US008952207B2

(12) United States Patent
Daugulis et al.

(10) Patent No.: US 8,952,207 B2
(45) Date of Patent: Feb. 10, 2015

(54) COPPER-CATALYZED C—H BOND ARYLATION

(75) Inventors: Olafs Daugulis, Houston, TX (US); Hien-Quang Do, Houston, TX (US)

(73) Assignee: The University of Houston System, Houston, TX (US)

( * ) Notice: Subject to any disclaimer, the term of this patent is extended or adjusted under 35 U.S.C. 154(b) by 255 days.

(21) Appl. No.: 12/208,286

(22) Filed: Sep. 10, 2008

(65) Prior Publication Data

US 2009/0076266 A1 Mar. 19, 2009

Related U.S. Application Data

(60) Provisional application No. 60/971,466, filed on Sep. 11, 2007.

(51) Int. Cl.
| | |
|---|---|
| C07C 22/00 | (2006.01) |
| C07C 25/13 | (2006.01) |
| C07F 9/02 | (2006.01) |
| C07D 333/00 | (2006.01) |
| C07D 409/02 | (2006.01) |
| C07B 37/04 | (2006.01) |
| C07C 17/269 | (2006.01) |
| C07C 41/30 | (2006.01) |
| C07C 45/68 | (2006.01) |
| C07C 253/30 | (2006.01) |
| C07D 213/06 | (2006.01) |
| C07D 213/89 | (2006.01) |
| C07D 215/04 | (2006.01) |
| C07D 237/08 | (2006.01) |
| C07D 239/26 | (2006.01) |
| C07D 239/74 | (2006.01) |
| C07D 249/08 | (2006.01) |
| C07D 263/32 | (2006.01) |
| C07D 263/57 | (2006.01) |
| C07D 277/22 | (2006.01) |
| C07D 277/66 | (2006.01) |
| C07D 307/79 | (2006.01) |
| C07D 333/06 | (2006.01) |
| C07D 333/12 | (2006.01) |
| C07D 333/54 | (2006.01) |
| C07D 413/04 | (2006.01) |
| C07D 471/04 | (2006.01) |

(52) U.S. Cl.
CPC .............. *C07B 37/04* (2013.01); *C07C 17/269* (2013.01); *C07C 41/30* (2013.01); *C07C 45/68* (2013.01); *C07C 253/30* (2013.01); *C07D 213/06* (2013.01); *C07D 213/89* (2013.01); *C07D 215/04* (2013.01); *C07D 237/08* (2013.01); *C07D 239/26* (2013.01); *C07D 239/74* (2013.01); *C07D 249/08* (2013.01); *C07D 263/32* (2013.01); *C07D 263/57* (2013.01); *C07D 277/22* (2013.01); *C07D 277/66* (2013.01); *C07D 307/79* (2013.01); *C07D 333/06* (2013.01); *C07D 333/12* (2013.01); *C07D 333/54* (2013.01); *C07D 413/04* (2013.01); *C07D 471/04* (2013.01); *C07C 2101/14* (2013.01)
USPC .............................. 570/143; 544/224; 549/49

(58) Field of Classification Search
None
See application file for complete search history.

(56) References Cited

PUBLICATIONS

He et al. Tetrahedron Letters 45 (2004) 3237-3239.*
Fagnou et al. Angew. Chem. 2006, 7781-7786.*
Hassan et al. Chem. Rev. 2002, 102, No. 5, pp. 1359-1469.*
Ljusberg, H et al. Acta Chemica Scandinavica 27 (1973) 2717-2721.*
Harper et al. Journal of Organic Chemistry 1964, 2385-2389.*
Nilsson et al. Acta Chemica Scandinavia, 1968 22(7), 2336-2346.*
Jon C. Antilla, Jeremy M. Baskin, Timothy E. Barder, and Stephen L. Buchwald, "Copper-Diamine-Catalyzed N-Arylation of Pyrroles, Pyrazoles, Indazoles, Imidazoles, and Triazoles," J. Org. Chem. 2004, 69, 5578-5587.
Andrew Martins, Udo Marquardt, Neema Kasravi, Dino Alberico, and Mark Lautens, "Synthesis of Substituted Benzoxacycles via a Domino Ortho-Alkylation/Heck Coupling Sequence," J. Org. Chem. 2006, 71, 4937-4942.
Joseph S. Bair and Roger G. Harrison, "Synthesis and Optical Properties of Bifunctional Thiophene Molecules Coordinated to Ruthenium," J. Org. Chem. 2007, 72, 6653-6661.
Zhijian Liu and Richard C. Larock, "Highly Efficient Route to Fused Polycyclic Aromatics via Palladium-Catalyzed Aryne Annulation by Aryl Halides," J. Org. Chem. 2007, 72, 223-232.
Ryan A. Altman, Alexandr Shafir, Alice Choi, Phillip A. Lichtor, and Stephen L. Buchwald, "An Improved Cu-Based Catalyst System for the Reactions of Alcohols with Aryl Halides," J. Org. Chem. 2008, 73, 284-286.
Leandro A. Estrada, Victor A. Montes, Grigory Zyryanov, and Pavel Anzenbacher, Jr., "Triplet Energy Studies of Thiophene and para-Phenylene Based Oligomers," J. Phys. Chem. B, vol. 111, No. 25, 2007, 6983-6986.
Ji-Chang Xiao, Chengfeng Ye, and Jean'ne M. Shreeve, "Bipyridinium Ionic Liquid-Promoted Cross-Coupling Reactions between Perfluoroalkyl or Pentafluorophenyl Halides and Aryl Iodides," Org. Lett., vol. 7, No. 10, 2005, 1963-1965.
Yun Liang, Shi Tang, Xu-Dong Zhang, Li-Qiu Mao, Ye-Xiang Xie, and Jin-Heng Li, "Novel and Selective Palladium-Catalyzed Annulations of 2-Alkynylphenols to Form 2-Substituted 3-Halobenzo[b]furans," Org. Lett., vol. 8, No. 14, 2006, 3017-3020.

(Continued)

*Primary Examiner* — Clinton Brooks
(74) *Attorney, Agent, or Firm* — Robert W Strozier

(57) ABSTRACT

The present invention is a one-step method for efficiently converting carbon-hydrogen bonds into carbon-carbon bonds using a combination of aryl halides, a substrate, and a copper salt as catalyst. This method allows faster introduction of complex molecular entities, a process that would otherwise require many more steps. This invention is particularly relevant for the organic synthesis of complex molecules such as, but not limited to, pharmacophores and explosives.

12 Claims, 81 Drawing Sheets

(56) References Cited

PUBLICATIONS

Timothy A. Dwight, Nicholas R. Rue, Dagmara Charyk, Ryan Josselyn, and Brenton DeBoel, "C—C Bond Formation via Double C—H Functionalization: Aerobic Oxidative Coupling as a Method for Synthesizing Heterocoupled Biaryls," Org. Lett., vol. 9, No. 16, 2007, 3137-3139.

Marc Lafrance, Daniel Shore, and Keith Fagnou, "Mild and General Conditions for the Cross-Coupling of Aryl Halides with Pentafluorobenzene and Other Perfluoroaromatics," Org. Lett., vol. 8, No. 22, 2006, 5097-5100.

Matthew J. Campbell and Jeffrey S. Johnson, "Mechanistic Studies of the Copper-Catalyzed Electrophilic Amination of Diorganozinc Reagents and Development of a Zinc-Free Protocol," Org. Lett., vol. 9, No. 8, 2007, 1521-1524.

Gordon Brasche, Jorge Garcia-Fortanet, and Stephen L. Buchwald, "Twofold C—H Functionalization: Palladium-Catalyzed Ortho Arylation of Anilides," Org. Lett., vol. 10, No. 11, 2008, 2207-2210.

Anand Sundararaman, Roger A. Lalancette, Lev N. Zakharov, Arnold L. Rheingold, and Frieder Jäkle, "Structural Diversity of Pentafluorophenylcopper Complexes. First Evidence of ô-Coordination of Unsupported Arenes to Organocopper Aggregates," Organometallics 2003, 22, 3526-3532.

Lily J. Ackerman, Joseph P. Sadighi, David M. Kurtz, Jay A. Labinger, and John E. Bercaw, "Arene C—H Bond Activation and Arene Oxidative Coupling by Cationic Palladium(II) Complexes," Organometallics 2003, 22, 3884-3890.

Satoshi Haneda, Zhibin Gan, Kazuo Eda, and Masahiko Hayashi, "Ligand Effects of 2-(2-Pyridyl)benzazole-Pd Complexes on the X-ray Crystallographic Structures, 1H NMR Spectra, and Catalytic Activities in Mizoroki-Heck Reactions," Organometallics 2007, 26, 6551-6555.

Helene Pellissier* and Maurice Santelli, "The use of arynes in organic synthesis," Tetrahedron 59 (2003) 701-730.

Kuang Shen, Yao Fu, Jia-Ning Li, Lei Liu and Qing-Xiang Guo, "What are the pKa values of C—H bonds in aromatic heterocyclic compounds in DMSO?," Tetrahedron 63 (2007) 1568-1576.

Dipannita Kalyani, Allison R. Dick, Waseem Q. Anani and Melanie S. Sanford, "Scope and selectivity in palladium-catalyzed directed C—H bond halogenation reactions," Tetrahedron 62 (2006) 11483-11498.

Katritzky, A. R.; Hands, A. R. "N-Oxides and related compounds. XIV. Infrared spectra of 2-substituted pyridine 1-oxides" J. Chem. Soc. 1958, 2195—abstract only.

Anklam, E. Asmus, K. D.; Robertson, L. W. "Pulse radiolysis of monohalogenated biphenyls. Correlation of absorption spectra of the radical cations with photoelectron spectroscopic data." J. Chem. Soc., Perkin Transactions 2 1989, 1573—abstract only.

Vollmann, K.; Muller, C. E. "Synthesis of 8-substituted xanthine derivatives" Heterocycles 2002, 57, 871—abstract only.

Bagley, M. C.; Lubinu, M. C.; Mason, C. "Regioselective microwave-assisted synthesis of substituted pyrazoles from ethynyl ketones" Synlett 2007, 704.—abstract only.

Fuchita, Y.; Oka, H.; Okamura, M. "Direct formation of arylpalladium(II) complexes from aromatic hydrocarbons via carbonhydrogen bond activation by the palladium(II) acetate-dipropyl selenide system" Inorg. Chim. Acta 1992, 194, 213—abstract only.

Jintoku, T.; Fujiwara, Y.; Kawata, I.; Kawauchi, T.; Taniguchi, H. "Palladium-catalyzed synthesis of aromatic acids from carbon monoxide and aromatic compounds via the aromatic carbon—hydrogen bond activation" J. Organomet. Chem. 1990, 385, 297—abstract only.

Stuart, D. R.; Fagnou, K. "The catalytic cross-coupling of unactivated arenes.(REPORTS)" Science 2007, 316, 1172.

Beckwith, A. L. J.; Gara, W. B. "Mechanism of cyclization of aryl radicals containing unsaturated ortho-substituents" J. Chem. Soc. Perkin Trans. 2 1975, 7, 795.

Camus, A.; Marsich, N. "Organocopper(I) complexes containing nitrogen and phosphorus bidentate ligands" J. Organomet. Chem. 1970. 21, 249.—abstract only.

Cho, J.-Y.; Tse, M. K.; Holmes, D.; Maleczka Jr., R. E.; Smith III, M. R. "Remarkably Selective Iridium Catalysts for the Elaboration of Aromatic C—H Bonds" Science 2002, 295, 305.

Anctil, E. J.-G.; Snieckus, V. "The directed ortho metalation-cross coupling symbiosis. Regioselective methodologies for biaryls and heterobiaryls. Deployment in aromatic and heteroaromatic natural product synthesis" J. Organomet. Chem. 2002, 653, 150.—abstract only.

Takeshi Uemura, Shinya Imot, and Naoto Chatani, "Amination of the Ortho C—H Bonds by the Cu(OAc)2-mediated Reaction of 2-Phenylpyridines with Anilines," Chemistry Letters vol. 35, No. 8 (2006), 842.

M. Nakada, C. Miura, H. Hishiyama, F. Higashi, T. Mori, M. Hirota, T. Ishii, "Photoreaction of Polyhalobenzenes in Benzene, Formation of Terphenyls," Bull. Chem. Soc. Jpn., 62, 3122-3126 (1989).

S. Pisva-Art, T. Satoh, Y. Kawamura, M. Miura, M. Nomura, "Palladium-Catalyzed Arylation of Azole Compounds with Aryl Halides in the Presence of Alkali Metal Carbonates and the Use of Copper Iodide in the Reaction," Bull. Chem. Soc. Jpn., 71, 467-473 (1998).

Marc Taillefer, Ning Xia, and Armelle Ouali, "Efficient Iron/Copper Co-Catalyzed Arylation of Nitrogen Nucleophiles," Angew. Chem. Int. Ed. 2007, 46, 934-936.

Fumitoshi Kakiuchi, Naoto Chatani, "Catalytic Methods for C—H Bond Functionalization: Application in Organic Synthesis," Adv. Synth. Catal. 2003, 345, 1077-1101.

Qian Cai, Benli Zou, and Dawei Ma, "Mild Ullmann-Type Biaryl Ether Formation Reaction by Combination of ortho-Substituent and Ligand Effects," Angew. Chem. Int. Ed. 2006, 45, 1276-1279.

Gordon Brasche and Stephen L. Buchwald, "C—H Functionalization/CN Bond Formation: Copper-Catalyzed Synthesis of Benzimidazoles from Amidines," Angew. Chem. Int. Ed. 2008, 47, 1932-1934.

Yuhua Zhang and Chao-Jun Li. "Highly Efficient Cross-Dehydrogenative-Coupling between Ethers and Active Methylene Compounds," Angew. Chem. Int. Ed. 2006, 45, 1949-1952.

Yuri Bolshan and Robert A. Batey, "Enamide Synthesis by Copper-Catalyzed Cross-Coupling of Amides and Potassium Alkenyltrifluoroborate Salts," Angew. Chem. Int. Ed. 2008, 47, 2109-2112.

M. Angels Carvajal, Santiago Alvarez, and Juan J. Novoa, "The Nature of Intermolecular CuI . . . CuI Interactions: A Combined Theoretical and Structural Database Analysis," Chem. Eur. J. 2004, 10, 2117 ± 2132.

Masahiro Miura, "Rational Ligand Design in Constructing Efficient Catalyst Systems for Suzuki-Miyaura Coupling," Angew. Chem. Int. Ed. 2004, 43, 2201-2203.

Keigo Kamata, Syuhei Yamaguchi, Miyuki Kotani, Kazuya Yamaguchi, and Noritaka Mizuno, "Efficient Oxidative Alkyne Homocoupling Catalyzed by a Monomeric Dicopper-Substituted Silicotungstate," Angew. Chem. Int. Ed. 2008, 47, 2407-2410.

Barbara Branchi, Carlo Galli, and Patrizia Gentili, "Reactivity of Aryl and Vinyl Radicals: Abstraction of Hydrogen Atom or Reaction with a Nucleophile," Eur. J. Org. Chem. 2002, 28442854.

Sebastian Proch and Rhett Kempe, "An Efficient Bimetallic Rhodium Catalyst for the Direct Arylation of Unactivated Arenes," Angew. Chem. Int. Ed. 2007, 46, 3135-3138.

Matthew D. Helm, Jane E. Moore, Andrew Plant, and Joseph P. A. Harrity, "Synthesis of Highly Substituted Pyridazines through Alkynyl Boronic Ester Cycloaddition Reactions," Angew. Chem. Int. Ed. 2005, 44, 3889-3892.

K. C. Nicolaou, Paul G. Bulger, and David Sarlah, "Palladium-Catalyzed Cross-Coupling Reactions in Total Synthesis," Angew. Chem. Int. Ed. 2005, 44, 4442-4489.

Zhiping Li, Lin Cao, and Chao-Jun Li, "FeCl2-Catalyzed Selective CC Bond Formation by Oxidative Activation of a Benzylic CH Bond," Angew. Chem. Int. Ed. 2007, 46, 6505-6507.

(56) References Cited

OTHER PUBLICATIONS

Vicente del Amo, Srinivas Reddy Dubbaka, Arkady Krasovskiy, and Paul Knochel, "General Preparation of Primary, Secondary, and Tertiary Aryl Amines by the Oxidative Coupling of Polyfunctional Aryl and Heteroaryl Amidocuprates," Angew. Chem. Int. Ed. 2006, 45, 7838-7842.
J. M. Birchall, R, N. Haszeldine, and J. G. Speight, "Polyfluoroarenes. Part XIIP Further Hornolytic Reactions of Polyfluoroiodobenzenes," J. Chem. Soc. (C), 1970, 2187-2191.
Gaston Vernin, Henri J. M. Dou, and Jacques Metzger, "Homolytic Aromatic Substitution by Heterocyclic Free Radicals. Part 1V.I Reaction of 5-Substituted Thiazol-2-yl Radicals with Alkylbenzenes," J.C.S. Perkin 11, 1973, 1093-1095.
Antonia Black, John M. Brown* and Christophe Pichon, Regiochemical control of the catalytic asymmetric hydroboration of 1,2-diarylalkenes, Chem. Commun., 2005, 5284-5286.
Fredericgk. B Ordwell, "Equilibrium Acidities in Dimethyl Sulfoxide Solution," Acc. Chem. Res. 1988,21, 456-463.
Jared C. Lewis, Robert G. Bergman, and Jonathan A. Ellman, "Direct Functionalization of Nitrogen Heterocycles via Rh-Catalyzed C—H Bond Activation," Accounts of Chemical Research 1013-1025 Aug. 2008 vol. 41, No. 8.
Dawei Ma and Feng Liu, "Cul-catalyzed coupling reaction of aryl halides with terminal alkynes in the absence of palladium and phosphine,", Chem. Commun., 2004, 1934-1935.
Akira Suzuki, "Carbon—carbon bonding made easy," Chem. Commun., 2005, 4759-4763 | 4759.
Louis-Charles Campeau and Keith Fagnou, "Palladium-catalyzed direct arylation of simple arenes in synthesis of biaryl molecules," Chem. Commun., 2006, 1253-1264.
Ilya V. Seregin and Vladimir Gevorgyan, "Direct transition metal-catalyzed functionalization of heteroaromatic compounds," Chem. Soc. Rev., 2007, 36, 1173-1193.
Jin-Quan Yu, Ramesh Giri and Xiao Chen, "sigma-Chelation-directed C—H functionalizations using Pd(II) and Cu(II) catalysts: regioselectivity, stereoselectivity and catalytic turnover," Org. Biomol. Chem., 2006, 4, 4041-4047.
Victor Snieckus, "Directed Ortho Metalation. Tertiary Amide and &Carbamate Directors in Synthetic Strategies for Polysubstituted Aromatics," Chem. Rev. 1990, 90, 879-933.
Jwanro Hassan, Marc Se'vignon, Christel Gozzi, Emmanuelle Schulz, and Marc Lemaire, "Aryl-Aryl Bond Formation One Century after the Discovery of the Ullmann Reaction," Chem. Rev. 2002, 102, 1359-1469.
Vincent Ritleng, Claude Sirlin, and Michel Pfeffer, "Ru-, Rh-, and Pd-Catalyzed C—C Bond Formation Involving C—H Activation and Addition on Unsaturated Substrates: Reactions and Mechanistic Aspects," Chem. Rev. 2002, 102, 1731-1769.
Dino Alberico, Mark E. Scott, and Mark Lautens, "Aryl-Aryl Bond Formation by Transition-Metal-Catalyzed Direct Arylation," Chem. Rev. 2007, 107, 174-238.
Ken-ichi Fujita, Mitsuru Nonogawa and Ryohei Yamaguchi, "Direct arylation of aromatic C—H bonds catalyzed by Cp*Ir complexes,", Chem. Commun., 2004, 1926-1927.
Anand Sundararaman, Lev N. Zakharov, Arnold L. Rheingold and Frieder Jäkle, "Cuprophilic and p-stacking interactions in the formation of supramolecular stacks from dicoordinate organocopper complexes," Chem. Commun., 2005, 1708-1710.
A. Bondi, "van der Waals Volumes and Radii," The Journal of Phusical Chemistry, vol. 68, No. 3 Mar. 16, 441-451, 1964.
Herbert C. Brown, Bruce A. Carlson,lo Rolf H. Prager, "Alkoxide-Induced Reactions of Tri-n-butylborane with Chlorodifluoromethane and Related Trisubstituted Methanes. A New, Facile Route from Organoboranes to the Corresponding Trialkylcarbinols," Journal of the American Chemical Society / 93:8 / Apr. 21, 1971, 2070-2071.
J. W. Seasea~ND L. Zechmeister, "Chromatographic and Spectral Characteristics of Some Polythienyls," [Contribution No. 1079 From the Gatesa ND Crellin Laboratories of Chemistry, California Institute of Technology, vol. 69, 270-273, 1979.
Artis Klapars, Jon C. Antilla, Xiaohua Huang, and Stephen L. Buchwald, "A General and Efficient Copper Catalyst for the Amidation of Aryl Halides and the N-Arylation of Nitrogen Heterocycles," J. Am. Chem. Soc. 2001, 123, 7727-7729.

Mehul B. Thathagar, Jurriaan Beckers, and Gadi Rothenberg, "Copper-Catalyzed Suzuki Cross-Coupling Using Mixed Nanocluster Catalysts," J. Am. Chem. Soc. 2002, 124, 11858-11859.
Jesse W. Tye, Zhiqiang Weng, Adam M. Johns, Christopher D. Incarvito, and John F. Hartwig, "Copper Complexes of Anionic Nitrogen Ligands in the Amidation and Imidation of Aryl Halides," J. Am. Chem. Soc. 2008, 130, 9971-9983.
Tetsuya Hamada, Xuan Ye, and Shannon S. Stahl, "Copper-Catalyzed Aerobic Oxidative Amidation of Terminal Alkynes: Efficient Synthesis of Ynamides," J. Am. Chem. Soc. 2008, 130, 833-835.
Hien-Quang Do and Olafs Daugulis, "Copper-Catalyzed Arylation and Alkenylation of Polyfluoroarene C—H Bonds", J. Am. Chem. Soc. 2008, 130, 1128-1129.
Tatsuo Ishiyama, Jun Takagi, Kousaku Ishida, and Norio Miyaura, "Mild Iridium-Catalyzed Borylation of Arenes. High Turnover Numbers, Room Temperature Reactions, and Isolation of a Potential Intermediate," J. Am. Chem. Soc. 9 vol. 124, No. 3, 2002, 390-391.
Jakob Norinder, Arimasa Matsumoto, Naohiko Yoshikai, and Eiichi Nakamura, "Iron-Catalyzed Direct Arylation through Directed C—H Bond Activation," J. Am. Chem. Soc. 2008, 130, 5858-5859.
Robert J. Phipps, Neil P. Grimster, and Matthew J. Gaunt, "Cu(II)-Catalyzed Direct and Site-Selective Arylation of Indoles Under Mild," J. Am. Chem. Soc. 2008, 130, 8172-8174.
Gary D. Allred and Lanny S. Liebeskind, "Copper-Mediated Cross-Coupling of Organostannanes with Organic Iodides at or below Room Temperature," J. Am. Chem. Soc. 1996, 118, 2748-2749.
Dale L. Boger, Robert S. Coleman, James S. Panek, and Daniel Yohannes, "Thermal Cycloaddition of Dimethyl 1,2,4,5-Tetrazine-3,6-dicarboxylate with Electron-Rich Olefins: 1,2-Diazine and Pyrrole Introduction. Preparation of Octamethylporphin (OMP)," J. Org. Chenz. 1984,49, 4405-4409.
Thomas J. Delia, Marvin J . Olsen and George Bosworth Brown, "Cytosine 3-N—Oxide and Its Rearrangement on Acetylation," J. Org. Chem. 1965, 30, 2766.
Masayuki Tani, Satoshi Sakaguchi, and Yasutaka Ishii, "Pd(OAc)2-Catalyzed Oxidative Coupling Reaction of Benzenes with Olefins in the Presence of Molybdovanadophosphoric Acid under Atmospheric Dioxygen and Air," J. Org. Chem., vol. 69, No. 4, 2004, 1221-1226.
Takashi Mino, Yoshiaki Shirae, Masami Sakamoto, and Tsutomu Fujita, "Phosphine-Free Hydrazone-Pd Complex as the Catalyst Precursor for a Suzuki-Miyaura Reaction under Mild Aerobic Conditions," J. Org. Chem. 2005, 70, 2191-2194 2191.
Tiecco, M.; Testaferri, L.; Bagnoli, L.; Marini, F.; Santi, C.; Temperini, A. "Selenium catalyzed conversion of d-phenyl-g-alkenyl oximes into 2-phenylpyridines" Heterocycles 1996, 43, 2679.—abstract only.
Burukin, A. S.; Vasil'ev, A. A.; Chizhov, A. O.; Zlotin, S. G. "Cross-coupling of polychloroarenes with phenylboronic acid and organozinc compounds catalyzed by palladium complexes" Russ. Chem. Bull. 2005, 54, 970.—abstract only.
Ullmann, F.; Bielecki, J. "Over syntheses in the diphenyl line" Chem. Ber. 1901, 34, 2174—abstract only.
Stanforth, S. P. "Catalytic cross-coupling reactions in biaryl synthesis." Tetrahedron 1998, 54, 263.—abstract only.
Steinkopf, W.; Leitsmann, R.; Hofmann, K. H. Liebigs "Thiophene series. LVII. 2-Polythienyls" Ann. Chem. 1941, 546, 180—abstract only.
Dyker, G. "Transition metal catalyzed coupling reactions under C—H activation" Angew. Chem. Int. Ed. 1999, 38, 1698.—abstract only.
Ackermann, L. "Catalytic arylations with challenging substrates: from air-stable HASPO preligands to indole syntheses and C—H-bond functionalizations" Synlett 2007, 507.—abstract only.
Björklund, C.; Nilsson, M. "Preparation of 2,6-dinitrobiphenyls from m-dinitrobenzene and iodoarenes with copper(I) oxide in quinoline" Acta Chem. Scand. 1968, 22, 2338—abstract only.
Ljusberg, H.; Wahren, R. "Copper-promoted arylation of pentafl" Acta Chem. Scand. 1973, 27, 2717—abstract only.
Nilsson, M. "Reaction of 2-thienylcopper with iodobenzene" Tetrahedron Lett. 1966, 7, 679—abstract only.
Forrest, J. "Ilmann biaryl synthesis. II. The effect of m-dinitrated diluents on the self condensation of iodobenzene" J. Chem. Soc. 1960, 574.—abstract only.

\* cited by examiner

¹H NMR Spectrum of 2-phenylbenzoxazole

FIG. 3 — 1H NMR Spectrum of 2-(4-(trifluoromethyl)phenyl)benzoxazole

1H NMR Spectrum of 2-(4-fluorophenyl)benzoxazole

¹H NMR Spectrum of 2-o-tolylbenzoxazole

1H NMR Spectrum of 2-mesitylbenzoxazole

1H NMR Spectrum of 2-(2-pyridyl)benzoxazole

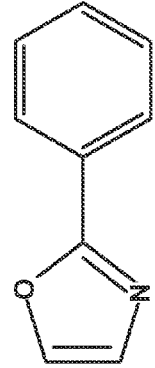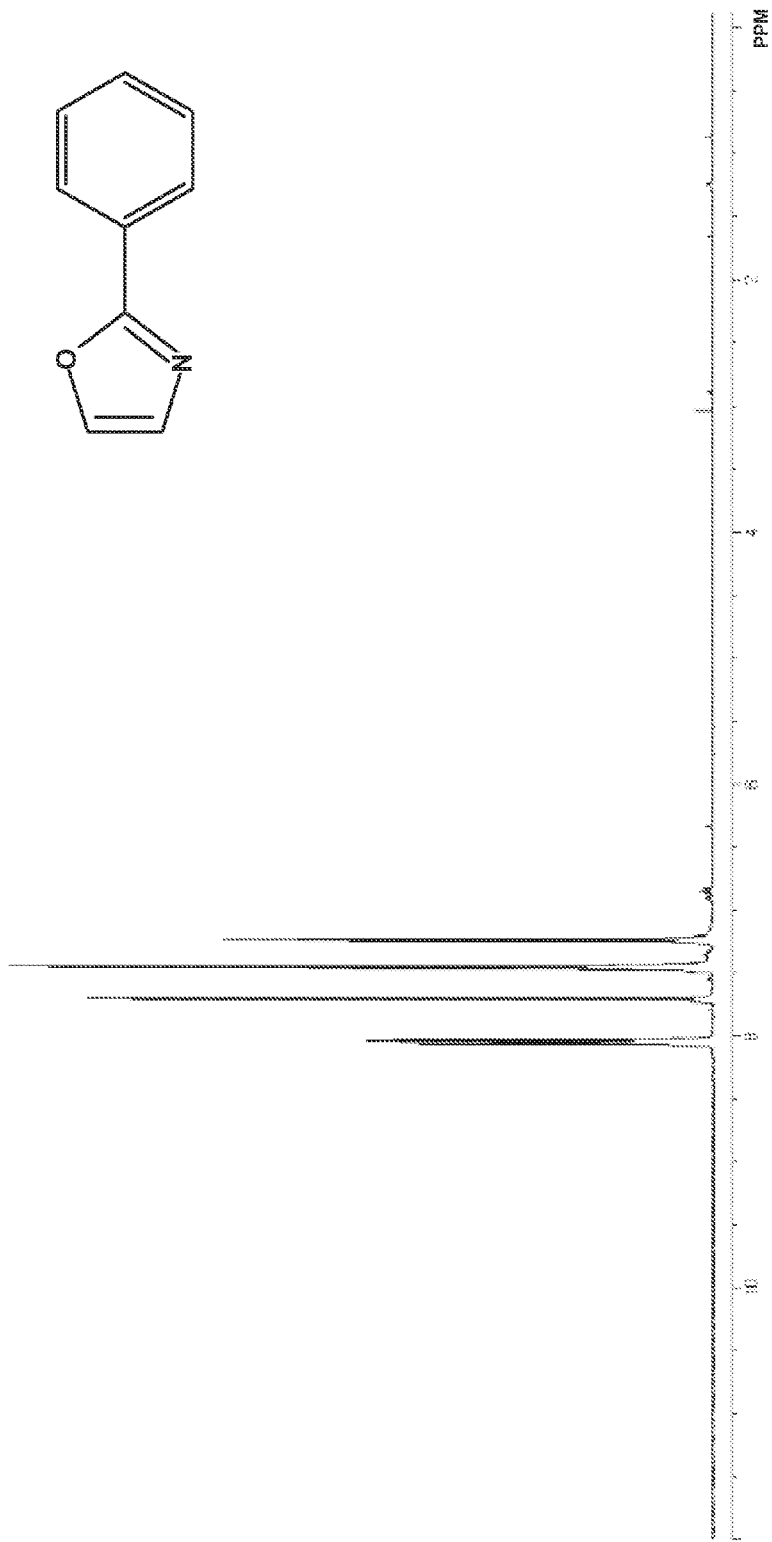
FIG. 11
1H NMR Spectrum of 2-phenyloxazole

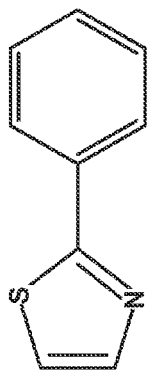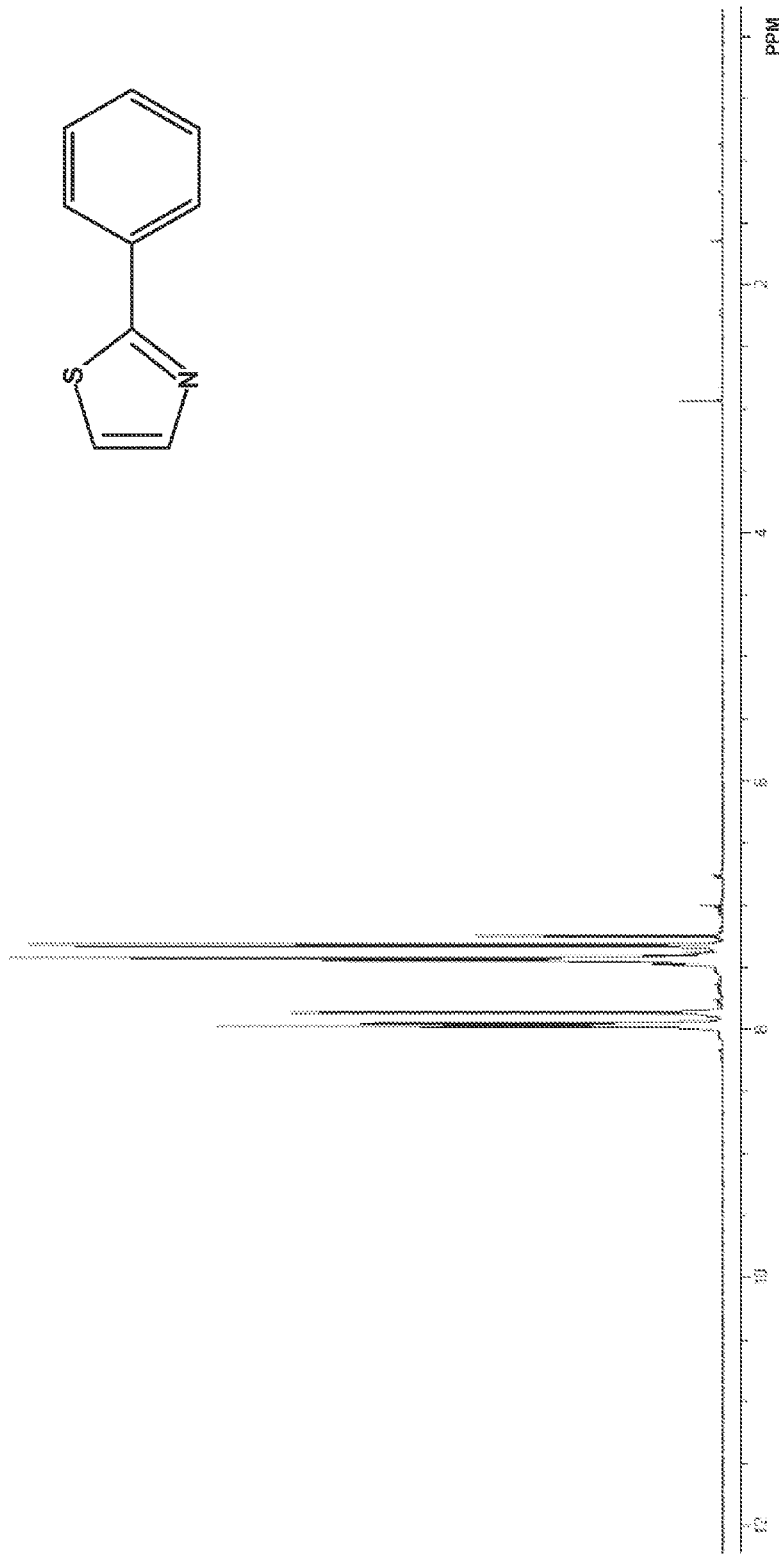
FIG. 12
1H NMR Spectrum of 2-phenylthiazole

1H NMR Spectrum of 4,5-dimethyl-2-phenylthiazole

1H NMR Spectrum of 2-phenylbenzothiazole

1H NMR Spectrum of 1-methyl-2-phenylbenzimidazole

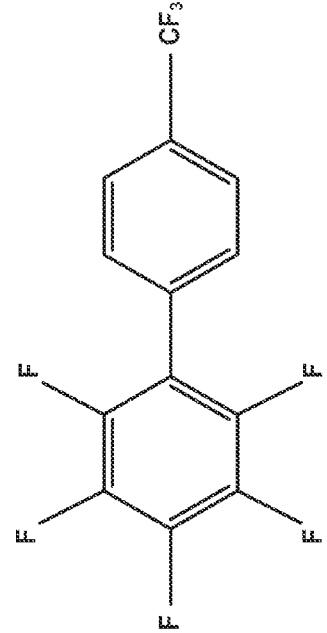
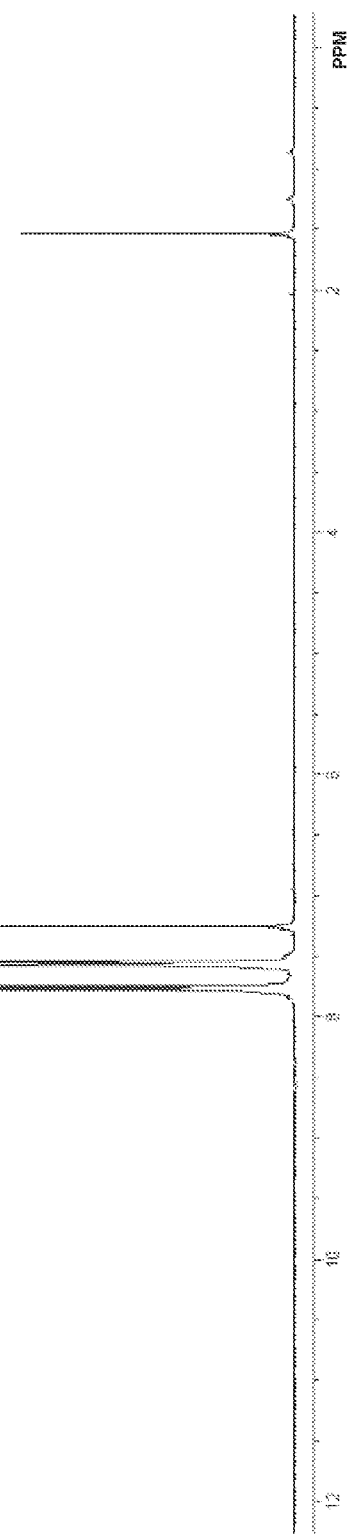
FIG. 24
1H NMR Spectrum of 2,3,4,5,6-pentafluoro-4'-(trifluoromethyl)biphenyl 1H NMR Spectrum of 3-(perfluorophenyl)pyridine ¹H NMR Spectrum of 2,3,5,6-tetrafluoro-4'-methylbiphenyl ¹H NMR Spectrum of 2,3,4,5-tetrafluoro-4'-methylbiphenyl

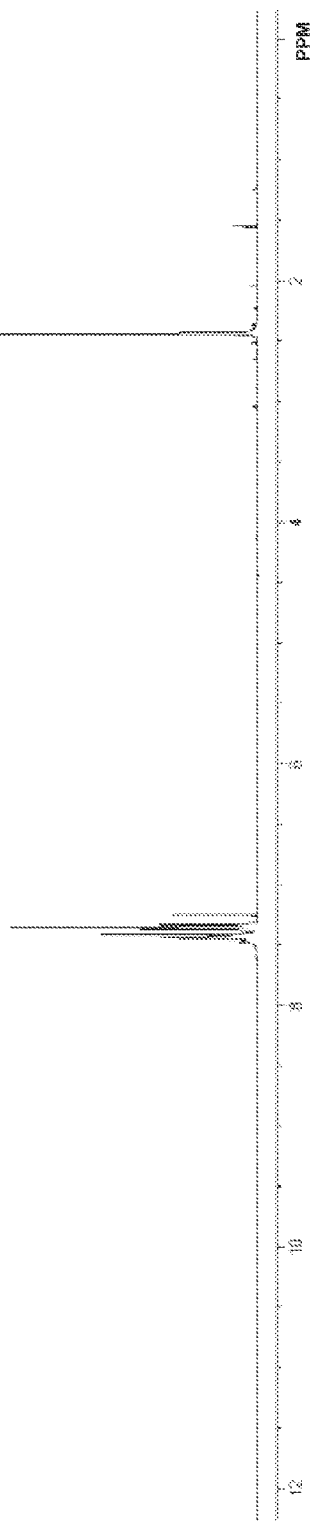
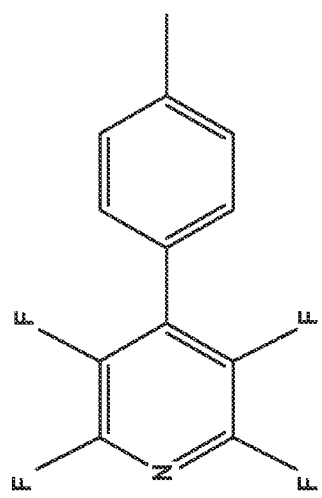
FIG. 39

1H NMR Spectrum of 2,4,6-trifluoro-4'-methylbiphenyl

1H NMR Spectrum of 2,5-difluoro-4'-methylbiphenyl

1H NMR Spectrum of 3-fluoro-2-p-tolylpyridine

Molecule Structure of 4-Methoxytetrafluorophenylcopper-phenanthroline Complex 2 and Its ¹H NMR Spectrum.

Molecule Structure of 4,5-Dimethyl-2-*m*-tolylthiazole and its $^1$H NMR spectrum.

Molecule Structure of 2-(pyridin-2-yl)benzo[d]thiazole and Its $^1$H NMR Spectrum.

FIG. 49 Molecule Structure of 1,3,7-Trimethyl-8-phenyl-1H-purine-2,6(3H,7H)-dione and Its ¹H NMR Spectrum.

FIG. 50 Molecule Structure of 1-Methyl-5-phenyl-1H-1,2,4-triazole and Its $^1$H NMR Spectrum.

Molecule Structure of 1-Methyl-2-phenylimidazole and Its ¹H NMR Spectrum.

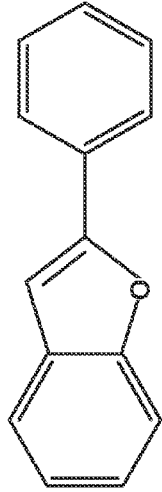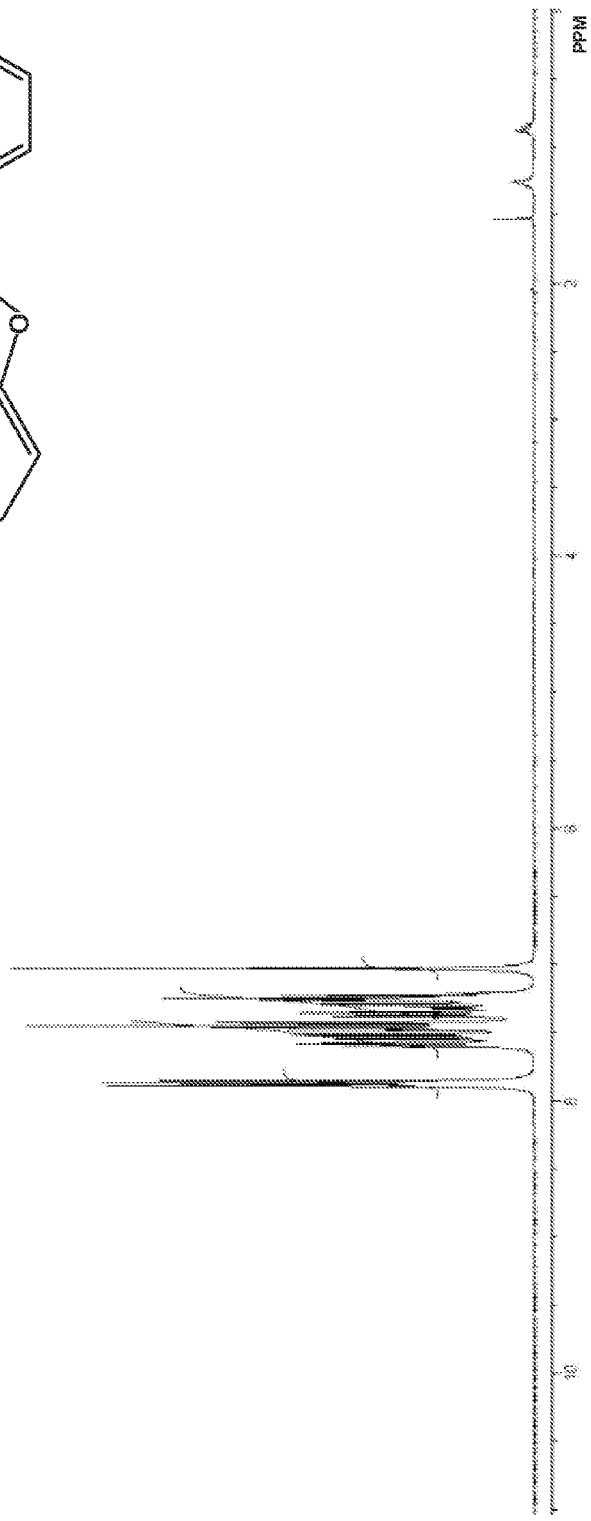
Molecule Structure of 2-Phenylbenzofuran and Its $^1$H NMR Spectrum
FIG. 56

Molecule Structure of 2-Chloro-5-*m*-tolylthiophene and Its $^1$H NMR Spectrum

Molecule Structure of 4-Phenylpyridazine and Its $^1$H NMR Spectrum

FIG. 68 Molecule Structure of 2-(Pentafluorophenyl)quinoline and its $^1$H NMR Spectrum Molecule Structure of Phenyl(2',3',5',6'-tetrafluorobiphenyl-4-yl)methanone and Its ¹H NMR Spectrum Molecule Structure of 2,3,4,6-Tetrafluoro-4'-phenylbiphenyl and Its $^1$H NMR spectrum Molecule Structure of 1-(Cyclohexylidenemethyl)-2,3,5,6-tetrafluoro-4-methylbenzene and Its $^1$H NMR Spectrum Molecule Structure of 2,4-Difluoro-3-(pyridin-2-yl)benzophenone and Its $^1$H NMR Spectrum Molecule Structure of 2,6-Dichlorobiphenyl and Its $^1$H NMR Spectrum

COPPER-CATALYZED C—H BOND ARYLATION

CROSS-REFERENCES TO RELATED APPLICATIONS

This application claim priority to and the benefit of U.S. Provisional Application Ser. No. 60/971,466 filed Sep. 11, 2007.

GOVERNMENTAL SPONSORSHIP

The U.S. Government has a paid-up license in this invention and the right in limited circumstances to require the patent owners to license others on reasonable terms as provided for by the terms of Contract No. 1R01GM077635-01A1 awarded by the National Health Institute—National Institute of General Medicine Sciences.

REFERENCE TO A SEQUENTIAL LISTING

Not Applicable.

BACKGROUND OF THE INVENTION

1. Field of the Invention

The present invention relates generally to a new method for the formation of carbon-carbon bonds.

More specifically, the invention relates to a one-step method for converting a carbon-hydrogen bond into carbon-carbon bond by contacting an aryl halide, a substrate, and a copper (I) salt as a catalyst.

2. Description of the Related Art

Because many pharmaceuticals contain heterocycle-aryl linkages, the arylation of heterocycles has received significant attention in the recent years. The shortest and most efficient route to synthesize these compounds involves the direct functionalization of heterocycle C—H bonds. So far, most efforts in cross-coupling methodologies consist in replacing aryl iodides with cheaper aryl chlorides. However, for realistic catalyst loadings it is more cost-efficient to replace the expensive transition metal catalyst, usually palladium or rhodium, with a cheaper one. Prior art teaches the use of copper catalysts in amination reactions—that is the formation of carbon-nitrogen bonds—and for Stille-type or Suzuki-type couplings. The formation of carbon-carbon bonds by the arylation of b-dicarbonyl compounds is known; however, the formation of carbon-carbon bond using copper-catalyzed direct heterocycle or electron-poor arene C—H arylation reactions has not been developed.

Thus, there is a need in the art for a general method for the copper-catalyzed C—H bond arylation by aryl halides including electron-rich five-membered heterocycles, electron-deficient heterocycles, electron-poor arene is also disclosed that shortens organic synthetic pathways.

SUMMARY OF THE INVENTION

The present invention also provides a method for a one-step arylation of C—H bonds, where the method includes contacting a substrate selected from the group consisting of electron-rich heterocyclic substrates, electron-poor heterocyclic substrates, electron-poor aromatic substrates, and mixtures or combinations thereof and an aryl halide in the presence of a copper catalyst.

The present invention also provides a method for a one-step arylation of C—H bonds, where the method includes contacting an electron-rich heterocyclic substrate, an aryl halide, and a copper catalyst.

The present invention also provides a method for a one-step arylation of C—H bonds, where the method includes contacting an electron-poor heterocyclic substrate, electron-poor aromatic compounds, where the method includes contacting an aryl halide, a substrate, and a copper salt as a catalyst.

The present invention also provides a method for a one-step arylation of C—H bonds, where the method contacting includes a electron-poor aromatic substrate, an aryl halide, and a copper catalyst.

The present invention also provides a method for a one-step dimerization of heterocycles or electron-poor arenes, where the method includes contacting a substrate selected from the group consisting of electron-rich heterocyclic substrates, electron-poor heterocyclic substrates, electron-poor aromatic substrates, and mixtures or combinations thereof in the presence of a copper catalyst and stoichiometric oxygen or air reoxidant.

BRIEF DESCRIPTION OF THE FIGURES

FIG. 11 depicts the molecular structure of 2-phenyloxazole and $^1$H NMR Spectrum of 2-phenyloxazole.

FIG. 12 depicts the molecular structure of 2-phenylthiazole and $^1$H NMR Spectrum of 2-phenylthiazole

FIG. 24 depicts the molecular structure of 2,3,4,5,6-pentafluoro-4'-(trifluoromethyl)biphenyl and $^1$H NMR Spectrum of 2,3,4,5,6-pentafluoro-4'-(trifluoromethyl)biphenyl.

FIG. 39 depicts the molecular structure of 2,3,5,6-tetrafluoro-4-p-tolylpyridine and $^1$H NMR Spectrum of 2,3,5,6-tetrafluoro-4-p-tolylpyridine.

FIG. 56 depicts the molecule structure of 2-phenylbenzofuran and its $^1$H NMR spectrum.

DESCRIPTION OF THE PREFERRED EMBODIMENTS

Figure 1:
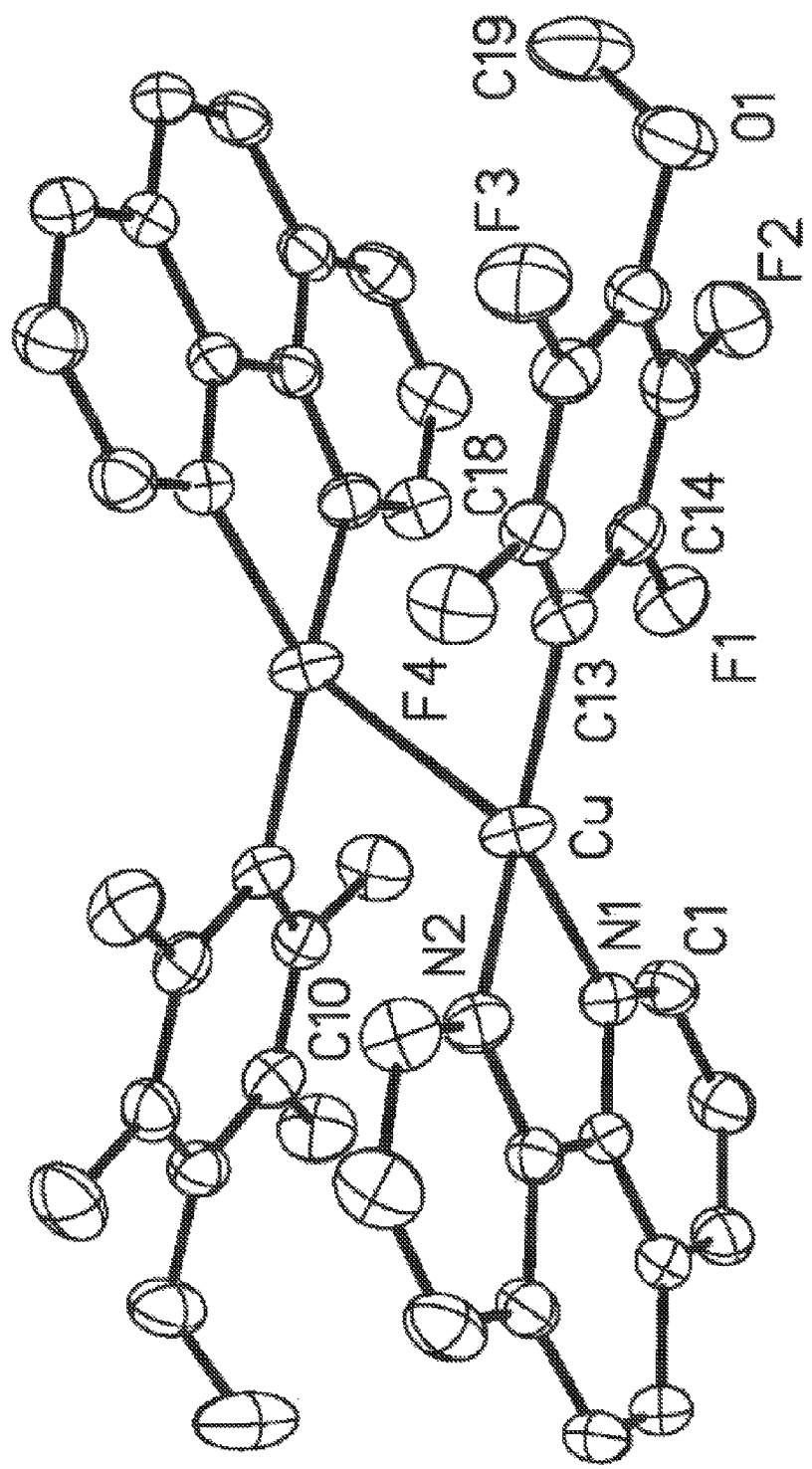
FIG. 1 depicts an ORTEP view of 4-methoxy-2,3,5,6-tetrafluorophenylcopper phenanthroline complex 2: selected interatomic distances (Å) and angles (deg): Cu—C(13) =1.932(2), Cu—N(1)=2.0720(18), Cu—N(2)=2.0949(19), Cu—Cu=2.5770(6), C(13)-Cu—N(1)=135.68(9), C(13)-Cu—N(2)=132.69(8).

The present invention is a method for the direct formation of carbon-carbon bonds in electron-rich and electron-poor heterocycles, as well as electron-poor arenes using a combination of an aryl halide, a substrate, and a copper salt as catalyst. The present invention is particularly relevant for the organic synthesis of complex molecules such as, but not limited to, pharmacophores and explosives. The methods of this invention are generally carried out at atmospheric pressure; however, the reaction can be performed at reduced pressure or at an elevated pressure up to many atmospheres. The methods of this invention are generally carried out at an elevated temperature. In certain embodiments, the temperature is between about 20° C. and about 200° C. In other embodiments, the temperature is between about 80° C. and about 150° C. In other embodiments, the temperature is between about 90° C. and about 140° C.

The present invention broadly relates to a method for the direct conversion of C—H bonds to carbon-carbon bonds comprising the step of contacting a substrate and an aryl halide in the presence of a catalyst including a copper(I) salt, where the substrate is selected from the group consisting of electron-rich heterocyclic substrates, electron-poor heterocyclic substrates, electronic-poor aromatic substrates, and mixtures or combinations thereof. The catalyst can further include a ligand. The ligand can comprise a nitrogen, sulfur, oxygen ligand or mixtures or combinations thereof. The ligand can be selected from the group consisting of, but not limited to, dimethylformamide, dimethylacetamide, N-methylpyrrolidone, bipyridine and its derivatives, phenanthroline and its derivatives, cyclohexanediamine and its derivatives, ethylenediamine and its derivatives, and mixtures or combinations thereof, as well as other nitrogen, oxygen, or sulfur containing ligands.

The present invention also broadly relates to a method for the direct conversion of C—H bonds to carbon-carbon bonds comprising the step of contacting a substrate and an aryl halide in the presence of a catalyst including a copper(I) salt, where the substrate comprises an electron-rich heterocyclic substrate or a plurality of electron-rich heterocyclic substrates. The catalyst can further includes a ligand. The ligand can comprise a nitrogen, sulfur, oxygen ligand or mixtures or combinations thereof. The ligand can be selected from the group consisting of, but not limited to, dimethylformamide, dimethylacetamide, N-methylpyrrolidone, bipyridine and its derivatives, phenanthroline and its derivatives, cyclohexanediamine and its derivatives, ethylenediamine and its derivatives, and mixtures or combinations thereof, as well as other nitrogen, oxygen, or sulfur containing ligands.

The present invention also broadly relates to a method for the direct conversion of C—H bonds to carbon-carbon bonds comprising the step of contacting a substrate and an aryl halide in the presence of a catalyst including a copper(I) salt, where the substrate comprises an electron-poor heterocyclic substrate or a plurality of electron-poor heterocyclic substrates. The catalyst can further includes a ligand. The ligand can comprise a nitrogen, sulfur, oxygen ligand or mixtures or combinations thereof. The ligand can be selected from the group consisting of, but not limited to, dimethylformamide, dimethylacetamide, N-methylpyrrolidone, bipyridine and its derivatives, phenanthroline and its derivatives, cyclohexanediamine and its derivatives, ethylenediamine and its derivatives, and mixtures or combinations thereof, as well as other nitrogen, oxygen, or sulfur containing ligands.

The present invention also broadly relates method for the direct conversion of C—H bonds to carbon-carbon bonds comprising the step of contacting a substrate and an aryl halide in the presence of a catalyst including a copper(I) salt, where the substrate comprises a electron-poor aromatic substrate or a plurality of electron-poor aromatic substrates. The catalyst can further includes a ligand. The ligand can comprise a nitrogen, sulfur, oxygen ligand or mixtures or combinations thereof. The ligand can be selected from the group consisting of, but not limited to, dimethylformamide, dimethylacetamide, N-methylpyrrolidone, bipyridine and its derivatives, phenanthroline and its derivatives, cyclohexanediamine and its derivatives, ethylenediamine and its derivatives, and mixtures or combinations thereof, as well as other nitrogen, oxygen, or sulfur containing ligands.

The present invention also broadly relates method for dimerizing electron-poor or electron-deficient arenes comprising the step of contacting a substrate selected from the group consisting of electron-rich heterocyclic substrates, electron-poor heterocyclic substrates, electron-poor aromatic substrates, and mixtures or combinations thereof in the presence of a copper catalyst and stoichiometric oxygen or air reoxidant. The catalyst can further includes a ligand. The ligand can comprise a nitrogen, sulfur, oxygen ligand or mixtures or combinations thereof. The ligand can be selected from the group consisting of, but not limited to, dimethylformamide, dimethylacetamide, N-methylpyrrolidone, bipyridine and its derivatives, phenanthroline and its derivatives, cyclohexanediamine and its derivatives, ethylenediamine and its derivatives, and mixtures or combinations thereof, as well as other nitrogen, oxygen, or sulfur containing ligands.

Exemplary example of electron-poor or electron-deficient arenes include, without limitation, halogenated arenes such as fluorinated arenes, perfluorinated arenes, chlorinated arenes, perchlorinated arenes, fluorinated/chlorinated arenes, or mixtures or combinations thereof, nitrile substituted arenes, nitrile and halogen substituted arenes, nitro substituted arenes, nitro and nitrile substituted arenes, nitro, nitrile and halogen substituted arenes, arenes bearing halogenated substitutents such as halogenated alkyl groups, e.g., fluorinated alkyl groups, perfluoroalkyl group, chlorinated alkyl groups, perchloroalkyl group, fluorinated/chlorinated alkyl groups, any other type of electron-poor or electron-deficient arenes or mixtures or combinations thereof.

In addition to monomeric substrates, the substrates can be part of a polymer, where the resulting polymer have modified chemical and/or physical properties.

One preferred embodiment of the present invention includes a general procedure for the phenylation of benzoxazole using copper iodide as catalyst, where a phenyl group is introduced into an electron-rich heterocycle:

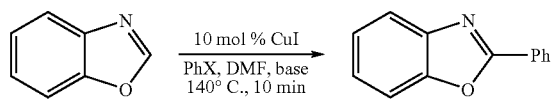 [SMILES: c1ccc2ocnc2c1 ; c1ccc(-c2nc3ccccc3o2)cc1]

Reactions are performed in 1-dram vials with polyvinyl lined caps. Flash chromatography is performed on 60 Å silica gel (Sorbent Technologies). Purification by preparative HPLC is performed on a Shimadzu Prominence LC (LC-20AB) equipped with a SPD-20A UV-Vis detector and a Varian Dynamax (250 mm×21.4 mm) column. GC-MS analyses are performed on a Shimadzu GCMS-QP5000 chromatograph equipped with a Restek column (Rtx-XLB, 30 m×0.25 mm I.D.). The $^1$H and $^{13}$C NMR spectra are recorded on a GE QE-300 spectrometer using residual solvent peak as a reference. Melting points are measured on a Mel-Temp apparatus and are uncorrected. Elemental analyses are performed by Atlantic Microlab Inc. of Norcross, Ga. IR spectra are obtained using ThermoNicolet Avatar 370 FT-IR instrument.

The following starting materials are obtained from commercial sources and are used without further purification: 1-fluoro-4-iodobenzene, 4-iodobenzotrifluoride and iodobenzene benzoxazole, benzothiazole, 4,5-dimethylthiazole, 5-iodo-m-xylene, copper(I) iodide, DMF, 1-iodonapthalene, oxazole, thiazole, potassium t-butoxide, 1-methylbenzimidazole, 4-iodoanisole, 2-iodopyridine, powdered lithium t-butoxide, 2-iodotoluene, caffeine, 1-methyl-1,2,4-triazole, 2-iodo-1,3,5-trimethylbenzene The 2-phenylpyridine oxide is prepared from 2-phenylpyridine.

A general method for the arylation of benzoxazole is presented here. Outside the glovebox a 1-dram vial equipped with a magnetic stir bar is charged with heterocycle (1.0 mmol), iodoarene (3.0 equiv) and DMF (1 mL). The vial is flushed with argon, capped and placed inside a glovebox. To this mixture is added CuI (10 mol %) and t-BuOLi (2.0 equiv). The sealed vial is taken out of the glovebox, stirred at room temperature for 5 min and placed in a preheated oil bath (140° C.) for 10 minutes. The reaction mixture is allowed to cool to room temperature and diluted with ethyl acetate (50 mL). The resulting solution is washed with brine (3×15 mL), dried over anhydrous MgSO$_4$, and concentrated under vacuum to a volume of about 2 mL. The mixture containing the product is subjected to flash chromatography on silica gel (hexanes followed by appropriate solvent to elute the products). After concentrating the fractions containing the product, the residue is dried under reduced pressure to yield pure arylation product. Table I tabulates a list of phenylated benzoxazole products prepared using Cu(I)I as the catalyst studying the effect of base and aryl halide on reaction yield.

TABLE I

Phenylation of Benzoxazole[a] Using Copper Iodide as Catalyst: Effect of the Base and Aryl Halide on the Reaction Yield

| Entry | Base | PhX | Yield % |
|---|---|---|---|
| 1 | KOtBu | PhF or PhOTs | No Arylation |
| 2[b] | KOtBu | PhCl | 40 |
| 3 | KOtBu | PhBr | 51 |
| 4 | KOtBu | PhI | 61 |
| 5 | LiOtBu | Phd, PhBr or PhOTs | No Arylation |
| 6 | LiOtBu | PhI | 93 |

[a]Substrate is benzoxazole (1 equiv.), aryl halide (3 equiv.), base (2 equiv.)
[b]PhCl (4 equiv.), base (3 equiv.)
OTs—Tosylate
Yields are isolated yields Table II tabulates a list of phenylated benzoxazole products prepared using Cu(I)I as the catalyst studying the effect of aryl iodides on reaction yield.

TABLE II

Arylation of Benzoxazole Using Copper Iodide as Catalyst Effect of Aryl Iodides[a]

| Entry | Aryl | Product | Yield % |
|---|---|---|---|
| 1 | 4-CF$_3$C$_6$H$_4$I | benzoxazole-4-CF$_3$-phenyl | 91 |
| 2 | 4-FC$_6$H$_4$I | benzoxazole-4-F-phenyl | 90 |
| 3 | 4-OMeC$_6$H$_4$I | benzoxazole-4-OMe-phenyl | 80 |
| 4 | 3,5-Me$_2$C$_6$H$_3$I | benzoxazole-3,5-Me$_2$-phenyl | 85 |
| 5 | 2-MeC$_6$H$_4$I | benzoxazole-2-Me-phenyl | 91 |

TABLE II-continued

Arylation of Benzoxazole Using Copper Iodide as Catalyst
Effect of Aryl Iodides[a]

| Entry | Aryl | Product | Yield % |
|---|---|---|---|
| 6 | 2,4,6-Me$_3$C$_6$H$_2$I | 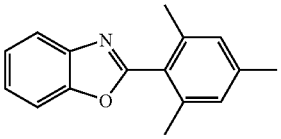 [SMILES: Cc1cc(C)c(-c2nc3ccccc3o2)c(C)c1] | 55 |
| 7 | 1-Iodonaphthalene | 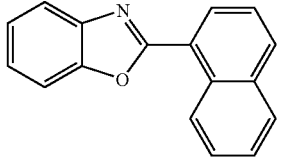 [SMILES: c1ccc2c(-c3nc4ccccc4o3)cccc2c1] | 90 |
| 8 | 2-Iodopyridine | 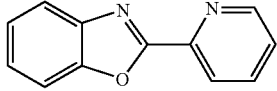 [SMILES: c1ccc(-c2nc3ccccc3o2)nc1] | 89 |

[a]Substrate (1 equiv.), aryl iodide (3 equiv.), base (2 equiv.). Yields are isolated yields Table III tabulates a list of phenylated benzoxazole products prepared using Cu(I)I as the catalyst studying the effect of heterocyclic compounds on reaction yield.

TABLE III

Arylation of Benzoxazole Using Copper Iodide as Catalyst
Effect of Heterocyclic Compounds

| Entry | Aryl | Product | Yield % |
|---|---|---|---|
| 1[b] |  | 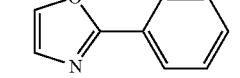 | 59 |
| 2[c] |  | 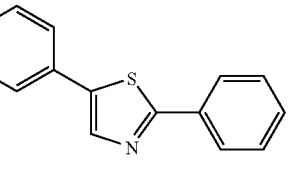 | 59 |
| 3 |  | 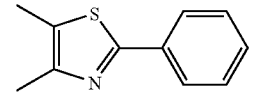 | 84 |
| 4 | 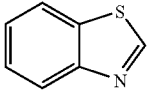 | 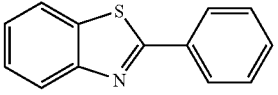 | 82 |
| 5[d] | 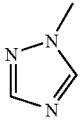 | 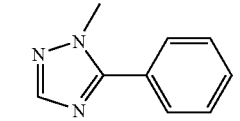 | 57 |
| 6[e] | 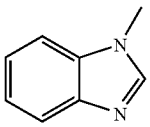 | 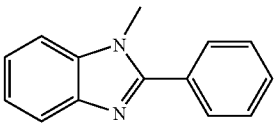 [SMILES: Cn1c(-c2ccccc2)nc2ccccc21] | 89 |
| 7[d] | 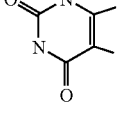 | 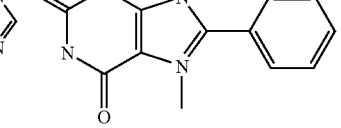 | 78 |
| 8 | 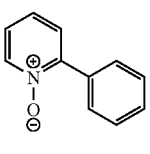 | 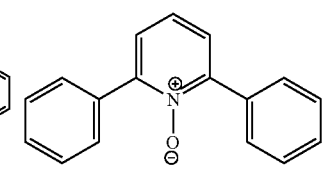 | 70 |

[a]Substrate (1 equiv.), iodobenzene (3 equiv.), base (2 equiv.). Yields are isolated yields.
[b]2,5-Diphenyloxazole also isolated (7%)
[c]2-Phenylthiazole also isolated (37%).
[d]KOtBu base.
[e]LiOtBu/KOtBu base (1:1).

A general method for copper-catalyzed arylation of sp$^2$ C—H bonds with pKa's below 35 has been developed. The method employs aryl halide as the coupling partner, lithium alkoxide or K$_3$PO$_4$ base, and DMF, DMPU, or mixed DMF/xylenes solvent. A variety of electron-rich and electron-poor heterocycles such as azoles, caffeine, thiophenes, benzofuran, pyridine oxides, pyridazine, and pyrimidine can be arylated. Furthermore, electron-poor arenes possessing at least two electron-withdrawing groups on benzene ring can also be arylated.

Introduction

Compounds containing polyaryl moieties are common among natural products, pharmaceuticals, and dyes. As a consequence, regioselective formation of aryl-aryl bonds has attracted substantial interest over the last century.[1] The copper-promoted biaryl synthesis was pioneered by Ullmann more than a hundred years ago.[2] Until the development of Stille, Suzuki, and Kumada reactions[3] in 1970's copper was the only metal widely used for the formation of aryl-aryl bonds. Recently, copper-catalyzed crosscoupling reactions are undergoing resurgence. Efficient methods for carbon-carbon,[4] carbon-nitrogen,[5] and carbon-oxygen[6] bond formation have been demonstrated by using copper complexes. However, copper appears to be underutilized as a catalyst for C—H bond functionalization even though it was the first transition metal shown to promote carbon-hydrogen bond arylation.[7] In the last few years palladium-, rhodium-, and ruthenium-catalyzed sp$^2$ C—H bond arylation has undergone explosive growth.[8] In contrast, only scattered examples of copper-promoted carbon-hydrogen bond arylation have been described with most reports dating back to 1960's and 1970's.[9]

Majority of the palladium-, rhodium-, or ruthenium-catalyzed C—H bond functionalization examples involve regioselective arylation of directing-group-containing arenes (Scheme 1A) or electron-rich heterocycles. Several recent reports describe functionalization of arenes possessing no conventional directing groups.[10] In the latter case the regioselectivity issues are often unsolved and sometimes only symmetrical arenes can be employed as the C—H coupling component due to the possibility of regioisomer formation (Scheme 1B). Perhaps the only general exception is found in recent elegant work by Fagnou who showed that fluorinated arenes can be regioselectively arylated by aryl halides under palladium catalysis.[11] The regioselectivity is imparted by the acidification of the C—H bonds by ortho-fluorine substituents (Scheme 1A, DG=F). Thus, two issues that need to be solved are apparent. First, regioselectivity of arylation is often problematic unless the coupling C—H component contains a directing group. Second, expensive transition metals such as palladium, rhodium, and ruthenium are routinely employed as arylation catalysts. Cheap copper and iron complexes are only rarely used in non-carbene C—H bond functionalization chemistry.[12]

Scheme 1A&B
Regioselectivity in C—H Bond Functionalization

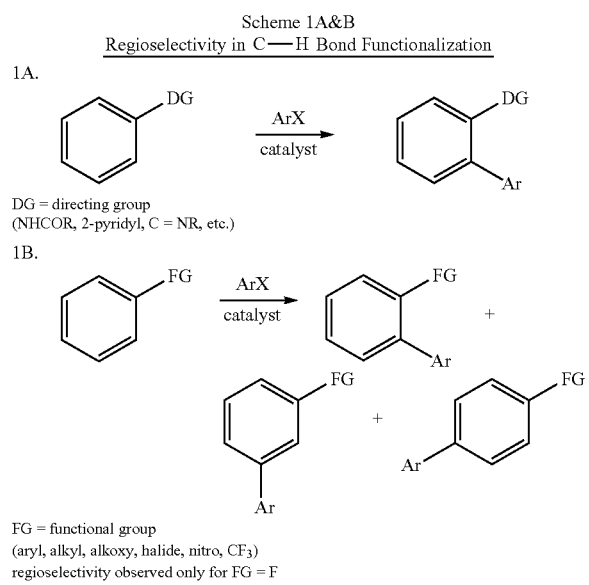

FG = functional group
(aryl, alkyl, alkoxy, halide, nitro, CF₃)
regioselectivity observed only for FG = F We have recently disclosed a method for copper-catalyzed arylation of C—H bonds in electron-poor and electron-rich heterocycles as well as polyfluorobenzenes.[13] The reactions proceed by initial deprotonation of a relatively acidic sp² C—H bond by an alkali metal base (or tBuOCu) followed by transmetallation and coupling with an aryl or vinyl halide (Scheme 2). Even 1,4-difluorobenzene derivatives can be arylated, although the efficiency is low, presumably due to insufficient acidity. If pKa of the C—H bond is the major factor determining the arylation efficiency, copper-catalyzed cross-coupling method should be very general.

Scheme 2
Copper-Catalyzed Arylation

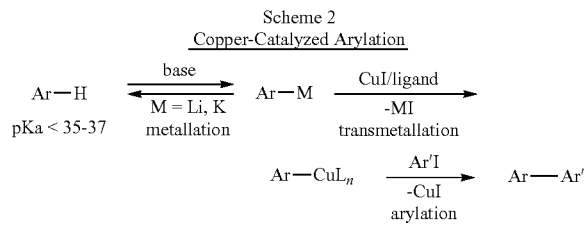

We report here a general method for copper-catalyzed, highly regioselective arylation and alkenylation of electron-rich and electron-poor heterocycles as well as benzenes possessing at least two electronwithdrawing groups. Mechanistic investigations of the arylation process are also described.

Results
Arylation of Electron-Rich Heterocycles

Our initial attempts were directed towards developing optimized conditions for electron-rich heterocycle arylation. We have recently reported a method for copper-catalyzed heterocycle arylation by aryl iodides.[13a] The best results were obtained by employing lithium t-butoxide base and relatively acidic heterocycle substrates such as oxazoles and thiazoles. For less acidic imidazole and 1,2,4-triazole derivatives a stronger tBuOK base is required and the reaction proceeds by a benzyne-type mechanism.[14] Regioisomer mixtures were formed if substituted aryl halides were used in combination with KOtBu base (Scheme 3). Additional issues that had to be considered are as follows. Formation of t-butyl aryl ether by the reaction of t-butoxide bases with aryl iodide was observed, resulting in decreased conversion to the arylation products. Copper catalyst was found to be relatively unstable at the temperature required for the arylation and thus only fast reactions were successful.

Scheme 3
Benzyne Mechanism

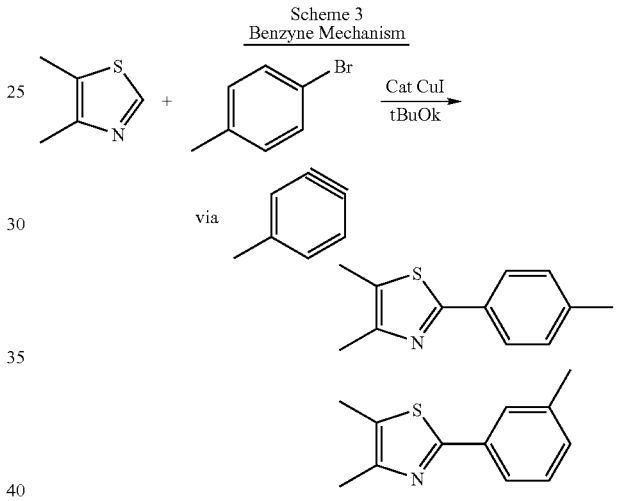

We reasoned that employing a phenanthroline ligand as described by Buchwald and coworkers 6a should allow for a more efficient heterocycle arylation by stabilizing the copper catalyst and facilitating the halide displacement step. Replacing tBuOK with a weaker lithium alkoxide or $K_3PO_4$ base should shut down the benzyne mechanism thus ensuring arylation regioselectivity. For less reactive substrates employing hindered Et₃COLi base instead of tBuOLi should be beneficial by slowing the nucleophilic substitution of aryl iodide while not influencing the arylation rate. We were pleased to discover that addition of phenanthroline ligand allows us to use lithium t-butoxide as a base for less acidic heterocycle arylation avoiding the problems associated with the benzyne mechanism. Additionally, the modified reaction conditions allow for the arylation of heterocycles that were not reactive under our previous conditions (Table IV). It is possible to employ $K_3PO_4$ base in the arylation of the most acidic heterocycles such as benzothiazole (Entry 1). Caffeine and N-methyl-1,2,4-triazole can be arylated by using tBuOLi base (Entries 2 and 3). Previously, tBuOK was required for the arylation of those substrates.[13a] For the least acidic heterocycles hindered Et₃COLi base is required for optimal results. Arylation of N-methylimidazole (Entry 4), thiophenes (Entries 5, 6, 10, and 11), N-phenylpyrazole (Entry 7), benzofuran and benzothiophene (Entries 8 and 9) can be accomplished in good yields. Reaction of 2-chlorothiophene with 2-iodotoluene afforded only the o-tolylated heterocycle (Entry 10). If the benzyne mechanism would be operative, either isomer mixture or m-isomer would be formed. Arylation of 2-chlorothiophene with 3-iodotoluene afforded only the m-tolylated isomer (Entry 11) in contrast with the previous results obtained by employing KOtBu base (Scheme 3). Furans and N-substituted indoles were found to be unreactive under any conditions tried while heterocycles possessing acidic N—H bonds were arylated on the nitrogen as reported by Buchwald.[5e] The following DMSO pKa's of heterocycle C—H bonds have been reported: N-alkylindoles, about 37; furan, 35; N-methylimidazole, 33.[15] It can be concluded that copper-catalyzed electron-rich heterocycle arylation is successful for compounds possessing pKa's below 35.

TABLE IV

Electron-rich Heterocycle Arylation[a]

Heterocycle $\xrightarrow[\text{100-125° C., 2-12 hours}]{\text{10 mol % CuI/phenanthroline}}$ Product

| Entry | Heterocycle | Arylhalide/base | Product | Yield % |
|---|---|---|---|---|
| 1 | benzothiazole | 2-bromopyridine, $K_3PO_4$ | 2-(benzothiazol-2-yl)pyridine | 89 |
| 2 | 1,3,7-trimethylxanthine | $C_6H_5I$/tBuOLi | 8-phenyl-1,3,7-trimethylxanthine | 85 |
| 3 | 1-methyl-1,2,4-triazole | $C_6H_5I$/tBuOLi | 1-methyl-5-phenyl-1,2,4-triazole | 88 |
| 4 | 1-methylimidazole | $C_6H_5I$/tEt$_3$COLi | 1-methyl-2-phenylimidazole | 82 |
| 5 | 3-chlorothiophene | $C_6H_5I$/tEt$_3$COLi | 3-chloro-2,5-diphenylthiophene | 87 |
| 6 | thiophene | $C_6H_5I$/tEt$_3$COLi | 2,5-diphenylthiophene | 85 |
| 7 | 1-phenylpyrazole | $C_6H_5I$/tEt$_3$COLi | 1,5-diphenylpyrazole | 52 |
| 8 | benzothiophene | $C_6H_5I$/tEt$_3$COLi | 2-phenylbenzothiophene | 86 |

TABLE IV-continued

Electron-rich Heterocycle Arylation[a]

Heterocycle $\xrightarrow[\text{ArX, solvent, base}]{\text{10 mol \% CuI/phenanthroline}}$ Product
100-125° C., 2-12 hours

| Entry | Heterocycle | Arylhalide/base | Product | Yield % |
|---|---|---|---|---|
| 9 | benzofuran | C$_6$H$_5$I/tEt$_3$COLi | 2-phenylbenzofuran | 60 |
| 10 | 2-chlorothiophene | 2-iodotoluene / tBuOLi | 5-chloro-2-(2-methylphenyl)thiophene | 89 |
| 11 | 2-chlorothiophene | 3-iodotoluene / tBuOLi | 5-chloro-2-(3-methylphenyl)thiophene | 91 |

[a]Copper (I) iodide (0.1 mmol), phenanthroline (0.1 mmol), aryl halide (1-3 mmol), heterocycle (1-2 mmol), base (1.7-2 mmol), DMF or DMPU (0.5-0.6 mL). Yields are isolated yields.

Arylation of Electron-Poor Heterocycles

We have previously reported one example of coppercatalyzed electron-poor heterocycle arylation.[13a] If the mechanistic considerations presented in Scheme 2 are correct, arylation of electron-poor heterocycles with C—H bond DMSO pKa's below 35 should be feasible. Gratifyingly, conditions developed for electron-rich heterocycle arylation worked well also in this case (Table V). While most pyridines are not reactive, more acidic pyridine oxides can be arylated by using either tBuOLi or K$_3$PO$_4$ base (Entries 1-5). 2-Iodopyridine is incompatible with alkoxides due to the formation of 2-t-butoxypyridine under the reaction conditions and K$_3$PO$_4$ base has to be used (Entry 2). 2-Methylpyridine oxide is also reactive, but the yield is diminished compared to other substrates, presumably due to acidic benzylic protons decreasing effective concentration of the arylcopper intermediate. 2-Phenylpyridine oxide is efficiently arylated by substituted aryl iodides and the products are obtained in excellent yield (Entries 4 and 5). More interestingly, pyridazine can be arylated in a good yield (Entry 6). A four-step synthesis of 4-phenylpyridazine has been reported.[16] In contrast, direct arylation methodology allows to synthesize this compound in a single step from commercially available starting materials. Pyrimidine is arylated in a low yield, presumably due to insufficient acidity (pKa=37;[15] Entry 7). Cyanidine and 1,2,3-triazine decompose under the reaction conditions.

TABLE V

Electron-poor Heterocycle Arylation[a]

Heterocycle $\xrightarrow[\text{ArI, solvent, base}]{\text{10 mol \% CuI/phenanthroline}}$ Product
120-125° C., 1-12 hours

| Entry | Heterocycle | Arylhalide/Base | Product | Yield % |
|---|---|---|---|---|
| 1 | pyridine N-oxide | C$_6$H$_5$I/tBuOLi | 2-phenylpyridine N-oxide | 58 |
| 2 | pyridine N-oxide | 2-iodopyridine /K$_3$PO$_4$ | 2-(2-pyridyl)pyridine N-oxide | 41 |

TABLE V-continued

Electron-poor Heterocycle Arylation[a]

Heterocycle $\xrightarrow[\text{ArI, solvent, base}]{\text{10 mol \% CuI/phenanthroline}}$ Product
120-125° C., 1-12 hours

| Entry | Heterocycle | Arylhalide/Base | Product | Yield % |
|---|---|---|---|---|
| 3 | 2-methylpyridine N-oxide | C₆H₅I/tBuOLi | 2-methyl-6-phenylpyridine N-oxide | 43 |
| 4 | 2-phenylpyridine N-oxide | 4-iodo-(trifluoromethyl)benzene /tBuOLi | 2-phenyl-6-(4-trifluoromethylphenyl)pyridine N-oxide | 80 |
| 5 | 2-phenylpyridine N-oxide | 1-iodonaphthalene /tBuOLi | 2-phenyl-6-(1-naphthyl)pyridine N-oxide | 91 |
| 6 | pyridazine | C₆H₅I/tEt₃COLi | 4-phenylpyridazine | 60 |
| 7 | pyrimidine | C₆H₅I/tEt₃COLi | 5-phenylpyrimidine | 31 |

[a]Copper (I) iodide (0.1 mmol), phenanthroline (0.1 mmol), aryl halide (1-2 mmol), heterocycle (1-2 mmol), base (1.7-2 mmol), DMF or DMPU solvent (0.5-0.6 mL). Yields are isolated yields.
[b]2,6-Diphenylpyridine oxide also isolated (20%).

Arylation of Electron-Poor Benzenes

We have recently disclosed preliminary results showing that polyfluorobenzene derivatives can be arylated and alkenylated under copper catalysis.[13b] Both aryl iodide and bromide reagents can be employed. The reactivity parallels the acidity of C—H bonds, with the most acidic C—H bonds, those flanked by two C—F bonds, arylated most efficiently. The arylation of C—H bonds that are not flanked by two C—F bonds was inefficient and only 10% yield was obtained in the reaction of 4-iodotoluene with 1,2,3,4-tetrafluorobenzene. Since introduction of electron-withdrawing substituents in aromatic ring is expected to decrease the pKa of C—H bonds, we reasoned that arylation of a variety of other electron-deficient arenes should be possible. The improved conditions for arylation of electron-rich heterocycles were successfully applied to the arylation of electron-deficient arenes (Table VI). Pentafluorobenzene and tetrafluoroarenes can be arylated by aryl iodides (Entries 2 and 6) as well as aryl bromides (Entries 1, 7, 8). Even some hetaryl chlorides can be used (Entries 3 and 4) although for 2-pyridyl chloride 150° C. reaction temperature is required. Alkenylation is also possible (Entries 5 and 9). Potassium phosphate can be used as a base if arene contains more than two fluorine substituents or two fluorine substituents and an additional electron-withdrawing group (Entry 11). For 1,4-difluorobenzene arylation, hindered Et₃COLi base is required. Previously we were unable to efficiently arylate such compounds by using tBuOLi base due to formation of tBuOAr byproduct. Penta- and tetrachlorobenzenes can be phenylated in excellent yield (Entries 12 and 13). Less acidic 1,3-dichlorobenzene is regioselectively phenylated in an acceptable 43% yield by employing Et₃COLi base (Entry 14). If tBuOLi base was used, arylation product was isolated in only 18% yield. 1,3-Dinitrobenzene and 3-nitrobenzonitrile are also reactive affording the arylation products in moderate yields (Entries 15 and 16). The latter two arenes are slowly decomposed by the base and thus only the most reactive aryl iodides can be used. High arylation yield and absence of cyclized products for Entry 6 suggests that $S_{RN}1$ mechanism is unlikely.[17] Recent data obtained by Hartwig and coworkers argue against intermediacy of aryl radicals for copper-catalyzed C—N bond formation reactions.[18] The following limitations have been observed. If aryl bromides are used in combination with lithium alkoxide bases, low yields of arylation products are obtained. Low conversions (<5%) are obtained in arylation of fluorobenzene, nitrobenzene, and α,α,α-trifluorotoluene.

TABLE VI

Arylation of Electron-poor Arenes[a]

Arene —10 mol % CuI/phenanthroline, RI or RBr, base, 120-150° C., 12-24 hours→ Product

| Entry | Arene | Arylhalide/Base | Product | Yield % |
|---|---|---|---|---|
| 1[b] | $C_6F_5H$ | 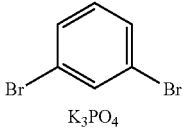 1,3-dibromobenzene; $K_3PO_4$ | 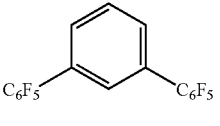 1,3-bis(pentafluorophenyl)benzene | 51 |
| 2[b] | $C_6F_5H$ | 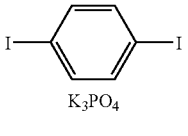 1,4-diiodobenzene; $K_3PO_4$ | 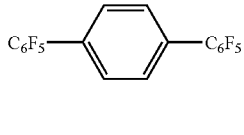 1,4-bis(pentafluorophenyl)benzene | 73 |
| 3 | $C_6F_5H$ |  2-chloroquinoline; $K_3PO_4$ | 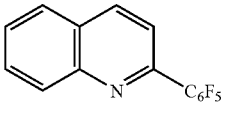 2-(pentafluorophenyl)quinoline | 85 |
| 4 | $C_6F_5H$ | 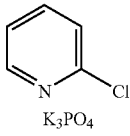 2-chloropyridine; $K_3PO_4$ | 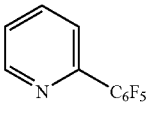 2-(pentafluorophenyl)pyridine | 41 |
| 5 | $C_6F_5H$ | 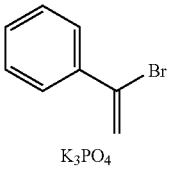 α-bromostyrene; $K_3PO_4$ | 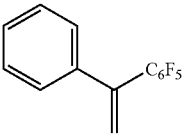 | 81 |
| 6 | $C_6F_5H$ | 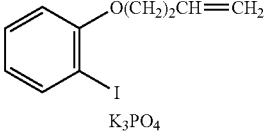 $K_3PO_4$ | 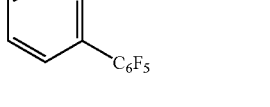 | 89 |
| 7 | 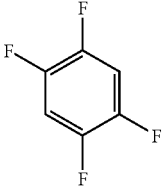 1,2,4,5-tetrafluorobenzene | 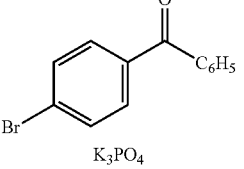 4'-bromo-benzophenone; $K_3PO_4$ | 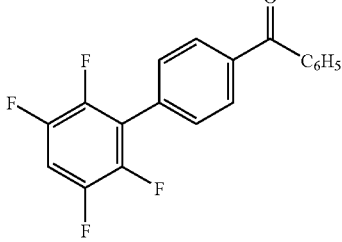 | 52 |
| 8 | 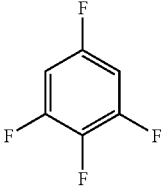 1,2,3,5-tetrafluorobenzene | 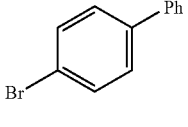 4-bromobiphenyl | 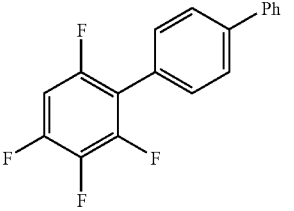 [SMILES: Fc1cc(F)c(-c2ccc(-c3ccccc3)cc2)c(F)c1F] | 70 |

TABLE VI-continued
Arylation of Electron-poor Arenes[a]
Arene $\xrightarrow[\text{RI or RBr, base}]{\text{10 mol \% CuI/phenanthroline}}$ Product
120-150° C., 12-24 hours
| Entry | Arene | Arylhalide/Base | Product | Yield % |
|---|---|---|---|---|
| 9 | 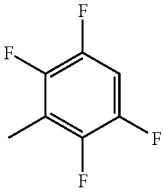 | 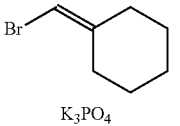 K$_3$PO$_4$ | 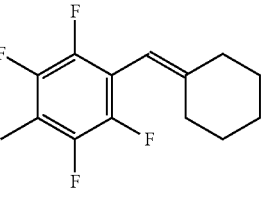 | 95 |
| 10 | 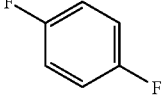 | 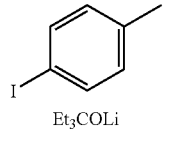 Et$_3$COLi | 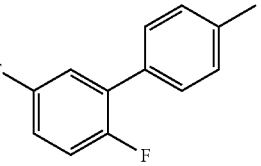 | 54 |
| 11 | 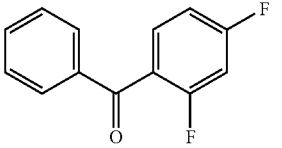 [SMILES: O=C(c1ccccc1)c1ccc(F)cc1F] | 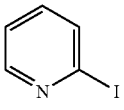 K$_3$PO$_4$ | 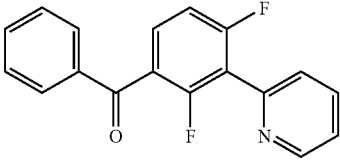 [SMILES: O=C(c1ccccc1)c1ccc(F)c(-c2ccccn2)c1F] | 68 |
| 12 | C$_6$Cl$_5$H | C$_6$H$_5$I/tBuOLi | 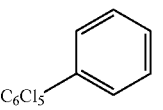 | 91 |
| 13 | 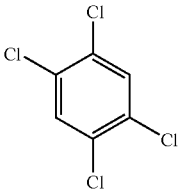 | C$_6$H$_5$I/tBuOLi | 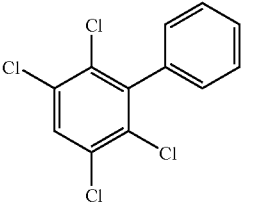 [SMILES: Clc1cc(Cl)c(Cl)c(-c2ccccc2)c1Cl] | 74 |
| 14 | 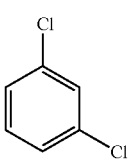 | C$_6$H$_5$I/Et$_3$COLi | 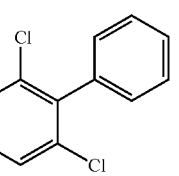 | 43<br>18[c] |
| 15 | 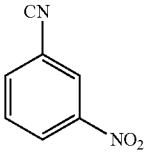 | 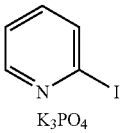 K$_3$PO$_4$ | 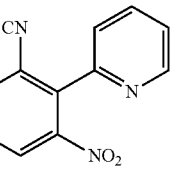 | 51 |

TABLE VI-continued

Arylation of Electron-poor Arenes[a]

Arene $\xrightarrow[\text{RI or RBr, base}]{\text{10 mol \% CuI/phenanthroline}}$ Product
120-150° C., 12-24 hours

| Entry | Arene | Arylhalide/Base | Product | Yield % |
|---|---|---|---|---|
| 16 | 1,3-dinitrobenzene | 2-iodopyridine / K₃PO₄ | 2-(2,6-dinitrophenyl)pyridine | 72 |

[a]Copper (I) iodide (0.1 mmol), phenanthroline (0.1 mmol), halide (1-2 mmol), arene (1-3 mmol), base (1.7-4 mmol), DMF, DMPU, or DMF/xylenes solvent (0.5-0.8 mL). Yields are isolated yields.
[b]Copper (I) iodide (0.15 mmol), phenanthroline (0.15 mmol), halide (1 mmol), arene (3 mmol), base (4 mmol).
[c]tBuOLi base.

Mechanistic Considerations

As shown in Scheme 2, the arylation reaction can be divided into three parts: metallation, transmetallation with copper halide, and reaction of arylcopper with haloarene. Metallation and reaction of arylcopper with haloarene steps will be discussed in more detail.

Metallation Step

One can expect that metallation step may be facilitated by coordination of copper species to Lewis-basic heteroatoms of the substrate. However, base-promoted H/D exchange in polyfluoroarenes, electron-rich, and electron-poor heterocycles occurs with the same efficiency both in the presence or absence of CuI (Scheme 4). Consequently, the acidity of substrate determines the position and efficiency of metallation even though the substrates belong to different classes of compounds and some of them possess heteroatoms capable of coordinating transition metals. Copper tbutoxide is a competent metallating reagent under the arylation conditions (Scheme 4B) complicating the mechanistic situation. The lifetime of aryllithium and arylpotassium species must be short since formation of benzyne-derived products has not been observed for polyfluoro- or polychloroarenes under catalytic or H/D exchange conditions.

Schemes 4A-D
H/D Exchange Experiments

A.
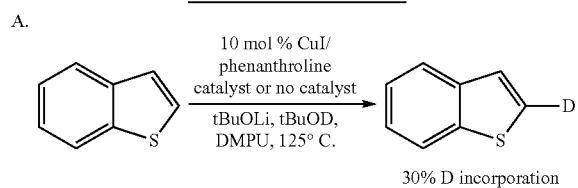
30% D incorporation

B.
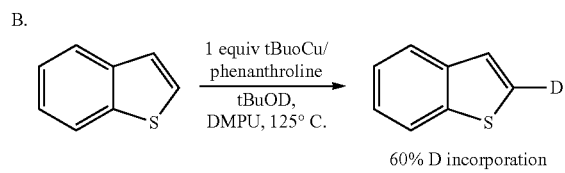
60% D incorporation

C.
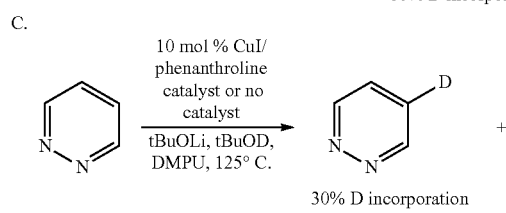
30% D incorporation

D.
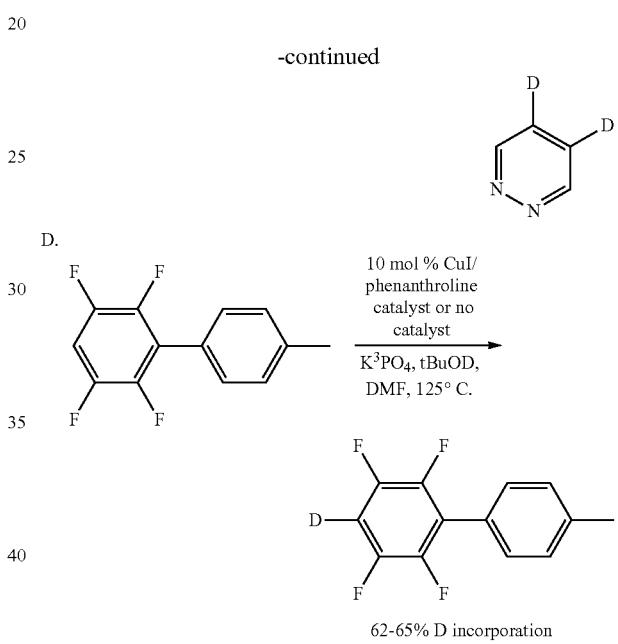
62-65% D incorporation

The rate of metallation/demetallation relative to subsequent reaction steps also has been considered (Scheme 5). If benzothiophene is arylated under the usual reaction conditions but with added tBuOD, incorporation of deuterium in the unreacted starting material is observed. The protonation of aryllithium and/or arylcopper intermediates by relatively weak t-butanol acid is competitive with the arylation step.

Scheme 5
Deuteration under Reaction Conditions

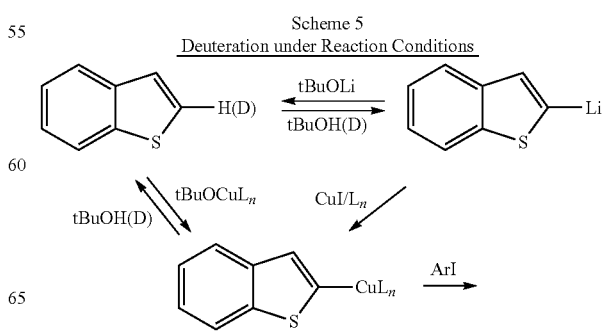

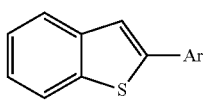

The ease of electron-deficient arene metallation demonstrated in this work may have other synthetic implications since strong alkyllithium bases and cryogenic conditions are not required. For substrates possessing DMSO pKa's below 27 even $K_3PO_4$ base is an efficient metallating agent.

Arylcopper Reaction with Haloarene Step

Several competition experiments were undertaken to determine relative reactivities of aryl iodides and arenes. The intermediate arylcopper species were identified by NMR as well as independently synthesized.

Relative Reactivities

Competition between arylation of pentafluorobenzene and tetrafluorobenzene by 4-iodotoluene results in preferential functionalization of pentafluorobenzene (Scheme 6). This result may be explained by the higher concentration of arylmetal intermediate for the more acidic pentafluorobenzene.

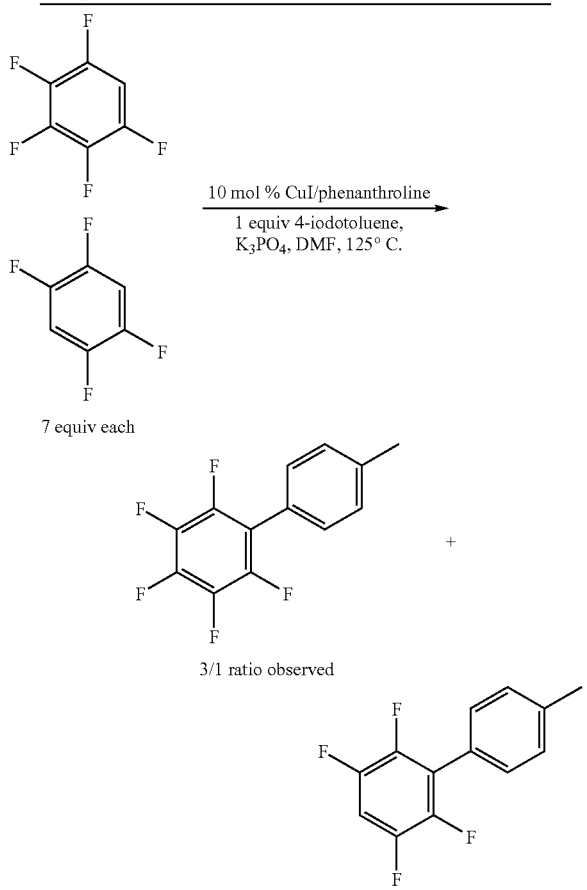

The reactivity of electron-rich and electron-poor aryl halides was compared by reacting a mixture of 4-trifluoromethylhalobenzene and 4-halotoluene with pentafluorobenzene (Scheme 7). A 4/1 product ratio was observed favoring trifluoromethylphenylation for both Hal=I and Br. Thus, electron-deficient aryl halides are more reactive as reported earlier.[9b]

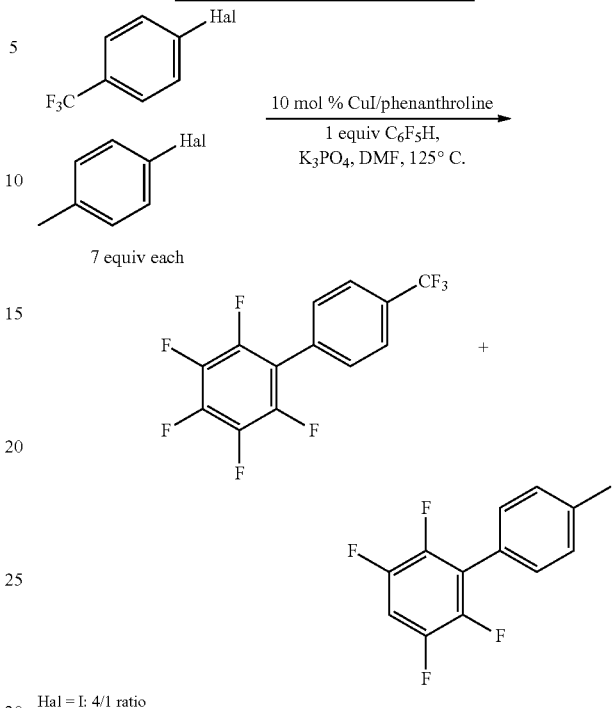

Arylcopper Intermediates

We independently synthesized one of the presumed arylation intermediates, pentafluorophenylcopper-phenanthroline complex 1 (Scheme 8). It exists as a moisture-sensitive and temperature-sensitive dark orange solid that is either insoluble or poorly soluble in most common organic solvents. The connectivity was verified by X-ray crystallography; however, it was not possible to fully refine the structure due to twinning of the crystals. The reaction of copper iodide, potassium phosphate, pentafluorobenzene, and phenanthroline in DMF under the conditions of the catalytic process afforded complex 1 as determined by $^{19}F$ NMR of the crude reaction mixture. The complex reacts with aryl iodides producing cross-coupled biaryls. An analogous 4-methoxy-2,3,5,6-tetrafluorophenylcopperphenanthroline complex 2 was prepared as dark rust-colored crystals by reacting tBuOCu with 2,3,5,6-tetrafluoroanisole followed by addition of phenanthroline ligand. The complex is stable in solid state under inert atmosphere at −20° C.; however, slow decomposition is observed in $CH_2Cl_2$ solution. It is sparingly soluble in most organic solvents and can be recrystallized from dichloromethane at −30° C. The structure of 2 was verified by single-crystal X-ray diffraction analysis. The ORTEP diagram of 2 is shown in FIG. 1. The complex exists as a dimer in solid state with a Cu—Cu distance of 2.5570(6) Å that is shorter than the van der Waals radii sum of 2.80 Å signifying a Cu—Cu bonding interaction.19 Copper assumes a distorted tetrahedral geometry with C(13)-Cu—N(1) angle of 135.68(9) Å. As expected, phenanthroline complexes to Cu in a bidentate fashion with Cu—N(1) distance of 2.0720(18) Å and Cu—N(2) distance of 2.0949(19) Å. The copper-C(aryl) bond length is 1.932(2)Å, which is slightly shortened compared to the corresponding Cu—C distance in tetrameric pentafluorophenylcopper (1.962(2) to 2.007(2)Å).[20] However, Cu—C distance in pentafluorophenylcopper-pyridine complex is shorter at 1.8913(17)Å.[21] No arylcopper-phenanthroline complexes appear to have been crystalographically characterized. Isomeric tolylcopper-phenanthroline complexes are known.[22]

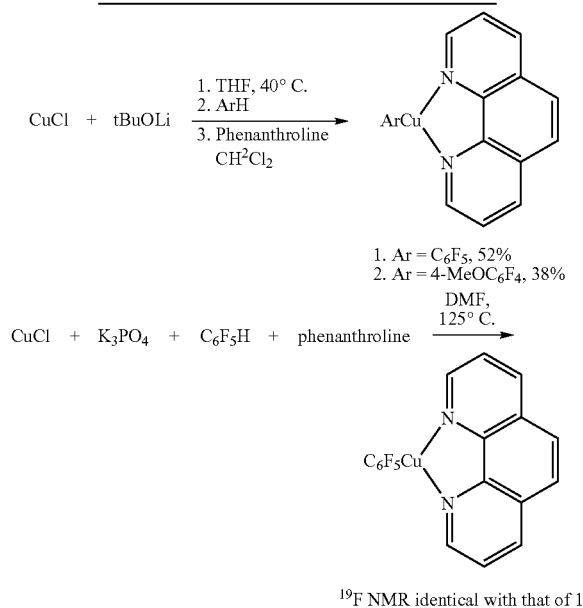

Scheme 8
Polyfluorophenylcopper-Phenanthroline Complexes

SUMMARY

A general method for copper-catalyzed arylation of $SP_2$ C—H bonds possessing DMSO pKa's below 35 has been developed. The choice of base is dependent on the acidity of the C—H bond to be arylated. For comparatively acidic C—H bonds with pKa below 27 $K_3PO_4$ base may be employed. If the substrates are less acidic (pKa 27-35), a stronger lithium alkoxide base is required. A variety of electronrich and electron-poor heterocycles such as azoles, caffeine, thiophenes, benzofuran, pyridine oxides, pyridazine, and pyrimidine can be arylated. Furthermore, electron-poor arenes possessing at least two electron-withdrawing groups on benzene ring can also be arylated. Unusual regioselectivity has been achieved allowing the arylation of the most hindered position. This method supplements the well-known C—H activation/borylation methodology[23] where functionalization usually occurs at the least hindered position. Additionally, the copper-catalyzed arylation methodology is complementary to existing lithiationiboronation/cross-coupling methods and in some cases may offer advantages with regards to the number of synthetic steps and functional group tolerance.[24]

EXPERIMENTS OF THE INVENTION

General Procedure for Coupling Reactions

Outside the glovebox a 1-dram vial equipped with a magnetic stir bar was charged with haloarene, phenanthroline (10 mol %), substrate, and solvent (DMF or a 1/1 mixture of DMF and xylenes). If anhydrous DMPU was used, the reaction was set up inside the glovebox. The vial was flushed with argon, capped and placed inside a glovebox. To this mixture was added CuI (10 mol %) and base (1.7-2.5 equiv). The sealed vial was taken out of the glovebox, stirred at room temperature for 5 min and placed in a preheated oil bath. After the completion of the reaction, the mixture was cooled to room temperature and diluted with ethyl acetate (50 mL). The resulting solution was washed with brine (15 mL), dried over anhydrous MgSO4, and concentrated under vacuum to a volume of about 1 mL. The mixture containing the product was subjected to column chromatography on silica gel (hexanes followed by appropriate solvent to elute the products). After concentrating the fractions containing the product, the residue was dried under reduced pressure to yield pure product. The results of this general coupling reaction are shown in Table I (supra).

First Set of Reactions

Figure 2:
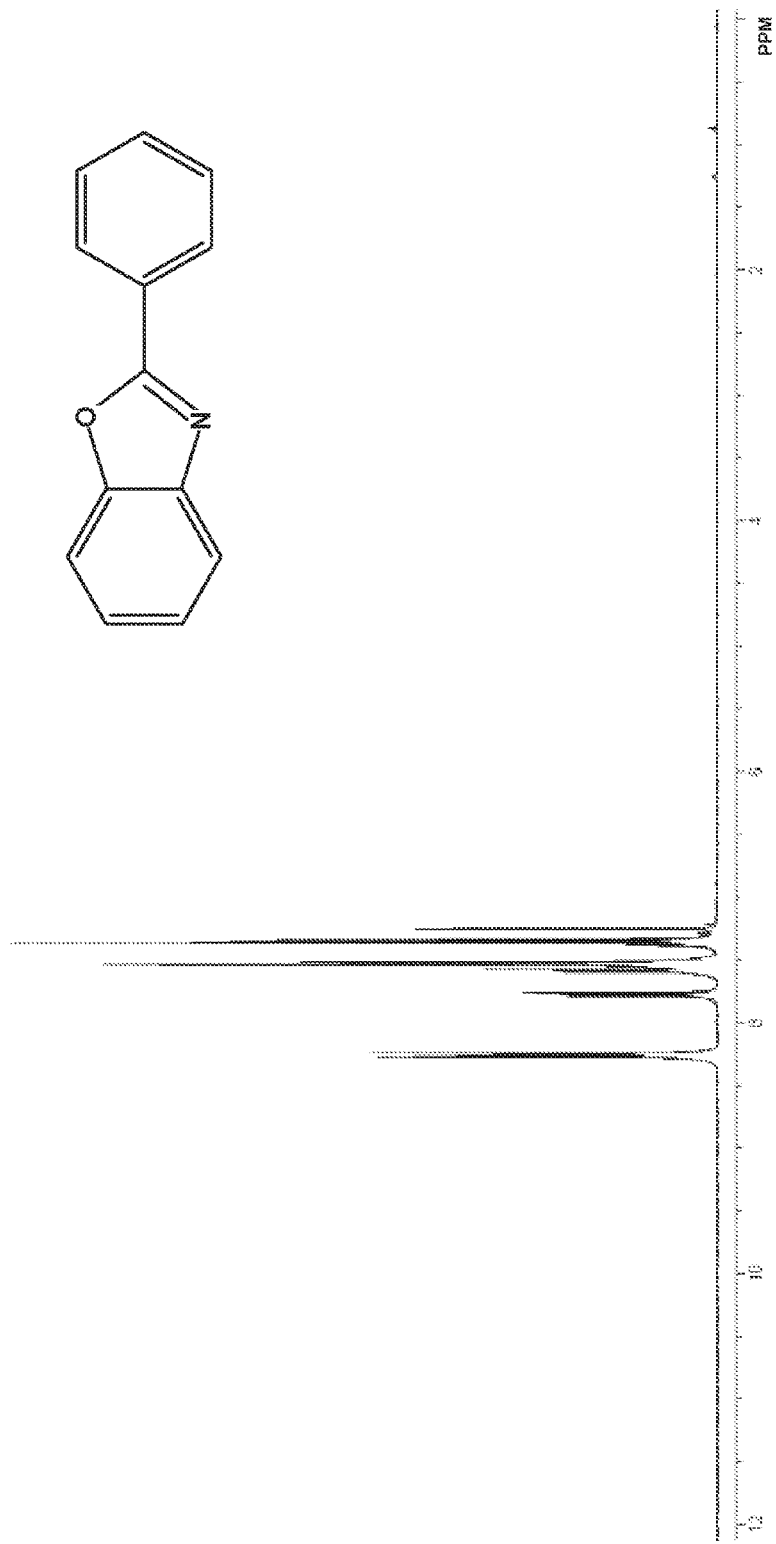
FIG. 2 depicts the molecular structure of 2-phenylbenzoxazole and $^1$H NMR Spectrum of 2-phenylbenzoxazole.

FIG. 2 shows the chemical structure of the resultant molecule 2-phenylbenzoxazole, and its NMR spectrum. 2-Phenylbenzoxazole is synthesized using copper(I) iodide (19.1 mg, 0.1 mmol), benzoxazole (119 mg, 1.0 mmol), iodobenzene (612 mg, 3.0 mmol), t-BuOLi (160 mg, 2.0 mmol), and DMF (1.0 mL). After column chromatography (hexanes, then 10% ethyl acetate in hexanes) 181 mg (93%) of a white solid is obtained. $R_f$=0.43 (1/9 ethyl acetate/hexanes). $^1$H NMR (CDCl$_3$, 300 MHz) δ 8.25-8.30 (m, 2H), 7.75-7.80 (m, 1H), 7.50-7.56 (m, 3H), 7.56-7.62 (m, 1H), 7.33-7.40 (m, 2H).

Under similar conditions, reactions between benzoxazole and other halobenzenes such as PhF or PhBr using t-BuOLi as a base does not lead to 2-phenylbenzoxazole, using copper(I) iodide (19.1 mg, 0.1 mmol), benzoxazole (119 mg, 1.0 mmol), halobenzene (3.0 mmol), t-BuOLi (160 mg, 2.0 mmol), and DMF (1.0 mL). The arylation results are presented in Table 1. However, yields over 40% are obtained when the reactions between benzoxazole and halobenzenes—except with fluorobenzene—are conducted using t-BuOK as a base. The reaction conditions are as follows:

For Fluorobenzene:

Copper(I) iodide (19.1 mg, 0.1 mmol), benzoxazole (119 mg, 1.0 mmol), fluorobenzene (288 mg, 3.0 mmol), t-BuOK (224 mg, 2.0 mmol), and DMF (1.0 mL). No product is detected.

For Chlorobenzene:

Copper(I) iodide (19.1 mg, 0.1 mmol), benzoxazole (119 mg, 10.0 mmol), chlorobenzene (450 mg, 4.0 mmol), t-BuOK (336 mg, 3.0 mmol), and DMF (1.0 mL). After column chromatography (hexanes, then 10% ethyl acetate in hexanes) and preparative HPLC (5% ethyl acetate in hexanes) 78 mg (40%) of 2-phenylbenzoxazole is obtained. Table I, entry 1.

For Bromobenzene:

Copper(I) iodide (19.1 mg, 0.1 mmol), benzoxazole (119 mg, 10.0 mmol), bromobenzene (471 mg, 3.0 mmol), t-BuOK (224 mg, 2.0 mmol), and DMF (1.0 mL). After column chromatography (hexanes, then 10% ethyl acetate in hexanes) and preparative HPLC (5% ethyl acetate in hexanes) 99 mg (51%) of 2-phenylbenzoxazole is obtained. Table I, entry 2.

For Iodobenzene:

Copper(I) iodide (19.1 mg, 0.1 mmol), benzoxazole (119 mg, 1.0 mmol), iodobenzene (612 mg, 3.0 mmol), t-BuOK (224 mg, 2.0 mmol), and DMF (1.0 mL). After column chromatography (hexanes, then 10% ethyl acetate in hexanes) and preparative HPLC (5% ethyl acetate in hexanes) 119 mg (61%) of 2-phenylbenzoxazole is obtained. Table I, entry 3.

Another General Synthetic Procedure

Another preferred embodiment of the present invention includes a general procedure for the arylation of benzoxazole using copper iodide as catalyst as shown below:

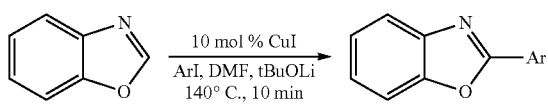

The results of this general coupling reaction are shown in Table II (supra).

Figure 3:
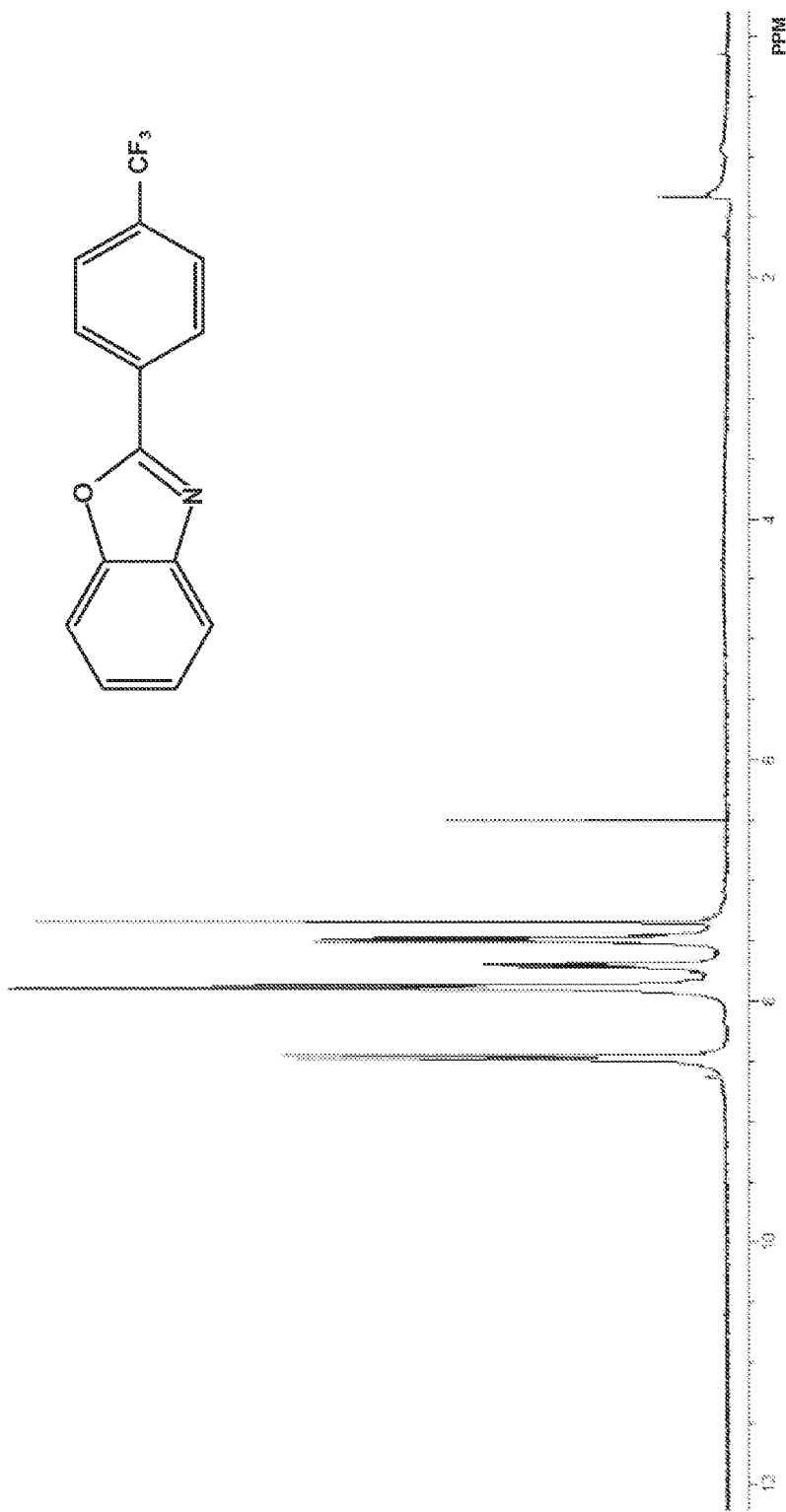
FIG. 3 depicts the molecular structure of 2-(4-(trifluoromethyl)phenyl)benzoxazole and $^1$H NMR Spectrum of 2-(4-(trifluoromethyl)phenyl)benzoxazole.

FIG. 3 shows the molecular structure of the resultant molecule 2-(4-(trifluoromethyl)phenyl)benzoxazole when ArI=4-CF$_3$C$_6$H$_4$I or 4-iodobenzotrifluoride, an electron deficient aryl iodide, and its $^1$H NMR spectrum. The synthesis of 2-(4-(trifluoromethyl)phenyl)benzoxazole is conducted using copper(I) iodide (19.1 mg, 0.1 mmol), benzoxazole (119 mg, 1.0 mmol), 4-iodobenzotrifluoride (816 mg, 3.0 mmol), t-BuOLi (160 mg, 2.0 mmol) and DMF (1.0 mL). After column chromatography (hexanes, then 10% ethyl acetate in hexanes) 239 mg (91%) of a white solid is obtained. R$_f$=0.46 (1/9 ethyl acetate/hexanes). $^1$H NMR (300 MHz, $_{CDCl3}$) δ 7.43-7.55 (m, 2H), 7.67-7.74 (m, 1H), 7.85-7.93 (m, 3H), 8.48 (d, J=9.0 Hz, 2H). Table II, entry 1.

Figure 4:
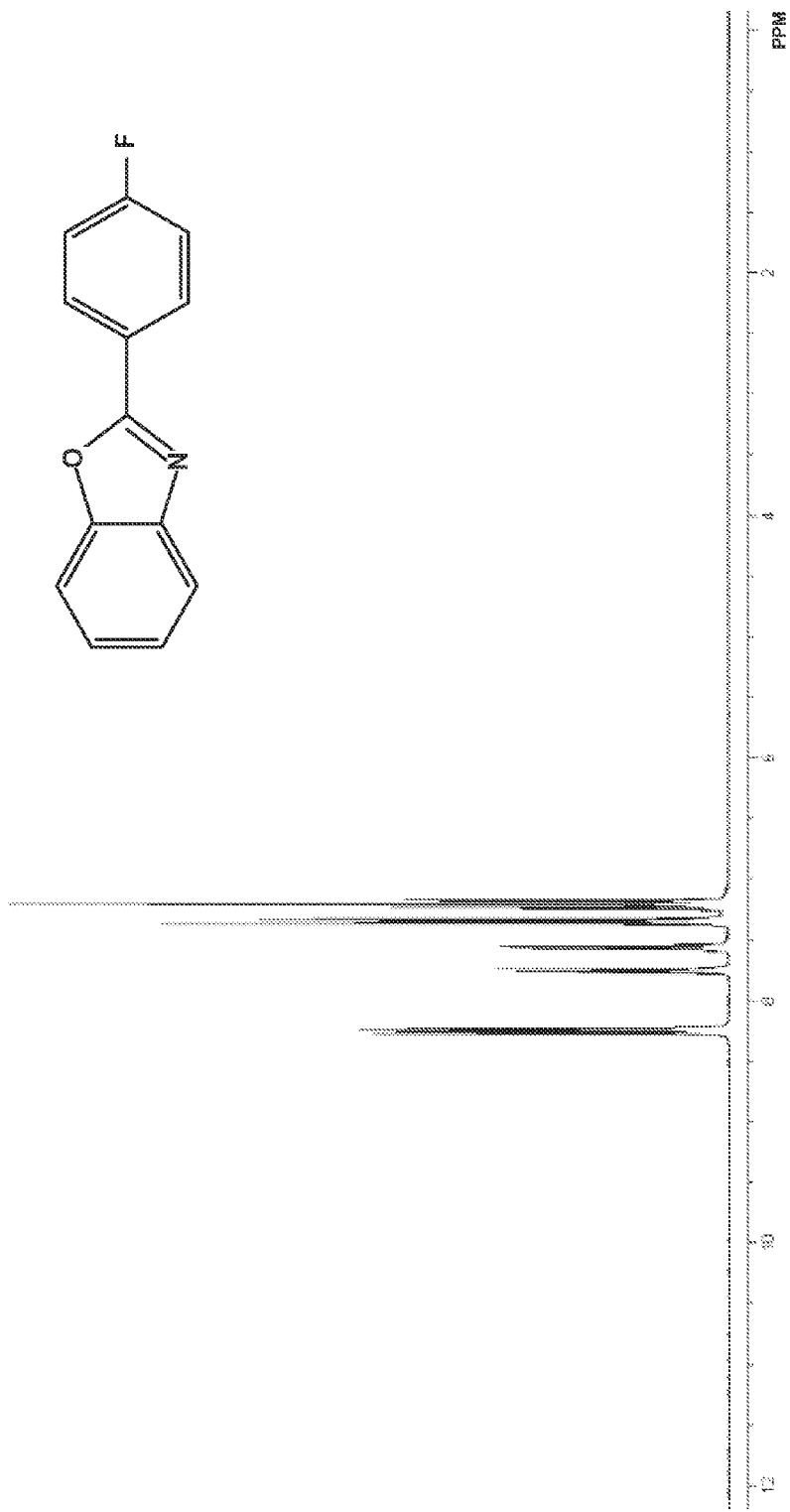
FIG. 4 depicts the molecular structure of 2-(4-fluorophenyl)benzoxazole and $^1$H NMR Spectrum of 2-(4-fluorophenyl)benzoxazole.

FIG. 4 shows the molecular structure of the resultant molecule 2-(4-fluorophenyl)benzoxazole when ArI=4-FC$_6$H$_4$I or 1-fluoro-4-iodobenzene, an electron deficient aryl iodide, and its $^1$H NMR spectrum. The synthesis of 2-(4-fluorophenyl)benzoxazole is conducted using copper(I) iodide (19.1 mg, 0.1 mmol), benzoxazole (119 mg, 1.0 mmol), 1-fluoro-4-iodobenzene (666 mg, 3.0 mmol), t-BuOLi (160 mg, 2.0 mmol), and DMF (1.0 mL). After column chromatography (hexanes, then 10% ethyl acetate in hexanes) 192 mg (90%) of a white solid is obtained. R$_f$=0.42 (1/9 ethyl acetate/hexanes). $^1$H NMR (300 MHz, $_{CDCl3}$) δ 7.16-7.26 (m, 2H), 7.31-7.39 (m, 2H), 7.53-7.60 (m, 1H), 7.72-7.79 (m, 1H), 8.21-8.29 (m, 2H). Table II, entry 2.

Figure 5:
FIG. 5 depicts the molecular structure of 2-(4-methoxyphenyl)benzoxazole and $^1$H NMR Spectrum of 2-(4-methoxyphenyl)benzoxazole.

FIG. 5 shows the molecular structure of the resultant molecule 2-(4-methoxyphenyl) benzoxazole when ArI=4-MeOC$_6$H$_4$I or 4-iodoanisole, an electron rich aryl iodide, and its $^1$H NMR spectrum. The synthesis of 2-(4-methoxyphenyl)benzoxazole is conducted using copper(I) iodide (19.1 mg, 0.1 mmol), benzoxazole (119 mg, 1.0 mmol), 4-iodoanisole (702 mg, 3.0 mmol), t-BuOLi (160 mg, 2.0 mmol), and DMF (1.0 mL). After column chromatography (hexanes, then 15% ethyl acetate in hexanes) 180 mg (80%) of a white solid is obtained. R$_f$=0.27 (1/9 ethyl acetate/hexanes). $^1$H NMR (300 MHz, $_{CDCl3}$) δ 3.98 (s, 3H), 7.12 (d, J=8.0 Hz, 2H), 7.37-7.45 (m, 2H), 7.62-7.67 (m, 1H), 7.80-7.85 (m, 1H), 8.29 (d, J=8.0 Hz, 2H). Table II, entry 3.

Figure 6:
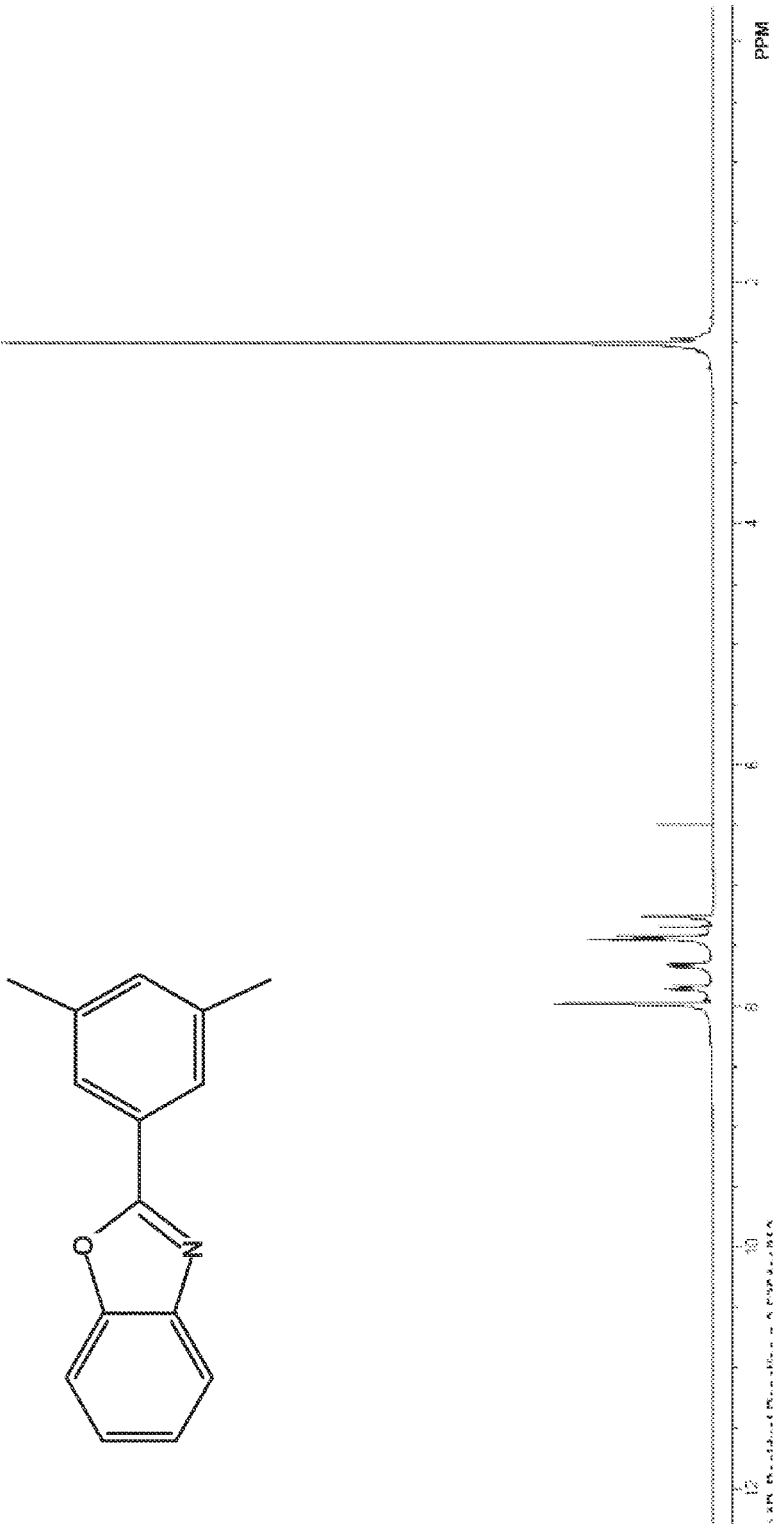
FIG. 6 depicts the molecular structure of 2-(3,5-dimethylphenyl)benzoxazole and $^1$H NMR Spectrum of 2-(3,5-dimethylphenyl)benzoxazole.

FIG. 6 shows the chemical structure of the resultant molecule 2-(3,5-dimethylphenyl)benzoxazole when ArI=3,5-Me$_2$C$_6$H$_3$I or 5-iodo-m-xylene, an electron rich aryl iodide, and its $^1$H NMR spectrum. The synthesis of 2-(3,5-dimethylphenyl)benzoxazole is conducted using copper(I) iodide (19.1 mg, 0.11 mmol), benzoxazole (119 mg, 1.0 mmol), 5-iodo-m-xylene (669 mg, 3.0 mmol), t-BuOLi (160 mg, 2.0 mmol), and DMF (1.0 mL). After column chromatography (hexanes, then 10% ethyl acetate in hexanes) 189 mg (85%) of a white solid is obtained. R$_f$=0.47 (1/9 ethyl acetate/hexanes). $^1$H NMR (300 MHz, $_{CDCl3}$) δ 2.50 (s, 6H), 7.26 (s, 1H), 7.40-7.47 (m, 2H), 7.64-7.68 (m, 1H), 7.83-7.88 (m, 1H), 7.98 (s, 2H). Table II, entry 4.

Figure 7:
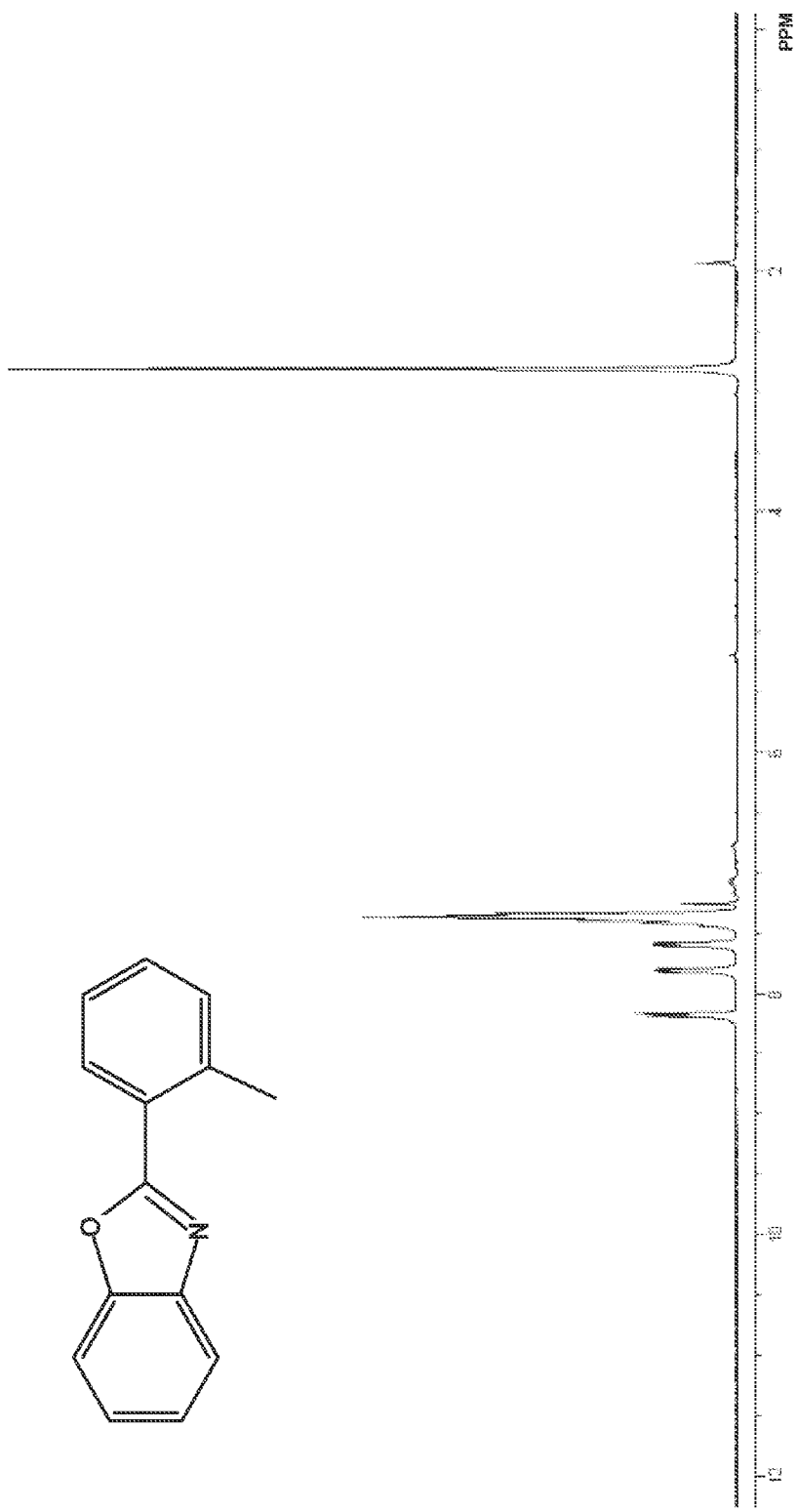
FIG. 7 depicts the molecular structure of 2-o-tolylbenzoxazole and $^1$H NMR Spectrum of 2-o-tolylbenzoxazole.

FIG. 7 shows the chemical structure of the resultant molecule 2-o-tolylbenzoxazole when ArI=2-MeC$_6$H$_4$I or 2-methyliodobenzene, an electron rich aryl iodide, and its $^1$H NMR spectrum. The synthesis of t-o-tolylbenzoxazole is conducted using copper(I) iodide (19.1 mg, 0.1 mmol), benzoxazole (119 mg, 1.0 mmol), 2-methyliodobenzene (654 mg, 3.0 mmol), t-BuOLi (160 mg, 2.0 mmol), and DMF (1.0 mL). After column chromatography (hexanes, then 10% ethyl acetate in hexanes) 190 mg (91%) of a white solid is obtained. R$_f$=0.50 (1/9 ethyl acetate/hexanes). $^1$H NMR (300 MHz, $_{CDCl3}$) δ 2.80 (s, 3H), 7.25-7.43 (m, 5H), 7.55-7.65 (m, 1H), 7.75-7.85 (m, 1H), 8.18 (d, J=8.0 Hz, 1H). Table II, entry 5.

Figure 8:
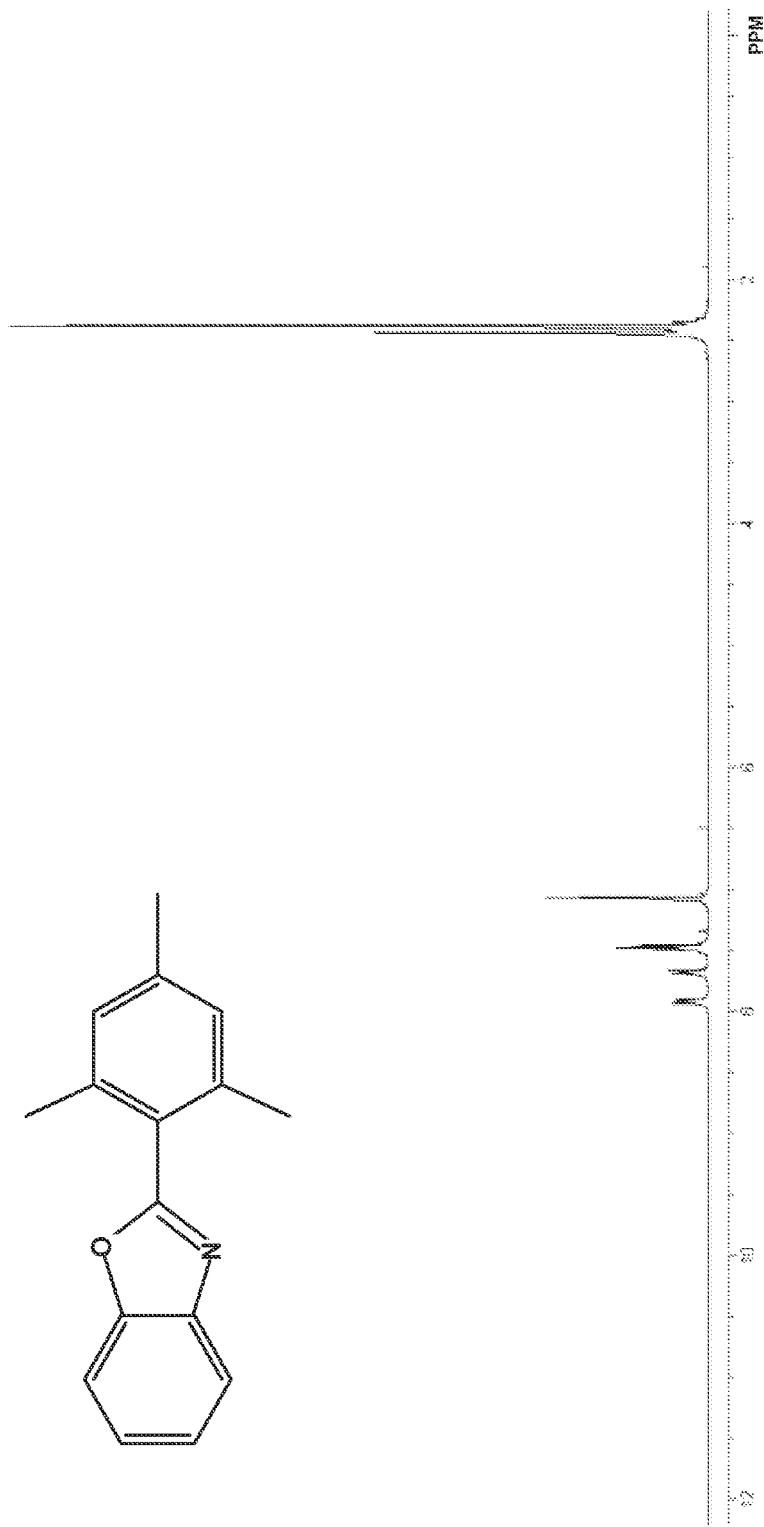
FIG. 8 depicts the molecular structure of 2-mesitylbenzoxazole and $^1$H NMR Spectrum of 2-mesitylbenzoxazole.

FIG. 8 shows the chemical structure of the resultant molecule 2-mesitylbenzoxazole when ArI=2,4,6-Me$_3$C$_6$H$_{21}$ or 2-iodo-1,3,5-trimethylbenzene, an electron rich aryl iodide, and its $^1$H NMR spectrum. The synthesis of 2-mesitylbenzoxazole is conducted using copper(I) iodide (19.1 mg, 0.1 mmol), benzoxazole (119 mg, 1.0 mmol), 2-iodo-1,3,5-trimethylbenzene (738 mg, 3.0 mmol), t-BuOLi (160 mg, 2.0 mmol), and DMF (1.0 mL). After column chromatography (hexanes, then 5% ethyl acetate in hexanes) 130 mg (55%) of a white solid is obtained, mp 63.5-65° C. R$_f$=0.58 (1/9 ethyl acetate/hexanes). $^1$H NMR (300 MHz, $_{CDCl3}$) δ 2.38 (s, 6H), 2.44 (s, 3H), 7.08 (s, 2H), 7.44-7.52 (m, 2H), 7.64-7.72 (m, 1H), 7.89-7.97 (m, 1H). $^{13}$C NMR (75 MHz, $_{CDCl3}$) δ 20.3, 21.3, 110.6, 120.1, 122.5, 124.3, 124.9, 128.7, 138.5, 140.3, 141.7, 150.6, 163.4. FT-IR (neat, cm$^{-1}$) u 1615, 1557, 1456. Table II, entry 6.

Figure 9:
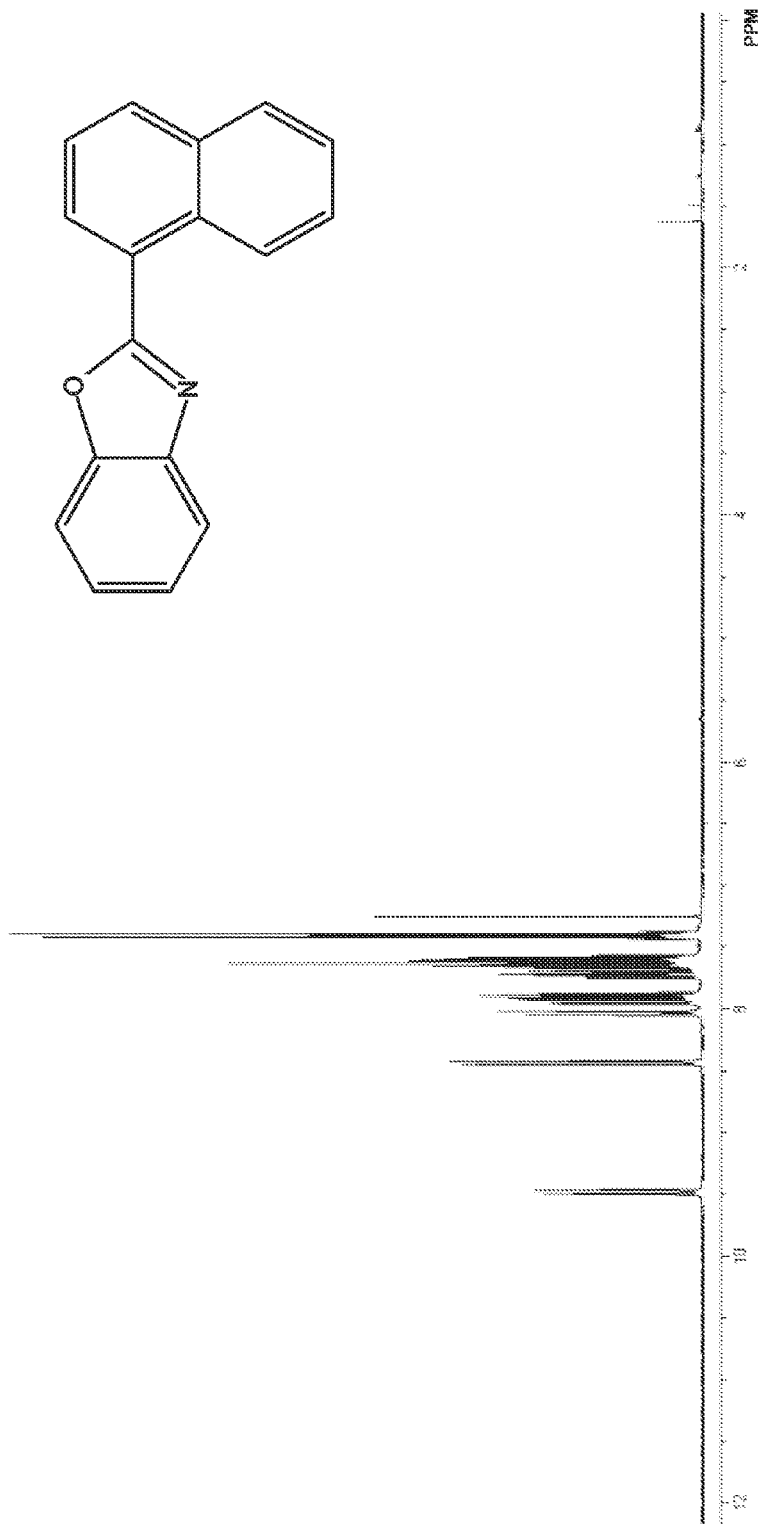
FIG. 9 depicts the molecular structure of 2-(1-naphthyl)benzoxazole and $^1$H NMR Spectrum of 2-(1-naphthyl)benzoxazole.

FIG. 9 shows the chemical structure of the resultant molecule 2-(1-naphthyl)benzoxazole when ArI=1-iodonaphthalene, an electron rich aryl iodide, and its $^1$H NMR spectrum. The synthesis of 2-(1-naphthyl)benzoxazole is conducted using copper(I) iodide (19.1 mg, 0.11 mmol), benzoxazole (119 mg, 1.0 mmol), 1-iodonapthalene (762 mg, 3.0 mmol), t-BuOLi (160 mg, 2.0 mmol) and DMF (1.0 mL). After column chromatography (hexanes, then 10% ethyl acetate in hexanes) 220 mg (90%) of a white solid is obtained. R$_f$=0.39 (1/9 ethyl acetate/hexanes). $^1$H NMR (300 MHz, $_{CDCl3}$) δ 7.36-7.44 (m, 2H), 7.56-7.76 (m, 4H), 7.86-7.96 (m, 2H), 8.03 (d, J=8.0 Hz, 1H), 8.44 (dd, J=8.0 Hz, 1.1 Hz, 1H), 9.48 (dd, J=8.0 Hz, 1.1 Hz, 1H). Table II, entry 7.

Figure 10:
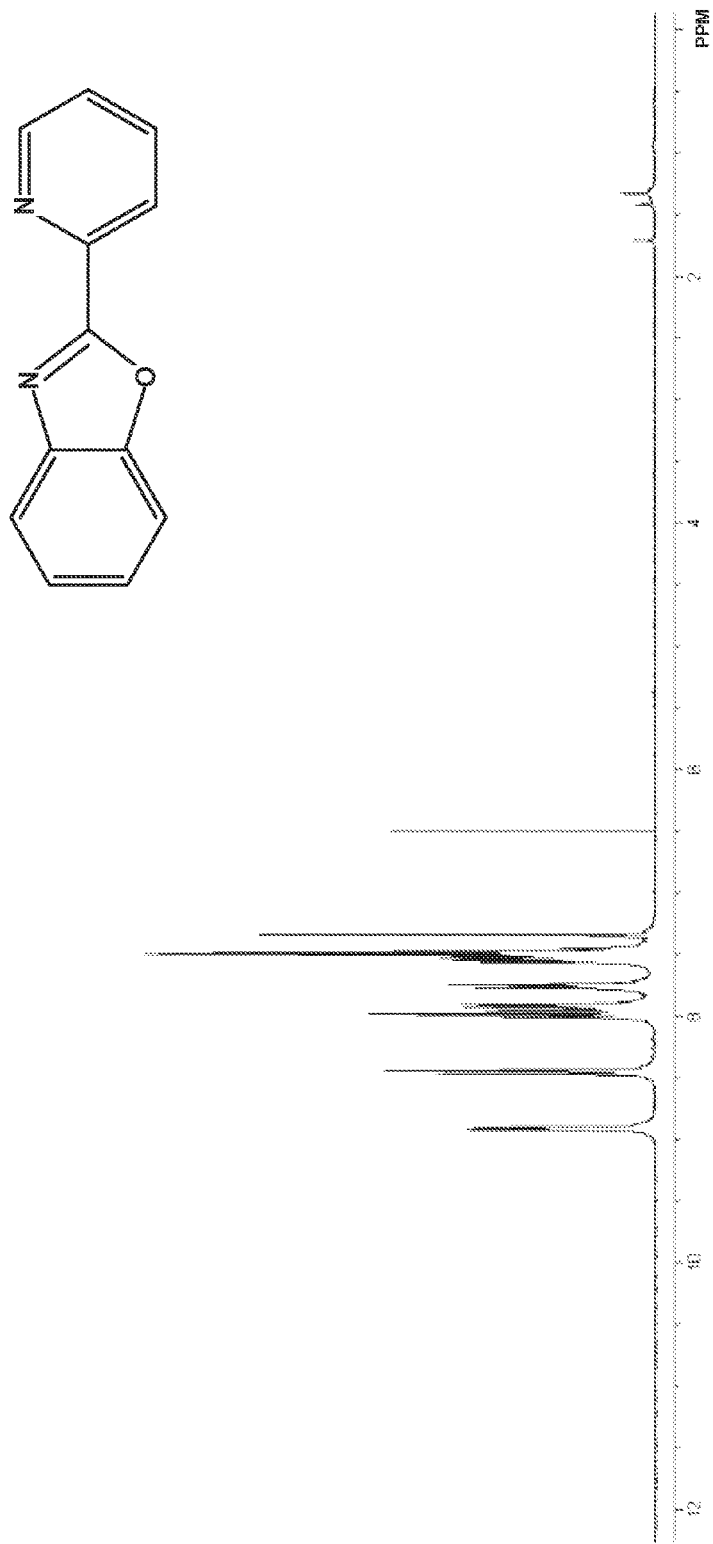
FIG. 10 depicts the molecular structure of 2-(2-pyridyl)benzoxazole and $^1$H NMR Spectrum of 2-(2-pyridyl)benzoxazole.

FIG. 10 shows the chemical structure of the resultant molecule 2-(2-pyridyl)benzoxazole when ArI=2-iodopyridine, and its $^1$H NMR spectrum. The synthesis of 2-(2-pyridyl)benzoxazole is conducted using copper(I) iodide (19.1 mg, 0.1 mmol), benzoxazole (119 mg, 1.0 mmol), 2-iodopyridine (615 mg, 3.0 mmol), t-BuOLi (160 mg, 2.0 mmol), and DMF (1.0 mL). After column chromatography (hexanes, then 30% ethyl acetate in hexanes) 174 mg (89%) of a white solid is obtained. R$_f$=0.34 (1/1 ethyl acetate/hexanes). $^1$H NMR (300 MHz, $_{CDCl3}$) δ 7.43-7.59 (m, 3H), 7.72-7.79 (m, 1H), 7.88-8.04 (m, 2H), 8.46 (d, J=8.0 Hz, 1H), 8.91 (d, J=4.3 Hz, 1H). Table II, entry 8.

Another General Synthetic Procedure

Another preferred embodiment of the present invention includes a general procedure for the arylation of a broad variety of heterocycles using copper iodide as catalyst as shown below:

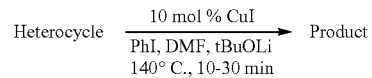

where a phenyl group is attached to either an electron-rich or electron-poor heterocycle. The results of this general coupling reaction are shown in Table III (supra).

The general procedure for the coupling of iodoarenes with heterocyclic compounds is presented here. Outside the glovebox a 1-dram vial equipped with a magnetic stir bar is charged with heterocycle (1.0 mmol), iodoarene (3.0 equiv) and DMF (1 mL). The vial is flushed with argon, capped and placed inside a glovebox. To this mixture is added CuI (10 mol %) and t-BuOLi (2.0 equiv). The sealed vial is taken out of the glovebox, stirred at room temperature for 5 minutes and placed in a preheated oil bath (140° C) for 10 minutes. The reaction mixture is allowed to cool to room temperature and diluted with ethyl acetate (50 mL). The resulting solution is washed with brine (3×15 mL), dried over anhydrous MgSO4, and concentrated under vacuum to a volume of about 2 mL. The mixture containing the product is subjected to flash chromatography on silica gel (hexanes followed by appropriate solvent to elute the products). After concentrating the fractions containing the product, the residue is dried under reduced pressure to yield pure arylation product.

FIG. 11 shows the molecular structures of the resultant molecule 2-phenyloxazole when the starting heterocycle is 1,3-oxazole, and its $^1$H NMR spectrum. 2,5-Diphenyloxazole is also produced in the synthesis. The synthesis of 2-phenyloxazole and 2,5-diphenyloxazole is conducted using copper (I) iodide (19.1 mg, 0.1 mmol), oxazole (69 mg, 1.0 mmol), iodobenzene (612 mg, 3.0 mmol), t-BuOLi (160 mg, 2.0 mmol), and DMF (1.0 mL). After column chromatography (hexanes, then 10% ethyl acetate in hexanes) and preparative HPLC (5% ethyl acetate in hexanes) 15 mg (7%) of a light tan solid (2,5-diphenyloxazole, $R_f$=0.30 (1/9 ethyl acetate/hexanes)) and 85 mg (59%) of a colorless oil (2-phenyloxazole, $R_f$=0.27 (1/9 ethyl acetate/hexanes)) are obtained. $^1$H NMR spectrum for 2-Phenyloxazole (300 MHz, $_{CDCl3}$): δ7.23 (s, 1H), 7.42-7.49 (m, 3H), 7.71 (s, 1H), 8.01-8.10 (m, 2H). $^1$H NMR spectrum for 2,5-Diphenyloxazole (300 MHz, $_{CDCl3}$): δ 7.31-7.38 (m, 1H), 7.40-7.52 (m, 6H), 7.70-7.75 (m, 2H), 8.08-8.15 (m, 2H). Table III, entry 1.

Figure 13:
FIG. 13 depicts the molecular structure of 2,5-diphenylthiazole and $^1$H NMR Spectrum of 2,5-diphenylthiazole.

FIG. 12 shows the molecular structures of the resultant molecule 2-phenylthiazole, when the heterocycle is 1,3-thiazole, and its $^1$H NMR spectrum. FIG. 13 shows the molecular structure of the resultant molecule 2,5-diphenylthiazole, and its $^1$H NMR spectrum. The synthesis of 2-phenylthiazole and 2,5-diphenylthiazole is conducted using copper(I) iodide (19.1 mg, 0.1 mmol), thiazole (85 mg, 1.0 mmol), iodobenzene (612 mg, 3.0 mmol), t-BuOLi (160 mg, 2.0 mmol), and DMF (1.0 mL). After column chromatography (hexanes, then 10% ethyl acetate in hexanes) and preparative HPLC (5% ethyl acetate in hexanes) 140 mg (59%) of a light tan solid (2,5-diphenylthiazole, $R_f$=0.37 (1/9 ethyl acetate/hexanes)) and 60 mg (37%) of a colorless oil (2-phenylthiazole, $R_f$=0.36 (1/9 ethyl acetate/hexanes)). $^1$H NMR spectrum for 2-phenylthiazole (300 MHz, $_{CDCl3}$): δ 7.32 (d, J=3.0 Hz, 1H), 7.40-7.49 (m, 3H), 7.87 (d, J=3.0 Hz, 1H), 7.92-8.01 (m, 2H). $^1$H NMR spectrum for 2,5-diphenylthiazole (300 MHz, $_{CDCl3}$): δ 7.35-7.47 (m, 6H), 7.58-7.65 (m, 2H), 7.94-8.00 (m, 2H), 8.02 (s, 1H). Table III, entry 2.

Figure 14:
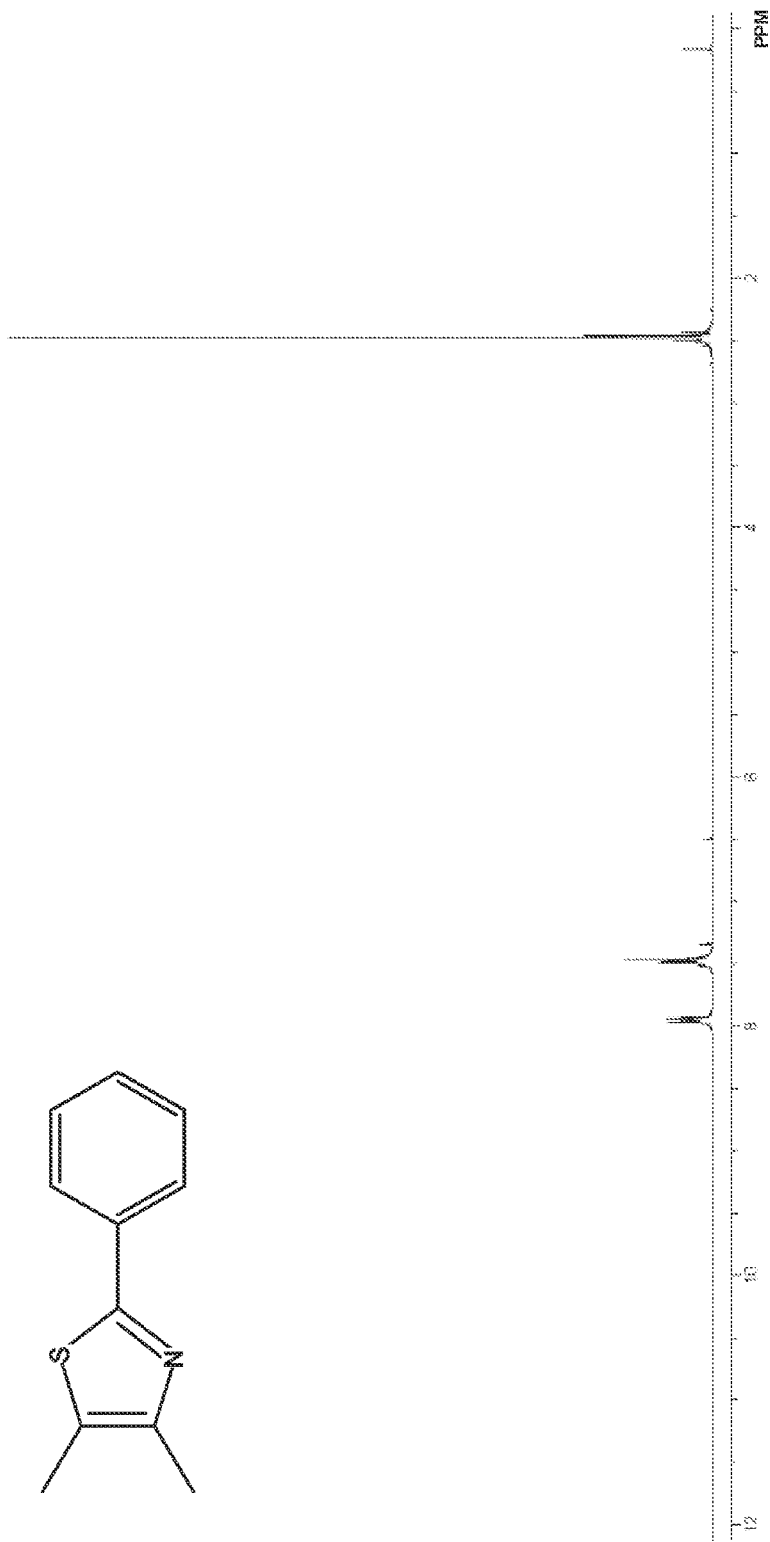
FIG. 14 depicts the molecular structure of 4,5-dimethyl-2-phenylthiazole and $^1$H NMR Spectrum of 4,5-dimethyl-2-phenylthiazole.

FIG. 14 shows the molecular structure of the resultant molecule 4,5-dimethyl-2-phenylthiazole, when the heterocycle is 4,5-dimethylthiazole, and its $^1$H NMR spectrum. The synthesis of 4,5-dimethyl-2-phenylthiazole is conducted using copper(I) iodide (19.1 mg, 0.1 mmol), 4,5-dimethylthiazole (113 mg, 1.0 mmol), iodobenzene (612 mg, 3.0 mmol), t-BuOLi (160 mg, 2.0 mmol), and DMF (1.0 mL). After column chromatography (hexanes, then 10% ethyl acetate in hexanes) 159 mg (84%) of a colorless oil is obtained. $R_f$=0.39 (1/9 ethyl acetate/hexanes). This compound is known.[14] $^1$H NMR (300 MHz, $_{CDCl3}$) δ 2.50 (s, 6H), 7.43-7.52 (m, 3H), 7.95 (dd, J=7.0 Hz, 1.2 Hz, 2H). Table III, entry 3.

Figure 15:
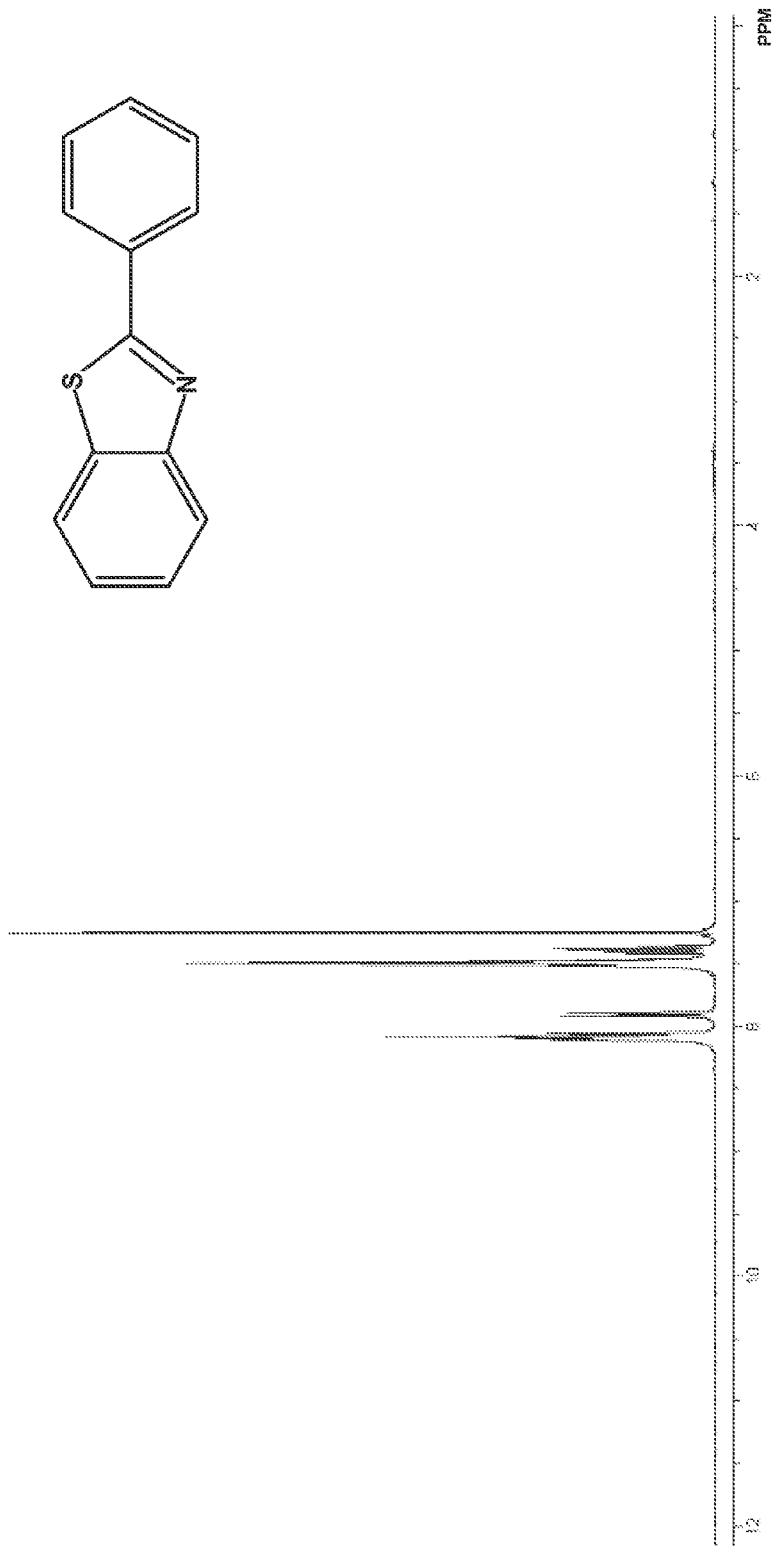
FIG. 15 depicts the molecular structure of 2-phenylbenzothiazole and $^1$H NMR Spectrum of 2-phenylbenzothiazole.

FIG. 15 shows the molecular structure of the resultant molecule 2-phenylbenzothiazole when the heterocycle is benzothiazole and its $^1$H NMR spectrum. The synthesis of 2-phenylbenzothiazole is conducted using copper(I) iodide (19.1 mg, 0.11 mmol), benzothiazole (135 mg, 1.0 mmol), iodobenzene (612 mg, 3.0 mmol), t-BuOLi (160 mg, 2.0 mmol), and DMF (1.0 mL). After column chromatography (hexanes, then 10% ethyl acetate in hexanes) 173 mg (82%) of a light tan solid is obtained. $R_f$=0.45 (1/9 ethyl acetate/hexanes). $^1$H NMR (300 MHz, $_{CDCl3}$) δ 8.05-8.13 (m, 3H), 7.92 (d, J=8.0 Hz, 1H), 7.42-7.53 (m, 4H), 7.38 (td, J=8.0 Hz, 1.1 Hz, 1H). Table III, entry 4.

Figure 16:
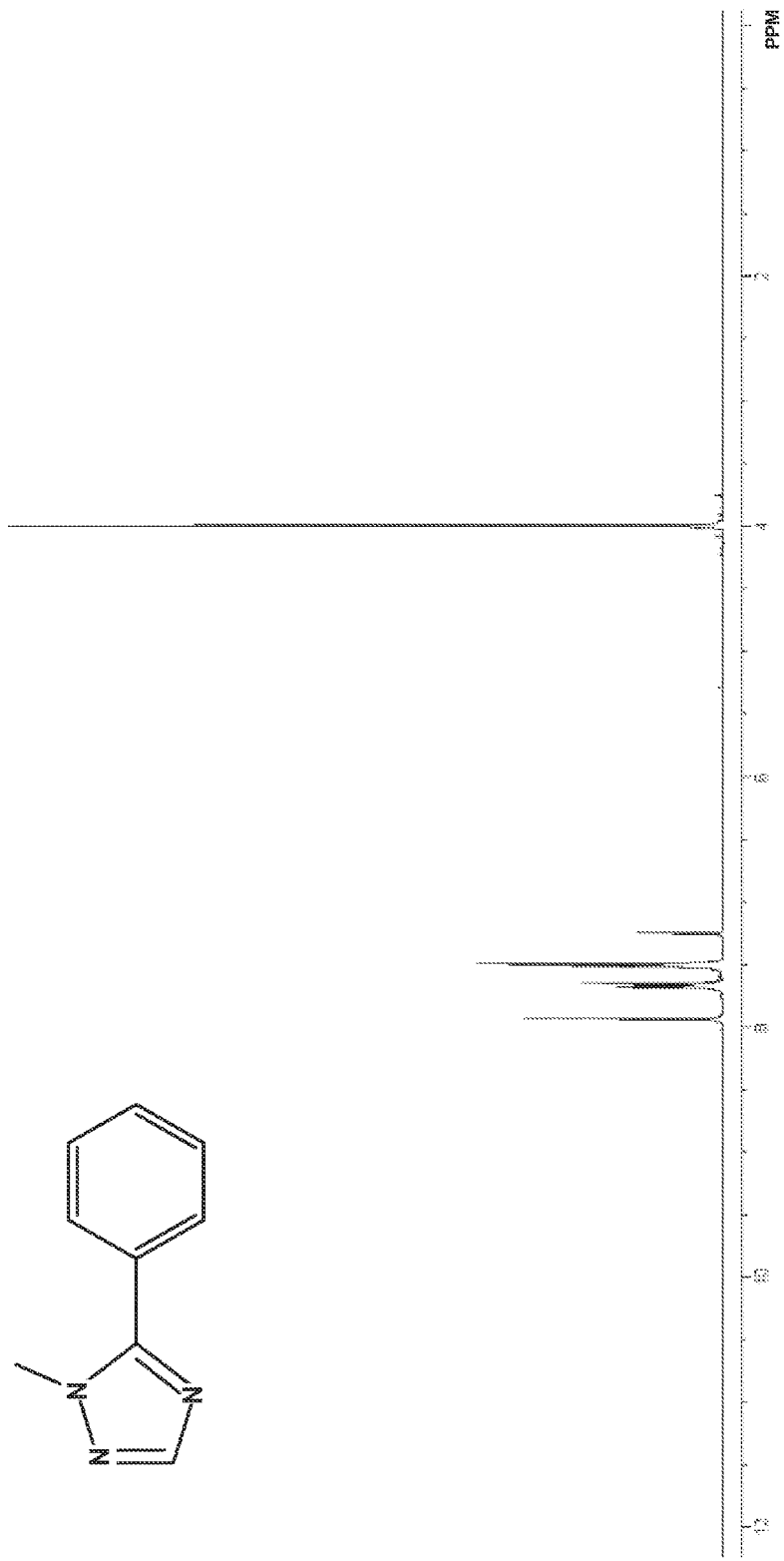
FIG. 16 depicts the molecular structure of 1-methyl-5-phenyl-1H-1,2,4-triazole and $^1$H NMR Spectrum of 1-methyl-5-phenyl-1H-1,2,4-triazole.

FIG. 16 shows the chemical structure of the resultant molecule 1-methyl-5-phenyl-1H-1,2,4-triazole, when the heterocycle is 1-methyl-1,2,4-triazole, and its $^1$H NMR spectrum. The synthesis of 1-methyl-5-phenyl-1H-1,2,4-triazole is conducted using copper(I) iodide (19.1 mg, 0.1 mmol), 1-methyl-1,2,4-triazole (83 mg, 1.0 mmol), iodobenzene (612 mg, 3.0 mmol), t-BuOK (224 mg, 2.0 mmol), and DMF (1.0 mL). After column chromatography (hexanes, then 10% hexanes in ethyl acetate) and preparative HPLC (1/1 ethyl acetate/hexanes) 91 mg (57%) of a light tan oil is obtained. $R_f$=0.23 (1/1 ethyl acetate/hexanes). $^1$H NMR (300 MHz, $_{CDCl3}$) δ 4.00 (s, 3H), 7.48-7.54 (m, 3H), 7.64-7.70 (m, 2H), 7.94 (s, 1H). $^{13}$C NMR (75 MHz, $_{CDCl3}$) δ 37.5, 128.4, 129.1, 129.4, 130.6, 151.3, 155.2. Table III, entry 5.

Figure 17:
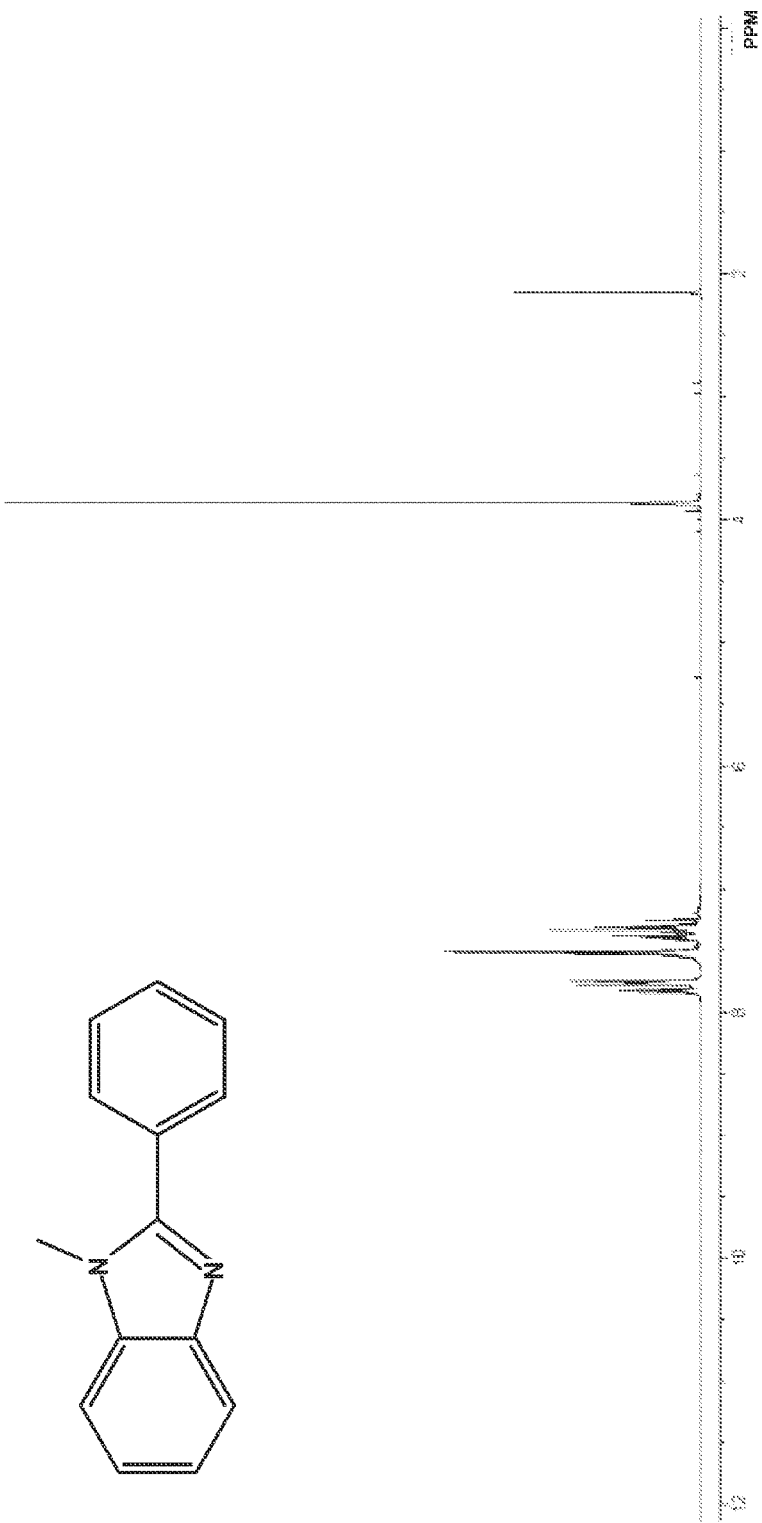
FIG. 17 depicts the molecular structure of 1-methyl-2-phenylbenzimidazole and $^1$H NMR Spectrum of 1-methyl-2-phenylbenzimidazole.

FIG. 17 shows the chemical structure of the resultant molecule 1-methyl-2-phenylbenzimidazole when the heterocycle is 1-methylbenzimidazole, and its $^1$H NMR spectrum. The synthesis of 1-methyl-2-phenylbenzimidazole is conducted using copper(I) iodide (19.1 mg, 0.1 mmol), 1-methylbenzimidazole (132 mg, 1.0 mmol), iodobenzene (612 mg, 3.0 mmol), t-BuOLi (80 mg, 1.0 mmol), t-BuOK (112 mg, 1.0 mmol), and DMF (0.5 mL), 30 minutes. After column chromatography (hexanes, then 25% ethyl acetate in hexanes) and preparative HPLC (1/1 ethyl acetate/hexanes) 186 mg (89%) of an off-white solid is obtained. $R_f$=0.36 (1/1 ethyl acetate/hexanes). $^1$H NMR (300 MHz, $_{CDCl3}$) δ 3.88 (s, 3H), 7.30-7.37 (m, 2H), 7.37-7.42 (m, 1H), 7.48-7.57 (m, 3H), 7.75-7.80 (m, 3H), 7.80-7.88 (m, 1H). Table III, entry 6.

Figure 18:
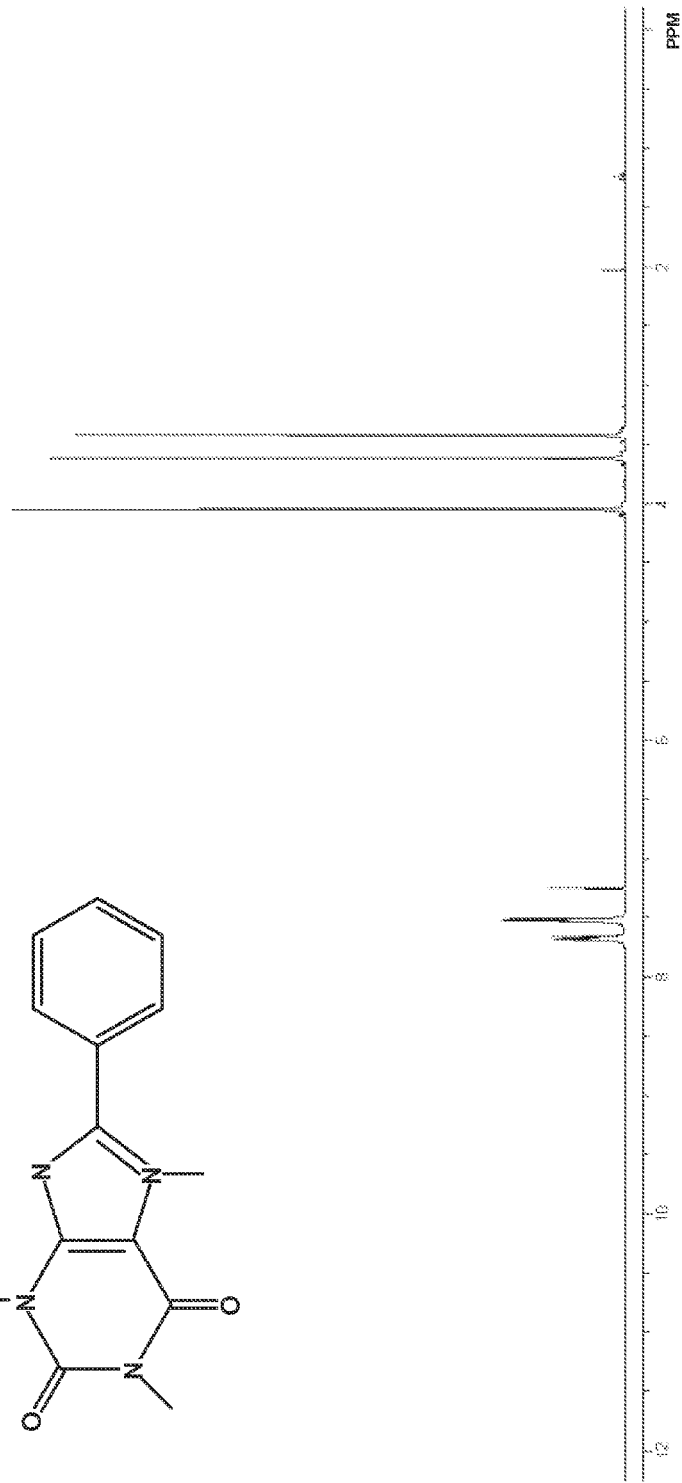
FIG. 18 depicts the molecular structure of 1,3,7-trimethyl-8-phenyl-1H-purine-2,6(3H, 7H)-dione and $^1$H NMR Spectrum of 1,3,7-trimethyl-8-phenyl-1H-purine-2,6(3H, 7H)-dione.

FIG. 18 shows the chemical structure of the resultant molecule 1,3,7-trimethyl-8-phenyl-1H-purine-2,6(3H,7H)-dione, when the heterocycle is caffeine, and its $^1$H NMR spectrum. The synthesis of 1,3,7-trimethyl-8-phenyl-1H-purine-2,6(3H,7H)-dione is conducted using copper(I) iodide (19.1 mg, 0.1 mmol), caffeine (194 mg, 1.0 mmol), iodobenzene (612 mg, 3.0 mmol), t-BuOK (224 mg, 2.0 mmol), and DMF (0.5 mL). After column chromatography (hexanes, then 30% hexanes in ethyl acetate) and preparative HPLC (50% ethyl acetate in hexanes) 210 mg (78%) of a white solid is obtained. $R_f$=0.25 (1/1 ethyl acetate/hexanes). $^1$H NMR (300 MHz, $_{CDCl3}$) δ 3.43 (s, 3H), 3.62 (s, 3H), 4.05 (s, 3H), 7.50-7.60 (m, 3H), 7.65-7.72 (m, 2H). Table III, entry 7.

Figure 19:
FIG. 19 depicts the molecular structure of 2,6-diphenylpyridine oxide and $^1$H NMR Spectrum of 2,6-diphenylpyridine oxide.

FIG. 19 shows the resultant molecule 2,6-diphenylpyridine oxide, when the heterocycle is 2-phenylpyridine oxide, and its $^1$H NMR spectrum. The synthesis of 2,6-diphenylpyridine oxide is conducted using copper(I) iodide (19.1 mg, 0.1 mmol), 2-phenylpyridine oxide (171 mg, 1.0 mmol), iodobenzene (612 mg, 3.0 mmol), t-BuOLi (160 mg, 2.0 mmol) and DMF (1.0 mL), 30 minutes. After column chromatography (hexanes, then 50% ethyl acetate in hexanes) 162 mg (66%) of an off-white solid is obtained. $R_f$=0.28 (1/1 ethyl acetate/hexanes). $^1$H NMR (300 MHz, $_{CDCl3}$) δ 7.30-7.60 (m, 9H), 7.80-7.86 (m, 4H). Table III, entry 8.

Another General Synthetic Procedure

Yet, another preferred embodiment of the present invention is a general procedure for the coupling of haloarenes with perfluorobenzenes.

Reactions are performed in 1-dram vials with PTFE/Liner caps. Flash chromatography is performed on 60 Å silica gel (Sorbent Technologies). Purification by preparative HPLC is performed on a Shimadzu Prominence LC (LC-20AB) equipped with a SPD-20A UV-Vis detector and a Varian Dynamax (250 mm×21.4 mm) column. GC-MS analyses are performed on a Shimadzu GCMS-QP5000 chromatograph equipped with a Restek column (Rtx-XLB, 30 m×0.25 mm I.D.). The $^1$H and $^{13}$C NMR are recorded on a GE QE-300 spectrometer using residual solvent peak as a reference. Melting points are measured on a Mel-Temp apparatus and are uncorrected. Elemental analyses are performed by Atlantic Microlab Inc. of Norcross, Ga. IR spectra are obtained using ThermoNicolet Avatar 370 FT-IR instrument.

The following starting materials are obtained from commercial sources and are used without further purification: 4-bromotoluen, 4-iodotoluene, 4-bromobenzotrifluoride, 4-bromobenzonitrile, 2-bromothiophene, 3-fluoropyridine, 1,4-difluorobenzene, 1,3,5-trifluorobenzene, 1,2,3,4-tetrafluorobenzene, 1,10-phenanthroline, copper(I) iodide, DMF, lithium t-butoxide, 1-bromonaphthalene, beta-bromostyrene (mixture of cis and trans isomers), potassium phosphate, m-xylene, 4-bromoanisole, 1-bromo-4-fluorobenzene, ethyl 4-bromobenzoate, 2-bromopyridine, 3-bromopyridine, 2-bromonaphthalene, 2-bromo-1,3,5-trimethylbenzene, fluorobenzene, 1,2,4,5-tetrafluorobenzene, 1,3,4,5-tetrafluorobenzene, 2,3,5,6-tetrafluorobenzene, 2-bromotoluene, 1,3-difluorobenzene, pentafluorobenzene, and 2-iodo-1,3,5-trimethylbenzene.

The general procedure for coupling of haloarenes with perfluorobenzenes is presented here. Outside the glovebox a 1-dram vial equipped with a magnetic stir bar is charged with haloarenes (1.0 mmol), phenanthroline (0.1 mmol), perfluorobenzenes (1.5 equiv) and a mixture (1/1) of DMF and xylene (0.6 mL). The vial is flushed with argon, capped and placed inside a glovebox. To this mixture is added CuI (10 mol %) and K$_3$PO$_4$ (2.0 equiv). The sealed vial is taken out of the glovebox, stirred at room temperature for 5 min and placed in a preheated oil bath (130° C.) for 24 hours. The reaction mixture is allowed to cool to room temperature and diluted with ethyl acetate (50 mL). The resulting solution is washed with brine (3×15 mL), dried over anhydrous MgSO$_4$, and concentrated under vacuum to a volume of about 2 mL. The mixture containing the product is subjected to flash chromatography on silica gel (hexanes followed by appropriate solvent to elute the products). After concentrating the fractions containing the product, the residue is dried under reduced pressure to yield pure arylation product.

Figure 20:
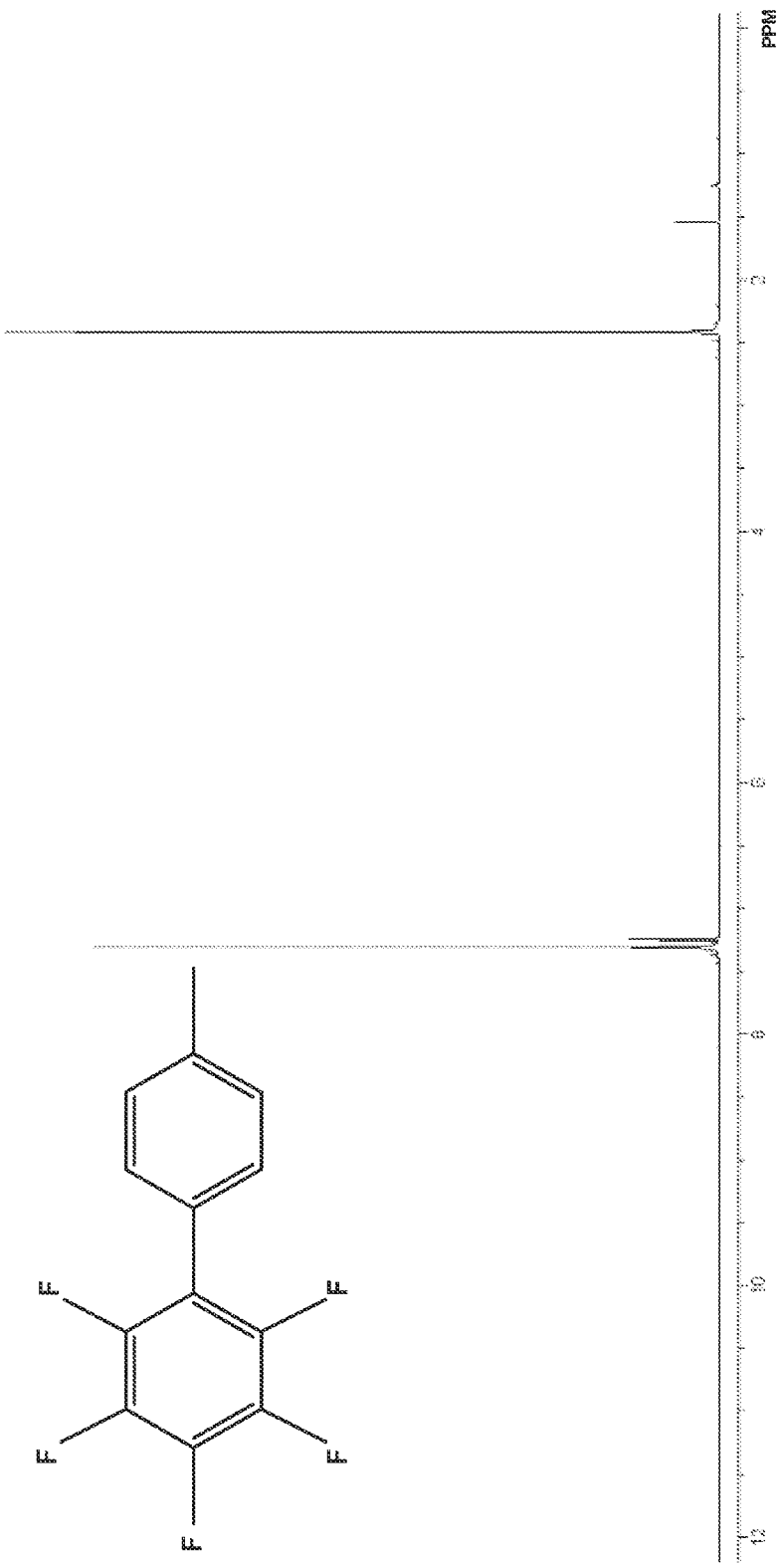
FIG. 20 depicts the molecular structure of 2,3,4,5,6-pentafluoro-4'-methylbiphenyl and $^1$H NMR Spectrum of 2,3,4,5,6-pentafluoro-4'-methylbiphenyl.

FIG. 20 shows the resultant molecule 2,3,4,5,6-pentafluoro-4'-methylbiphenyl, when the substrate is pentafluorobenzene and the haloarene is 4-bromotoluene, and its $^1$H NMR spectrum. The synthesis of 2,3,4,5,6-pentafluoro-4'-methylbiphenyl is conducted using copper(I) iodide (19.1 mg, 0.1 mmol), 4-bromotoluene (171 mg, 1.0 mmol), 1,10-phenanthroline (18 mg, 0.1 mmol), pentafluorobenzene (252 mg, 1.5 mmol), K$_3$PO$_4$ (424 mg, 2.0 mmol), and DMF/xylene (0.6 mL), 140° C. After column chromatography (hexanes) 235 mg (91%) of a white solid is obtained. $^1$H NMR (300 MHz, $_{CDCl3}$) δ 2.42 (s, 3H), 7.31 (s, 4H).

Figure 21:
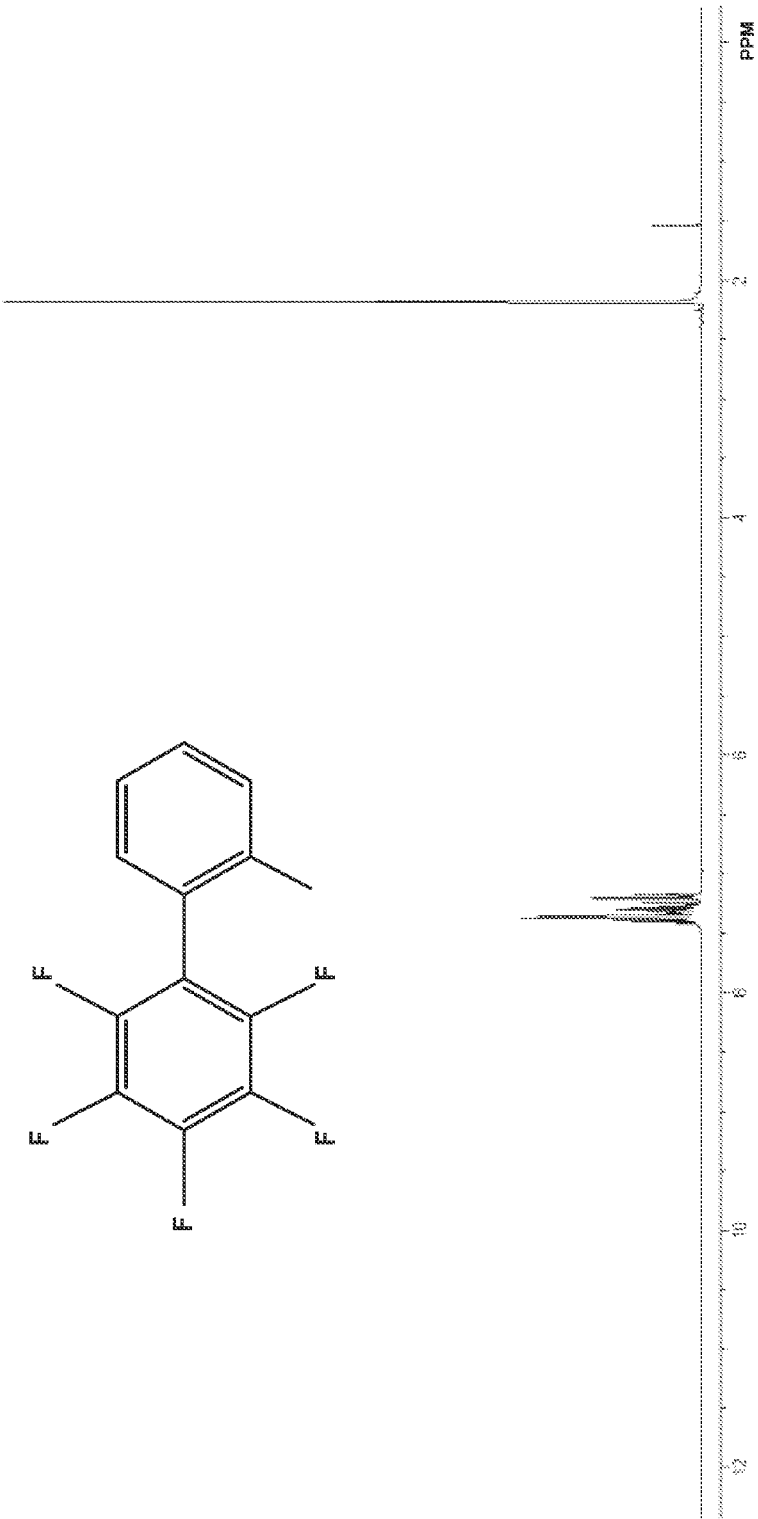
FIG. 21 depicts the molecular structure of 2,3,4,5,6-pentafluoro-2'-methylbiphenyl and $^1$H NMR Spectrum of 2,3,4,5,6-pentafluoro-2'-methylbiphenyl.

FIG. 21 shows the resultant molecule 2,3,4,5,6-pentafluoro-2'-methylbiphenyl when the substrate is pentafluorobenzene and the haloarene is 2-bromotoluene, and its $^1$H NMR spectrum. The synthesis of 2,3,4,5,6-pentafluoro-2'-methylbiphenyl is conducted using copper(I) iodide (19.1 mg, 0.1 mmol), 2-bromotoluene (171 mg, 1.0 mmol), 1,10-phenanthroline (18 mg, 0.1 mmol), pentafluorobenzene (252 mg, 1.5 mmol), K$_3$PO$_4$ (424 mg, 2.0 mmol), and DMF/xylene (0.6 mL), 140° C. After column chromatography (hexanes) 225 mg (87%) of a colorless oil is obtained. $^1$H NMR (300 MHz, $_{CDCl3}$) δ 2.18 (s, 3H), 7.16-7.43 (m, 4H).

Figure 22:
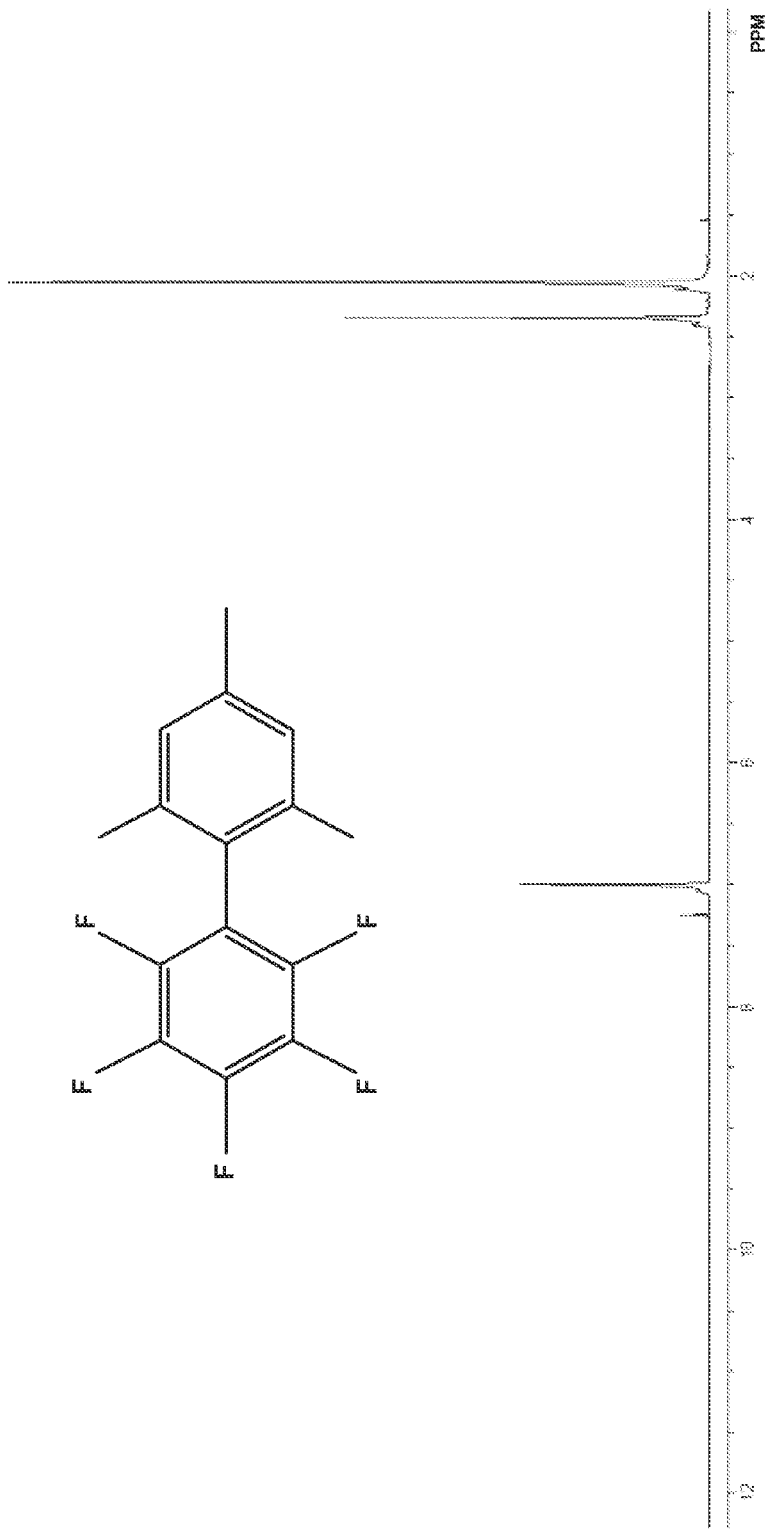
FIG. 22 depicts the molecular structure of 2,3,4,5,6-pentafluoro-2',4',6"-trimethylbiphenyl and $^1$H NMR Spectrum of 2,3,4,5,6-pentafluoro-2',4',6'-trimethylbiphenyl.

FIG. 22 shows the resultant molecule 2,3,4,5,6-pentafluoro-2',4',6'-trimethylbiphenyl when the substrate is pentafluorobenzene and the haloarene is 2-bromo-1,3,5-trimethylbenzene, and its $^1$H NMR spectrum. The synthesis of 2,3,4,5,6-pentafluoro-2',4',6'-trimethylbiphenyl is conducted using copper(I) iodide (19.1 mg, 0.1 mmol), 2-bromo-1,3,5-trimethylbenzene (199 mg, 1.0 mmol), 1,10-phenanthroline (18 mg, 0.1 mmol), pentafluorobenzene (252 mg, 1.5 mmol), K$_3$PO$_4$ (424 mg, 2.0 mmol), and DMF/xylene (0.6 mL), 140° C. After column chromatography (hexanes) and preparative HPLC (hexanes) 60 mg (20%) of a colorless oil is obtained. An alternative synthesis route involves the use of copper(I) iodide (19.1 mg, 0.1 mmol), 2-iodo-1,3,5-trimethylbenzene (246 mg, 1.0 mmol), 1,10-phenanthroline (18 mg, 0.1 mmol), pentafluorobenzene (252 mg, 1.5 mmol), K$_3$PO$_4$ (424 mg, 2.0 mmol), and DMF (0.6 mL). After column chromatography (hexanes) 250 mg (87%) of a colorless oil is obtained. $^1$H NMR (300 MHz, $_{CDCl3}$) δ 2.05 (s, 6H), 2.34 (s, 6H), 7.00 (s, 2H).

Figure 23:
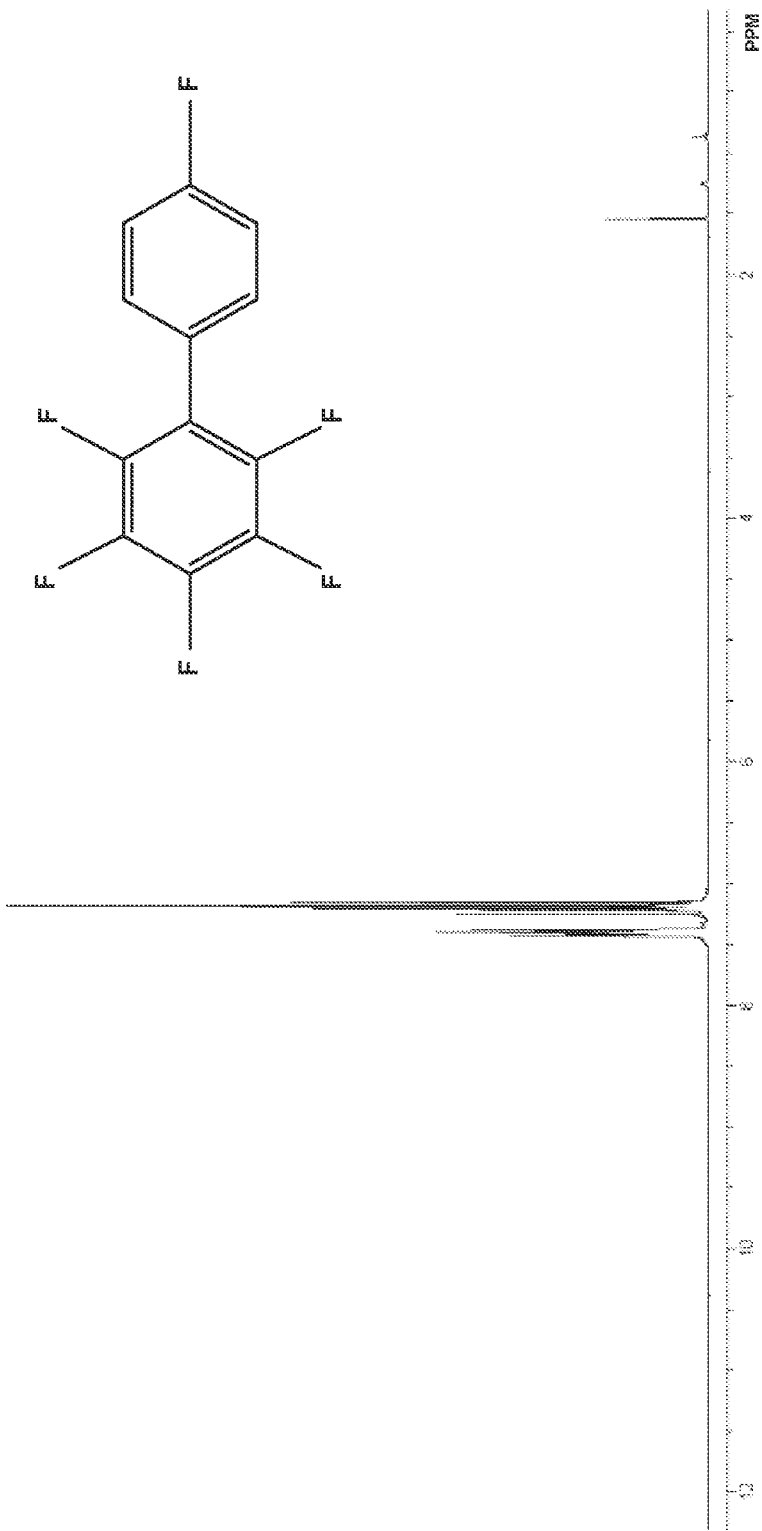
FIG. 23 depicts the molecular structure of 2,3,4,4',5,6-hexafluorobiphenyl and $^1$H NMR Spectrum of 2,3,4,4',5,6-hexafluorobiphenyl.

FIG. 23 shows the resultant molecules 2,3,4,4',5,6-hexafluorobiphenyl when the substrate is pentafluorobenzene and the haloarene is 1-bromo-4-fluorobenzene, and its $^1$H NMR spectrum. The synthesis of 2,3,4,4',5,6-hexafluorobiphenyl is conducted using copper(I) iodide (19.1 mg, 0.1 mmol), 1-bromo-4-fluorobenzene (175 mg, 1.0 mmol), 1,10-phenanthroline (18 mg, 0.1 mmol), pentafluorobenzene (252 mg, 1.5 mmol), K$_3$PO$_4$ (424 mg, 2.0 mmol), and DMF/xylene (0.6 mL), 140° C. After column chromatography (hexanes) 240 mg (92%) of a white solid was obtained. $^1$H NMR (300 MHz, $_{CDCl3}$) δ 7.14-7.24 (m, 2H), 7.36-7.45 (m, 2H).

FIG. 24 shows the resultant molecule 2,3,4,5,6-pentafluoro-4'-(trifluoromethyl)biphenyl when the substrate is pentafluorobenzene and the haloarene is 4-bromobenzotrifluoride, and its $^1$H NMR spectrum. The synthesis of 2,3,4,5,6-pentafluoro-4'-(trifluoromethyl)biphenyl is conducted using copper(I) iodide (19.1 mg, 0.1 mmol), 4-bromobenzotrifluoride (225 mg, 1.0 mmol), 1,10-phenanthroline (18 mg, 0.1 mmol), pentafluorobenzene (252 mg, 1.5 mmol), K$_3$PO$_4$ (424 mg, 2.0 mmol), and DMF/xylene (0.6 mL), 140° C. After column chromatography (hexanes) 275 mg (88%) of a white solid is obtained. $^1$H NMR (300 MHz, $_{CDCl3}$) δ 7.56 (d, J=8.0 Hz, 2H), 7.76 (d, J=8.0 Hz, 2H).

Figure 25:
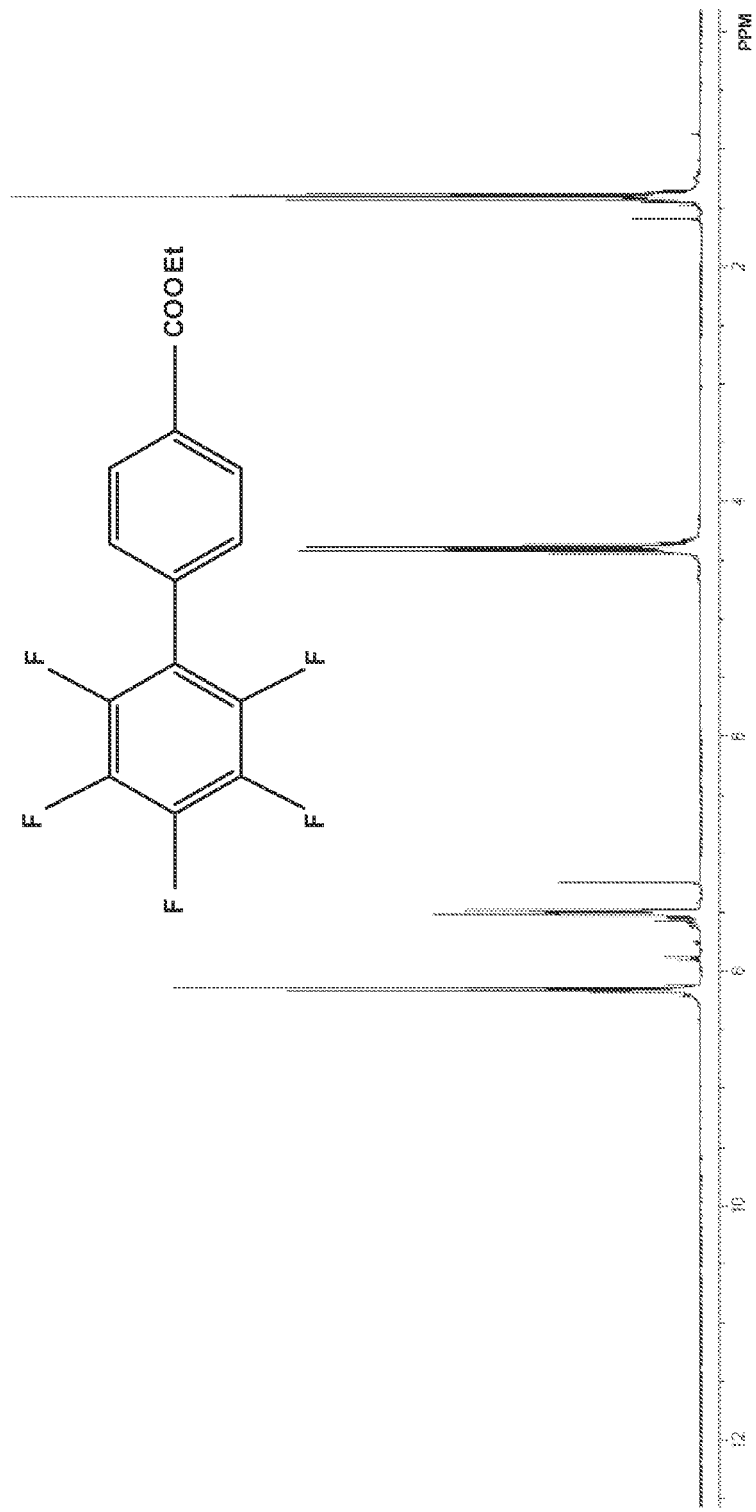
FIG. 25 depicts the molecular structure of ethyl 2',3',4',5',6'-pentafluorobiphenyl-4-carboxylate and $^1$H NMR Spectrum of ethyl 2',3',4',5',6'-pentafluorobiphenyl-4-carboxylate.

FIG. 25 shows the resultant molecule ethyl 2',3',4',5',6'-pentafluorobiphenyl-4-carboxylate when the substrate is pentafluorobenzene and the haloarene is ethyl 4-bromobenzoate, and its $^1$H NMR spectrum. The synthesis of ethyl 2',3',4',5',6'-pentafluorobiphenyl-4-carboxylate is conducted using copper(I) iodide (19.1 mg, 0.1 mmol), ethyl 4-bromobenzoate (229 mg, 1.0 mmol), 1,10-phenanthroline (18 mg, 0.1 mmol), pentafluorobenzene (252 mg, 1.5 mmol), K$_3$PO$_4$ (424 mg, 2.0 mmol), and DMF/xylene (0.6 mL). After column chromatography (10% ethyl acetate in hexanes) 285 mg (90%) of a white solid is obtained. $^1$H NMR (300 MHz, $_{CDCl3}$) δ 1.41 (t, J=7.0 Hz, 3H), 4.41 (q, J=7.0 Hz, 2H), 7.50 (d, J=8.0 Hz, 2H), 8.16 (d, J=8.0 Hz, 2H).

Figure 26:
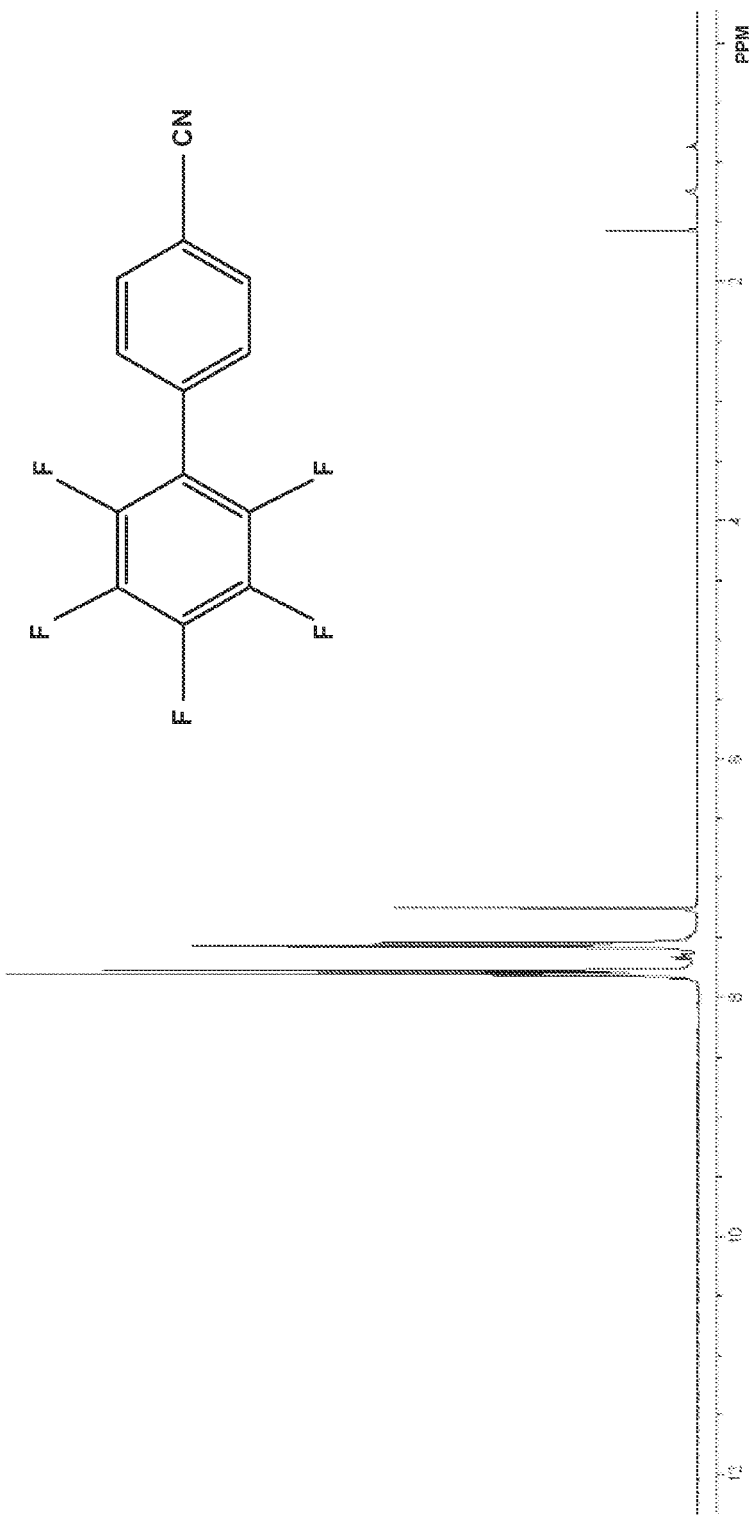
FIG. 26 depicts the molecular structure of 2',3',4',5',6'-pentafluorobiphenyl-4-carbonitrile and $^1$H NMR Spectrum of 2',3',4',5',6'-pentafluorobiphenyl-4-carbonitrile.

FIG. 26 shows the resultant molecule 2',3',4',5',6'-pentafluorobiphenyl-4-carbonitrile when the substrate is pentafluorobenzene and the haloarene is bromobenzonitrile, and its $^1$H NMR spectrum. The synthesis of 2',3',4',5',6'-pentafluorobiphenyl-4-carbonitrile is conducted using copper(I) iodide (19.1 mg, 0.1 mmol), 4-bromobenzonitrile (182 mg, 1.0 mmol), 1,10-phenanthroline (18 mg, 0.1 mmol), pentafluorobenzene (252 mg, 1.5 mmol), K$_3$PO$_4$ (424 mg, 2.0 mmol), and DMF/xylene (0.6 mL). After column chromatography (10% ethyl acetate in hexanes) 255 mg (95%) of a white solid is obtained. $^1$H NMR (300 MHz, $_{CDCl3}$) δ 7.53-7.59 (m, 2H), 7.77-7.84 (m, 2H).

Figure 27:
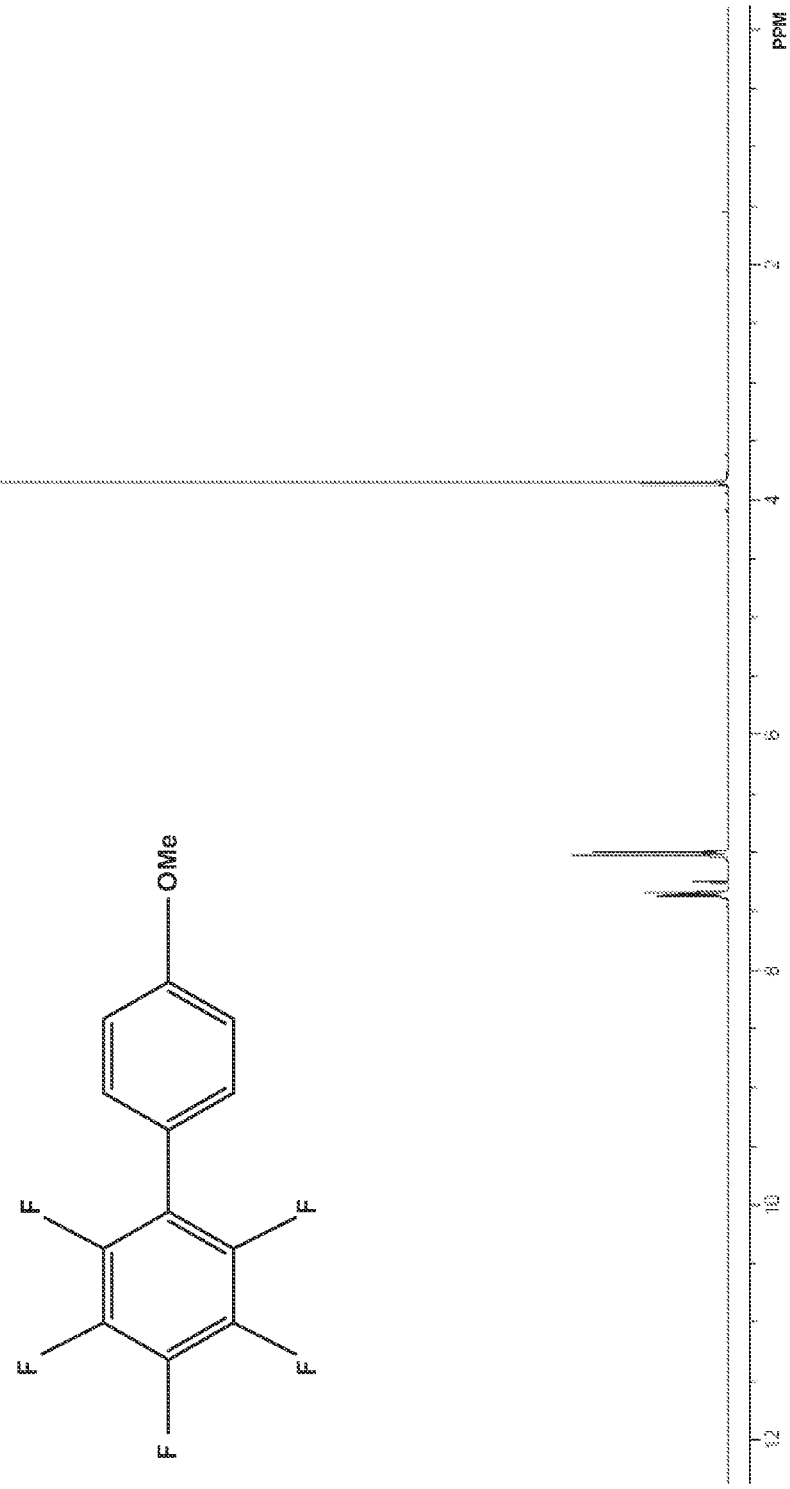
FIG. 27 depicts the molecular structure of 2,3,4,5,6-pentafluoro-4'-methoxybiphenyl and $^1$H NMR Spectrum of 2,3,4,5,6-pentafluoro-4'-methoxybiphenyl.

FIG. 27 shows the resultant molecule 2,3,4,5,6-pentafluoro-4'-methoxybiphenyl when the substrate is pentafluorobenzene and the haloarene is 4-bromoanisole, and its $^1$H NMR spectrum. The synthesis of 2,3,4,5,6-pentafluoro-4'-methoxybiphenyl is conducted using copper(I) iodide (19.1 mg, 0.1 mmol), 4-bromoanisole (187 mg, 1.0 mmol), 1,10-phenanthroline (18 mg, 0.1 mmol), pentafluorobenzene (252 mg, 1.5 mmol), K$_3$PO$_4$ (424 mg, 2.0 mmol), and DMF/xylene (0.6 mL), 140° C. After column chromatography (10% ethyl acetate in hexanes) 240 mg (88%) of a white solid is obtained. $^1$H NMR (300 MHz, $_{CDCl3}$) δ 3.86 (s, 3H), 6.98-7.04 (m, 2H), 7.33-7.38 (m, 2H).

Figure 28:
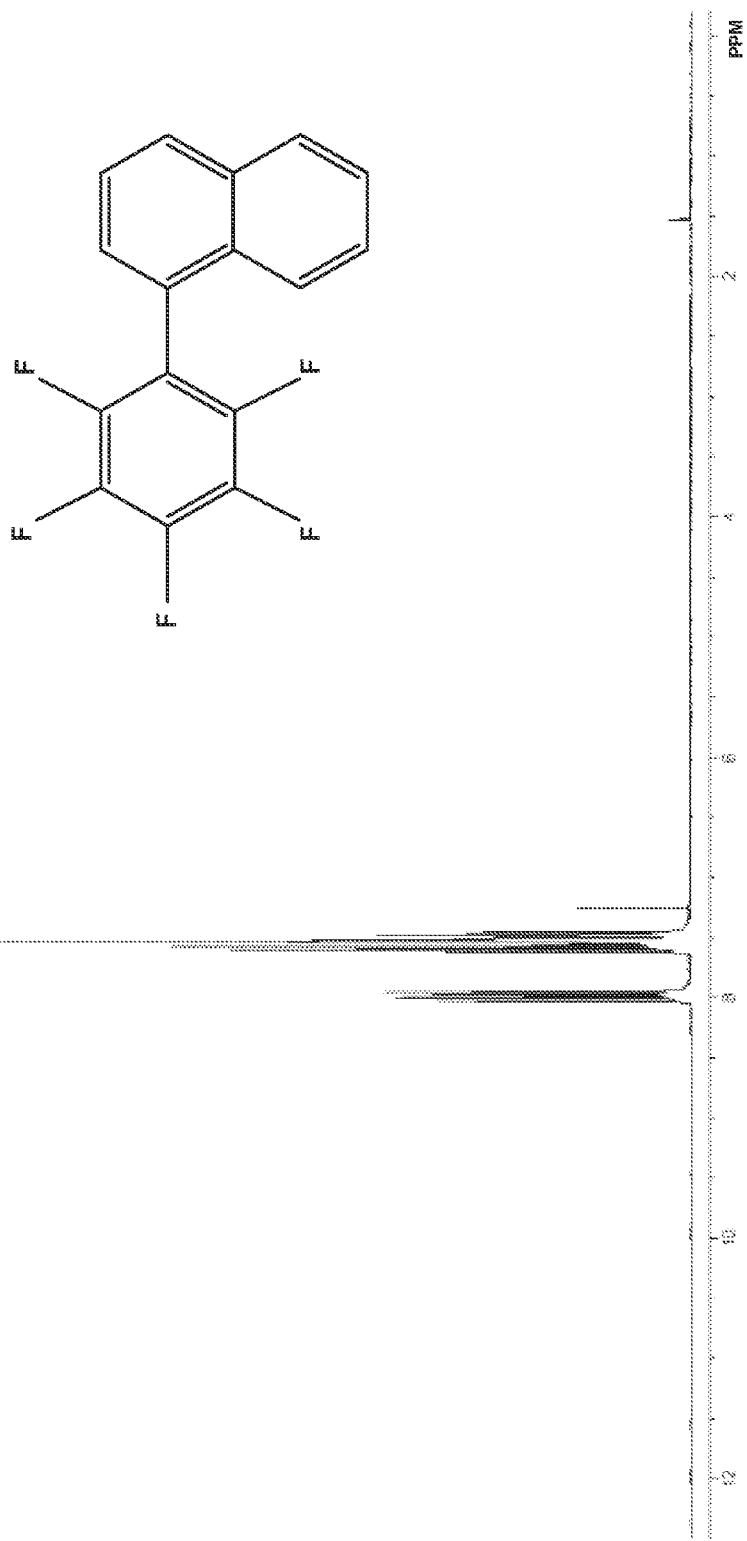
FIG. 28 depicts the molecular structure of 1-(perfluorophenyl)naphthalene and $^1$H NMR Spectrum of 1-(perfluorophenyl)naphthalene.

FIG. 28 shows the resultant molecule 1-(perfluorophenyl)naphthalene when the substrate is pentafluorobenzene and the haloarene is 1-bromonaphthalene, and its $^1$H NMR spectrum. The synthesis of 1-(perfluorophenyl)naphthalene is conducted using copper(I) iodide (19.1 mg, 0.1 mmol), 1-bromonaphthalene (207 mg, 1.0 mmol), 1,10-phenanthroline (18 mg, 0.1 mmol), pentafluorobenzene (252 mg, 1.5 mmol), K$_3$PO$_4$ (424 mg, 2.0 mmol), and DMF/xylene (0.6 mL), 140° C. After column chromatography (hexanes) and preparative HPLC (hexanes) 200 mg (68%) of a white solid is obtained. $^1$H NMR (300 MHz, $_{CDCl3}$) δ 7.45-7.63 (m, 5H), 7.94-8.04 (m, 2H).

Figure 29:
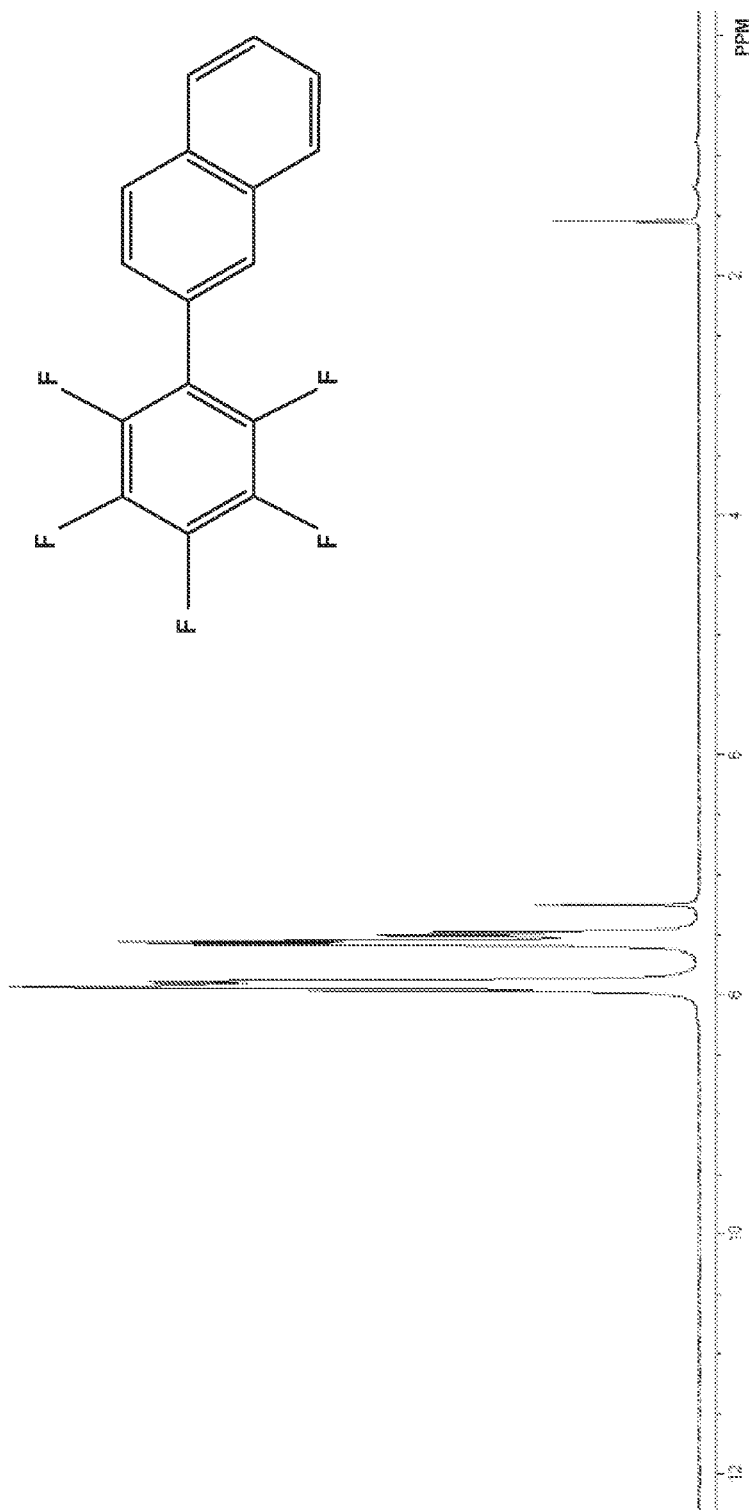
FIG. 29 depicts the molecular structure of 2-(perfluorophenyl)naphthalene and $^1$H NMR Spectrum of 2-(perfluorophenyl)naphthalene.

FIG. 29 shows the resultant molecule 2-(perfluorophenyl)naphthalene when the substrate is pentafluorobenzene and the haloarene is 2-bromonaphthalene, and its $^1$H NMR spectrum. The synthesis of 2-(perfluorophenyl)naphthalene is conducted using copper(I) iodide (19.1 mg, 0.1 mmol), 2-bromonaphthalene (207 mg, 1.0 mmol), 1,10-phenanthroline (18 mg, 0.1 mmol), pentafluorobenzene (252 mg, 1.5 mmol), K$_3$PO$_4$ (424 mg, 2.0 mmol), and DMF/xylene (0.6 mL). After column chromatography (10% ethyl acetate in hexanes) 265 mg (90%) of a white solid is obtained. $^1$H NMR (300 MHz, $_{CDCl3}$) δ 7.45-7.62 (m, 3H), 7.85-8.00 (m, 4H).

Figure 30:
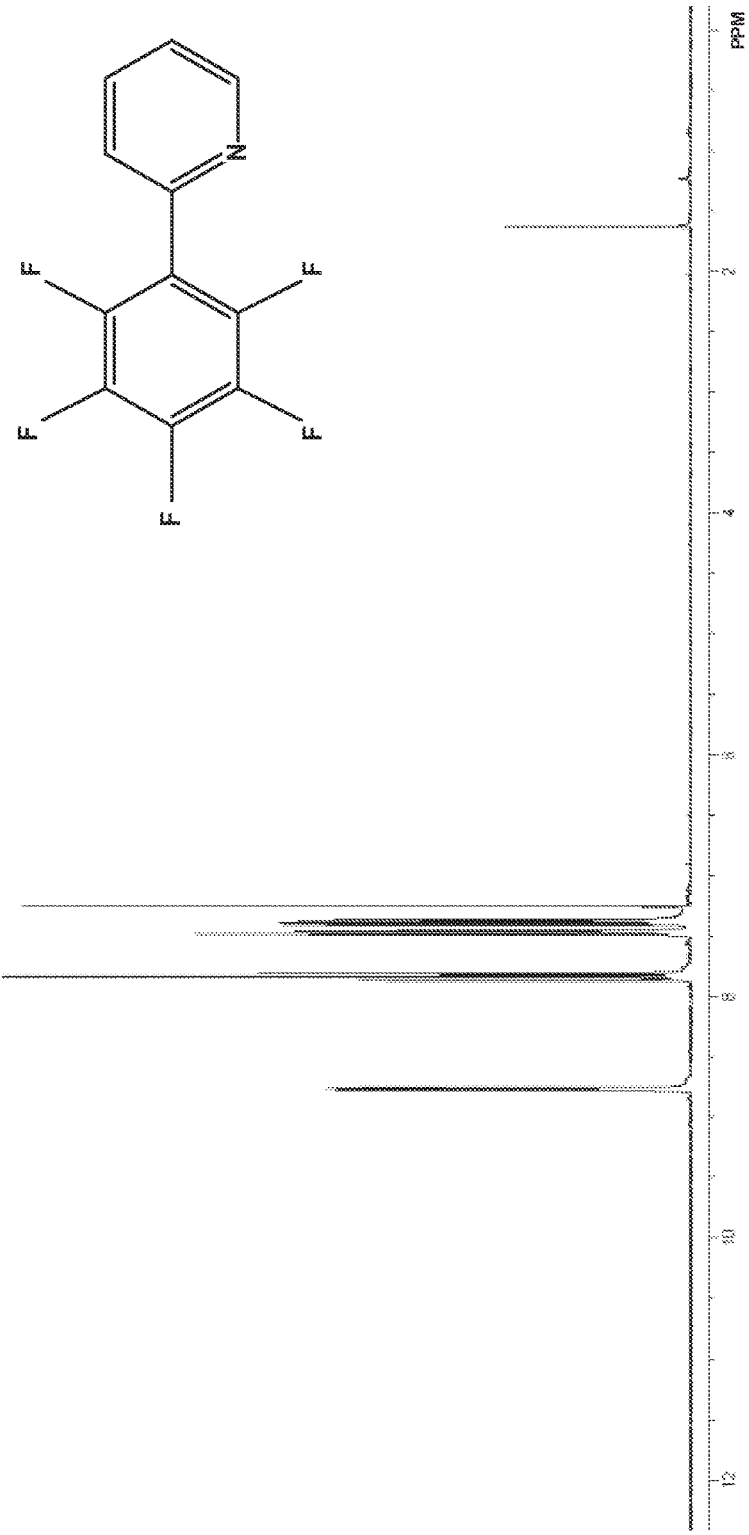
FIG. 30 depicts the molecular structure of 2-(perfluorophenyl)pyridine and $^1$H NMR Spectrum of 2-(perfluorophenyl)pyridine.

FIG. 30 shows the resultant molecule 2-(perfluorophenyl)pyridine when the substrate is pentafluorobenzene and the haloarene is 2-bromopyridine, and its $^1$H NMR spectrum. The synthesis of 2-(perfluorophenyl)pyridine is conducted using copper(I) iodide (19.1 mg, 0.1 mmol), 2-bromopyridine (158 mg, 1.0 mmol), 1,10-phenanthroline (18 mg, 0.1 μmol), pentafluorobenzene (252 mg, 1.5 mmol), K$_3$PO$_4$ (424 mg, 2.0 mmol), and DMF/xylene (0.6 mL), 120° C., 12 hours. After column chromatography (20% ethyl acetate in hexanes) 220 mg (90%) of a white solid is obtained. $^1$H NMR (300 MHz, $_{CDCl3}$) δ 7.38 (ddd, J=8.0 Hz, 5.0 Hz, 1.0 Hz, 1H), 7.45-7.50 (m, 1H), 7.84 (dt, J=1.6 Hz, 7.7 Hz, 1H), 8.75-8.78 (m, 1H).

Figure 31:
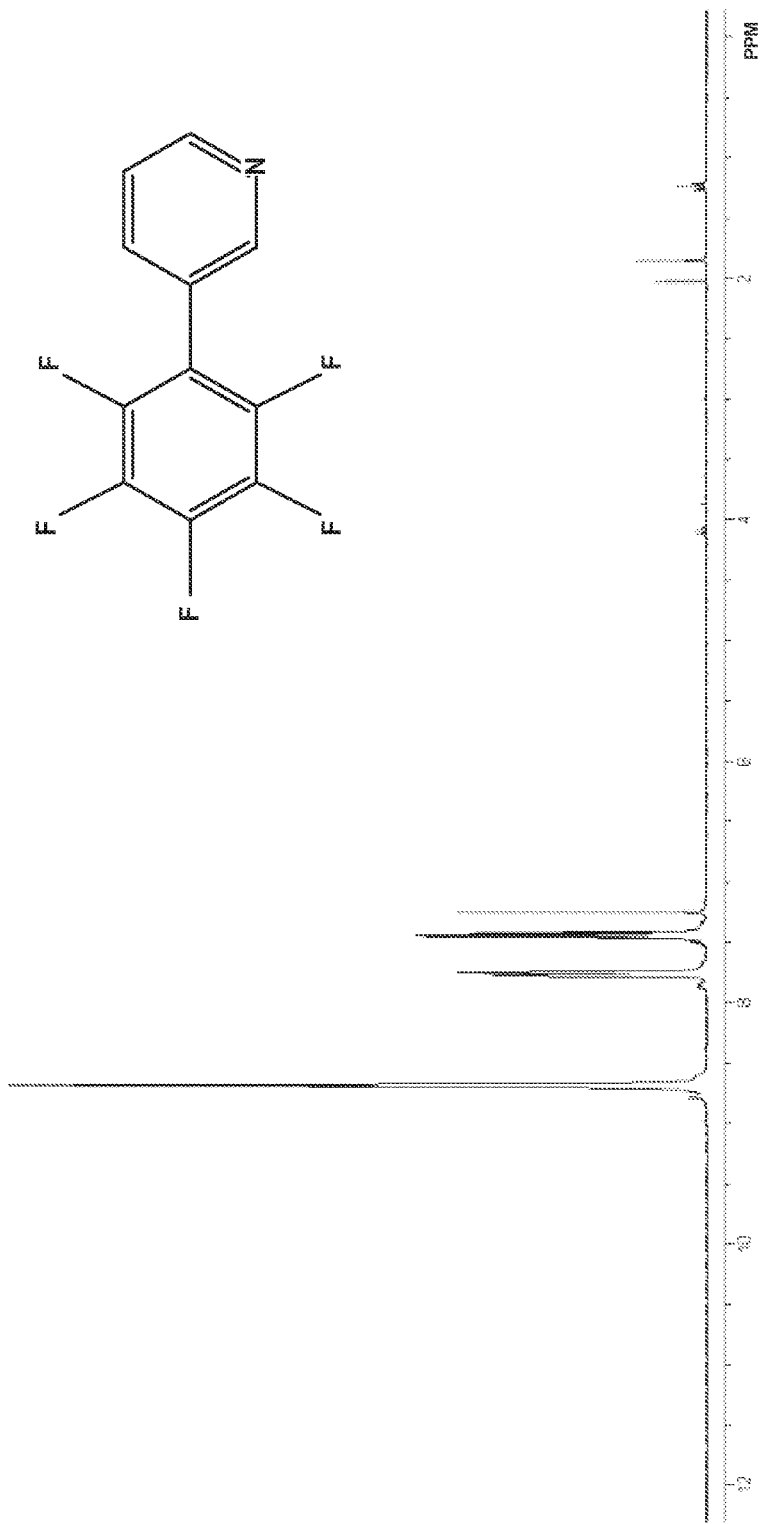
FIG. 31 depicts the molecular structure of 3-(perfluorophenyl)pyridine and $^1$H NMR Spectrum of 3-(perfluorophenyl)pyridine.

FIG. 31 shows the resultant molecule 3-(perfluorophenyl)pyridine when the substrate is pentafluorobenzene and the haloarene is 3-bromopyridine, and its $^1$H NMR spectrum. The synthesis of 3-(perfluorophenyl)pyridine is conducted using copper(I) iodide (19.1 mg, 0.1 mmol), 3-bromopyridine (158 mg, 1.0 mmol), 1,10-phenanthroline (18 mg, 0.11 mmol), pentafluorobenzene (252 mg, 1.5 mmol), K$_3$PO$_4$ (424 mg, 2.0 mmol), and DMF/xylene (0.6 mL). After column chromatography (1/1 ethyl acetate/hexanes) 210 mg (86%) of a light tan solid is obtained. $^1$H NMR (300 MHz, $_{CDCl3}$) δ 7.40-7.48 (m, 1H), 7.72-7.80 (m, 1H), 8.65-8.73 (m, 2H).

Figure 32:
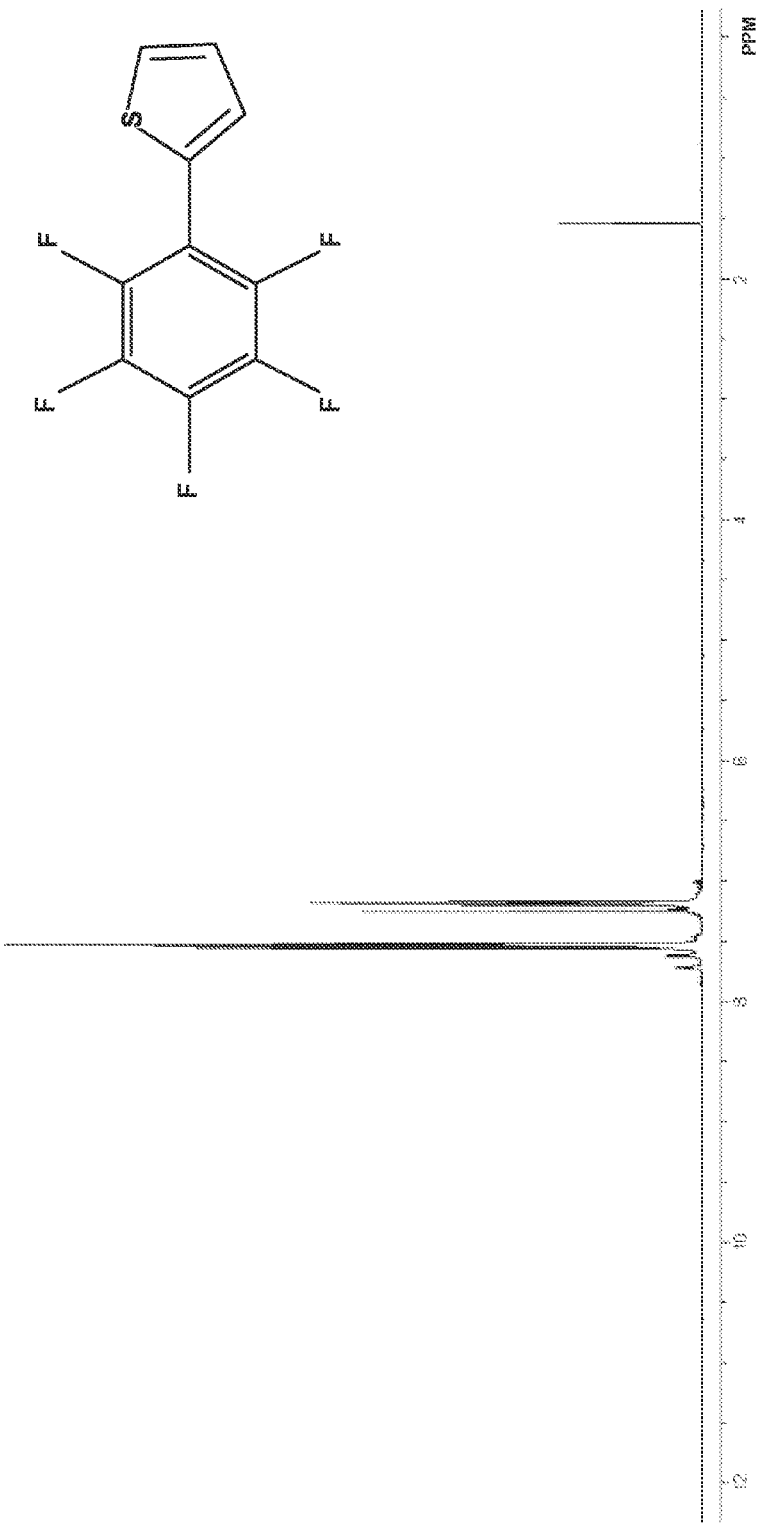
FIG. 32 depicts the molecular structure of 2-(perfluorophenyl)thiophene and $^1$H NMR Spectrum of 2-(perfluorophenyl)thiophene.

FIG. 32 shows the resultant molecule 2-(perfluorophenyl)thiophene when the substrate is pentafluorobenzene and the haloarene is 2-bromothiophene, and its $^1$H NMR spectrum. The synthesis of 2-(perfluorophenyl)thiophene is conducted using copper(I) iodide (19.1 mg, 0.1 mmol), 2-bromothiophene (163 mg, 1.0 mmol), 1,10-phenanthroline (18 mg, 0.1 mmol), pentafluorobenzene (252 mg, 1.5 mmol), K$_3$PO$_4$ (424 mg, 2.0 mmol), and DMF/xylene (0.6 mL), 120° C., 12 hours. After column chromatography (hexanes) 230 mg (92%) of a white solid is obtained. $^1$H NMR (300 MHz, $_{CDCl3}$) δ 7.16-7.21 (m, 1H), 7.50-7.57 (m, 2H).

Figure 33:
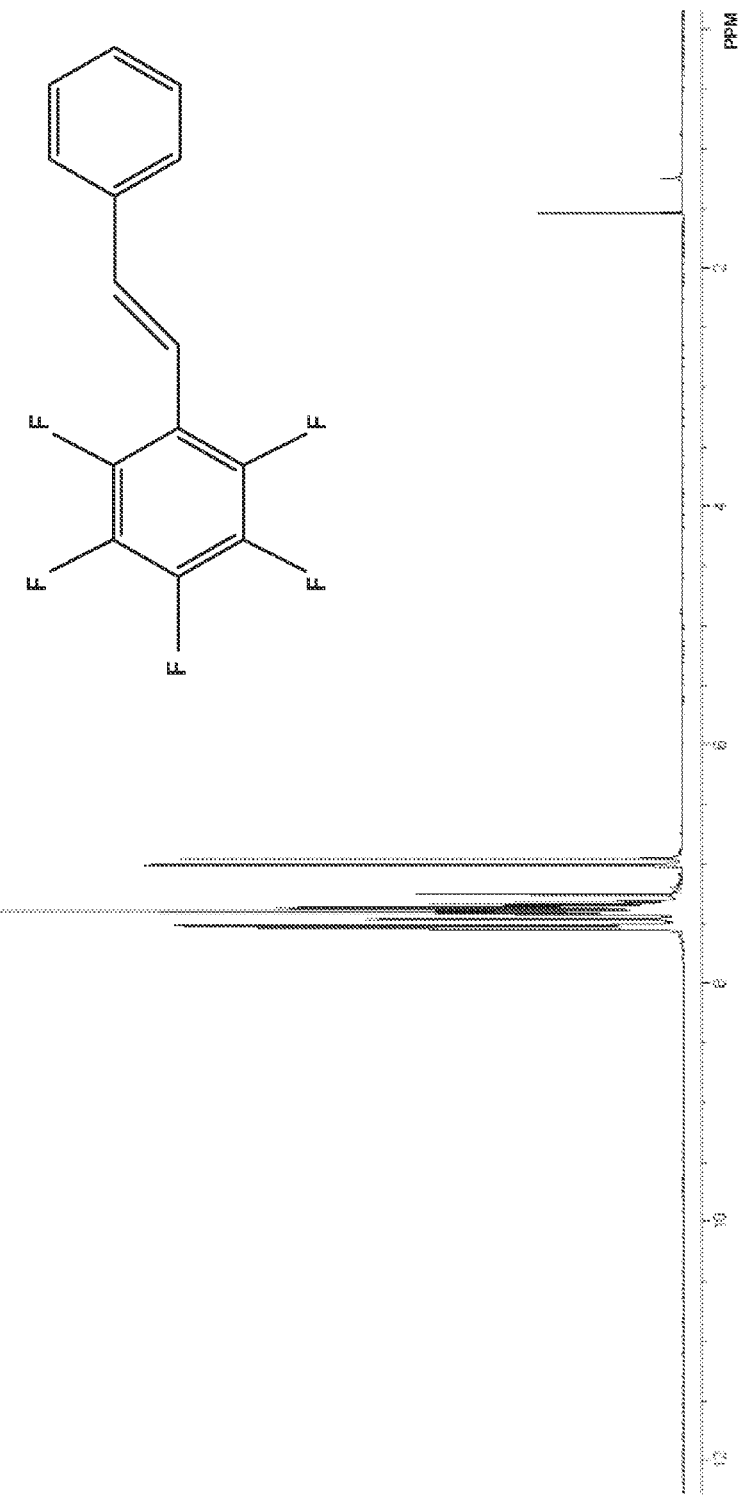
FIG. 33 molecular structure of (E)-1,2,3,4,5-pentafluoro-6-styrylbenzene and $^1$H NMR Spectrum of (E)-1,2,3,4,5-pentafluoro-6-styrylbenzene.

FIG. 33 shows the resultant molecules (E)-1,2,3,4,5-pentafluoro-6-styrylbenzene and when the substrate is pentafluorobenzene and the haloalkene is beta-bromostyrene, and its $^1$H NMR spectrum. (Z)-1,2,3,4,5-Pentafluoro-6-styrylbenzene is also produced in this synthesis. The synthesis of (E)-1,2,3,4,5-pentafluoro-6-styrylbenzene and (Z)-1,2,3,4,5-pentafluoro-6-styrylbenzene is conducted using copper(I) iodide (19.1 mg, 0.1 mmol), beta-bromostyrene (183 mg, 1.0 mmol), 1,10-phenanthroline (18 mg, 0.1 mmol), pentafluorobenzene (252 mg, 1.5 mmol), K$_3$PO$_4$ (424 mg, 2.0 mmol), and DMF/xylene (0.6 mL). After column chromatography (hexanes) and preparative HPLC (hexanes) 33 mg (12%) of an off-white solid ((Z)-1,2,3,4,5-pentafluoro-6-styrylbenzene) and 207 mg (77%) of a white solid ((E)-1,2,3,4,5-pentafluoro-6-styrylbenzene) are obtained. (E)-1,2,3,4,5-pentafluoro-6-styrylbenzene: $^1$H NMR (300 MHz, $_{CDCl3}$) δ 6.98 (d, J=16.6 Hz, 1H), 7.30-7.48 (m, 4H), 7.50-7.56 (m, 2H). Data not shown for (Z)-1,2,3,4,5-pentafluoro-6-styrylbenzene.

Figure 34:
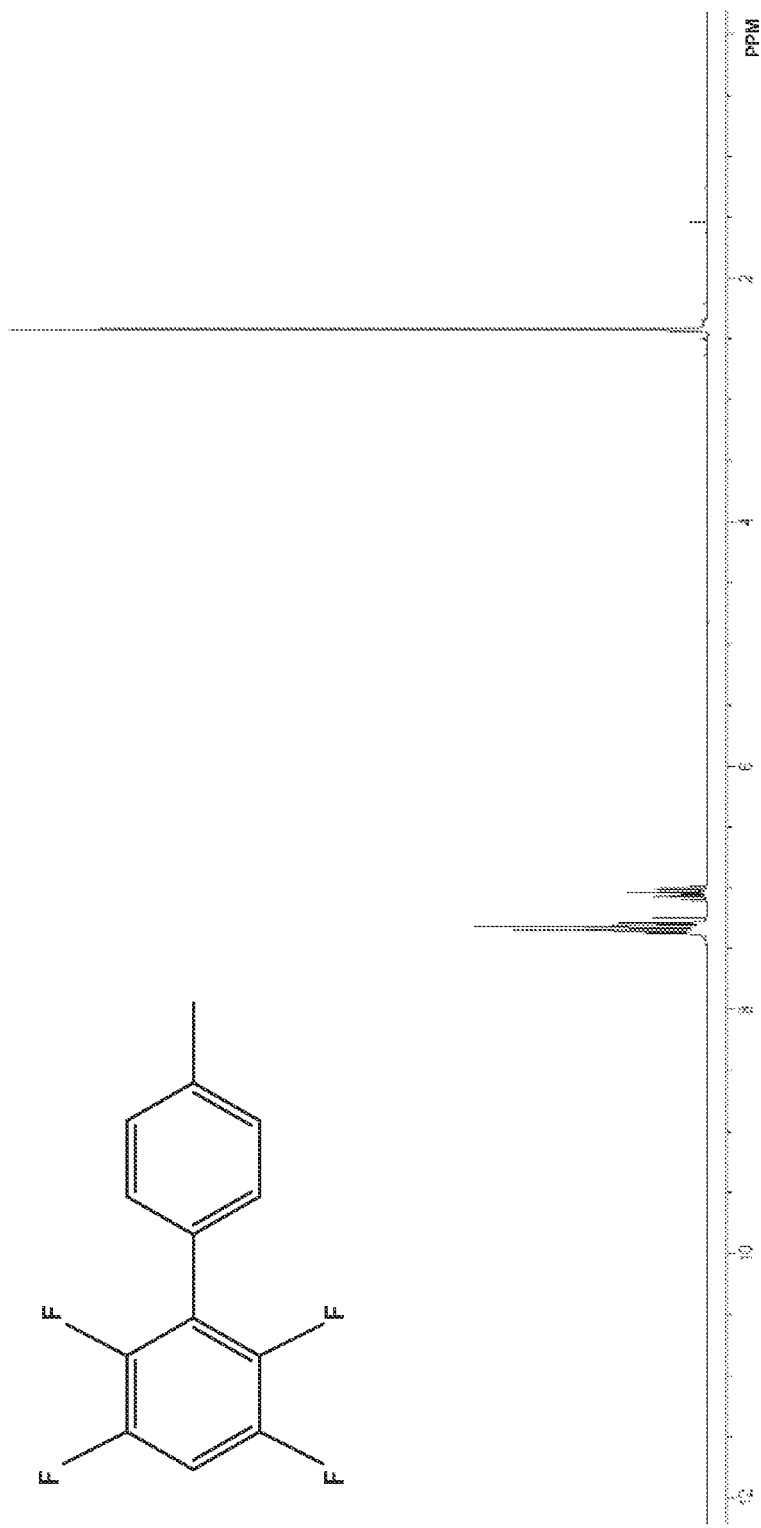
FIG. 34 depicts the molecular structure of 2,3,5,6-tetrafluoro-4'-methylbiphenyl and $^1$H NMR Spectrum of 2,3,5,6-tetrafluoro-4'-methylbiphenyl.
Figure 35:
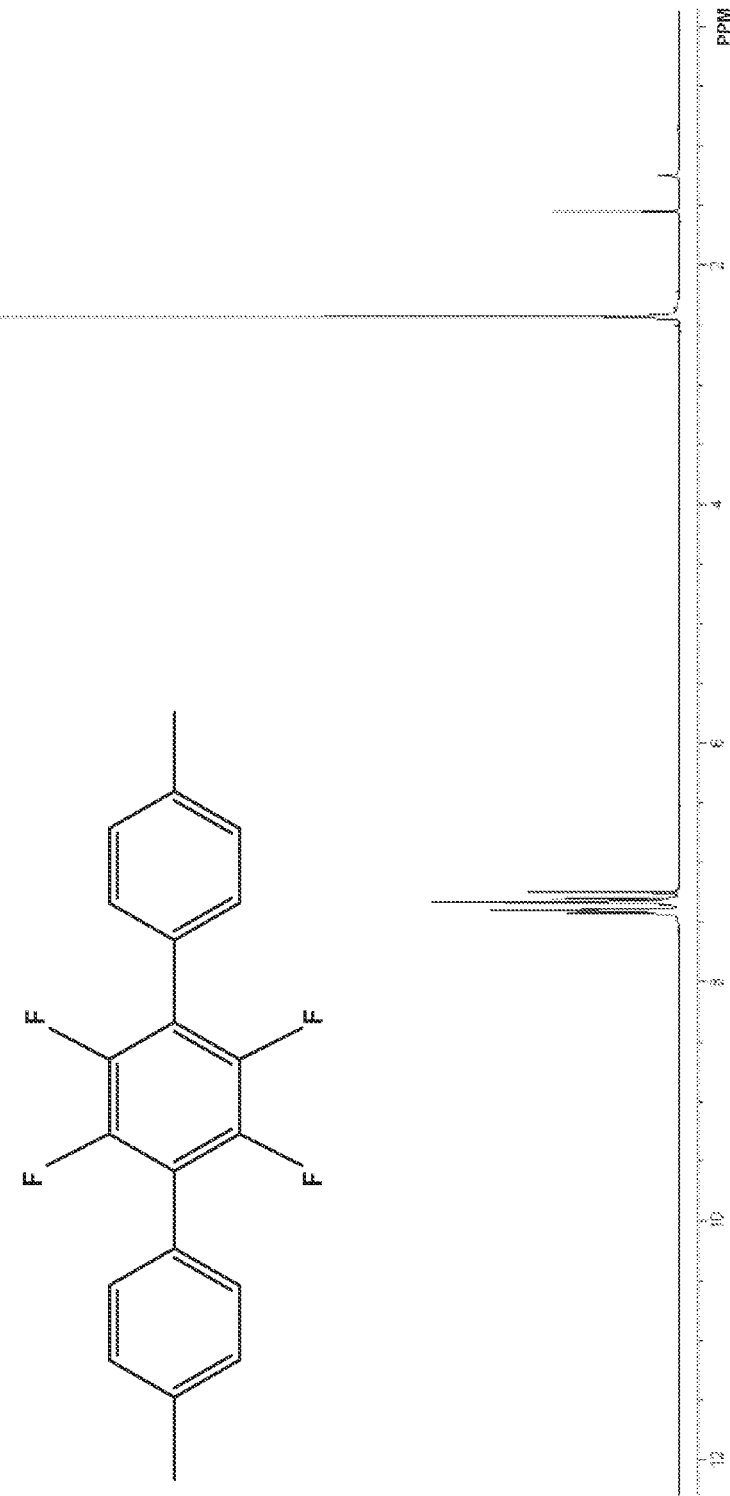
FIG. 35 depicts the molecular structure of 1,4-di-(p-tolyl)-2,3,5,6-tetrafluorobenzene and $^1$H NMR Spectrum of 1,4-di-(p-tolyl)-2,3,5,6-tetrafluorobenzene

FIG. 34 shows the resultant molecules 2,3,5,6-tetrafluoro-4'-methylbiphenyl when the substrate is 1,2,4,5-tetrafluorobenzene and the haloarene is 4-iodotoluene, and its $^1$H NMR. FIG. 35 shows the resultant molecules 1,4-di-(p-tolyl)-2,3,5,6-tetrafluorobenzene when the substrate is 1,2,4,5-tetrafluorobenzene and the haloarene is 4-iodotoluene, and its $^1$H NMR. The synthesis of 2,3,5,6-tetrafluoro-4'-methylbiphenyl and 1,4-di-(p-tolyl)-2,3,5,6-tetrafluorobenzene is conducted using copper(I) iodide (19.1 mg, 0.11 mmol), 4-iodotoluene (218 mg, 1.0 mmol), 1,10-phenanthroline (18 mg, 0.1 mmol), 1,2,4,5-tetrafluorobenzene (300 mg, 2.0 mmol), K$_3$PO$_4$ (488 mg, 2.3 mmol), and DMF (0.6 mL). After column chromatography (hexanes) and preparative HPLC (hexanes) 185 mg (77%) of a white solid (2,3,5,6-tetrafluoro-4'-methylbiphenyl) and 50 mg (15%) of another white solid (1,4-di-(p-tolyl)-2,3,5,6-tetrafluorobenzene) are obtained. Data for 2,3,5,6-tetrafluoro-4'-methylbiphenyl: $^1$H NMR (300 MHz, $_{CDCl3}$) δ 2.42 (s, 3H), 6.97-7.12 (m, 1H), 7.27-7.40 (m, 4H). Data for 1,4-di-(p-tolyl)-2,3,5,6-tetrafluorobenzene: $^1$H NMR (300 MHz, $_{CDCl3}$) δ 2.43 (s, 6H), 7.32 (d, J=8.0 Hz, 4H), 7.41 (d, J=8.0 Hz, 4H).

Figure 36:
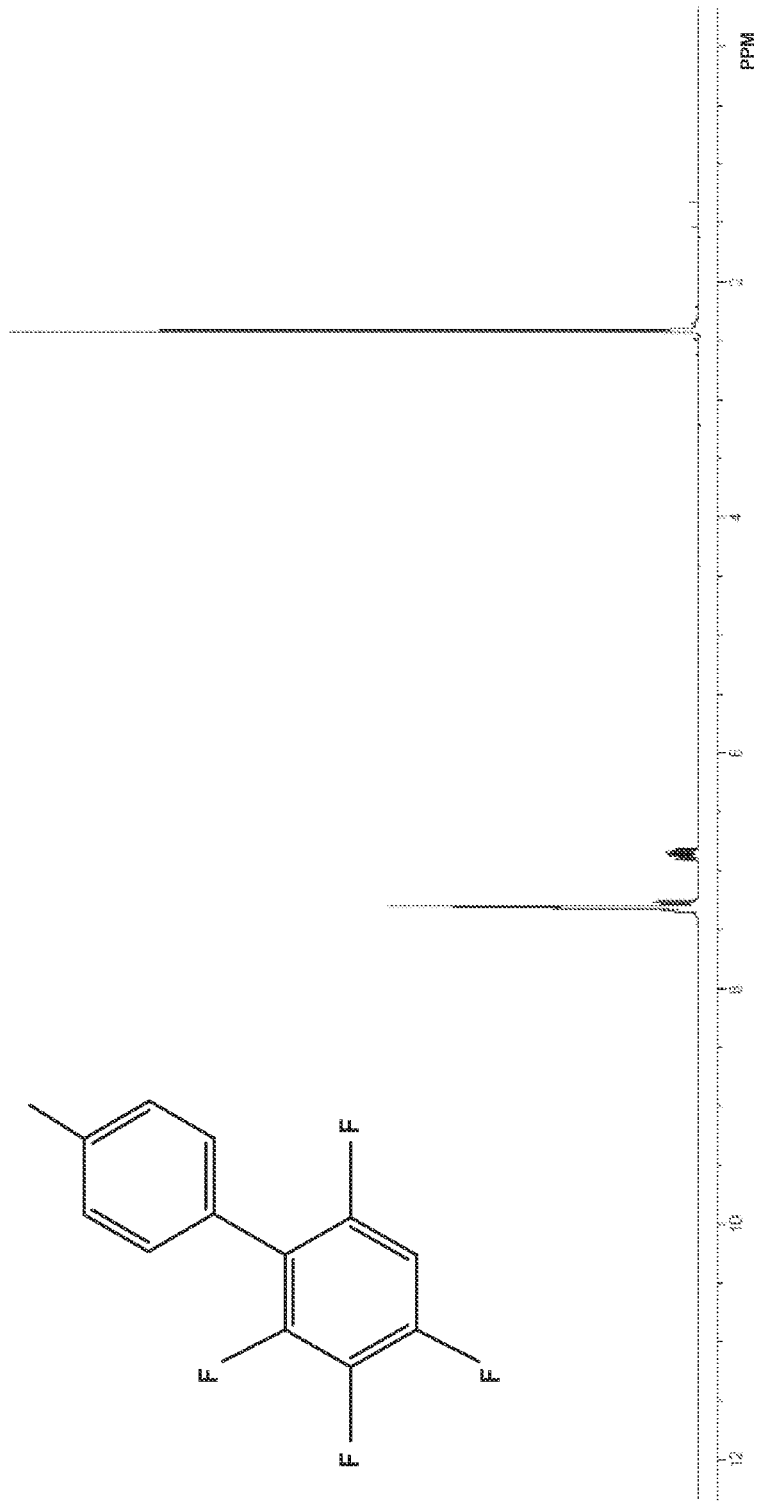
FIG. 36 depicts the molecular structure of 2,3,4,6-tetrafluoro-4'-methylbiphenyl and $^1$H NMR Spectrum of 2,3,4,6-tetrafluoro-4'-methylbiphenyl.
Figure 37:
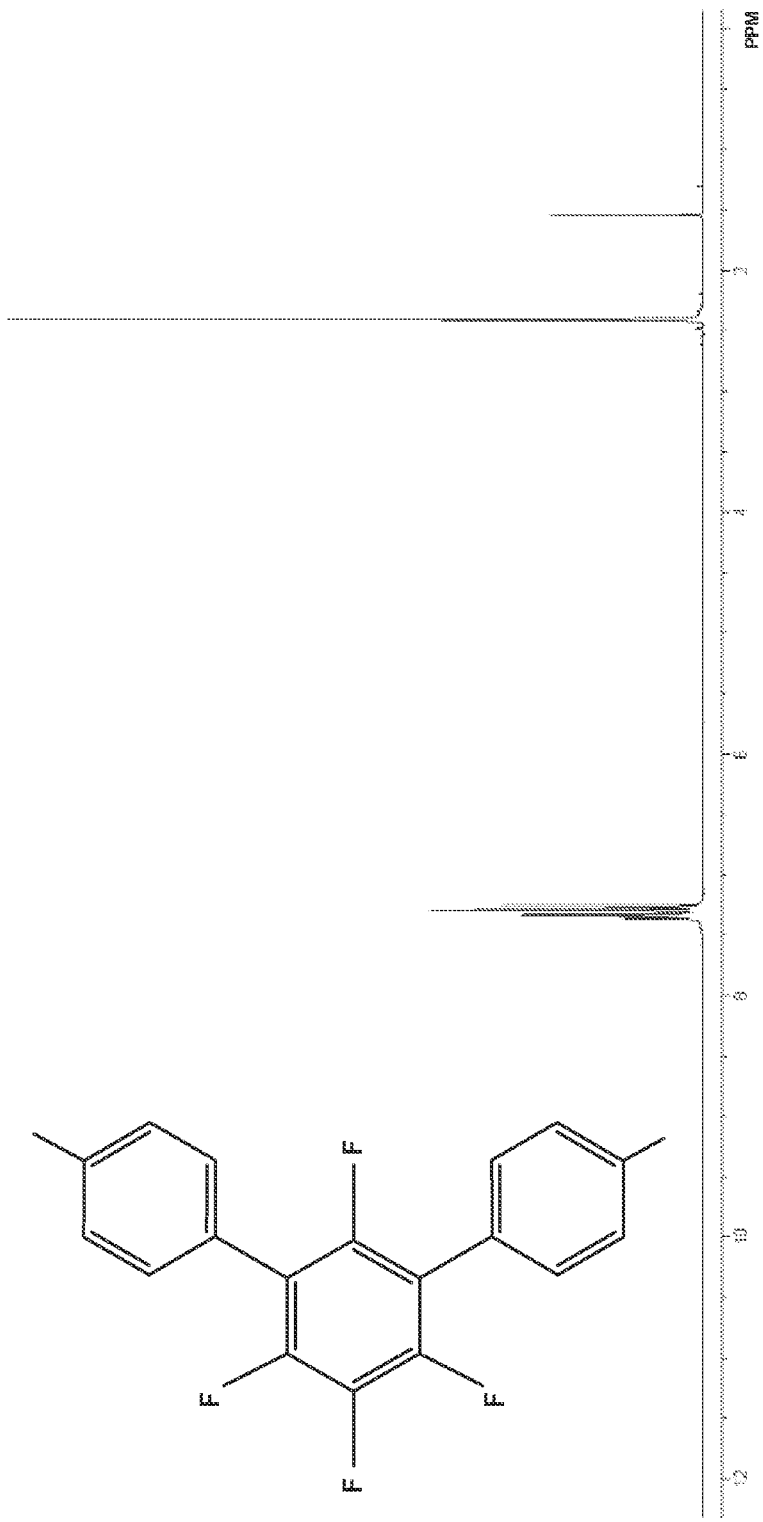
FIG. 37 depicts the molecular structure of 1,3-di-(p-tolyl)-2,4,5,6-tetrafluorobenzene and $^1$H NMR Spectrum of 1,3-di-(p-tolyl)-2,4,5,6-tetrafluorobenzene.

FIG. 36 shows the resultant molecules 2,3,4,6-tetrafluoro-4'-methylbiphenyl when the substrate is 1,3,4,5-tetrafluorobenzene and the haloarene is 4-iodotoluene, and its $^1$H NMR spectrum. FIG. 37 shows the resultant molecules 1,3-di-(p-tolyl)-2,4,5,6-tetrafluorobenzene when the substrate is 1,3,4,5-tetrafluorobenzene and the haloarene is 4-iodotoluene, and its $^1$H NMR spectrum. The synthesis of 2,3,4,6-tetrafluoro-4'-methylbiphenyl and 1,3-di-(p-tolyl)-2,4,5,6-tetrafluorobenzene is conducted using copper(I) iodide (19.1 mg, 0.1 mmol), 4-iodotoluene (218 mg, 1.0 mmol), 1,10-phenanthroline (18 mg, 0.1 mmol), 1,3,4,5-tetrafluorobenzene (300 mg, 2.0 mmol), K$_3$PO$_4$ (488 mg, 2.3 mmol), and DMF (0.6 mL). After column chromatography (hexanes) and preparative HPLC (hexanes) 175 mg (73%) of a white solid (2,3,4,6-tetrafluoro-4'-methylbiphenyl) and 55 mg (17%) of another white solid (1,3-di-(p-tolyl)-2,4,5,6-tetrafluorobenzene) are obtained. Data for 2,3,4,6-tetrafluoro-4'-methylbiphenyl: $^1$H NMR (300 MHz, $_{CDCl3}$) δ 2.42 (s, 3H), 6.80-6.92 (m, 1H), 7.27-7.36 (m, 4H). Data for 1,3-di-(p-tolyl)-2,4,5,6-tetrafluorobenzene: $^1$H NMR (300 MHz, $_{CDCl3}$) δ 2.41 (s, 6H), 7.28 (d, J=7.8 Hz, 4H), 7.35 (d, J=7.8 Hz, 4H).

Figure 38:
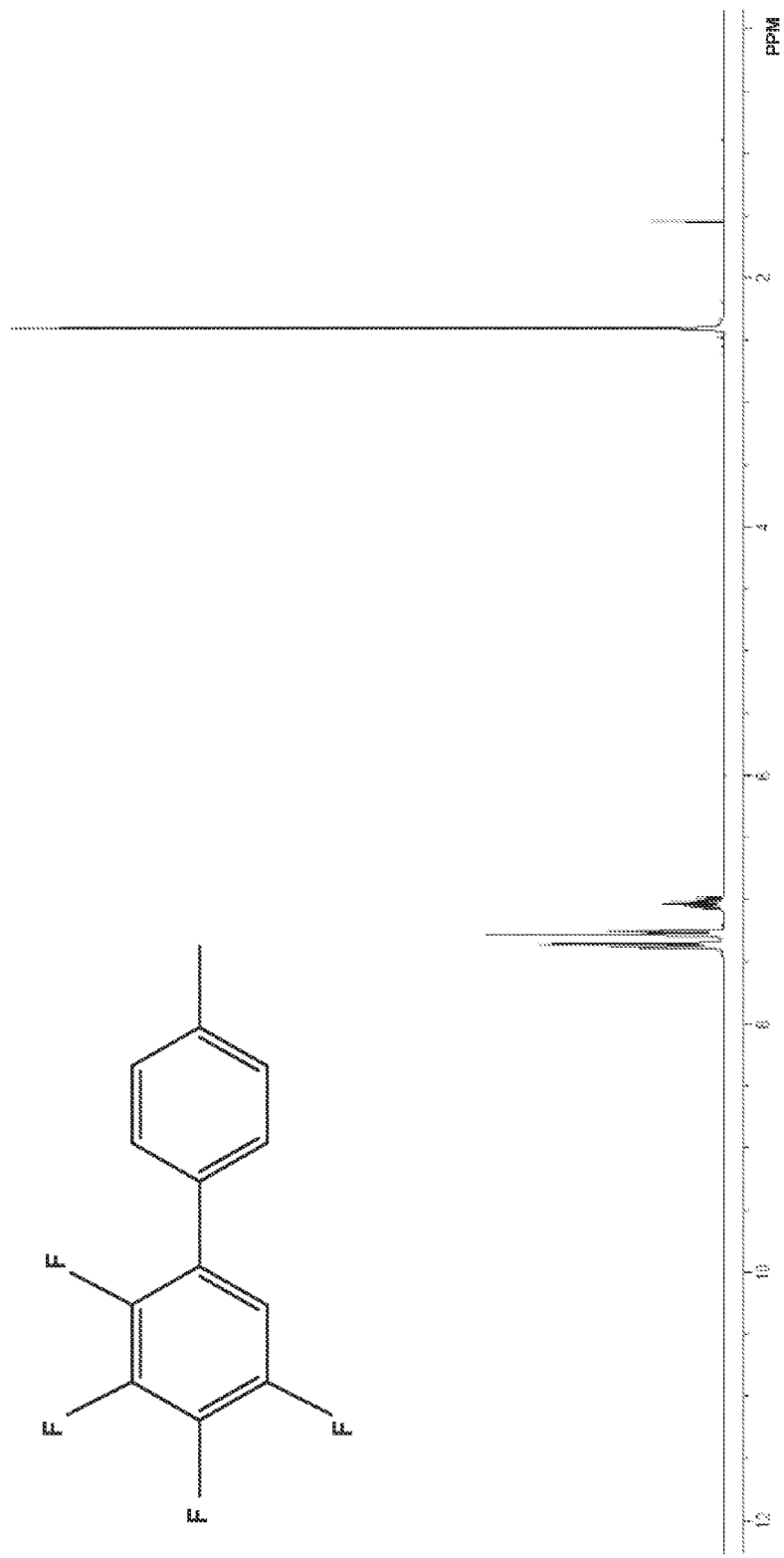
FIG. 38 depicts the molecular structure of 2,3,4,5-tetrafluoro-4'-methylbiphenyl and $^1$H NMR Spectrum of 2,3,4,5-tetrafluoro-4'-methylbiphenyl.

FIG. 38 shows the resultant molecule 2,3,4,5-tetrafluoro-4'-methylbiphenyl when the substrate is 1,2,3,4-tetrafluorobenzene and the haloarene is 4-iodotoluene, and its $^1$H NMR spectrum. The synthesis of 2,3,4,5-tetrafluoro-4'-methylbiphenyl is conducted using copper(I) iodide (19.1 mg, 0.1 mmol), 4-iodotoluene (218 mg, 1.0 mmol), 1,10-phenanthroline (18 mg, 0.1 mmol), 1,2,3,4-tetrafluorobenzene (300 mg, 2.0 mmol), $K_3PO_4$ (488 mg, 2.3 mmol), and DMF (0.6 mL), 140° C. After column chromatography (hexanes) and preparative HPLC (hexanes) 25 mg (10%) of a white solid is obtained. $^1$H NMR (300 MHz, $_{CDCl3}$) δ 2.41 (s, 3H), 6.98-7.09 (m, 1H), 7.24-7.30 (m, 2H), 7.34-7.40 (m, 2H).

FIG. 39 shows the resultant molecule 2,3,5,6-tetrafluoro-4-p-tolylpyridine when the substrate is 2,3,5,6-tetrafluoropyridine and the haloarene is 4-iodotoluene, and its $^1$H NMR spectrum. The synthesis of 2,3,5,6-tetrafluoro-4-p-tolylpyridine is conducted using copper(I) iodide (19.1 mg, 0.1 mmol), 4-iodotoluene (218 mg, 1.0 mmol), 1,10-phenanthroline (18 mg, 0.1 mmol), 2,3,5,6-tetrafluoropyridine (227 mg, 1.5 mmol), $K_3PO_4$ (424 mg, 2.0 mmol), and DMF (0.6 mL), 36 hours. After column chromatography (10% ethyl acetate in hexanes) 220 mg (91%) of a white solid is obtained. $^1$H NMR (300 MHz, $_{CDCl3}$) δ 2.44 (s, 3H), 7.35 (d, J=7.8 Hz, 2H), 7.40-7.46 (m, 2H).

Figure 40:
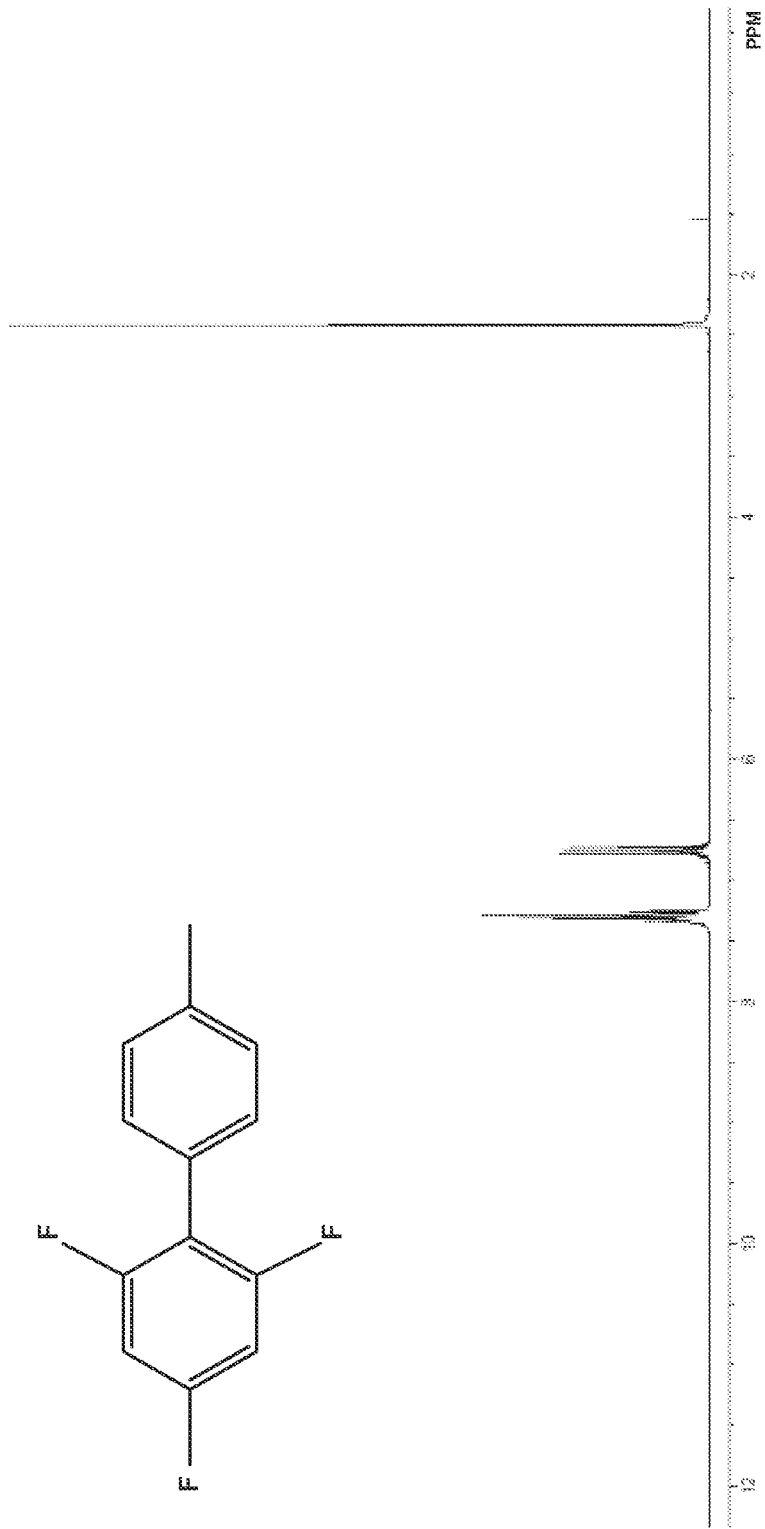
FIG. 40 depicts the molecular structure of 2,4,6-trifluoro-4'-methylbiphenyl and $^1$H NMR Spectrum of 2,4,6-trifluoro-4'-methylbiphenyl.

FIG. 40 shows the resultant molecule 2,4,6-trifluoro-4'-methylbiphenyl when the substrate is 1,3,5-trifluorobenzene and the haloarene is 4-iodotoluene, and its $^1$H NMR spectrum. The synthesis of 2,4,6-trifluoro-4'-methylbiphenyl is conducted using copper(I) iodide (19.1 mg, 0.1 mmol), 4-iodotoluene (218 mg, 1.0 mmol), 1,10-phenanthroline (18 mg, 0.1 mmol), 1,3,5-trifluorobenzene (396 mg, 3.0 mmol), $K_3PO_4$ (530 mg, 2.5 mmol), and DMF (0.6 mL). After column chromatography (hexanes) and preparative HPLC (hexanes) 90 mg (40%) of a white solid is obtained. $^1$H NMR (300 MHz, $_{CDCl3}$) δ 2.41 (s, 3H), 6.68-6.82 (m, 2H), 7.24-7.40 (m, 4H).

Figure 41:
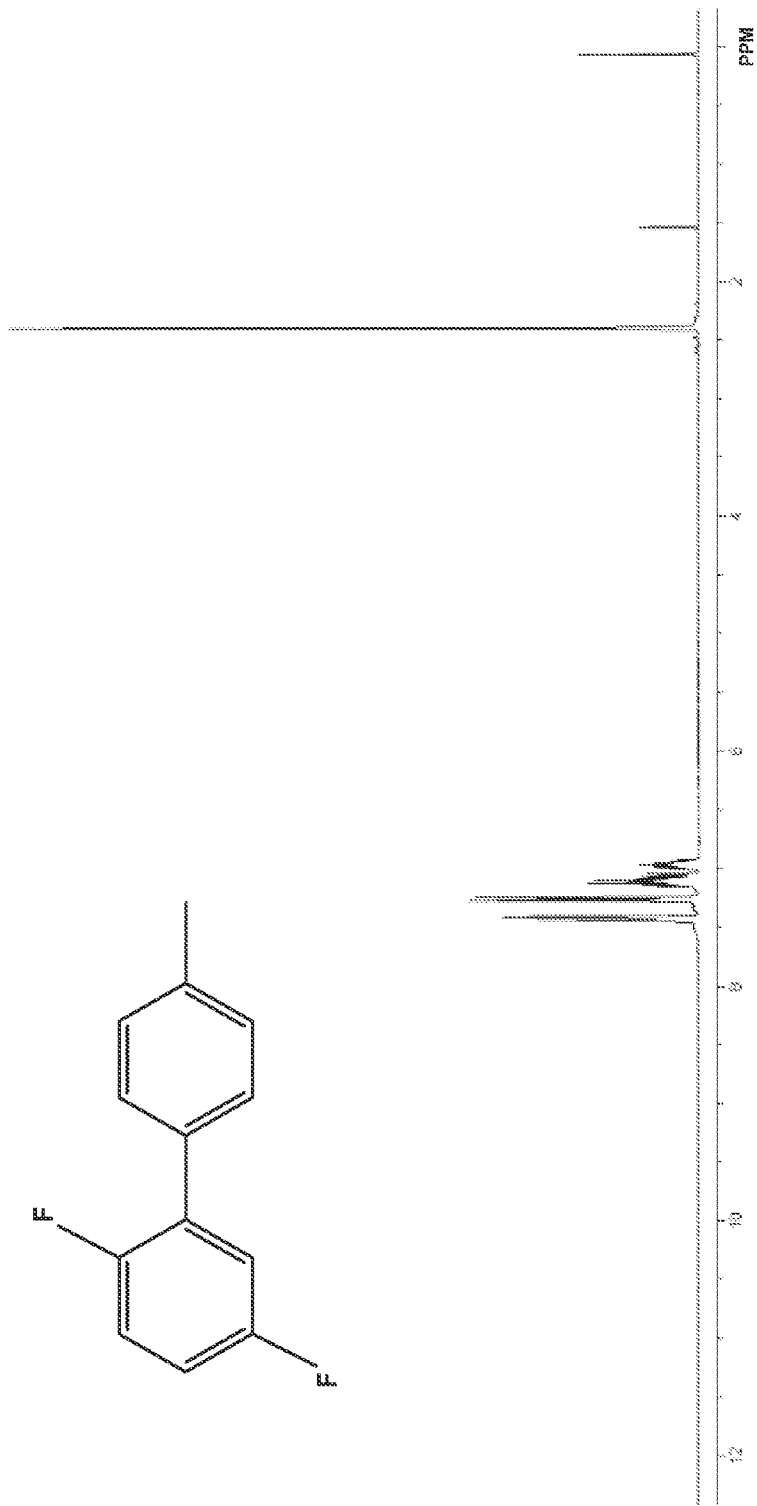
FIG. 41 depicts the molecular structure of 2,5-difluoro-4'-methylbiphenyl and $^1$H NMR Spectrum of 2,5-difluoro-4'-methylbiphenyl.

FIG. 41 shows the resultant molecule 2,5-difluoro-4'-methylbiphenyl when the substrate is 1,4-difluorobenzene and the haloarene is 4-iodotoluene, and its $^1$H NMR spectrum. The synthesis of 2,5-difluoro-4'-methylbiphenyl is conducted using copper(I) iodide (19.1 mg, 0.1 mmol), 4-iodotoluene (218 mg, 1.0 mmol), 1,10-phenanthroline (18 mg, 0.1 mmol), 1,4-difluorobenzene (342 mg, 3.0 mmol), t-BuOLi (160 mg, 2.0 mmol), and DMF (1.0 mL), 15 hours. After column chromatography (hexanes) and preparative HPLC (hexanes) 30 mg (15%) of a colorless oil is obtained. $^1$H NMR (300 MHz, $_{CDCl3}$) δ 2.40 (s, 3H), 6.91-7.01 (m, 1H), 7.04-7.16 (m, 2H), 7.26 (d, J=7.8 Hz, 2H), 7.40-7.46 (m, 2H).

Figure 42:
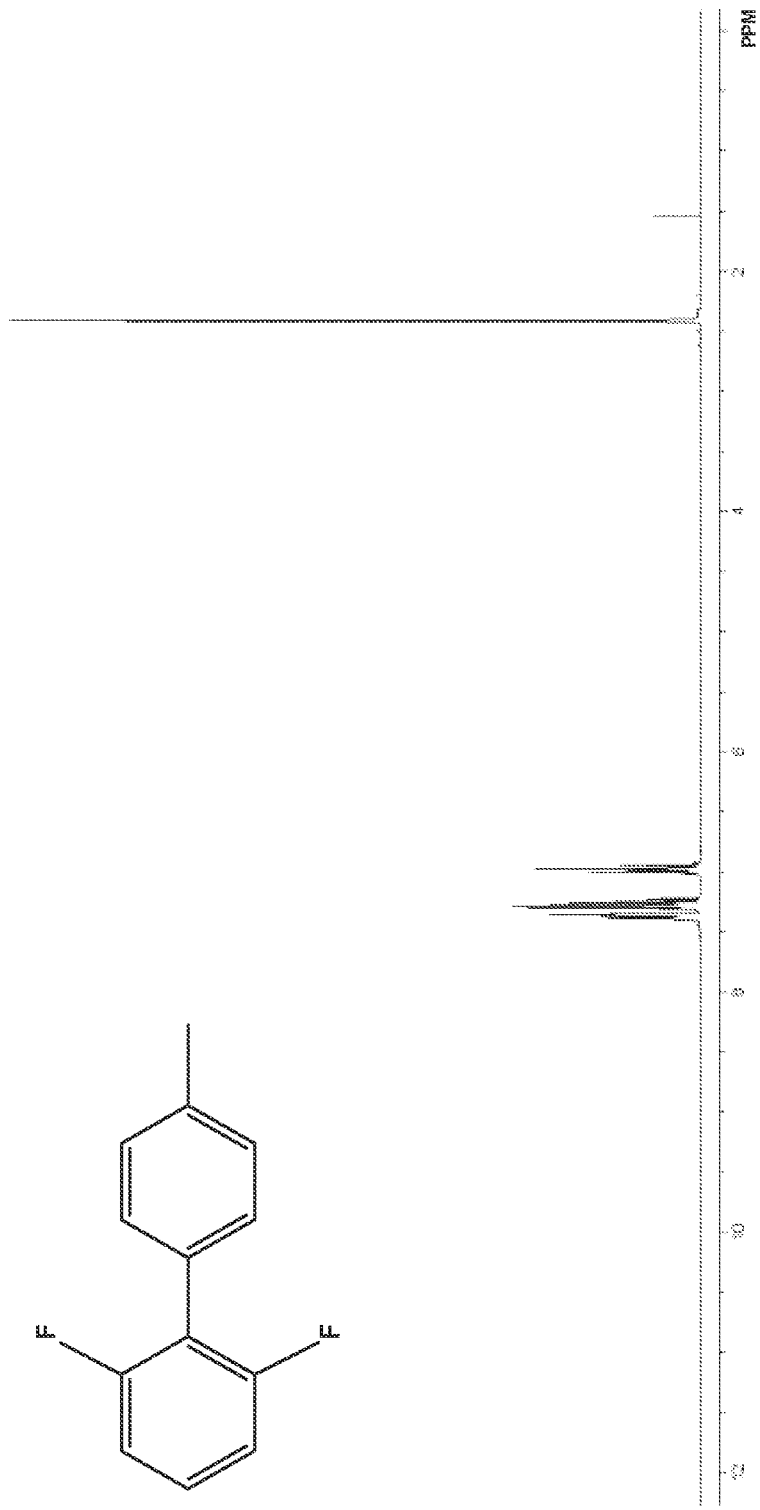
FIG. 42 depicts the molecular structure of 2,6-difluoro-4'-methylbiphenyl and $^1$H NMR Spectrum of 2,6-difluoro-4'-methylbiphenyl.

FIG. 42 shows the resultant molecule 2,6-difluoro-4'-methylbiphenyl when the substrate is 1,3-difluorobenzene and the haloarene is 4-iodotoluene, and its $^1$H NMR spectrum. The synthesis of 2,6-difluoro-4'-methylbiphenyl is conducted using copper(I) iodide (19.1 mg, 0.1 mmol), 4-iodotoluene (218 mg, 1.0 mmol), 1,10-phenanthroline (18 mg, 0.1 μmol), 1,3-difluorobenzene (342 mg, 3.0 mmol), t-BuOLi (160 mg, 2.0 mmol), and DMF (1.0 mL), 15 hours. After column chromatography (hexanes) and preparative HPLC (hexanes) 165 mg (81%) of a white solid is obtained. $^1$H NMR (300 MHz, $_{CDCl3}$) δ 2.41 (s, 3H), 6.91-7.04 (m, 2H), 7.20-7.32 (m, 3H), 7.34-7.40 (m, 2H).

Figure 43:
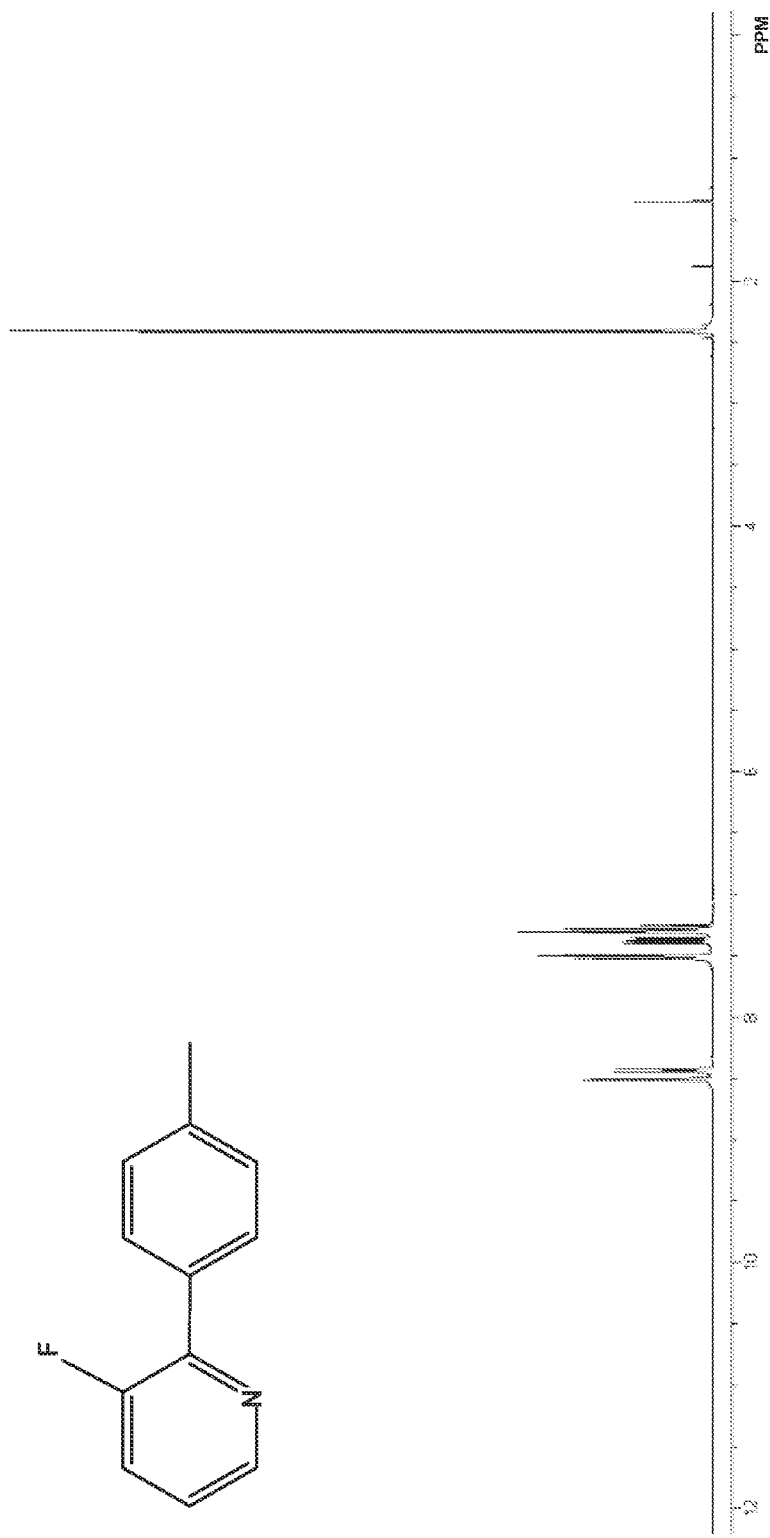
FIG. 43 depicts the molecular structure of 3-fluoro-2-p-tolylpyridine and $^1$H NMR Spectrum of 3-fluoro-2-p-tolylpyridine.

FIG. 43 shows the resultant molecule 3-fluoro-2-p-tolylpyridine when the substrate is 3-fluoropyridine and the haloarene is 4-iodotoluene, and its $^1$H NMR spectrum. The synthesis of 3-fluoro-2-p-tolylpyridine is conducted using copper(I) iodide (19.1 mg, 0.1 mmol), 4-iodotoluene (218 mg, 1.0 mmol), 1,10-phenanthroline (18 mg, 0.1 mmol), 3-fluoropyridine (291 mg, 3.0 mmol), t-BuOLi (160 mg, 2.0 mmol), and DMF (1.0 mL), 140° C., 12 hours. After column chromatography (40% ethyl acetate in hexanes) and preparative HPLC (40% ethyl acetate in hexanes) 70 mg (40%) of a light tan compound is obtained. $^1$H NMR (300 MHz, $_{CDCl3}$) δ 2.41 (s, 3H), 7.29 (d, J=8.0 Hz, 2H), 7.38 (dd, J=6.6 Hz, 5.0 Hz, 1H), 7.38 (dd, J=8.0 Hz, 1.5 Hz, 2H), 8.43 (d, J=5.0 Hz, 1H), 8.51 (d, J=2.8 Hz, 1H). $^{13}$C NMR (75 MHz, $_{CDCl3}$) δ 21.8, 124.6, 129.2, 130.1, 130.5, 136.4 (d), 139.3, 139.6, 139.9, 146.5, 155.5, 159.0. FT-IR (neat, cm$^{-1}$) u 1615, 1557, 1456.

General Considerations

Reactions were performed in 1-dram vials with PTFE/Liner caps. Flash chromatography was performed on 60 Å silica gel (Sorbent Technologies). Purification by preparative HPLC was performed on a Shimadzu Prominence LC (LC-20AB) equipped with a SPD-20A UV-Vis detector and a Varian Dynamax (250 mm×21.4 mm) column. GCMS analyses were performed on a Shimadzu GCMS-QP5000 chromatograph equipped with a Restek column (Rtx-XLB, 30 m×0.25 mm I.D.). The $^1$H, $^{19}$F and $^{13}$C NMR were recorded on a GE QE-300 spectrometer using residual solvent peak as a reference. Hexafluorobenzene (1% in $C_6D_6$, δ=−164.9) was employed as an external standard in $^{19}$F NMR spectra. Elemental analyses were performed by Atlantic Microlab Inc. of Norcross, Ga. IR spectra were obtained using ThermoNicolet Avatar 370 FT-IR instrument. Analytical thin layer chromatography was performed on silica gel IB-F (Baker-flex) by J. T. Baker.

Materials

The following starting materials were obtained from commercial sources and were used without further purification: 4-iodotoluene, 4-iodobenzotrifluoride, 4-bromotoluene, 4-bromobenzotrifluoride, 1,4-difluorobenzene, 1,2,4,5-tetrafluorobenzene, pentafluorobenzene, 4-bromobiphenyl, and 1,3-dibromobenzene were bought from Oakwood. 1,10-Phenanthroline, copper(I) iodide, DMF, 2,3-benzofuran, 1-iodonapthalene, 4,5-dimethylthiazole, 1-phenylpyrazole, benzothiophene, 2,3,5,6-tetrafluorotoluene, pyrimidine, 2-chloropyridine, 4-bromobenzophenone, 1,4-diiodobenzene, 2,4-difluorobenzophenone, and alpha-bromostyrene were obtained from Acros. Potassium phosphate, m-xylene, 2-bromopyridine, 1,3-dinitrobenzene, bromomethylenecyclohexane, 2-iodotoluene, 3-iodotoluene, pentachlorobenzene, 1,3-dichlorobenzene, 3-nitrobenzonitrile, pyridazine, pyridine N-oxide, 2-picoline N-oxide, anhydrous DMPU, n-butyllithium (2.0 M solution in cyclohexane), and 2-iodophenol were purchased from Aldrich. Iodobenzene, 1-methyl-1,2,4-triazole, 3-chlorothiophene, benzothiazole, caffeine, 2-chlorothiophene, thiophene, 2-chloroquinoline, 2,3,5,6-tetrafluoroanisole, and 3-ethyl-3-pentanol were from Alfa Aesar. Lithium t-butoxide was bought from Strem. 2-Iodopyridine and 4-bromo-1-butene were purchased from TCI. t-Butanol (OD) was from Cambridge Isotope Laboratories, Inc. 1,2,4,5-Tetrachlorobenzene was purchased from Eastman Organic Chemicals. 1-(But-3-enyloxy)-2-iodobenzene was prepared from o-iodophenol.[1] 2-Phenylpyridine oxide was synthesized from 2-phenylpyridine.[2]

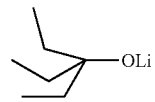

Lithium 3-ethyl-3-pentoxide

A flamed-dried 200 mL Schlenk flask was charged with a magnetic stirrer and phenanthroline indicator (5 mg). The flask was evacuated and backfilled three times by argon. Anhydrous pentane (20 mL) and a 2M solution of n-BuLi in cyclohexane (50 mL) were added at 0° C. to form a reddish-brown solution. 3-Ethyl-3-pentanol (predried by distillation from Mg turnings) was added dropwise with stirring until the solution became colorless. The reaction mixture was warmed up to room temperature following by solvent removal under vacuum affording a yellow solid. The crude product was dissolved in pentane (10 mL), filtered through Celite® under argon atmosphere. Celite® was washed by additional pentane (10 mL). The filtrate was kept at −20° C. for a week affording 9.5 g (78%) of a colorless crystalline product. This compound is known.[3]

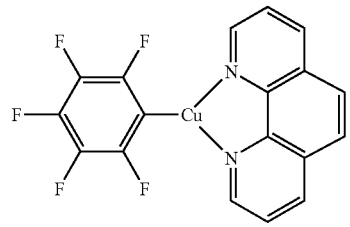

Pentafluorophenylcopper-phenanthroline Complex 1

Figure 44:
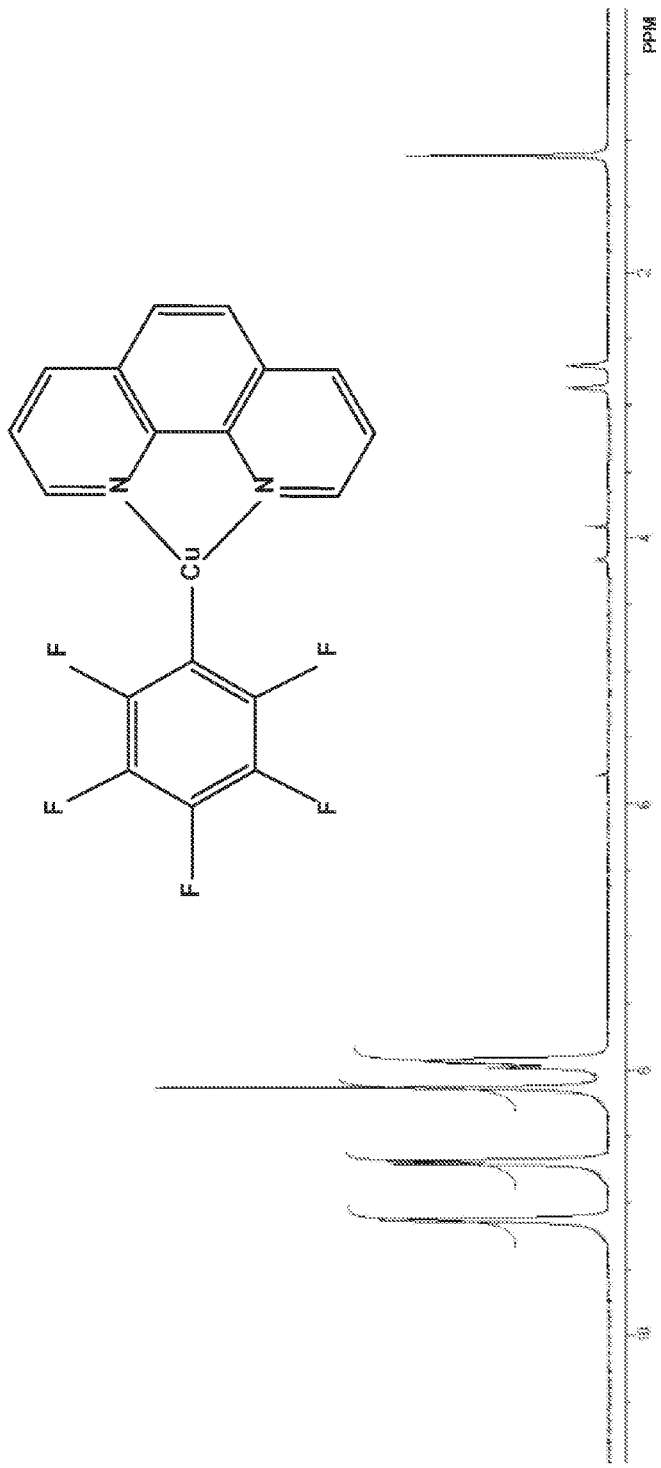
FIG. 44 depicts the molecule structure of pentafluorophenylcopper-phenanthroline complex 1 and its $^1$H NMR spectrum.

To a mixture of copper (I) chloride (1.99 g, 20 mmol) and t-BuOLi (1.50 g, 18.8 mmol) in a 50 mL Schlenk flask under Ar atmosphere was added dry THF (25 mL). The pale yellow reaction mixture was vigorously stirred at 40° C. for 4 hours followed by addition of pentafluorobenzene (5.04 g, 30 mmol) in one portion and stirring for an additional hour. The pale yellow solution was evaporated to dryness under reduced pressure and the residue was dissolved in dry toluene (30 mL) followed by filtration through a pad of Celite® under argon atmosphere. The filtrate was evaporated to dryness under reduced pressure at 45° C. and the residue was dissolved in dry $CH_2Cl_2$ (50 mL). To this mixture was added a solution of phenanthroline (3.60 g, 20 mmol) in $CH_2Cl_2$ (20 mL). An immediate precipitate of an orange solid was observed. The mixture was stirred for 5 minutes followed by filtration under argon atmosphere. An orange solid (4.0 g, 52% yield) was obtained. It can be recrystallized from a mixture (½) of DCM and DMPU at −30° C. affording dark orange needles. The connectivity was verified by X-ray crystallography as shown in FIG. 1; however, it was not possible to fully refine the structure due to twinning of the crystals. The molecule structure of pentafluorophenylcopper-phenanthroline complex 1 and its $^1H$ NMR spectrum are shown in FIG. 44. $^1H$ NMR (300 MHz, DMF-d7) δ 7.94 (dd, J=8.5 Hz, 4.2 Hz, 2H), 8.14 (s, 2H), 8.70 (d, J=8.5 Hz, 2H), 9.13 (d, J=2.2 Hz, 2H). $^{19}F$ NMR (282 MHz, DMF-d7) δ−166.2-165.9 (m, 2F), −165.2 (t, JF=20 Hz, 1F), −112.9-112.4 (m, 2F). $^{13}C$ NMR (75 MHz, DMFd7) δ 125.0, 127.5, 129.6, 134.2-138.3 (m), 137.7, 136.0-139.8 (m), 145.5, 148.0-151.6 (m), 150.5. FT-IR (neat, cm-1) ν 1511, 1486, 1432, 1423, 1416, 1035, 934, 839, 770, 725. The complex is sensitive to temperature and atmospheric moisture and satisfactory elemental analyses could not be obtained.

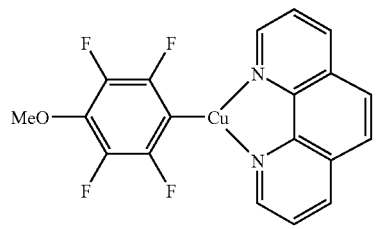

4-methoxytetrafluorophenylcopper-phenanthroline Complex 2

Figure 45:
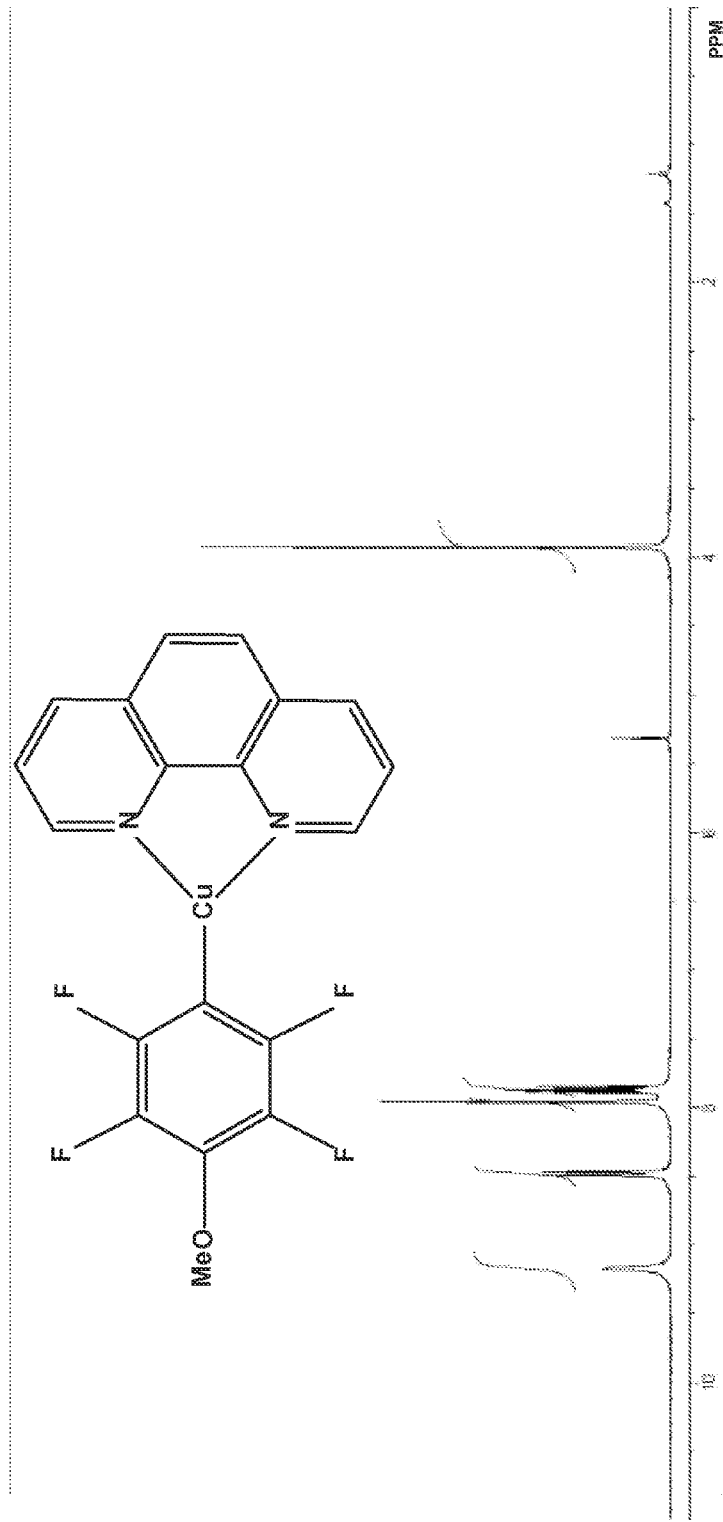
FIG. 45 depicts the molecule structure of 4-methoxytetrafluorophenylcopper-phenanthroline complex 2 and its $^1$H NMR spectrum.

To a mixture of copper (I) chloride (1.0 g, 10 mmol) and t-BuOLi (0.76 g, 9.5 mmol) in a 50 mL Schlenk flask under Ar atmosphere was added dry THF (12 mL). The pale yellow reaction mixture was vigorously stirred at 40° C. for 4 hours followed by addition of 2,3,5,6-tetrafluoroanisole (2.0 g, 11.1 mmol) in one portion and stirring overnight at 40° C. The pale yellow suspension was evaporated to dryness under reduced pressure and the residue was dissolved in dry toluene (20 mL) followed by filtration through a pad of Celite® under argon atmosphere. The filtrate was evaporated to dryness under reduced pressure at 45° C. and the residue was dissolved in dry $CH_2Cl_2$ (5 mL). To this mixture was added a solution of phenanthroline (0.58 g, 3.2 mmol) in $CH_2Cl_2$ (5 mL). The rust-colored solution was stirred for 5 minutes at room temperature and then kept at −30° C. for 2 days. Rust-colored crystals were collected and washed by a small amount of $CH_2Cl_2$ affording 0.52 g (38%) of the product. The structure was verified by X-ray crystallography. The molecule structure of 4-methoxytetrafluorophenylcopper-phenanthroline complex 2 and its $^1H$ NMR spectrum are shown in FIG. 45. $^1H$ NMR (300 MHz, $CD_2Cl_2$) δ 3.93 (s, 3H), 7.87 (dd, J=8.2 Hz, 4.5 Hz, 2H), 7.96 (s, 2H), 8.48 (dd, J=8.2 Hz, 1 Hz, 2H), 9.17 (s, 2H). $^{19}F$ NMR (282 MHz, $CD_2Cl_2$) δ−161.0-160.4 (m, 2F), −113.8-−113.0 (m, 2F). FT-IR (neat, cm-1) ν 1476, 1423, 1075, 949, 929, 841, 757, 727. It was impossible to obtain a good quality $^{13}C$ spectrum of 2 due to low solubility in common NMR solvents coupled with instability in solution. The complex is sensitive to temperature and atmospheric moisture and satisfactory elemental analyses could not be obtained.

General Procedure for Coupling Reactions

Outside the glovebox a 1-dram vial equipped with a magnetic stir bar was charged with haloarene, phenanthroline (10 mol %), substrate, and solvent (DMF or a 1/1 mixture of DMF and xylenes). If anhydrous DMPU was used, the reaction was set up inside the glovebox. The vial was flushed with argon, capped and placed inside a glovebox. To this mixture was added CuI (10 mol %) and base (1.7-2.5 equiv). The sealed vial was then taken out of the glovebox, stirred at room temperature for 5 min and placed in a preheated oil bath. After the completion of the reaction, the mixture was cooled to room temperature and diluted with ethyl acetate (50 mL). The resulting solution was washed with brine (15 mL), dried over anhydrous $MgSO_4$, and concentrated under vacuum to a volume of about 1 mL. The mixture containing the product was subjected to column chromatography on silica gel (hexanes followed by appropriate solvent to elute the products). After concentrating the fractions containing the product, the residue was dried under reduced pressure to yield pure product.

4,5-Dimethyl-2-p-tolylthiazole and 4,5-dimethyl-2-m-tolylthiazole (Scheme 3)

Figure 46:
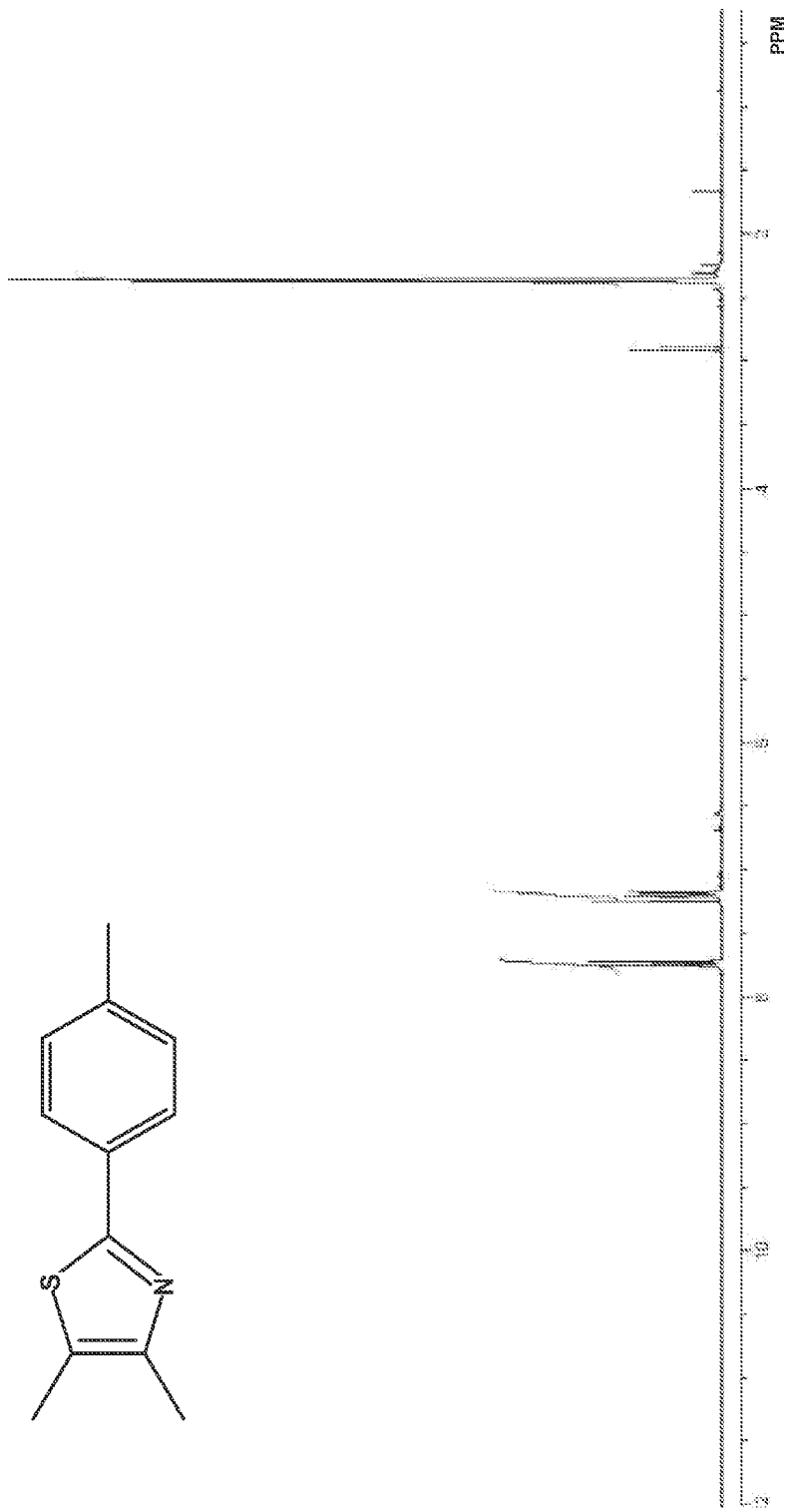
FIG. 46 depicts the molecule structure of 4,5-dimethyl-2-p-tolylthiazole and its $^1$H NMR spectrum.
Figure 47:
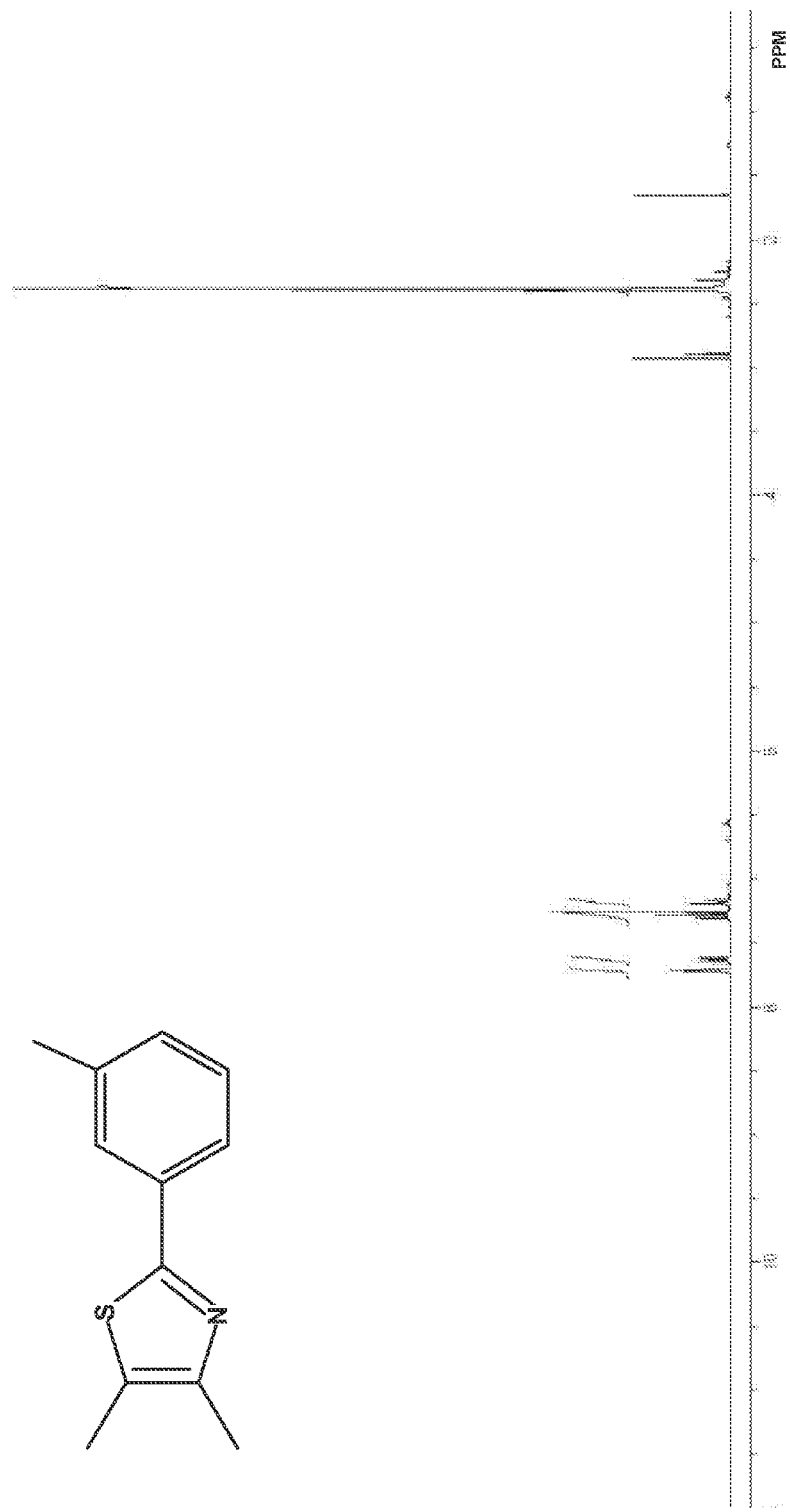
FIG. 47 depicts the molecule structure of 4,5-dimethyl-2-m-tolylthiazole and its $^1$H NMR spectrum.

Copper(I) iodide (19 mg, 0.1 mmol), 4,5-dimethylthiazole (113 mg, 1.0 mmol), p-bromotoluene (513 mg, 3.0 mmol), t-BuOK (224 mg, 2.0 mmol), and DMF (1.0 mL) at 140° C. in 10 minute. After column chromatography (hexanes, then 10% ethyl acetate in hexanes) and preparative HPLC (5% ethyl acetate in hexanes) 17 mg (8.4%) of a yellow solid (4,5-dimethyl-2-ptolylthiazole) and 15 mg (7.4%) of a colorless oil (4,5-dimethyl-2-m-tolylthiazole) were obtained. These compounds are known.[4] The molecule structure of 4,5-Dimethyl-2-p-tolylthiazole and the $^1H$ NMR spectrum are shown in FIG. 46. $^1H$ NMR (300 MHz, $CDCl_3$) δ 2.37 (s, 9H), 7.20 (d, J=8.0 Hz, 2H), 7.74 (d, J=8.0 Hz, 2H). The molecule structure of 4,5-Dimethyl-2-m-tolylthiazole and the ₁H NMR spectrum are shown in FIG. 47. ¹H NMR (300 MHz, CDCl₃) δ 2.39 (s, 9H), 7.18 (d, J=7.5 Hz, 1H), 7.25-7.32 (m, 1H), 7.63 (d, J=7.5 Hz, 1H), 7.71 (s, 1H).

2-(Pyridin-2-yl)benzo[d]thiazole (Entry 1, Table IV)

Figure 48:
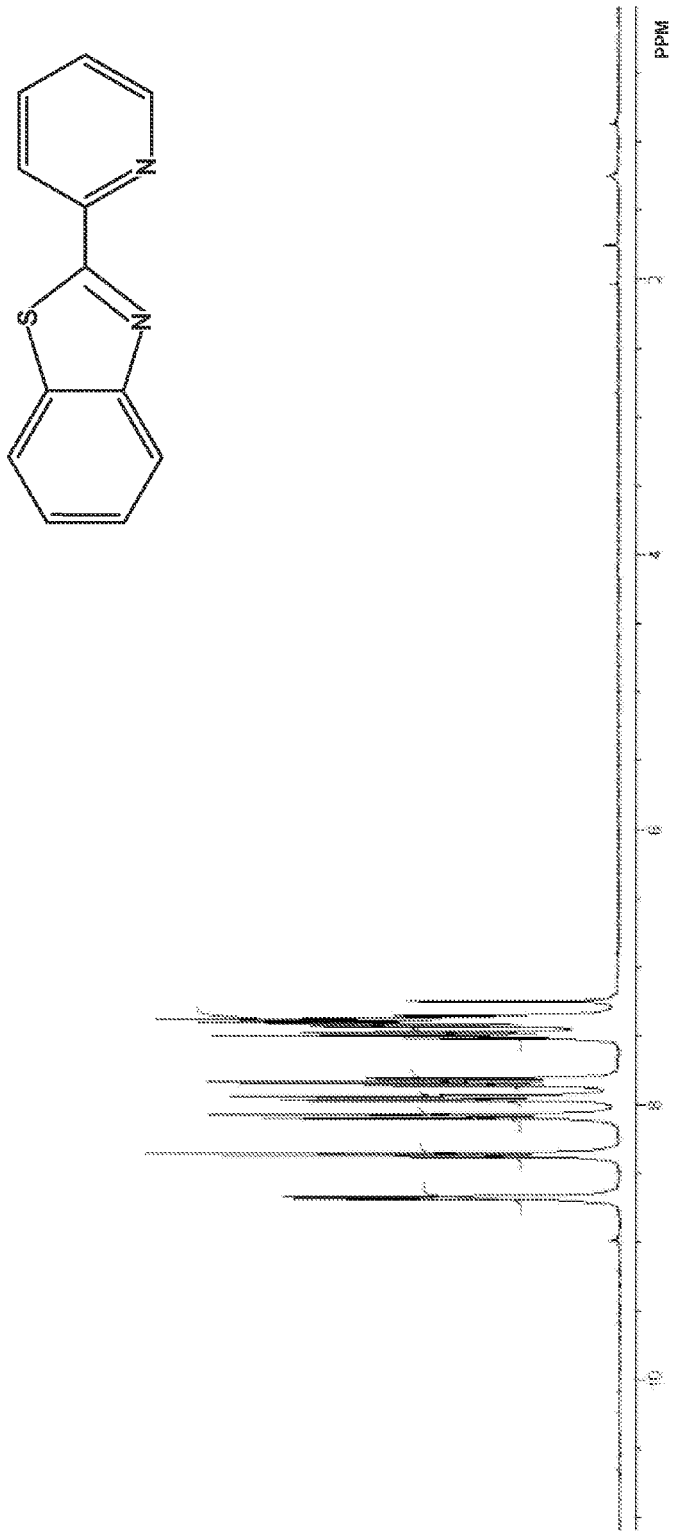
FIG. 48 depicts the molecule structure of 2-(pyridin-2-yl)benzo[d]thiazole and its $^1$H NMR spectrum.

Copper(I) iodide (19 mg, 0.1 mmol), 2-bromopyridine (316 mg, 2.0 mmol), 1,10-phenanthroline (18 mg, 0.1 mmol), benzothiazole (135 mg, 1.0 mmol), K₃PO₄ (424 mg, 2.0 mmol), and DMF (0.6 mL), 120° C., 5 hours. After column chromatography (hexanes, then 20% ethyl acetate in hexanes) 190 mg (89%) of a colorless solid was obtained. $R_f$=0.36 (1/4 ethyl acetate/hexanes). This compound is known.[5] The molecule structure of 2-(pyridin-2-yl)benzo[d]thiazole and its ¹H NMR spectrum are shown in FIG. 48. ¹H NMR (300 MHz, CDCl₃) δ 7.32-7.45 (m, 2H), 7.50 (t, J=7.7 Hz, 1H), 7.84 (dt, J=7.7 Hz, 1.6 Hz, 1H), 7.95 (d, J=7.7 Hz, 1H), 8.08 (d, J=7.7 Hz, 1H), 8.36 (d, J=7.7 Hz, 1H), 8.68 (d, J=4.4 Hz, 1H).

1,3,7-Trimethyl-8-phenyl-1H-purine-2,6(3H,7H)-dione (Entry 2, Table IV)

Figure 49:
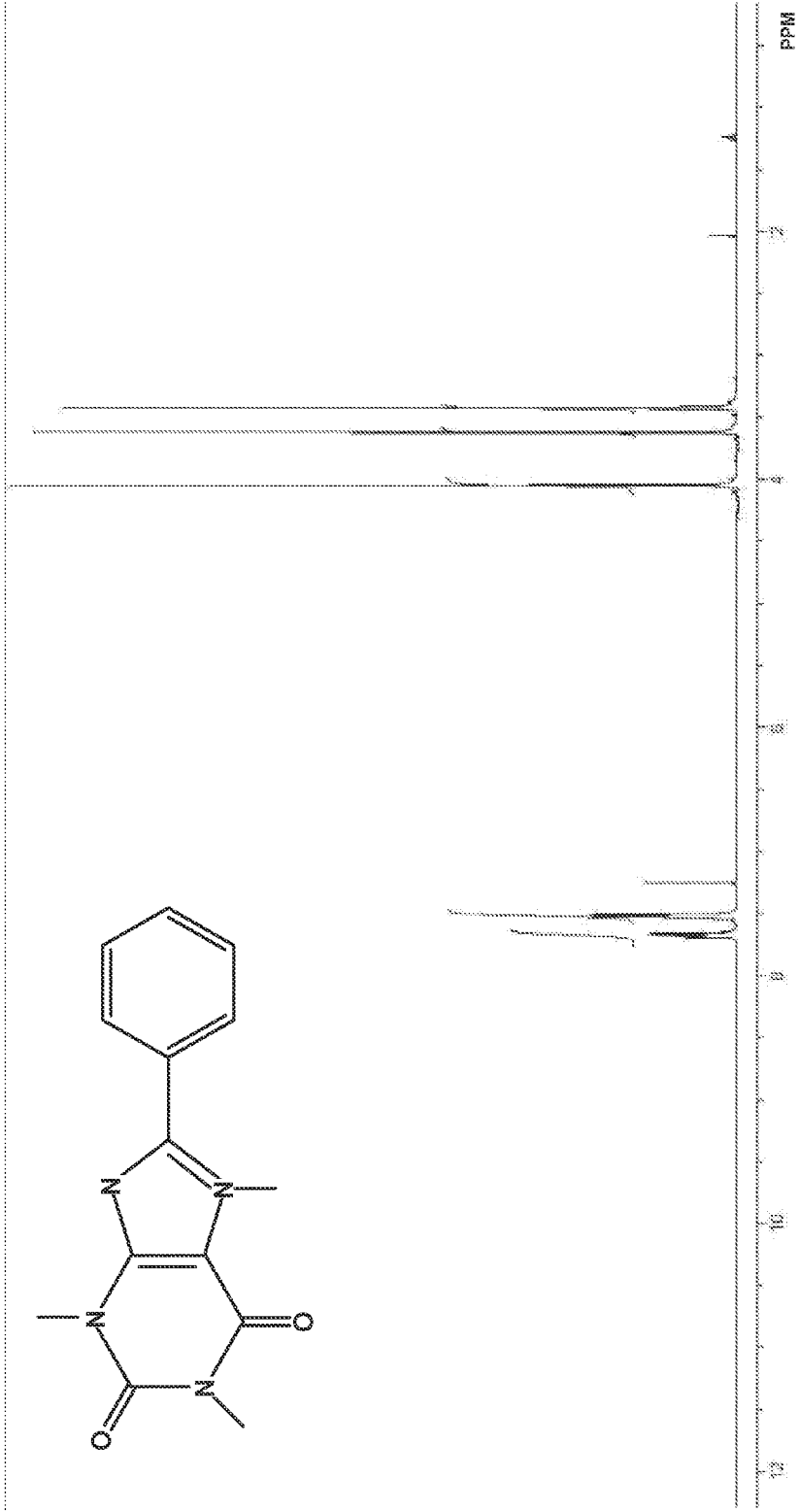
FIG. 49 depicts the molecule structure of 1,3,7-trimethyl-8-phenyl-1H-purine-2,6(3H, 7H)-dione and its $^1$H NMR spectrum.

Copper(I) iodide (19 mg, 0.1 mmol), caffeine (194 mg, 1.0 mmol), iodobenzene (408 mg, 2.0 mmol), 1,10-phenanthroline (18 mg, 0.1 mmol), t-BuOLi (160 mg, 2.0 mmol), and DMF (0.5 mL), 110° C., 5 hours. After column chromatography (hexanes, then 20% hexanes in ethyl acetate) 230 mg (85%) of a colorless solid was obtained. $R_f$=0.25 (1/1 ethyl acetate/hexanes). This compound is known.[6] The molecule structure of 1,3,7-Trimethyl-8-phenyl-1H-purine-2,6(3H,7H)-dione and its ¹H NMR spectrum are shown in FIG. 49. ¹H NMR (300 MHz, CDCl₃) δ 3.43 (s, 3H), 3.62 (s, 3H), 4.05 (s, 3H), 7.50-7.60 (m, 3H), 7.65-7.72 (m, 2H).

1-Methyl-5-phenyl-1H-1,2,4-triazole (Entry 3, Table IV)

Figure 50:
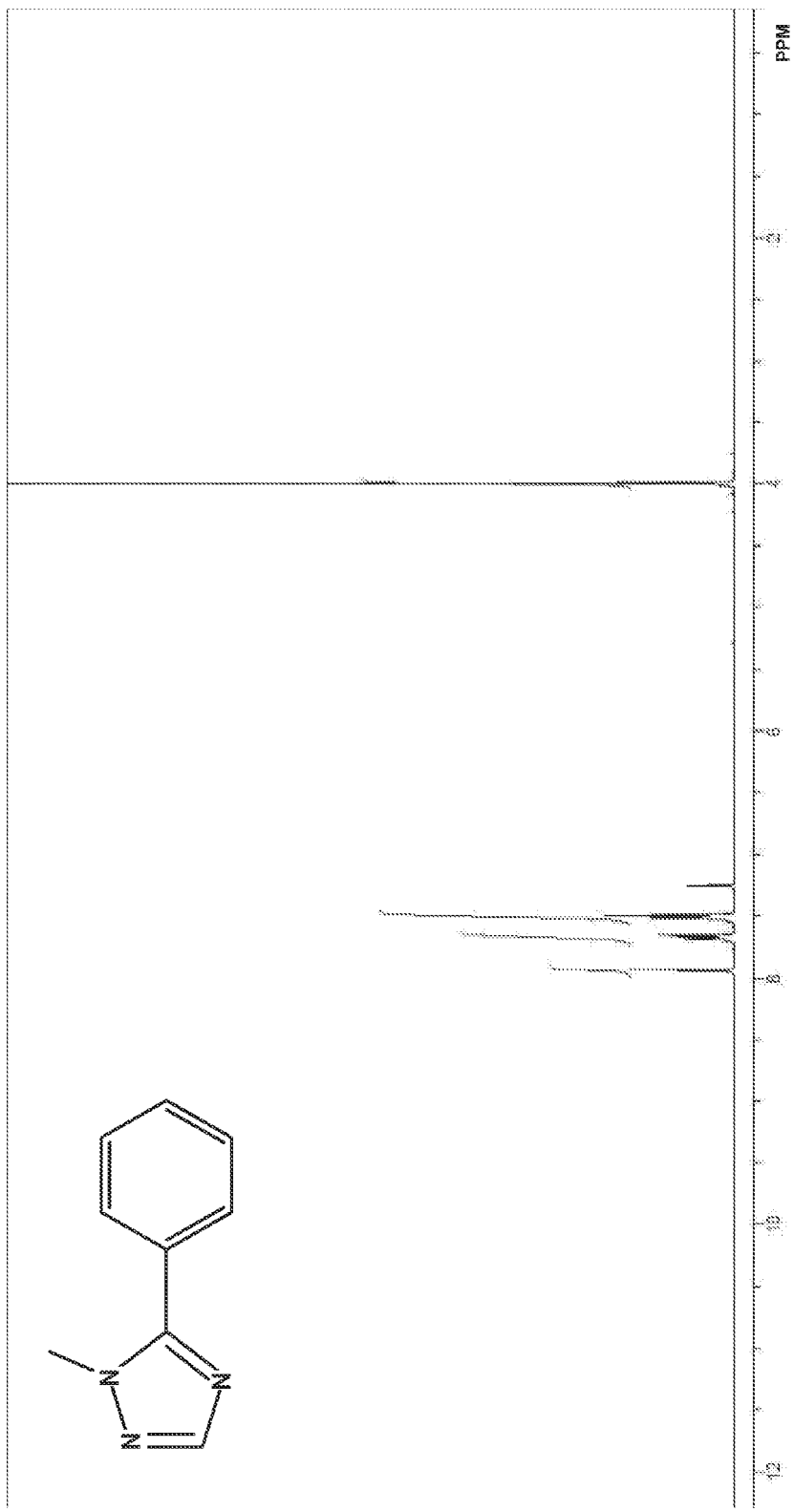
FIG. 50 depicts the molecule structure of 1-methyl-5-phenyl-1H-1,2,4-triazole and its $^1$H NMR spectrum.

Copper(I) iodide (19 mg, 0.1 mmol), iodobenzene (408 mg, 2.0 mmol), 1,10-phenanthroline (18 mg, 0.1 mmol), 1-methyl-1,2,4-triazole (83 mg, 1.0 mmol), t-BuOLi (160 mg, 1.7 mmol), and DMF (0.6 mL), 100° C., 5 hours. After column chromatography (hexanes, then 20% hexanes in ethyl acetate) 140 mg (88%) of a light tan oil was obtained. $R_f$=0.23 (1/1 ethyl acetate/hexanes). This compound is known.[7] The molecule structure of 1-Methyl-5-phenyl-1H-1,2,4-triazole and its ¹H NMR spectrum are shown in FIG. 50. ¹H NMR (300 MHz, CDCl₃) δ 4.00 (s, 3H), 7.48-7.54 (m, 3H), 7.64-7.70 (m, 2H), 7.94 (s, 1H).

1-Methyl-2-phenylimidazole (Entry 4, Table IV)

Figure 51:
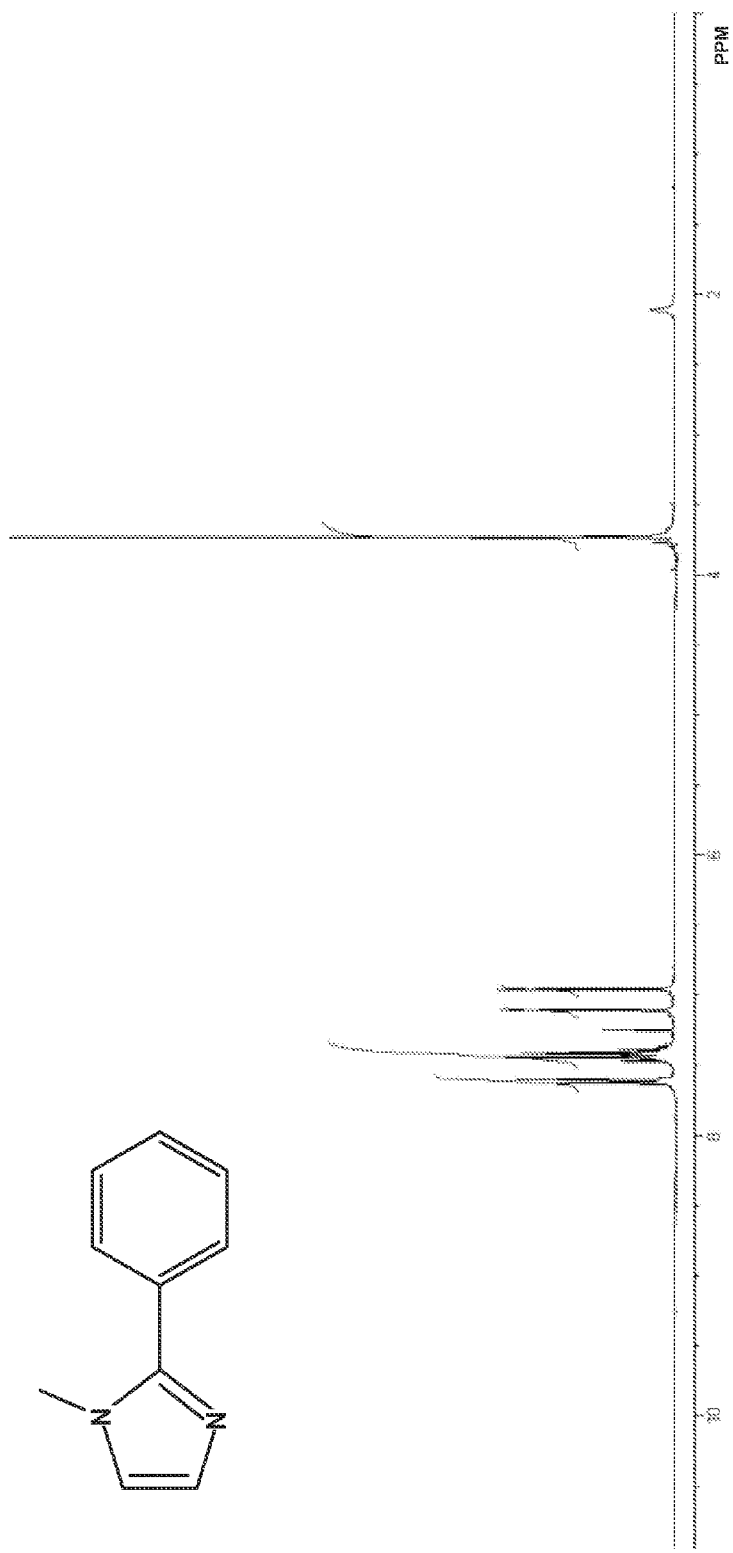
FIG. 51 depicts the molecule structure of 1-methyl-2-phenylimidazole and its $^1$H NMR spectrum.

Copper(I) iodide (19 mg, 0.1 mmol), iodobenzene (408 mg, 2.0 mmol), 1,10-phenanthroline (18 mg, 0.1 mmol), 1-methylimidazole (82 mg, 1.0 mmol), Et₃COLi (207 mg, 1.7 mmol), and anhydrous DMPU (0.5 mL), 125° C., 12 hours. After column chromatography (hexanes, then 1/1 ethyl acetate/hexanes) 130 mg (82%) of a colorless solid was obtained. $R_f$=0.56 (ethyl acetate). This compound is known.[8] The molecule structure of 1-Methyl-2-phenylimidazole and its ¹H NMR spectrum are shown in FIG. 51. ¹H NMR (300 MHz, CDCl₃) δ 3.73 (s, 3H), 6.96 (d, J=1.0 Hz, 1H), 7.11 (d, J=1.0 Hz, 1H), 7.38-7.48 (m, 3H), 7.59-7.64 (m, 2H).

3-Chloro-2,5-diphenylthiophene (Entry 5, Table IV)

Figure 52:
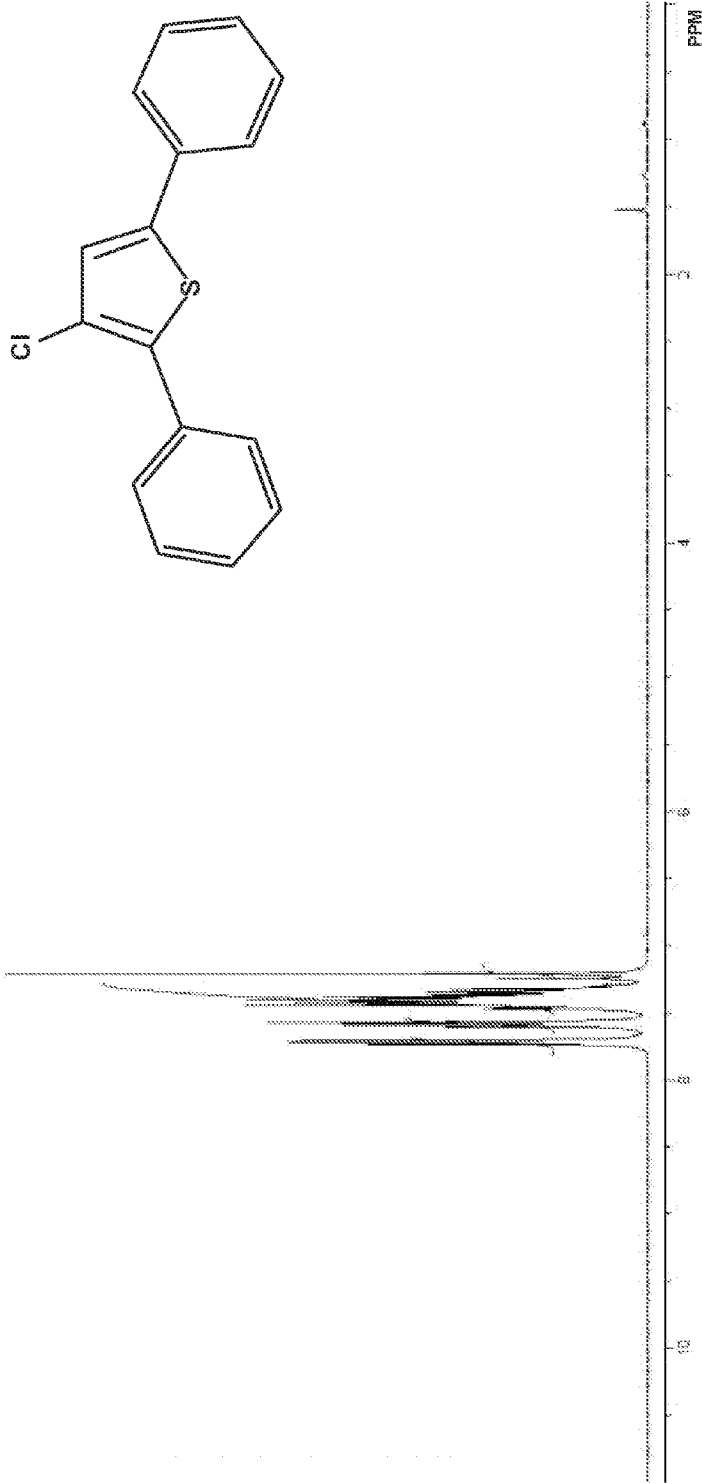
FIG. 52 depicts the molecule structure of 3-chloro-2,5-diphenylthiophene and its $^1$H NMR spectrum.

Copper(I) iodide (19 mg, 0.1 mmol), iodobenzene (612 mg, 3.0 mmol), 1,10-phenanthroline (18 mg, 0.11 mmol), 3-chlorothiophene (118.5 mg, 1.0 mmol), Et₃COLi (305 mg, 2.5 mmol), and anhydrous DMPU (0.6 mL), 125° C., 15 hours. After column chromatography (hexanes) 235 mg (87%) of a colorless solid was obtained. $R_f$=0.36 (hexanes), mp 63.5-64.5° C. (from pentane). The molecule structure of 3-chloro-2,5-diphenylthiophene and its ¹H NMR spectrum are shown in FIG. 52. ¹H NMR (300 MHz, CDCl₃) δ 7.21 (s, 1H), 7.29-7.49 (m, 6H), 7.55-7.62 (m, 2H), 7.69-7.76 (m, 2H). ¹³C NMR (75 MHz, CDCl₃) δ122.2, 125.6, 126.0, 128.6, 128.7, 129.0, 129.1, 129.5, 132.8, 133.8, 135.9, 142.6. FT-IR (neat, cm-1) u 1483, 863, 828, 756, 718, 694. Anal calcd for C₁₆H₁₁SCl (270.78 g/mol): C, 70.97; H, 4.09; S, 11.84. Found. C, 70.85; H, 4.04.

2,5-Diphenylthiophene and 2-phenylthiophene (Entry 6, Table IV)

Figure 53:
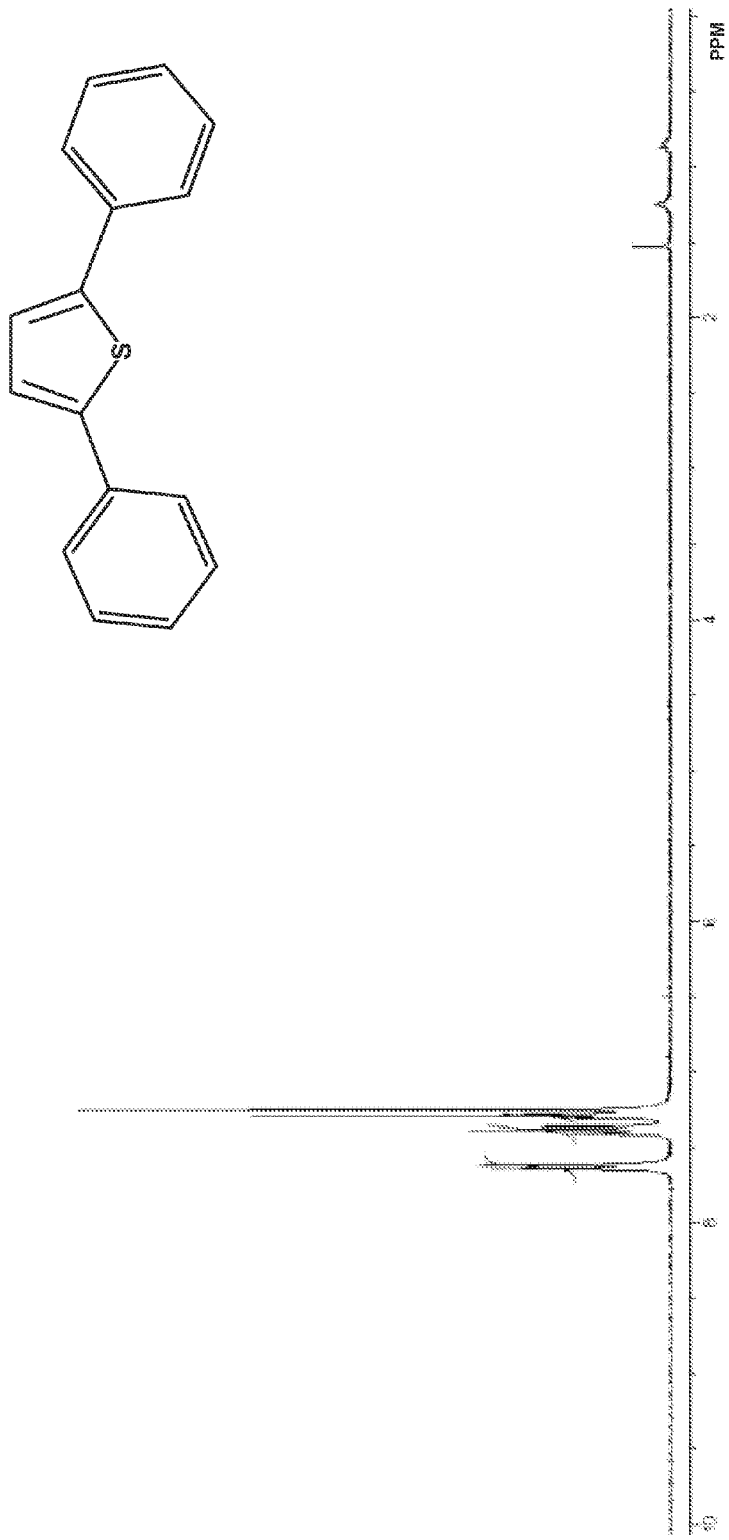
FIG. 53 depicts the molecule structure of 2,5-diphenylthiophene and its $^1$H NMR spectrum.

Copper(I) iodide (19 mg, 0.1 mmol), iodobenzene (612 mg, 3.0 mmol), 1,10-phenanthroline (18 mg, 0.1 mmol), thiophene (84 mg, 1.0 mmol), Et₃COLi (366 mg, 3.0 mmol), and anhydrous DMPU (0.6 mL), 125° C., 15 hours. After column chromatography (hexanes) 200 mg (85%) of a colorless solid was obtained. $R_f$=0.24 (SiO₂, hexanes). This compound is known.[9] The molecule structure of 2,5-diphenylthiophene and its ¹H NMR spectrum are shown in FIG. 53. ¹H NMR (300 MHz, CDCl₃) δ 7.27-7.32 (m, 4H), 7.39 (t, J=7.7 Hz, 4H), 7.63 (d, J=7.7 Hz, 4H).

1,5-Diphenyl-1H-pyrazole (Entry 7, Table IV)

Figure 54:
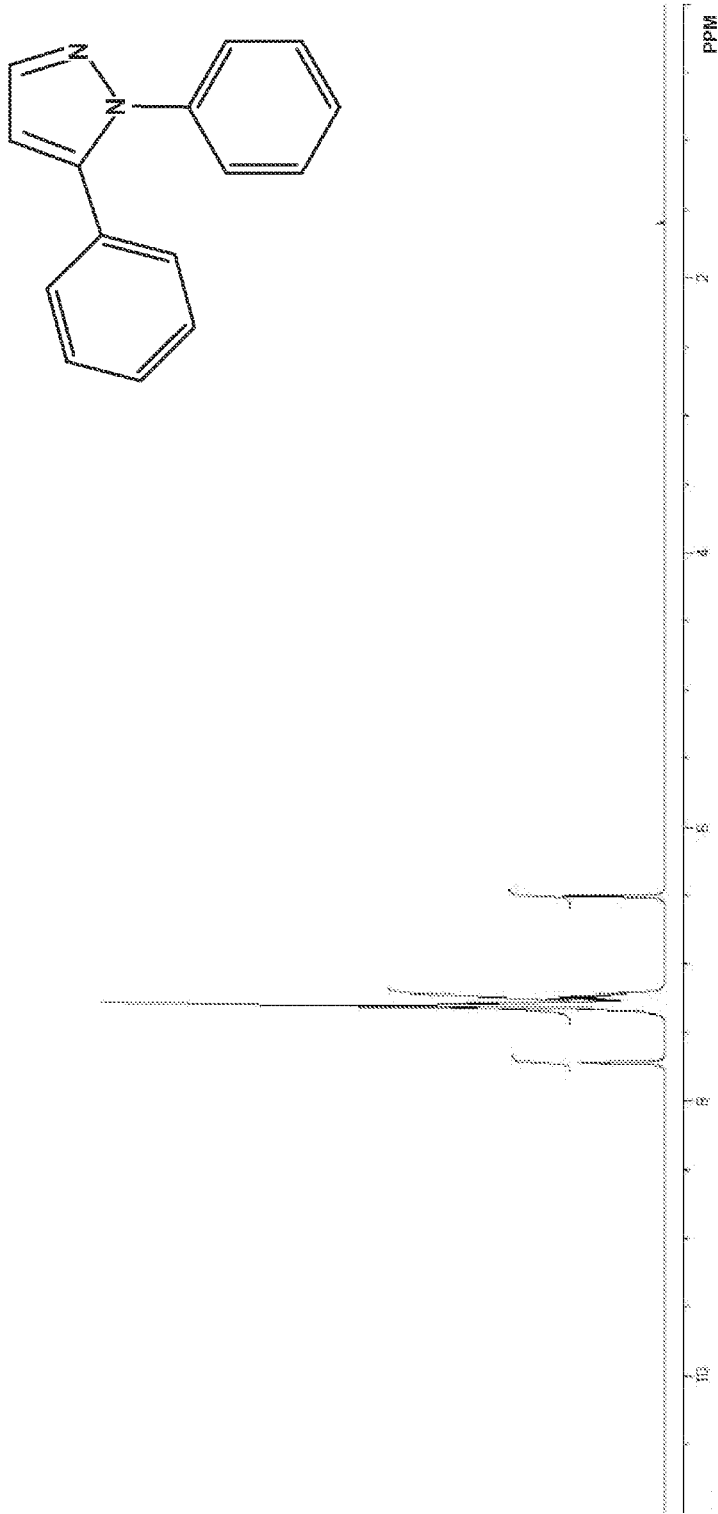
FIG. 54 depicts the molecule structure of 1,5-diphenyl-1H-pyrazole and its $^1$H NMR spectrum.

Copper(I) iodide (19 mg, 0.1 mmol), iodobenzene (408 mg, 2.0 mmol), 1,10-phenanthroline (18 mg, 0.1 mmol), 1-phenylpyrazole (144 mg, 1.0 mmol), Et₃COLi (207 mg, 1.7 mmol), and anhydrous DMPU (0.5 mL), 125° C., 12 hours. After column chromatography (hexanes, then 10% ethyl acetate in hexanes) 115 mg (52%) of a colorless solid was obtained. $R_f$=0.41 (1/4 ethyl acetate/hexanes). This compound is known.[10] The molecule structure of 1,5-diphenyl-1H-pyrazole and its ¹H NMR spectrum are shown in FIG. 54. ¹H NMR (300 MHz, CDCl₃) δ 6.51 (d, J=1.7 Hz, 1H), 7.20-7.26 (m, 2H), 7.26-7.35 (m, 8H), 7.72 (d, J=1.7 Hz, 1H).

2-Phenylbenzo[b]thiophene (Entry 8, Table IV)

Figure 55:
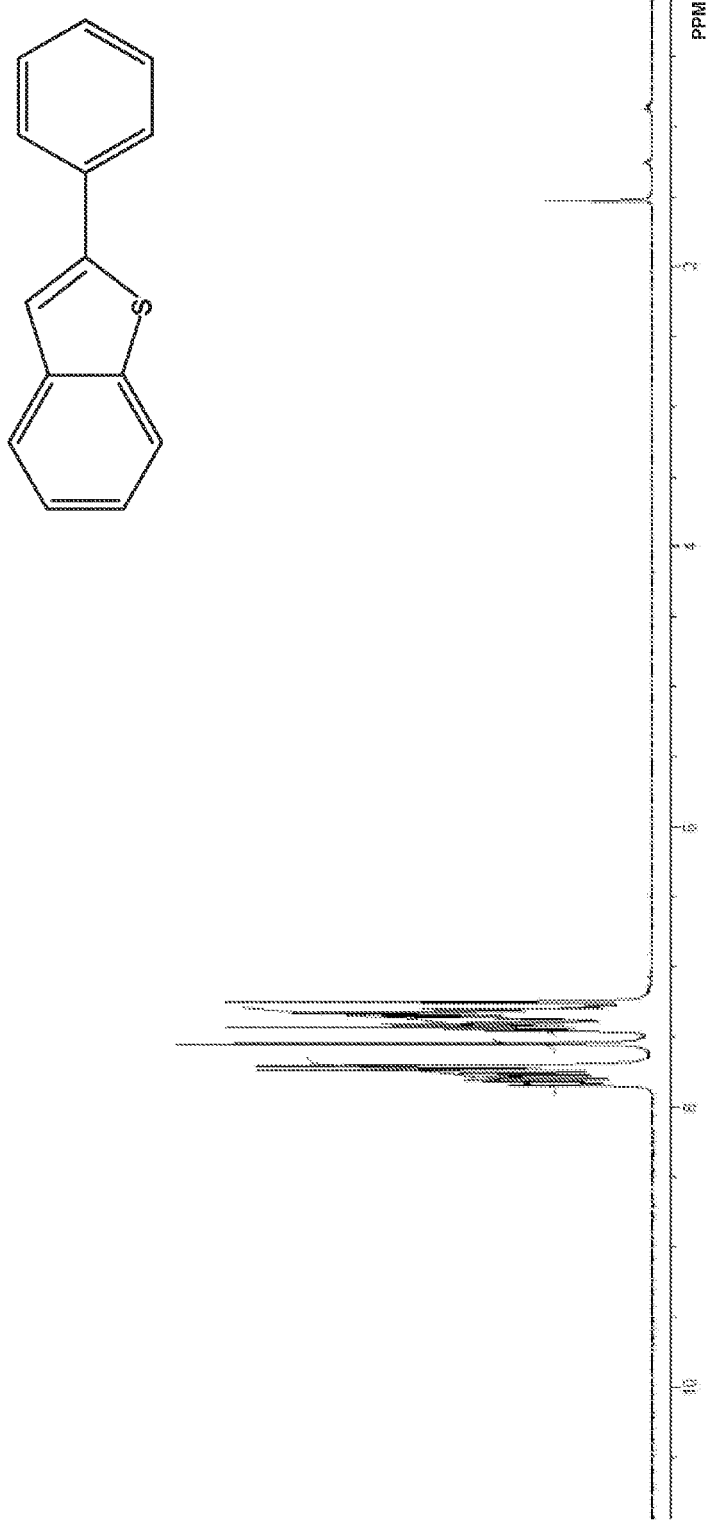
FIG. 55 depicts the molecule structure of 2-phenylbenzo[b]thiophene and its $^1$H NMR spectrum.

Copper(I) iodide (19 mg, 0.1 mmol), iodobenzene (408 mg, 2.0 mmol), 1,10-phenanthroline (18 mg, 0.1 mmol), benzo[b]thiophene (134 mg, 1.0 mmol), Et₃COLi (207 mg, 1.7 mmol), and anhydrous DMPU (0.5 mL), 125° C., 12 hours. After column chromatography (hexanes) 180 mg (86%) of a colorless solid was obtained. $R_f$=0.33 (hexanes). This compound is known.[8] The molecule structure of 2-phenylbenzo[b]thiophene and its ¹H NMR spectrum are shown in FIG. 55. ¹H NMR (300 MHz, CDCl₃) δ 7.27-7.47 (m, 5H), 7.55 (s, 1H), 7.67-7.86 (m, 4H).

2-Phenylbenzofuran (Entry 9, Table IV)

Copper(I) iodide (19 mg, 0.1 mmol), iodobenzene (408 mg, 2.0 mmol), 1,10-phenanthroline (18 mg, 0.11 mmol), benzofuran (118 mg, 1.0 mmol), Et₃COLi (207 mg, 1.7 mmol), and anhydrous DMPU (0.5 mL), 125° C., 12 hours. After column chromatography (hexanes) 117 mg (60%) of a colorless solid was obtained. $R_f$=0.27 (hexanes). This compound is known.[11] The molecule structure of 2-phenylbenzofuran and its ¹H NMR spectrum are shown in FIG. 56. ¹H NMR (300 MHz, CDCl₃) δ 7.03 (s, 1H), 7.20-7.40 (m, 3H), 7.45 (t, J=7.7 Hz, 2H), 7.53 (d, J=7.7 Hz, 1H), 7.59 (d, J=7.7 Hz, 1H), 7.88 (d, J=7.7 Hz, 2H).

2-Chloro-5-o-tolylthiophene (Entry 10, Table IV)

Figure 57:
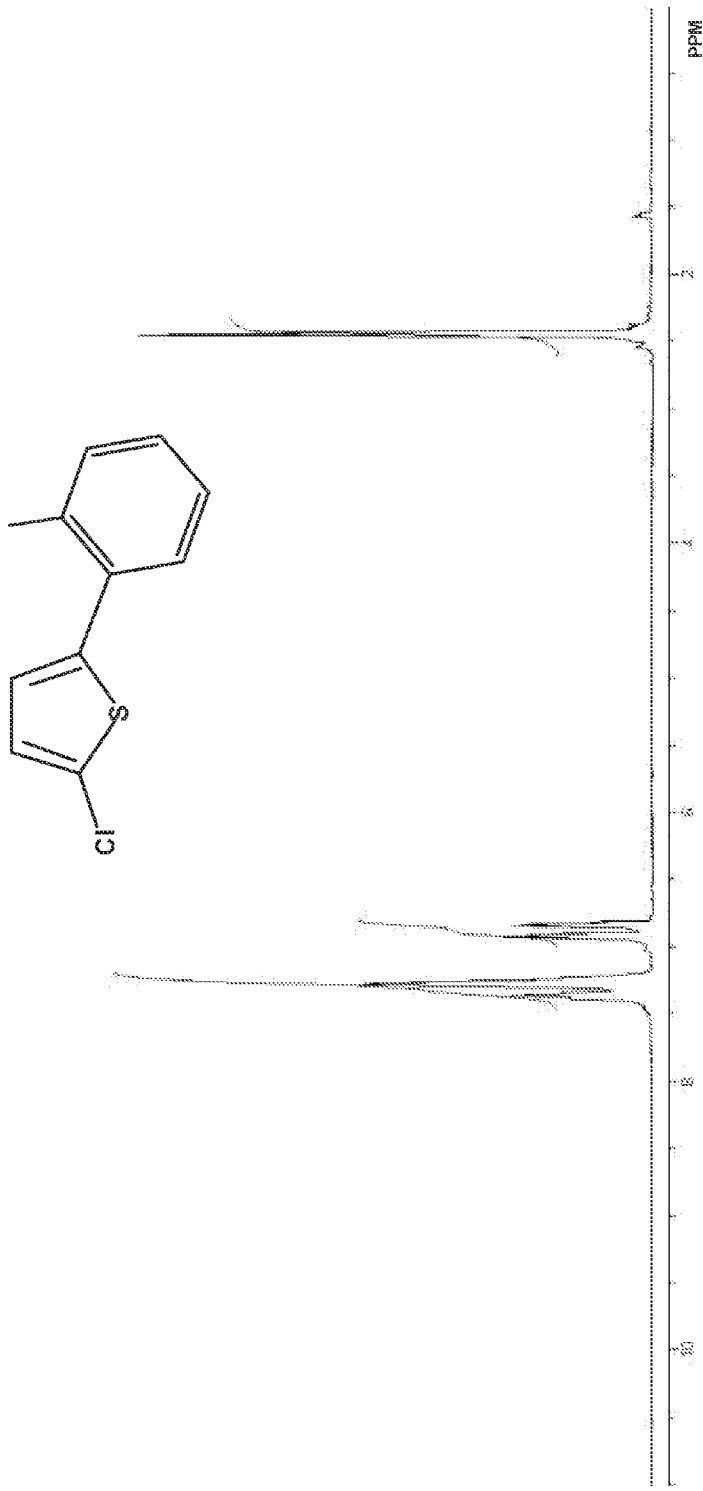
FIG. 57 depicts the molecule structure of 2-chloro-5-o-tolylthiophene and its $^1$H NMR spectrum.

Copper(I) iodide (19 mg, 0.1 mmol), 2-iodotoluene (218 mg, 1.0 mmol), 1,10-phenanthroline (18 mg, 0.1 mmol), 2-chlorothiophene (237 mg, 2.0 mmol), t-BuOLi (160 mg, 2.0 mmol), and anhydrous DMPU (0.6 mL), 125° C., 12 hours. After column chromatography (hexanes) 185 mg of a colorless oil (89%) was obtained. $R_f$=0.54 (hexanes). The molecule structure of 2-chloro-5-o-tolylthiophene and its $^1$H NMR spectrum are shown in FIG. 57. $^1$H NMR (300 MHz, CDCl$_3$) δ 2.34 (s, 3H), 6.73 (d, J=3.9 Hz, 1H), 6.82 (d, J=3.9 Hz, 1H), 7.10-7.20 (m, 3H), 7.24-7.29 (m, 1H). $^{13}$C NMR (75 MHz, CDCl$_3$) δ 21.5, 126.1, 126.5, 126.6, 128.7, 129.8, 130.8, 131.3, 133.8, 136.6, 142.3. FT-IR (neat, cm-1) u 1487, 1455, 1003, 799, 756, 721. Anal calcd for $C_{11}H_9ClS$ (208.71 g/mol): C, 63.30; H, 4.35; S, 15.36. Found. C, 62.83; H, 4.32.

2-Chloro-5-m-tolylthiophene (Entry 11, Table IV)

Figure 58:
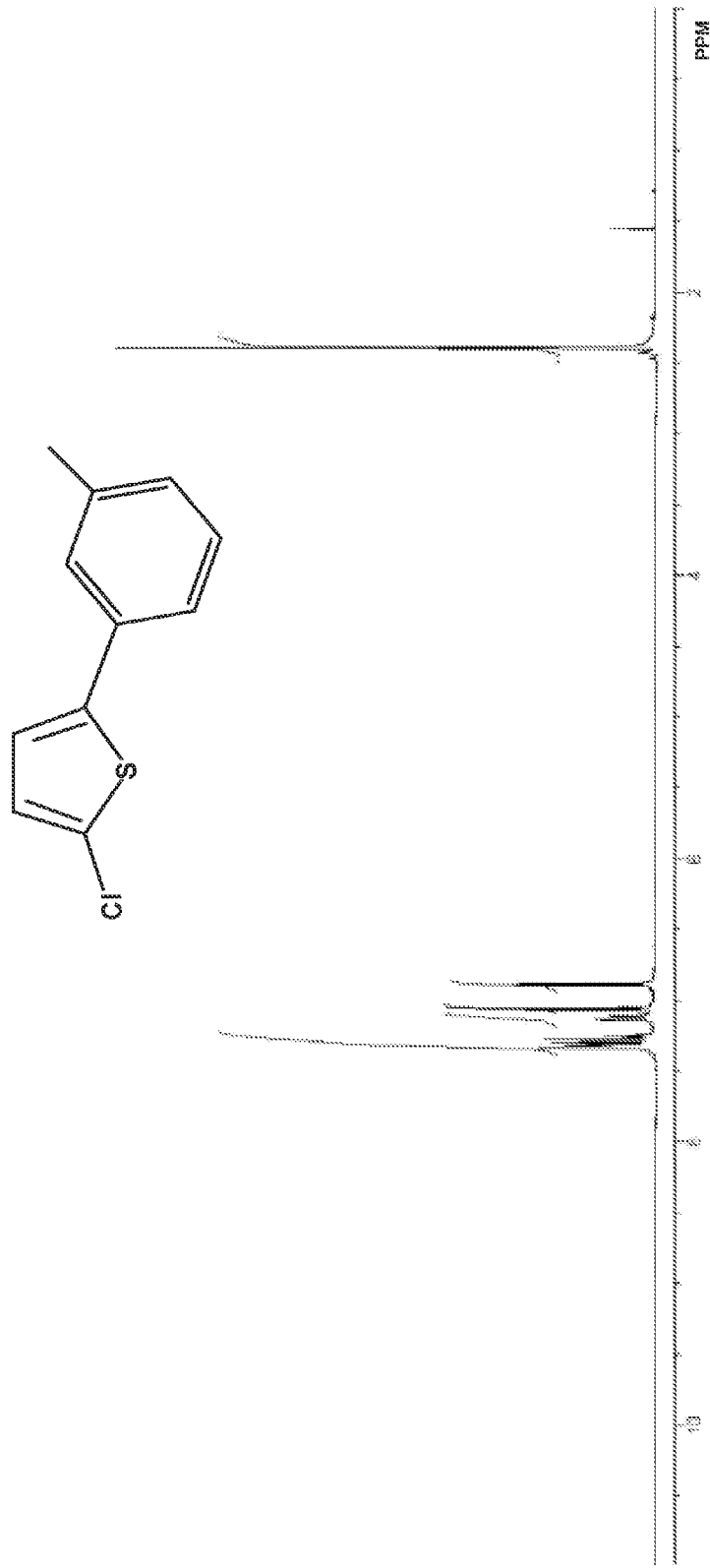
FIG. 58 depicts the molecule structure of 2-chloro-5-m-tolylthiophene and its $^1$H NMR spectrum.

Copper(I) iodide (19 mg, 0.1 mmol), 3-iodotoluene (218 mg, 1.0 mmol), 1,10-phenanthroline (18 mg, 0.1 mmol), 2-chlorothiophene (237 mg, 2.0 mmol), t-BuOLi (160 mg, 2.0 mmol), and anhydrous DMPU (0.6 mL), 125° C., 12 hours. After column chromatography (hexanes) 190 mg of a colorless solid (91%) was obtained. $R_f$=0.55 (hexanes), mp 37-38.5° C. (from hexanes). The molecule structure of 2-chloro-5-m-tolylthiophene and its $^1$H NMR spectrum are shown in FIG. 58. $^1$H NMR (300 MHz, CDCl$_3$) δ 2.39 (s, 3H), 6.89 (d, J=3.9 Hz, 1H), 7.06 (d, J=3.9 Hz, 1H), 7.12 (d, J=7.2 Hz, 1H), 7.24-7.35 (m, 3H). $^{13}$C NMR (75 MHz, CDCl$_3$) δ 22.0, 122.7, 123.3, 126.8, 127.6, 129.2, 129.4, 129.5, 134.2, 139.2, 143.7. FT-IR (neat, cm-1) u 1603, 1488, 1446, 1211, 796, 782, 688. Anal calcd for $C_{11}H_9ClS$ (208.71 g/mol): C, 63.30; H, 4.35; S, 15.36. Found. C, 63.28; H, 4.30.

2-Phenylpyridine 1-oxide and 2,6-diphenylpyridine 1-oxide (Entry 1, Table V)

Figure 59:
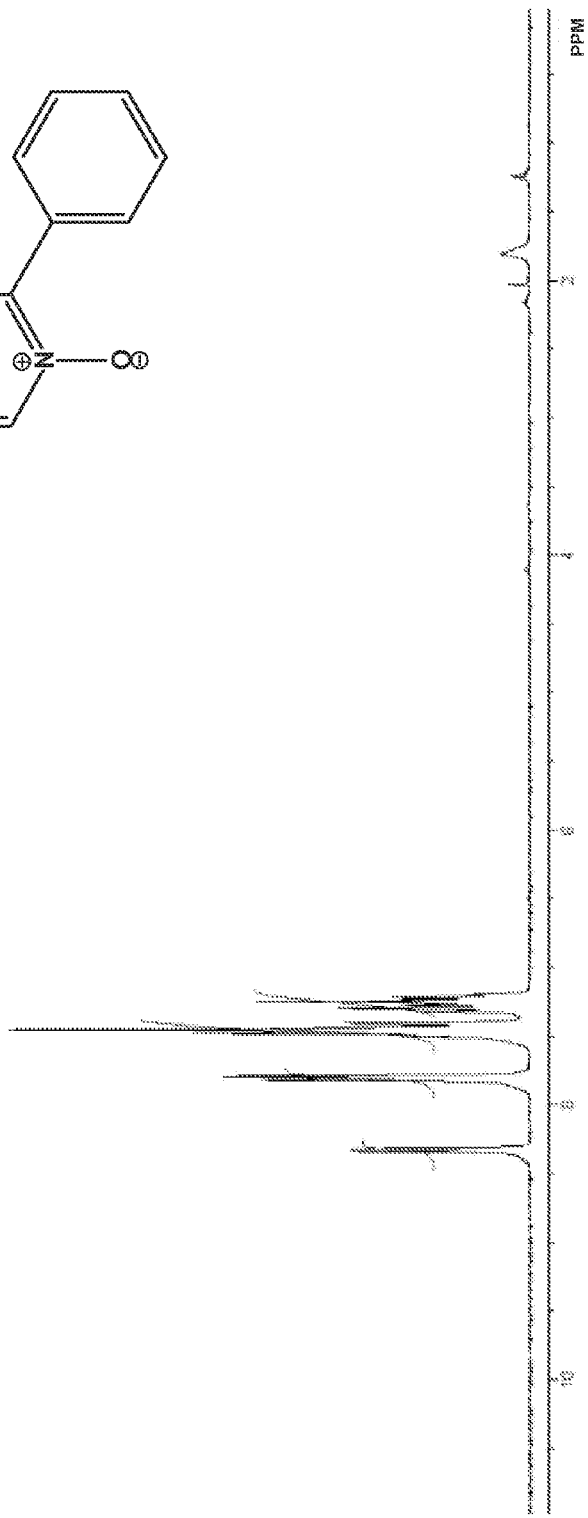
FIG. 59 depicts the molecule structure of 2-phenylpyridine 1-oxide and its $^1$H NMR spectrum.

Copper(I) iodide (19 mg, 0.1 mmol), iodobenzene (408 mg, 2.0 mmol), 1,10-phenanthroline (18 mg, 0.1 mmol), pyridine N-oxide (95 mg, 1.0 mmol), t-BuOLi (145 mg, 1.8 mmol), and anhydrous DMPU (0.5 mL), 125° C., 1 hour. After column chromatography (ethyl acetate, then 15% MeOH in ethyl acetate) 50 mg of 2,6-diphenylpyridine 1-oxide (20%) was obtained as an off-white solid. Additionally, 2-phenylpyridine 1-oxide (100 mg, 58%) was obtained as a colorless solid. These compounds are known.[7,12] 2-Phenylpyridine 1-oxide: $R_f$=0.46 (3/7 methanol/ethyl acetate). The molecule structure of 2-phenylpyridine 1-oxide and its $^1$H NMR spectrum are shown in FIG. 59. $^1$H NMR (300 MHz, CDCl$_3$) δ 7.17-7.34 (m, 2H), 7.38-7.53 (m, 4H), 7.80 (dd, J=7.7 Hz, 1.7 Hz, 2H), 8.33 (d, J=6.0 Hz, 1H). 2,6-Diphenylpyridine 1-oxide: $R_f$=0.30 (1/1 ethyl acetate/hexanes). $^1$H NMR (300 MHz, CDCl$_3$) δ 7.28-7.52 (m, 9H), 7.80-7.87 (m, 4H).

2,2'-Bipyridine 1-oxide (Entry 2, Table V)

Figure 60:
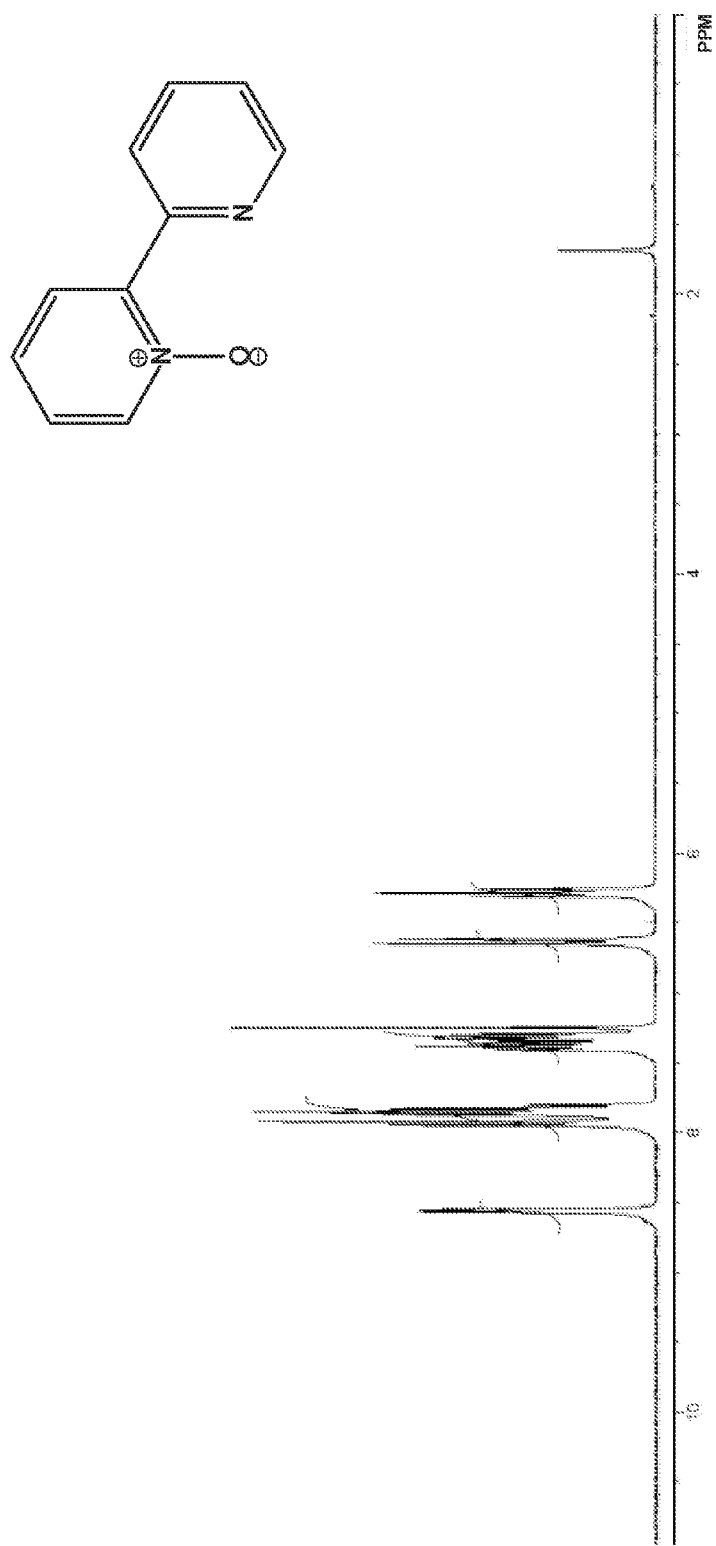
FIG. 60 depicts the molecule structure of 2,2'-bipyridine 1-oxide and its $^1$H NMR spectrum.

Copper(I) iodide (19 mg, 0.1 mmol), 2-iodopyridine (410 mg, 2.0 mmol), 1,10-phenanthroline (18 mg, 0.1 mmol), pyridine N-oxide (95 mg, 1.0 mmol), K$_3$PO$_4$ (424 mg, 2.0 mmol), and DMF (0.6 mL), 120° C., 5 hours. After column chromatography (hexanes, then 7/3 ethyl acetate/hexanes) 70 mg (41%) of a light tan solid was obtained. $R_f$=0.34 (ethyl acetate). This compound is known.[13] The molecule structure of 2,2'-bipyridine 1-oxide and its $^1$H NMR spectrum are shown in FIG. 60. $^1$H NMR (300 MHz, CDCl$_3$) δ 6.29 (t, J=6.7 Hz, 1H), 6.64 (d, J=8.5 Hz, 1H), 7.27-7.44 (m, 2H), 7.77-7.98 (m, 3H), 8.56 (dd, J=5.0 Hz, 1.0 Hz, 1H).

2-Methyl-6-phenylpyridine 1-oxide (Entry 3, Table V)

Figure 61:
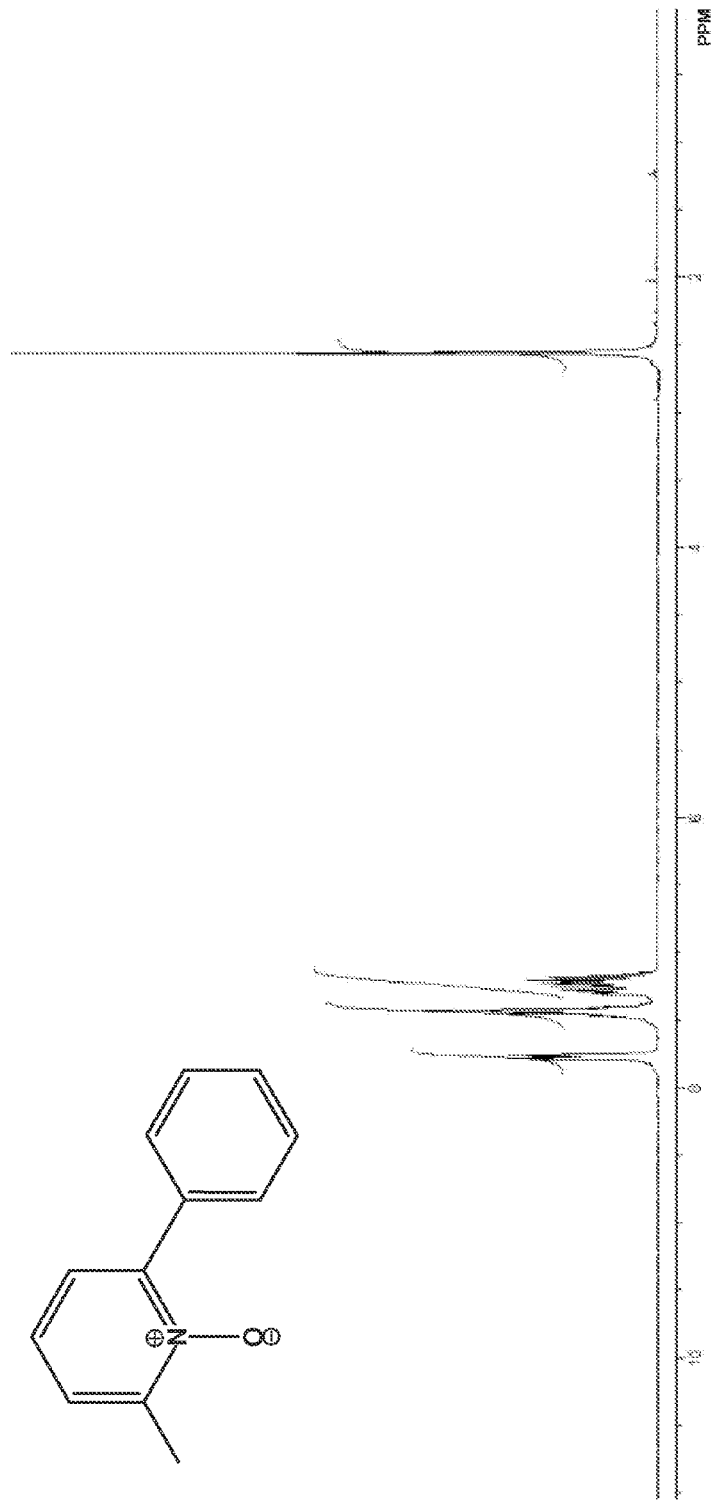
FIG. 61 depicts the molecule structure of 2-methyl-6-phenylpyridine 1-oxide and its $^1$H NMR spectrum.

Copper(I) iodide (19 mg, 0.1 mmol), iodobenzene (408 mg, 2.0 mmol), 1,10-phenanthroline (18 mg, 0.1 mmol), 2-picoline N-oxide (109 mg, 1.0 mmol), t-BuOLi (145 mg, 1.8 mmol), and anhydrous DMPU (0.5 mL), 125° C., 1 hour. After column chromatography (ethyl acetate, then 5% MeOH in ethyl acetate) and preparative HPLC (5% MeOH in ethyl acetate) 80 mg (43%) of a light tan solid was obtained. $R_f$=0.24 (ethyl acetate). This compound is known.[14] The molecule structure of 2-methyl-6-phenylpyridine 1-oxide and its $^1$H NMR spectrum are shown in FIG. 61. $^1$H NMR (300 MHz, CDCl$_3$) δ 2.56 (s, 3H), 7.13-7.34 (m, 3H), 7.37-7.51 (m, 3H), 7.77 (dd, J=7.8 Hz, 1.7 Hz, 2H).

2-Phenyl-6-(4-(trifluoromethyl)phenyl)pyridine 1-oxide (Entry 4, Table V)

Figure 62:
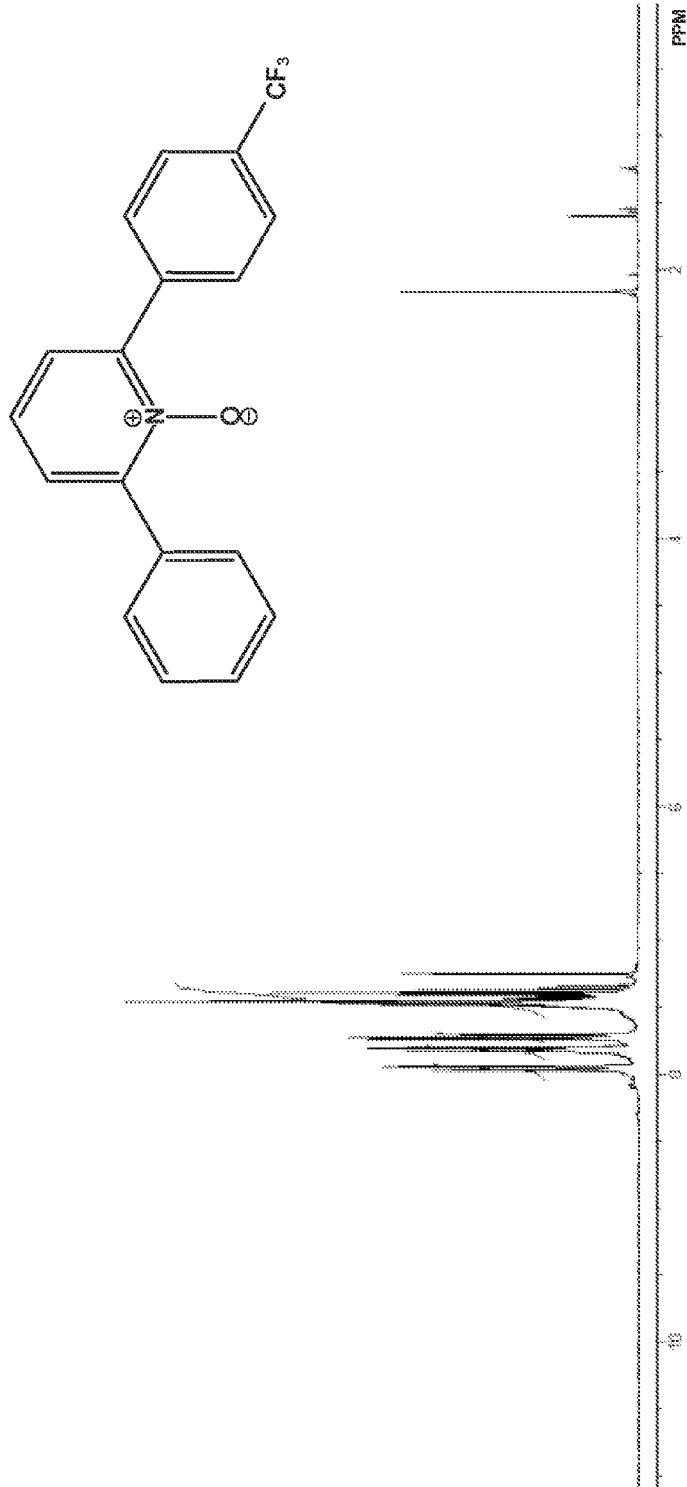
FIG. 62 depicts the molecule structure of 2-phenyl-6-(4-(trifluoromethyl)phenyl)pyridine 1-oxide and its $^1$H NMR spectrum.

Copper(I) iodide (19 mg, 0.1 mmol), 4-iodobenzotrifluoride (544 mg, 2.0 mmol), 1,10-phenanthroline (18 mg, 0.1 mmol), 2-phenylpyridine N-oxide (171 mg, 1.0 mmol), t-BuOLi (160 mg, 2.0 mmol), and anhydrous DMPU (0.6 mL), 125° C., 1 hour. After column chromatography (hexanes, then 1/1 ethyl acetate/hexanes) 252 mg (80%) of a light tan solid was obtained. $R_f$=0.44 (1/1 ethyl acetate/hexanes), mp 150-151° C. (from ether). The molecule structure of 2-phenyl-6-(4-(trifluoromethyl)phenyl)pyridine 1-oxide and its $^1$H NMR spectrum are shown in FIG. 62. $^1$H NMR (300 MHz, CDCl$_3$) δ 7.33-7.42 (m, 2H), 7.43-7.51 (m, 4H), 7.72 (d, J=8.5 Hz, 2H), 7.79-7.84 (m, 2H), 7.96 (d, J=8.5 Hz, 2H). $^{13}$C NMR (75 MHz, CDCl$_3$) δ 124.4 (q, JC-F=273 Hz), 125.4, 125.5, 125.6, 126.6, 127.4, 128.7, 130.0, 130.6, 131.6 (q, JC-F=33.5 Hz), 133.5, 137.4, 149.0, 150.7. FTIR (neat, cm-1) u 1372, 1327, 1281, 1165, 1121, 1071, 854, 844, 800, 768 Anal calcd for $C_{18}H_{12}F_3NO$ (315.29 g/mol): C, 68.57; H, 3.84; N, 4.44. Found. C, 68.71; H, 3.91; N, 4.41.

2-(Naphthalen-1-yl)-6-phenylpyridine 1-oxide (Entry 5, Table V)

Figure 63:
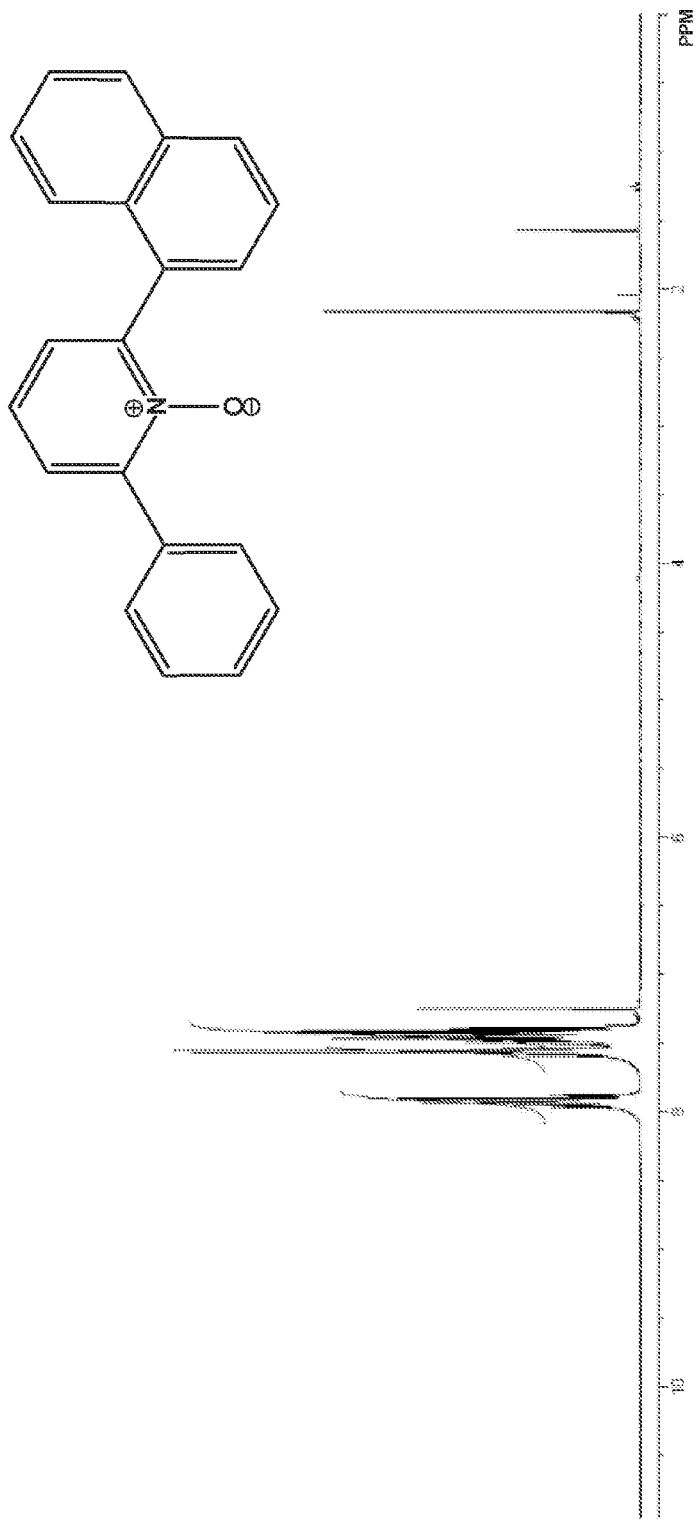
FIG. 63 depicts the molecule structure of 2-(naphthalen-1-yl)-6-phenylpyridine 1-oxide and its $^1$H NMR spectrum.

Copper(I) iodide (19 mg, 0.1 mmol), 1-iodonapthalene (508 mg, 2.0 mmol), 1,10-phenanthroline (18 mg, 0.1 mmol), 2-phenylpyridine N-oxide (171 mg, 1.0 mmol), t-BuOLi (160 mg, 2.0 mmol), and anhydrous DMPU (0.6 mL), 125° C., 1 hour. After column chromatography (hexanes, then 1/1 ethyl acetate/hexanes) 270 mg (91%) of a light tan solid was obtained. $R_f$=0.31 (1/1 ethyl acetate/hexanes), mp 167-168° C. (from ethyl acetate). The molecule structure of 2-(naphthalen-1-yl)-6-phenylpyridine 1-oxide and its $^1$H NMR spectrum are shown in FIG. 63. $^1$H NMR (300 MHz, CDCl$_3$) δ 7.38-7.50 (m, 7H), 7.52-7.60 (m, 4H), 7.86-7.98 (m, 4H). $^{13}$C NMR (75 MHz, CDCl$_3$) δ 122.5, 124.9, 125.8, 125.9, 126.6, 127.1, 127.3, 127.8, 128.2, 128.6, 129.0, 129.9, 130.1, 130.3, 131.7, 133.6, 134.0, 150.4, 151.0. FT-IR (neat, cm-1) u 1372, 1245, 843, 782, 764. Anal calcd for $C_{21}H_{15}NO$ (297.35 g/mol): C, 84.82; H, 5.08; N, 4.71. Found. C, 84.56; H, 5.05; N, 4.64.

4-Phenylpyridazine (Entry 6, Table V)

Figure 64:
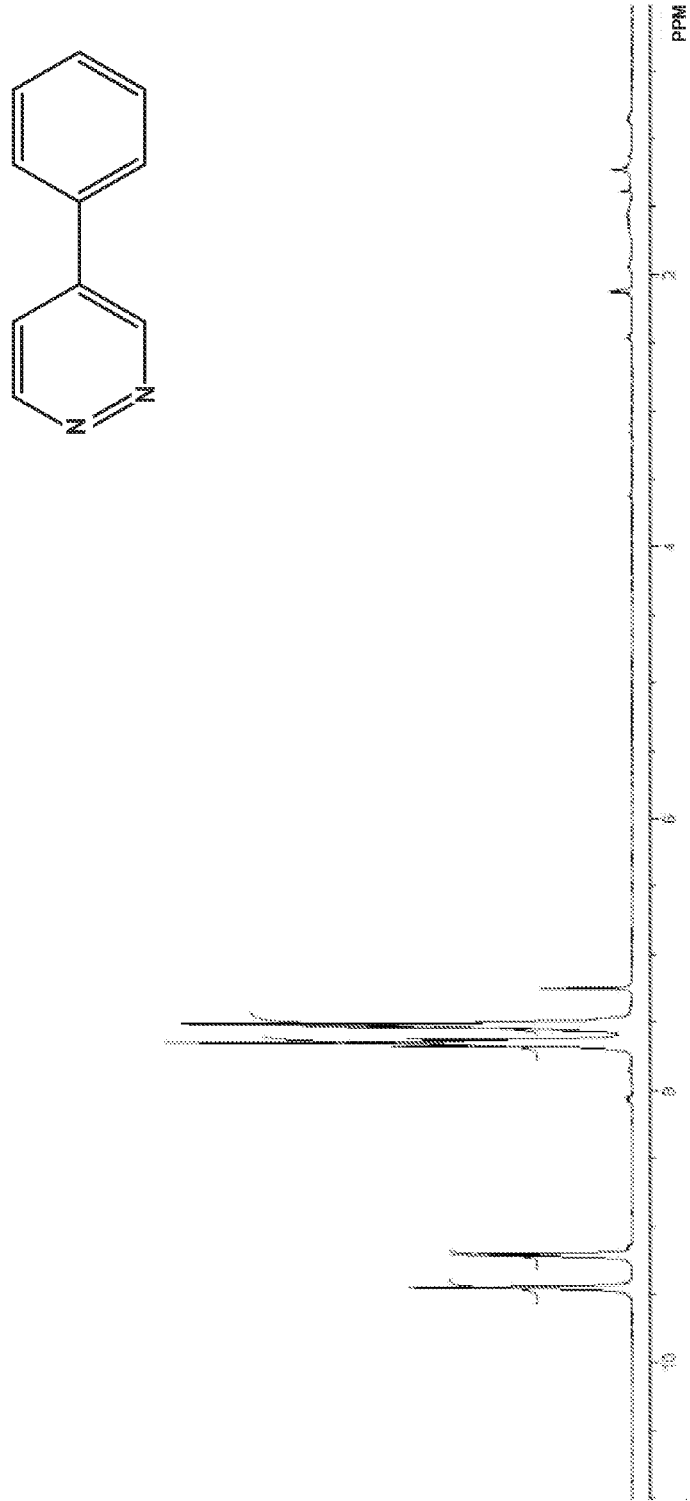
FIG. 64 depicts the molecule structure of 4-phenylpyridazine and its $^1$H NMR spectrum.

Copper(I) iodide (19 mg, 0.1 mmol), iodobenzene (204 mg, 1.0 mmol), 1,10-phenanthroline (18 mg, 0.1 mmol), pyridazine (160 mg, 2.0 mmol), Et$_3$COLi (207 mg, 1.7 mmol), and anhydrous DMPU (0.5 mL), 125° C., 12 hours. After column chromatography (hexanes, then 1/1 ethyl acetate/hexanes) 94 mg (60%) of a light tan solid was obtained. R$_f$=0.40 (ethyl acetate). This compound is known.[15] The molecule structure of 4-phenylpyridazine and its $^1$H NMR spectrum are shown in FIG. 64. $^1$H NMR (300 MHz, CDCl$_3$) δ 7.45-7.59 (m, 3H), 7.60-7.70 (m, 3H), 9.21 (dd, J=5.5 Hz, 1.0 Hz, 1H), 9.45 (dd, J=2.2 Hz, 1.0 Hz, 1H).

5-Phenylpyrimidine (Entry 7, Table V)

Figure 65:
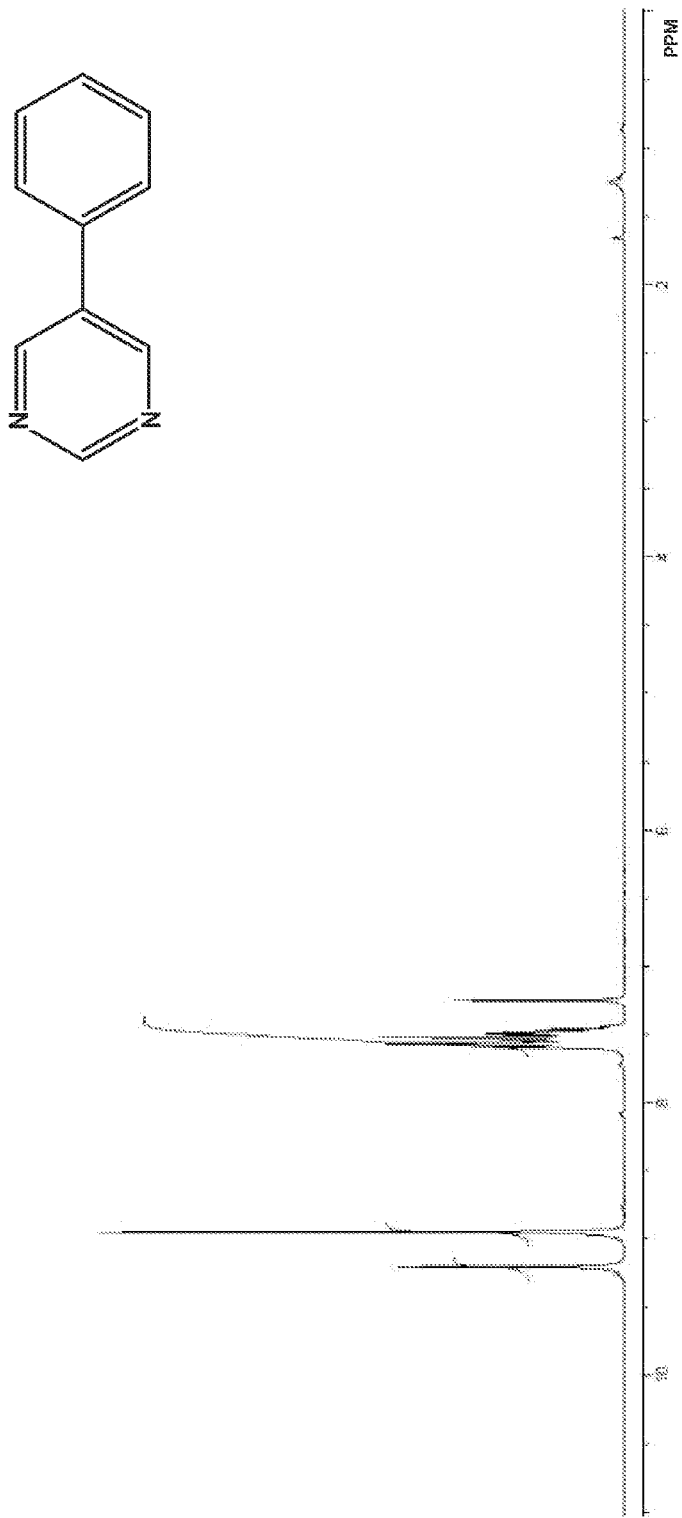
FIG. 65 depicts the molecule structure of 5-phenylpyrimidin and its $^1$H NMR spectrum.

Copper(I) iodide (19 mg, 0.1 mmol), iodobenzene (204 mg, 1.0 mmol), 1,10-phenanthroline (18 mg, 0.1 mmol), pyrimidine (160 mg, 2.0 mmol), Et$_3$COLi (207 mg, 1.7 mmol), and anhydrous DMPU (0.5 mL), 125° C., 12 hours. After column chromatography (hexanes, then 1/1 ethyl acetate/hexanes) 48 mg (31%) of a light tan solid was obtained. R$_f$=0.55 (ethyl acetate). This compound is known.[16] The molecule structure of 5-phenylpyrimidine and its $^1$H NMR spectrum are shown in FIG. 65. $^1$H NMR (300 MHz, CDCl$_3$) δ 7.42-7.61 (m, 5H), 8.95 (s, 2H), 9.20 (s, 1H).

1,3-Dipentafluorophenylbenzene (Entry 1, Table VI)

Figure 66:
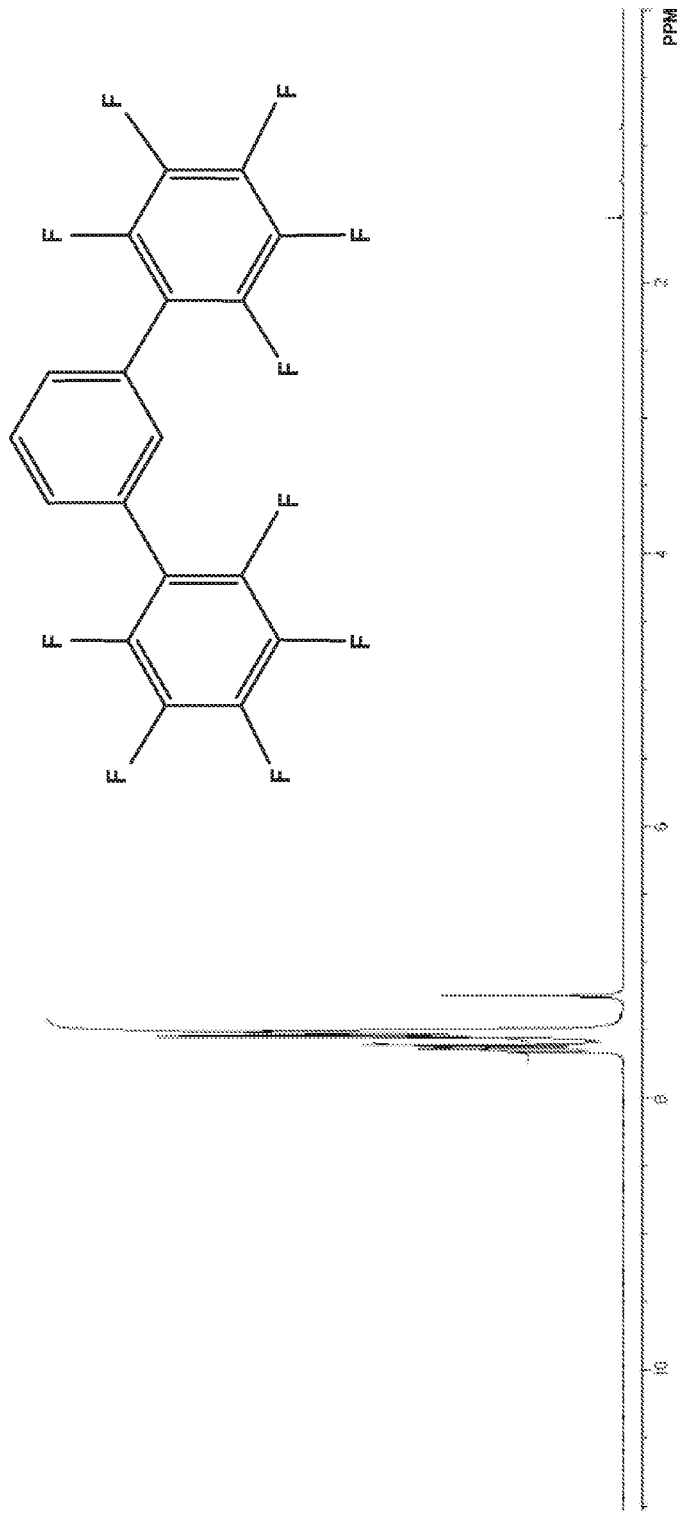
FIG. 66 depicts the molecule structure of 1,3-dipentafluorophenylbenzene and its $^1$H NMR spectrum.

Copper(I) iodide (29 mg, 0.15 mmol), pentafluorobenzene (504 mg, 3.0 mmol), 1,10-phenanthroline (27 mg, 0.15 mmol), 1,3-dibromobenzene (236 mg, 1.0 mmol), K$_3$PO$_4$ (848 mg, 4.0 mmol), and DMF/xylenes (1/1, 0.8 mL), 125° C., 24 hours. After column chromatography (hexanes) 210 mg (51%) of a colorless solid was obtained. R$_f$=0.38 (hexanes). This compound is known.[17] The molecule structure of 1,3-dipentafluorophenylbenzene and its $^1$H NMR spectrum are shown in FIG. 66. $^1$H NMR (300 MHz, CDCl$_3$) δ 7.47-7.58 (m, 3H), 7.60-7.67 (m, 1H). $^{19}$F NMR (282 MHz, CDCl$_3$) δ−163.8-163.5 (m, 4F), −156.4 (t, JF=21.0 Hz, 2F), −145.0 (dd, JF=7.6, 23.0 Hz, 4F).

1,4-Dipentafluorophenylbenzene (Entry 2, Table VI)

Figure 67:
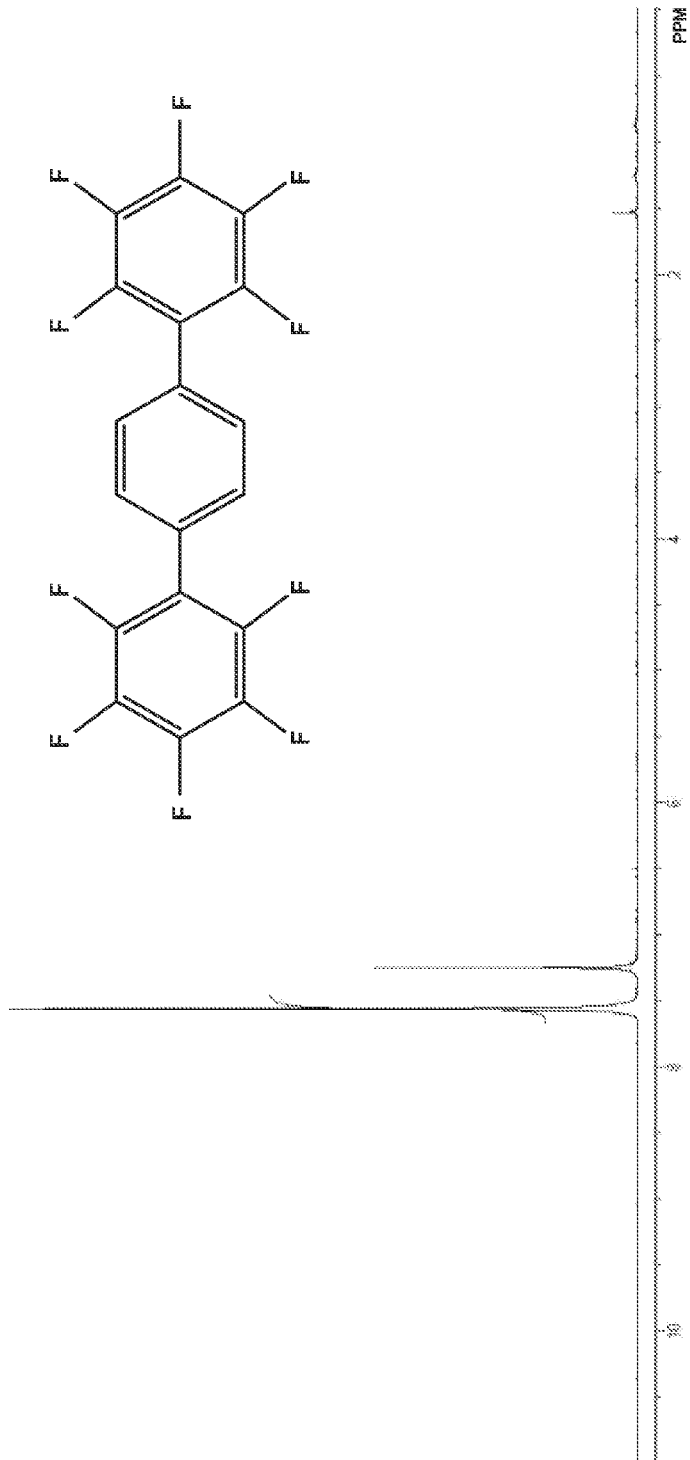
FIG. 67 depicts the molecule structure of 1,4-dipentafluorophenylbenzene and its $^1$H NMR spectrum.

Copper(I) iodide (29 mg, 0.15 mmol), pentafluorobenzene (504 mg, 3.0 mmol), 1,10-phenanthroline (27 mg, 0.15 mmol), 1,4-diiodobenzene (330 mg, 1.0 mmol), K$_3$PO$_4$ (848 mg, 4.0 mmol), and DMF (0.8 mL), 125° C., 12 hours. After column chromatography (hexanes) 300 mg (73%) of a colorless solid was obtained. R$_f$=0.30 (hexanes). This compound is known.[18] The molecule structure of 1,4-dipentafluorophenylbenzene and its $^1$H NMR spectrum are shown in FIG. 67. $^1$H NMR (300 MHz, CDCl$_3$) δ 7.56 (s, 4H). $^{19}$F NMR (282 MHz, CDCl$_3$) δ−163.4-163.0 (m, 4F), −156.2-155.8 (m, 2F), −144.6 (dd, JF=7.6, 23.0 Hz, 4F).

2-(Pentafluorophenyl)quinoline (Entry 3, Table VI)

Figure 68:
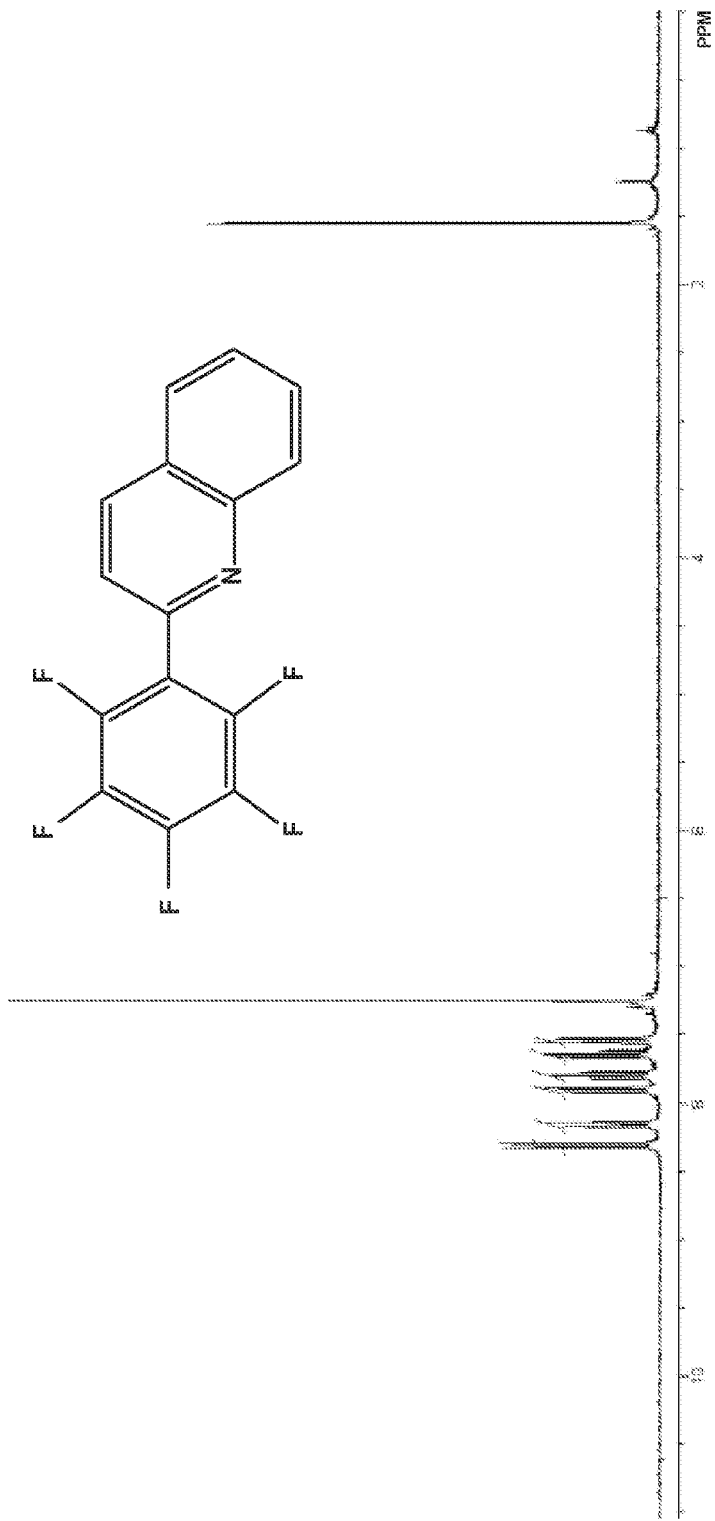
FIG. 68 depicts the molecule structure of 2-(pentafluorophenyl)quinoline and its $^1$H NMR spectrum.

Copper(I) iodide (19 mg, 0.1 mmol), pentafluorobenzene (252 mg, 1.5 mmol), 1,10-phenanthroline (18 mg, 0.1 mmol), 2-chloroquinoline (163.5 mg, 1.0 mmol), K$_3$PO$_4$ (424 mg, 2.0 mmol), and DMF/xylenes (1/1, 0.5 mL), 125° C., 24 hours. After column chromatography (hexanes) 250 mg (85%) of a colorless solid was obtained. R$_f$=0.42 (1/9 ethyl acetate/hexanes), mp 168-169.5° C. (from pentane). The molecule structure of 2-(pentafluorophenyl)quinoline and its $^1$H NMR spectrum are shown in FIG. 68. $^1$H NMR (300 MHz, CDCl$_3$) δ 7.53 (d, J=8.5 Hz, 1H), 7.63 (dt, J=7.8 Hz, 0.5 Hz, 1H), 7.79 (dt, J=7.8 Hz, 0.5 Hz, 1H), 7.89 (d, J=7.8 Hz, 1H), 8.16 (d, J=8.5 Hz, 1H), 8.29 (d, J=8.5 Hz, 1H). $^{19}$F NMR (282 MHz, CDCl$_3$) δ−163.5-162.9 (m, 2F), −155.3-154.9 (m, 1F), −144.4 (d, JF=21.0 Hz, 2F). FT-IR (neat, cm-1) υ 1493, 1077, 986, 906, 836, 789 Anal calcd for C$_{15}$H$_6$NF$_5$ (295.21 g/mol): C, 61.03; H, 2.05; N, 4.74. Found. C, 61.03; H, 1.97; N, 4.61.

2-(Pentafluorophenyl)pyridine (Entry 4, Table VI)

Figure 69:
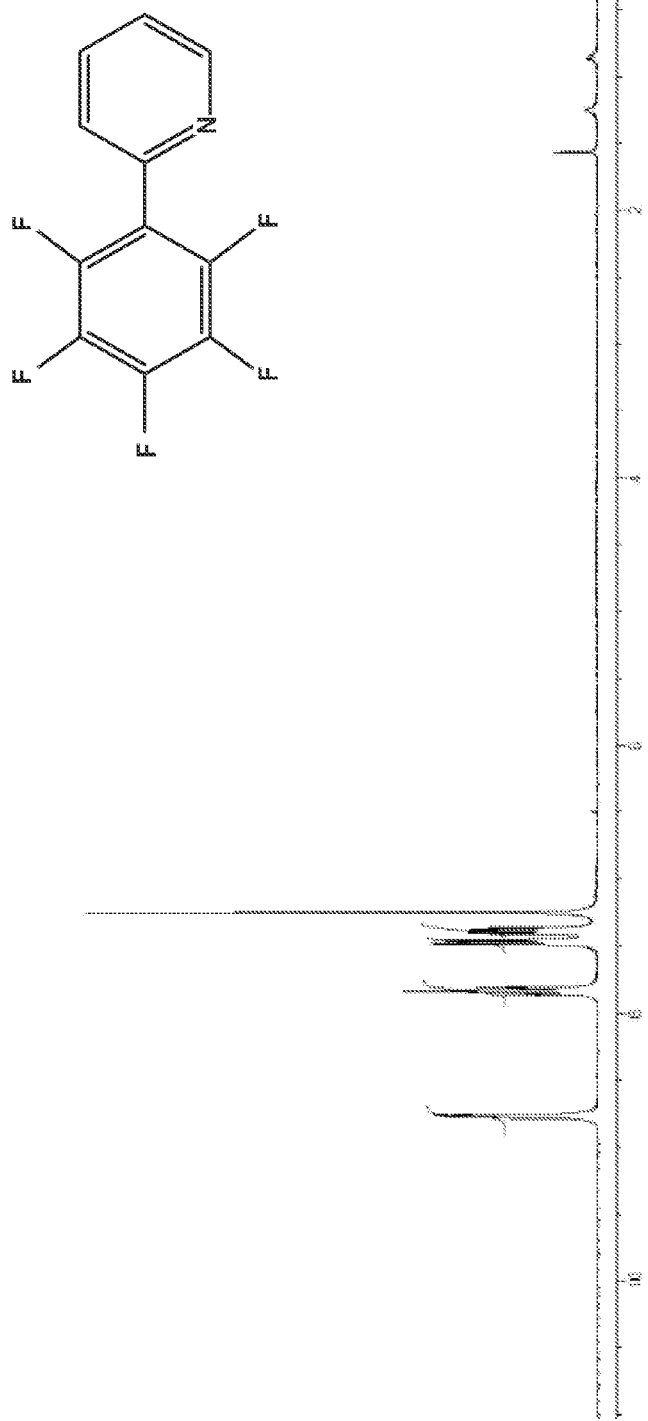
FIG. 69 depicts the molecule structure of 2-(pentafluorophenyl)pyridine and its $^1$H NMR spectrum.

Copper(I) iodide (19 mg, 0.1 mmol), 2-chloropyridine (113.5 mg, 1.0 mmol), 1,10-phenanthroline (18 mg, 0.11 mmol), pentafluorobenzene (252 mg, 1.5 mmol), K$_3$PO$_4$ (424 mg, 2.0 mmol), and DMF/xylenes (0.6 mL), 150° C., 24 hours. After column chromatography (hexanes, then 10% ethyl acetate in hexanes) 100 mg (41%) of a colorless solid was obtained. R$_f$=0.41 (1/4 AcOEt/hexanes). This compound is known.[17] The molecule structure of 2-(pentafluorophenyl)pyridine and its $^1$H NMR spectrum are shown in FIG. 69. $^1$H NMR (300 MHz, CDCl$_3$) δ 7.38 (ddd, J=8.0 Hz, 5.0 Hz, 1.0 Hz, 1H), 7.47 (d, J=8.0 Hz, 1H), 7.80-7.88 (m, 1H), 8.74-8.80 (m, 1H). $^{19}$F NMR (282 MHz, CDCl$_3$) δ−163.6-163.3 (m, 2F), −155.5-155.1 (m, 1F), −144.9 (dd, JF=7.6, 23.0 Hz, 2F).

1,2,3,4,5-Pentafluoro-6-(1-phenylvinyl)benzene (Entry 5, Table VI)

Figure 70:
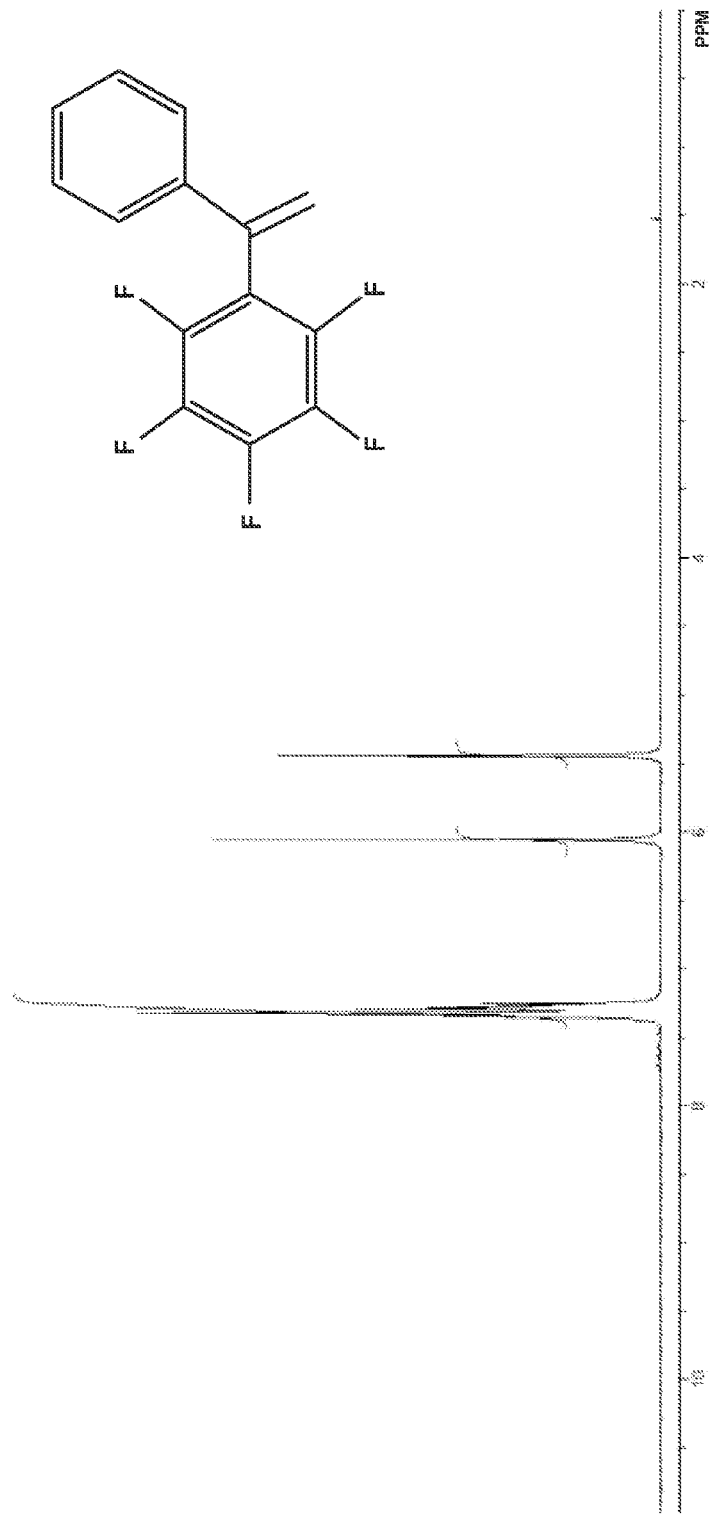
FIG. 70 depicts the molecule structure of 1,2,3,4,5-pentafluoro-6-(1-phenylvinyl)benzene and its $^1$H NMR spectrum.

Copper(I) iodide (19 mg, 0.1 mmol), a-bromostyrene (183 mg, 1.0 mmol), 1,10-phenanthroline (18 mg, 0.1 mmol), pentafluorobenzene (252 mg, 1.5 mmol), K$_3$PO$_4$ (424 mg, 2.0 mmol), and DMF/xylenes (1/1, 0.6 mL), 125° C., 24 hours. After column chromatography (hexanes) 220 mg (81%) of a colorless oil was obtained. R$_f$=0.42 (hexanes). This compound is known.[19] The molecule structure of 1,2,3,4,5-pentafluoro-6-(1-phenylvinyl)benzene and its $^1$H NMR spectrum are shown in FIG. 70. $^1$H NMR (300 MHz, CDCl$_3$) δ 5.44 (s, 1H), 6.06 (s, 1H), 7.22-7.39 (m, 5H). $^{19}$F NMR (282 MHz, CDCl$_3$) δ−163.9-163.4 (m, 2F), −156.9-156.5 (m, 1F), −141.9 (dd, JF=7.6, 23.0 Hz, 2F).

2'-(But-3-enyloxy)-2,3,4,5,6-pentafluorobiphenyl (Entry 6, Table VI)

Figure 71:
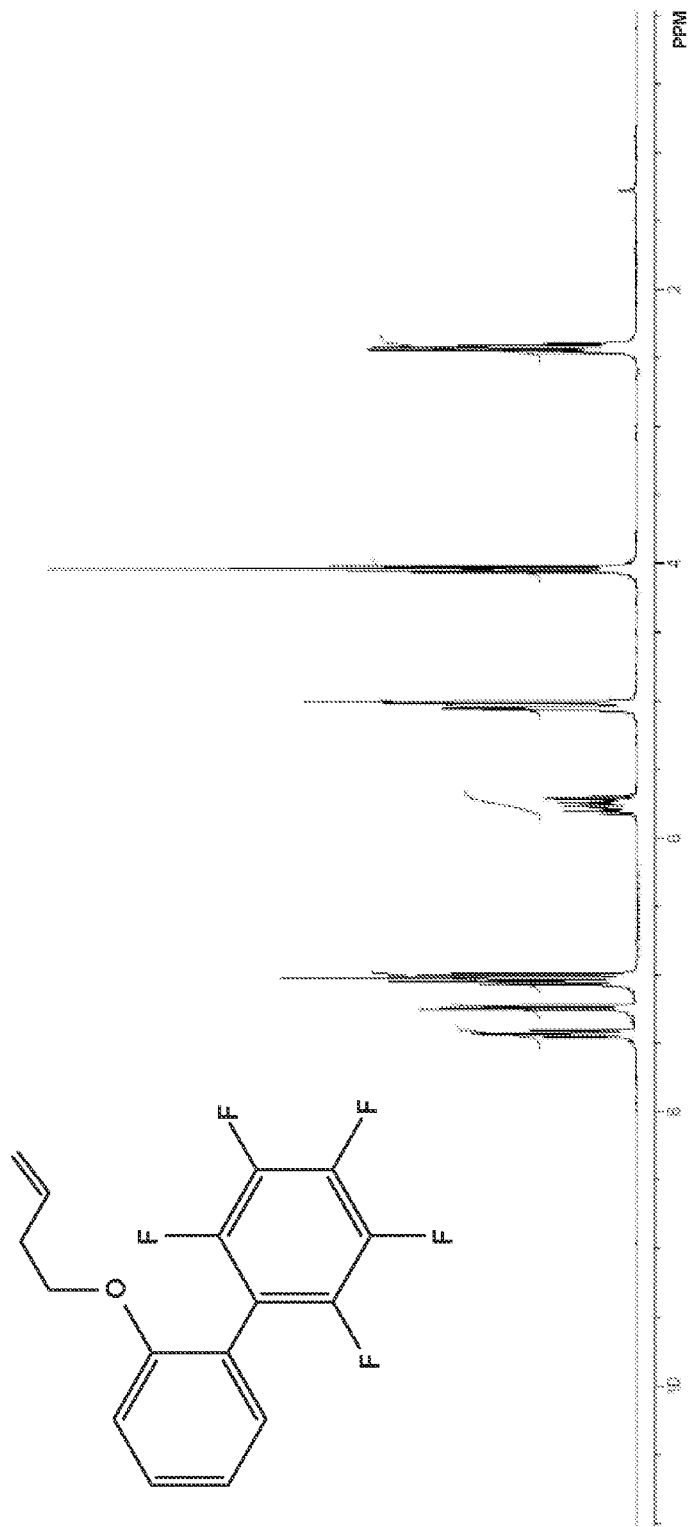
FIG. 71 depicts the molecule structure of 2'-(but-3-enyloxy)-2,3,4,5,6-pentafluorobiphenyl and its $^1$H NMR spectrum.

Copper(I) iodide (19 mg, 0.1 mmol), 1-(but-3-enyloxy)-2-iodobenzene (274 mg, 1.0 mmol), 1,10-phenanthroline (18 mg, 0.1 mmol), pentafluorobenzene (252 mg, 1.5 mmol), K$_3$PO$_4$ (424 mg, 2.0 mmol), and DMF (0.6 mL), 125° C., 12 hours. After column chromatography (hexanes, then 10% ethyl acetate in hexanes) 280 mg (89%) of a colorless oil was obtained. R$_f$=0.33 (hexanes). The molecule structure of 2'-(but-3-enyloxy)-2,3,4,5,6-pentafluorobiphenyl and its $^1$H NMR spectrum are shown in FIG. 71. $^1$H NMR (300 MHz, CDCl$_3$) δ 2.43 (q, J=6.6 Hz, 2H), 4.04 (t, J=6.6 Hz, 2H), 5.01 (s, 1H), 5.06 (d, J=5.5 Hz, 1H), 5.68-5.85 (m, 1H), 7.02 (d, J=7.8 Hz, 1H), 7.06 (d, J=7.8 Hz, 1H), 7.24 (d, J=6.6 Hz, 1H), 7.43 (dt, J=7.8 Hz, 1.5 Hz, 1H). $^{19}$F NMR (282 MHz, CDCl$_3$) δ−165.3-164.9 (m, 2F), −158.2-157.8 (m, 1F), −141.8-141.4 (m, 2F). $^{13}$C NMR (75 MHz, CDCl$_3$) δ 34.1, 68.1, 112.8, 113.4 (t, JC-F=15.7 Hz), 116.2, 117.4, 121.2, 131.5, 132.2, 136.4, 136.1-139.5 (m), 139.5-142.9 (m), 143.1-146.9 (m), 157.0. FT-IR (neat, cm-1) ν 1493, 1250, 1063, 987, 752 Anal calcd for C$_{16}$H$_{11}$OF$_5$ (314.25 g/mol): C, 61.15; H, 3.53; O, 5.09. Found. C, 61.58; H, 3.50.

Phenyl(2',3',5',6'-tetrafluorobiphenyl-4-yl)methanone (Entry 7, Table VI)

Figure 72:
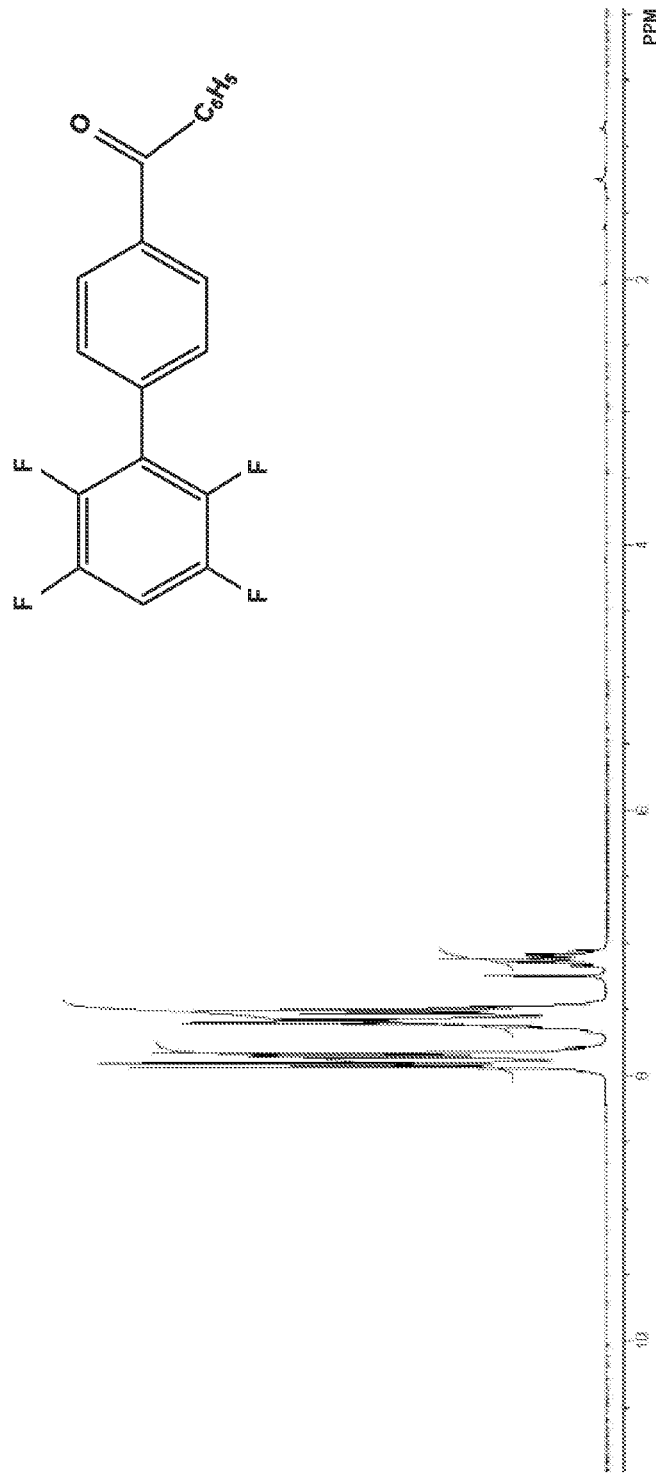
FIG. 72 depicts the molecule structure of phenyl(2',3',5',6'-tetrafluorobiphenyl-4-yl)methanone and its $^1$H NMR spectrum.

Copper(I) iodide (19 mg, 0.1 mmol), 1,2,4,5-tetrafluorobenzene (300 mg, 2.0 mmol), 1,10-phenanthroline (18 mg, 0.1 mmol), 4-bromobenzophenone (261 mg, 1.0 mmol), K$_3$PO$_4$ (500 mg, 2.4 mmol), and anhydrous DMPU (0.5 mL), 120° C., 12 hours. After column chromatography (hexanes, then 5% ethyl acetate in hexanes) 170 mg (52%) of a colorless solid was obtained. R$_f$=0.42 (1/9 ethyl acetate/hexanes), mp 108-111° C. (from pentane). The molecule structure of phenyl(2',3',5',6'-tetrafluorobiphenyl-4-yl)methanone and its $^1$H NMR spectrum are shown in FIG. 72. $^1$H NMR (300 MHz, CDCl$_3$) δ 7.05-7.18 (m, 1H), 7.45-7.65 (m, 5H), 7.80-7.88 (m, 2H), 7.92 (d, J=7.5 Hz, 2H). $^{19}$F NMR (282 MHz, CDCl$_3$) δ–145.5-145.3 (m, 2F), –140.5-140.2 (m, 2F). $^{13}$C NMR (75 MHz, CDCl$_3$) δ 106.0 (t, JC-F=21.5 Hz), 121.1 (t, JC-F=16.8 Hz), 128.7, 128.9, 130.5, 130.6, 131.9, 133.0, 137.9, 138.8, 142.4-146.2 (m), 145.0-148.8 (m), 196.2. FT-IR (neat, cm-1) ν 1645, 1492, 1283, 936, 852, 701 Anal calcd for C$_{19}$H$_{10}$OF$_4$ (330.28 g/mol): C, 69.09; H, 3.05; 0, 4.84. Found. C, 68.99; H, 3.02.

2,3,4,6-Tetrafluoro-4'-phenylbiphenyl (Entry 8, Table VI)

Figure 73:
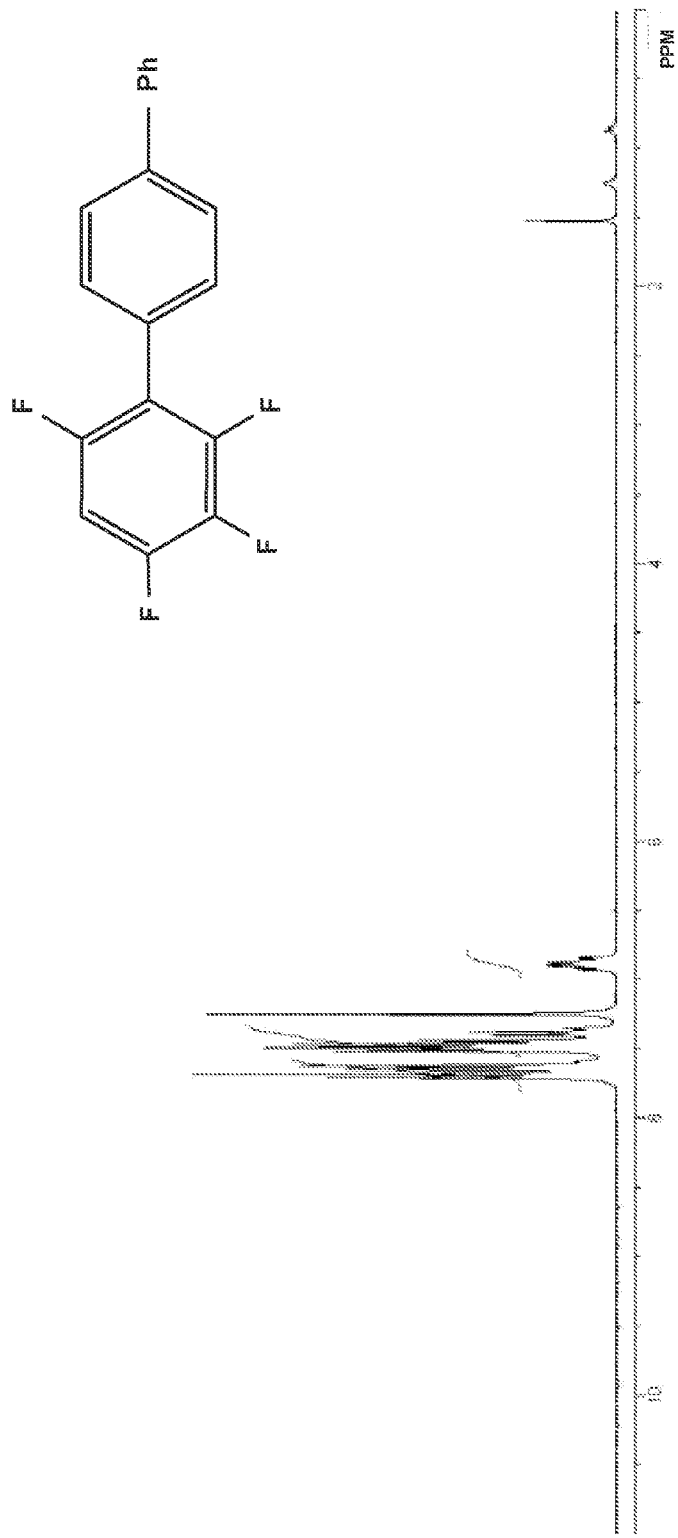
FIG. 73 depicts the molecule structure of 2,3,4,6-tetrafluoro-4'-phenylbiphenyl and its $^1$H NMR spectrum.

Copper(I) iodide (19 mg, 0.1 mmol), 1,2,3,5-tetrafluorobenzene (300 mg, 2.0 mmol), 1,10-phenanthroline (18 mg, 0.1 mmol), 4-bromobiphenyl (231 mg, 1.0 mmol), K$_3$PO$_4$ (500 mg, 2.4 mmol), and anhydrous DMPU (0.5 mL), 125° C., 24 hours. After column chromatography (hexanes) 210 mg (70%) of a colorless solid was obtained. R$_f$=0.23 (hexanes). This compound is known.[20] The molecule structure of 2,3,4,6-tetrafluoro-4'-phenylbiphenyl and its $^1$H NMR spectrum are shown in FIG. 73. $^1$H NMR (300 MHz, CDCl$_3$) δ 6.83-6.95 (m, 1H), 7.34-7.55 (m, 5H), 7.60-7.74 (m, 4H). $^{19}$F NMR (282 MHz, CDCl$_3$) δ–166.8-166.3 (m, 1F), –137.3 (d, JF=21.0 Hz, 1F), –135.3-135.0 (m, 1F), –120.0 (t, JF=10.0 Hz, 1F).

1-(Cyclohexylidenemethyl)-2,3,5,6-tetrafluoro-4-methylbenzene (Entry 9, Table VI)

Figure 74:
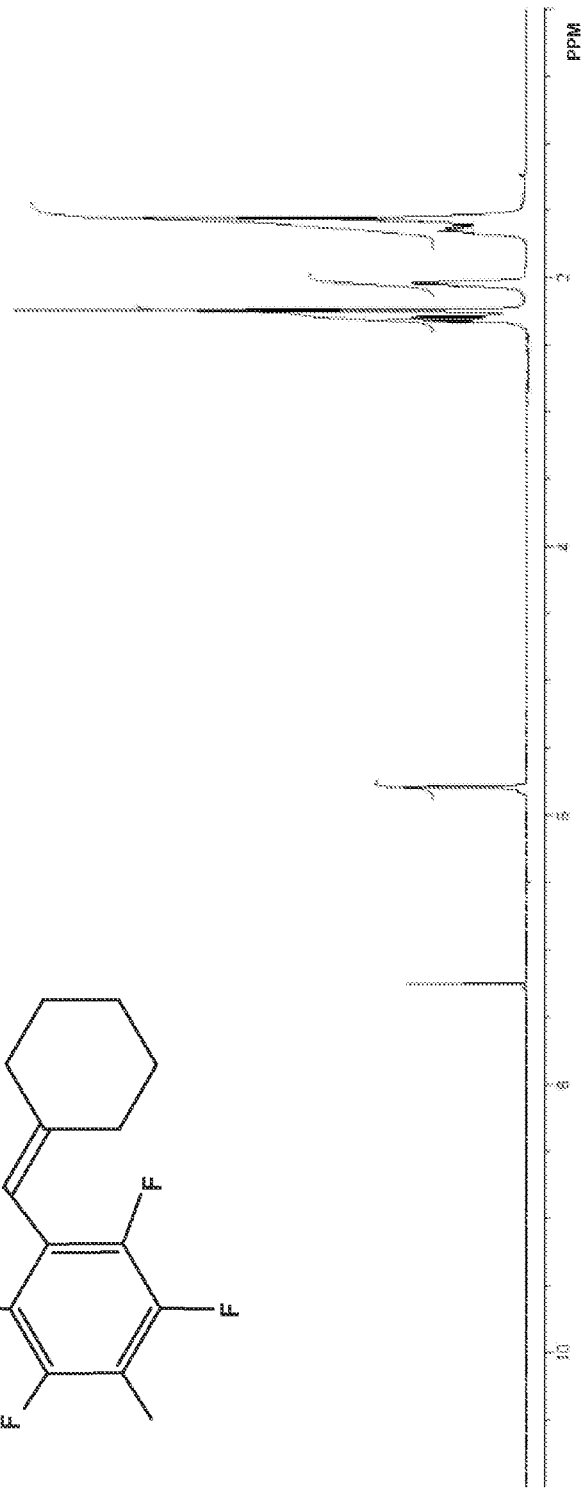
FIG. 74 depicts the molecule structure of 1-(cyclohexylidenemethyl)-2,3,5,6-tetrafluoro-4-methylbenzene and its $^1$H NMR spectrum.

Copper(I) iodide (19 mg, 0.1 mmol), 2,3,5,6-tetrafluorotoluene (245 mg, 1.5 mmol), 1,10-phenanthroline (18 mg, 0.1 mmol), bromomethylenecyclohexane (175 mg, 1.0 mmol), K$_3$PO$_4$ (424 mg, 2.0 mmol), and anhydrous DMPU (0.6 mL), 125° C., 12 hours. After column chromatography (hexanes) 245 mg (95%) of a colorless oil was obtained. R$_f$=0.60 (hexanes). The molecule structure of 1-(cyclohexylidenemethyl)-2,3,5,6-tetrafluoro-4-methylbenzene and its $^1$H NMR spectrum are shown in FIG. 74. $^1$H NMR (300 MHz, CDCl$_3$) δ 1.50-1.70 (m, 6H), 2.05 (s, 2H), 2.24 (t, J=2.2 Hz, 3H), 2.31 (t, J=6.0 Hz, 2H), 5.79 (s, 1H). $^{19}$F NMR (282 MHz, CDCl$_3$) δ-147.3 (dd, JF=21.0, 13.3 Hz, 1F), –147.3 (dd, JF=21.0, 13.3 Hz, 1F). $^{13}$C NMR (75 MHz, CDCl$_3$) δ 7.9, 26.8, 27.9, 28.9, 31.6, 37.5, 106.6, 114.2 (t, J=19.5 Hz), 115.3 (t, J=19.5 Hz), 142.3-146.0 (m), 143.6-147.4 (m), 151.0. FT-IR (neat, cm-1) u 2934, 2857, 1475, 1287, 1064, 951, 922 Anal calcd for C$_{14}$H$_{14}$F$_4$ (258.25 g/mol): C, 65.11; H, 5.46. Found. C, 64.74; H, 5.33.

2,5-Difluoro-4'-methylbiphenyl (Entry 10, Table VI)

Figure 75:
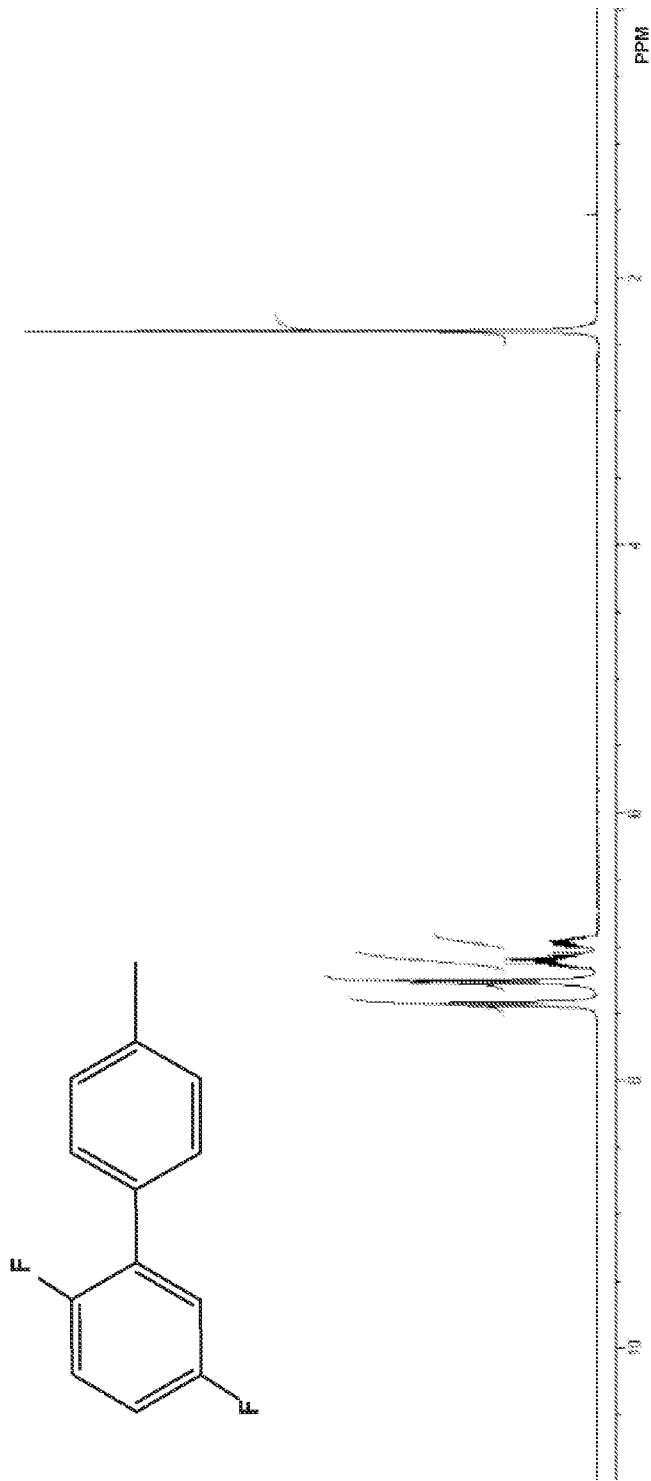
FIG. 75 depicts the molecule structure of 2,5-difluoro-4'-methylbiphenyl and its $^1$H NMR spectrum.

Copper(I) iodide (19 mg, 0.1 mmol), 4-iodotoluene (218 mg, 1.0 mmol), 1,10-phenanthroline (18 mg, 0.1 mmol), 1,4-difluorobenzene (228 mg, 2.0 mmol), Et$_3$COLi (207 mg, 1.7 mmol), and anhydrous DMPU (0.5 mL), 125° C., 12 hours. After column chromatography (hexanes) 110 mg (54%) of a colorless oil was obtained. R$_f$=0.42 (hexanes). This compound is known.[17] The molecule structure of 2,5-difluoro-4'-methylbiphenyl and its $^1$H NMR spectrum are shown in FIG. 75. $^1$H NMR (300 MHz, CDCl$_3$) δ 2.40 (s, 3H), 6.91-7.02 (m, 1H), 7.03-7.18 (m, 2H), 7.26 (d, J=7.8 Hz, 2H), 7.43 (dd, J=7.8 Hz, 1.2 Hz, 2H). $^{19}$F NMR (282 MHz, CDCl$_3$) δ–125.9 (br s, 1F), –120.9 (br s, 1F).

2,4-Difluoro-3-(pyridin-2-yl)benzophenone (Entry 11, Table VI)

Figure 76:
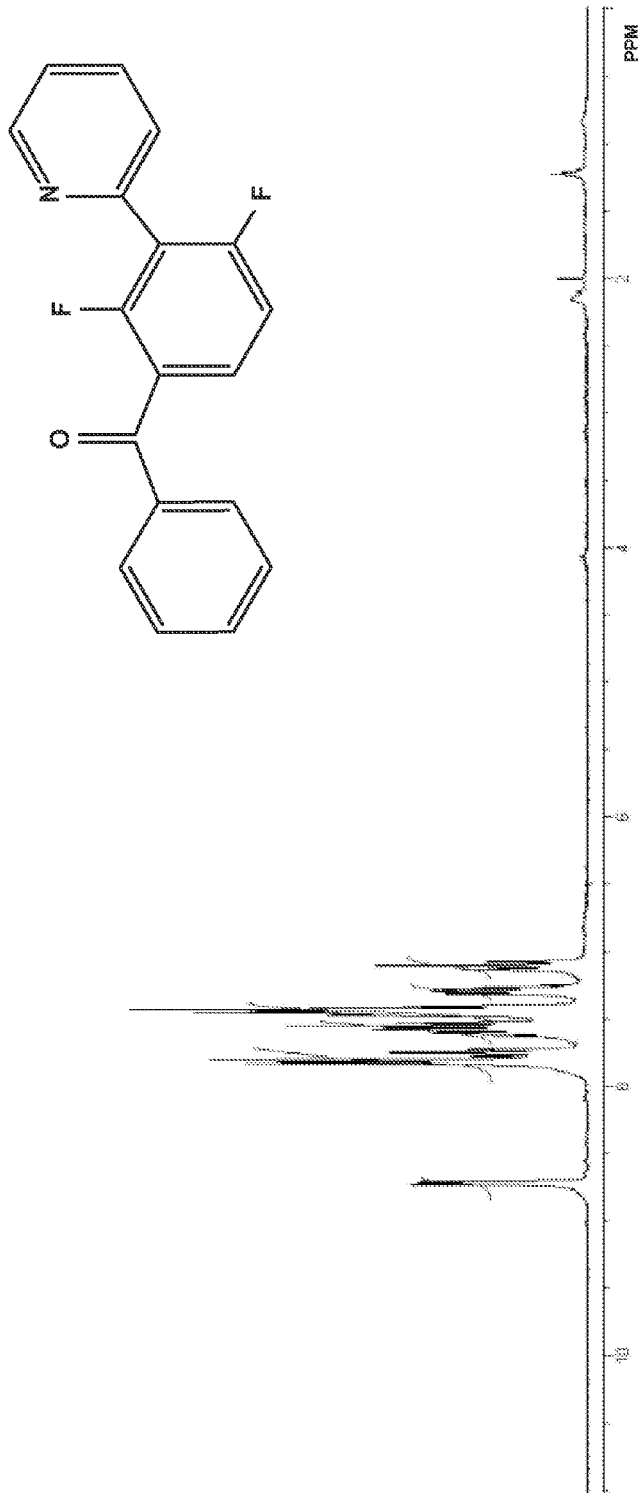
FIG. 76 depicts the molecule structure of 2,4-difluoro-3-(pyridin-2-yl)benzophenone and its $^1$H NMR spectrum.

Copper(I) iodide (19 mg, 0.1 mmol), 2-iodopyridine (205 mg, 1.0 mmol), 1,10-phenanthroline (18 mg, 0.1 mmol), 2,4-difluorobenzophenone (436 mg, 2.0 mmol), K$_3$PO$_4$ (424 mg, 2.0 mmol), and anhydrous DMPU (0.6 mL), 125° C., 24 hours. After column chromatography (hexanes, then 1/1 ethyl acetate/hexanes) 200 mg (68%) of a light tan oil was obtained. R$_f$=0.45 (1/1 ethyl acetate/hexanes). The molecule structure of 2,4-difluoro-3-(pyridin-2-yl)benzophenone and its $^1$H NMR spectrum are shown in FIG. 76. $^1$H NMR (300 MHz, CDCl$_3$) δ 7.11 (dt, J=8.8, 1.2 Hz, 1H), 7.26-7.33 (m, 1H), 7.39-7.50 (m, 3H), 7.51-7.64 (m, 2H), 7.75 (dt, J=7.8, 2.0 Hz, 1H), 7.82 (d, J=7.8 Hz, 2H), 8.72 (d, J=4.4 Hz, 2H). $^{19}$F NMR (282 MHz, CDCl$_3$) δ–113.3-113.2 (m, 1F), –110.2-110.0 (m, 1F). $^{13}$C NMR (75 MHz, CDCl$_3$) δ 112.8 (dd, J=24.0, 4.5 Hz), 119.2 (t, J=18.5, Hz), 121.9, 123.8, 124.3 (dd, J=15.5, 3.5 Hz), 126.5, 129.1, 130.2, 132.1 (dd, J=10.8, 6.8 Hz), 134.0, 137.0, 137.9, 149.1, 150.4, 158.7 (dd, J=257.3, 7.0 Hz), 162.7 (dd, J=257.3, 7.0 Hz), 192.8. FT-IR (neat, cm-1) u 1667, 1618, 1592, 1448, 1420, 1321, 1269, 1013, 832, 797, 789, 748, 719 Anal calcd for C$_{18}$H$_{11}$F$_2$NO (295.28 g/mol): C, 73.22; H, 3.75; N, 4.74. Found. C, 72.55; H, 3.88; N, 4.74.

2,3,4,5,6-Pentachlorobiphenyl (Entry 12, Table VI)

Figure 77:
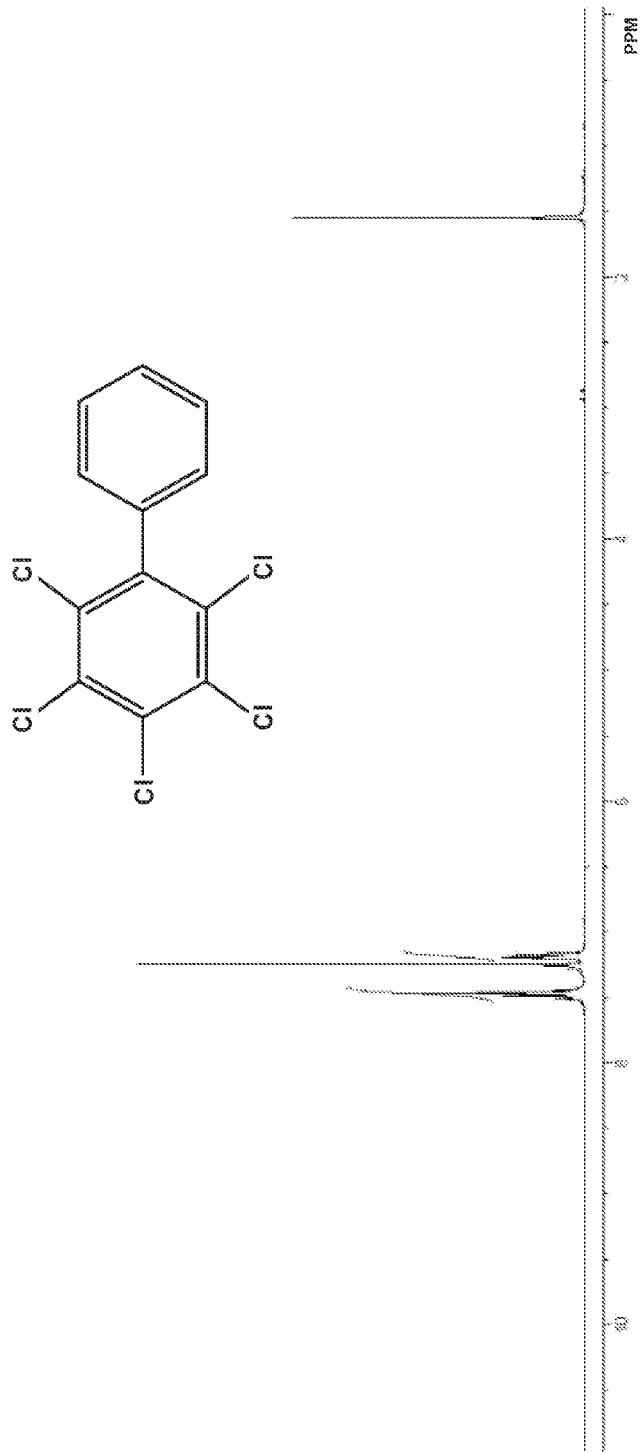
FIG. 77 depicts the molecule structure of 2,3,4,5,6-pentachlorobiphenyl and its $^1$H NMR spectrum.

Copper(I) iodide (19 mg, 0.1 mmol), iodobenzene (408 mg, 2.0 mmol), 1,10-phenanthroline (18 mg, 0.1 mmol), 1,2,3,4,5-pentachlorobenzene (250 mg, 1.0 mmol), t-BuOLi (160 mg, 2 mmol), and DMF (0.5 mL), 120° C., 12 hours. After column chromatography (hexanes) 297 mg (91%) of a colorless solid was obtained. R$_f$=0.54 (hexanes). This compound is known.[21] The molecule structure of 2,3,4,5,6-pentachlorobiphenyl and its $^1$H NMR spectrum are shown in FIG. 77. $^1$H NMR (300 MHz, CDCl$_3$) δ 7.16-7.21 (m, 2H), 7.44-7.52 (m, 3H).

2,3,5,6-Tetrachlorobiphenyl (Entry 13, Table VI)

Figure 78:
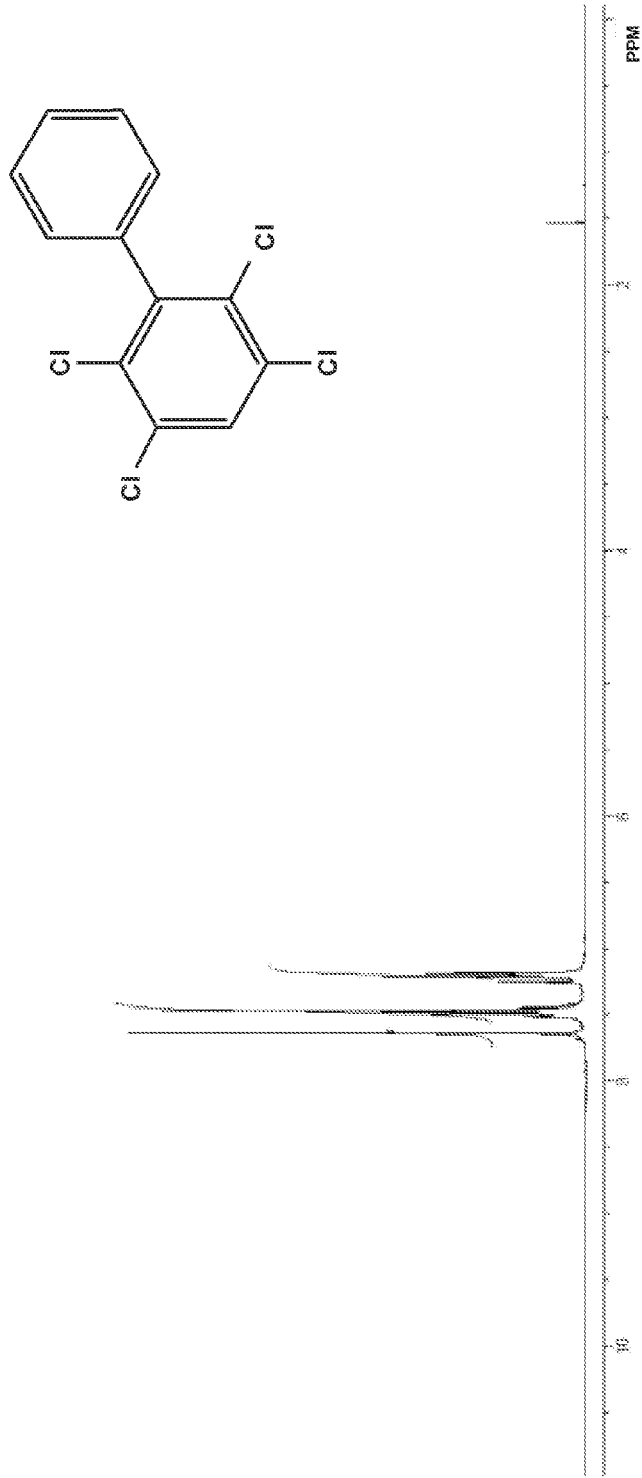
FIG. 78 depicts the molecule structure of 2,3,5,6-tetrachlorobiphenyl and its $^1$H NMR spectrum.

Copper(I) iodide (19 mg, 0.11 mmol), iodobenzene (204 mg, 1.0 mmol), 1,10-phenanthroline (18 mg, 0.1 mmol), 1,2,4,5-tetrachlorobenzene (432 mg, 2.0 mmol), t-BuOLi (160 mg, 2 mmol), and DMPU (0.6 mL), 125° C., 12 hours. After column chromatography (hexanes) 217 mg (74%) of a colorless solid was obtained. R$_f$=0.51 (hexanes). This compound is known.[22] The molecule structure of 2,3,5,6-tetrachlorobiphenyl and its $^1$H NMR spectrum are shown in FIG. 78. $^1$H NMR (300 MHz, CDCl$_3$) δ 7.17-7.22 (m, 2H), 7.44-7.52 (m, 3H), 7.64 (s, 1H).

2,6-Dichlorobiphenyl (Entry 14, Table VI)

Figure 79:
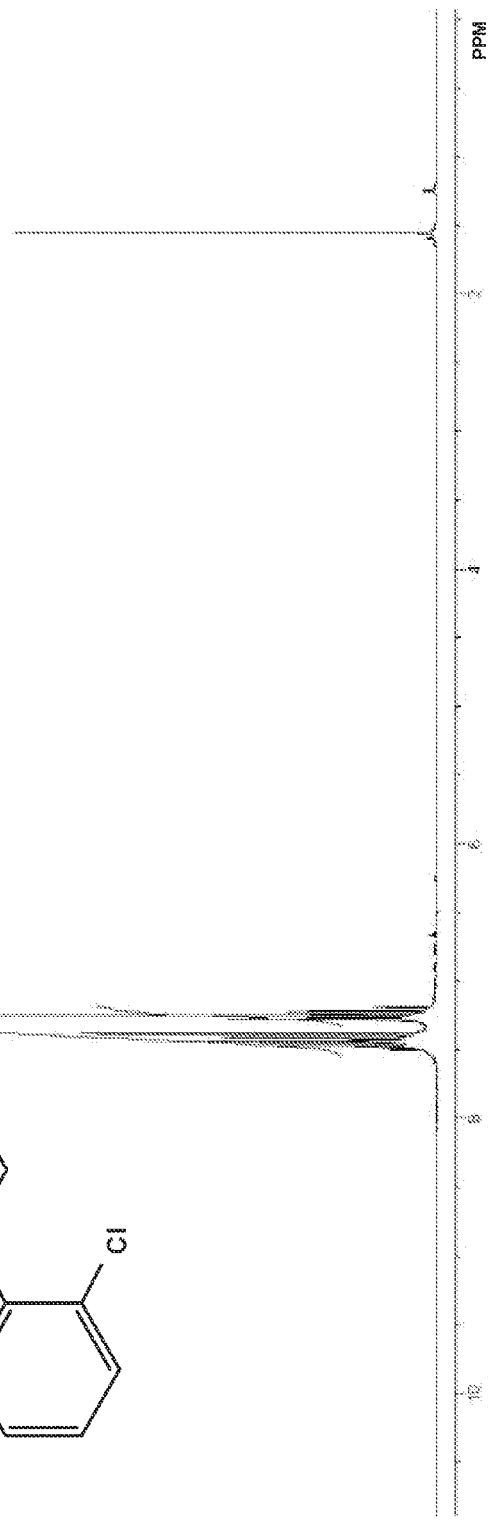
FIG. 79 depicts the molecule structure of 2,6-dichlorobiphenyl and its $^1$H NMR spectrum.

Using Et$_3$COLi Base:
Copper(I) iodide (19 mg, 0.1 mmol), iodobenzene (204 mg, 1.0 mmol), 1,10-phenanthroline (18 mg, 0.1 mmol), 1,3-dichlorobenzene (220 mg, 1.5 mmol), Et$_3$COLi (207 mg, 1.7 mmol), and anhydrous DMPU (0.5 mL), 125° C., 12 hours. After column chromatography (hexanes) 96 mg (43%) of a colorless oil was obtained. R$_f$=0.49 (hexanes). This compound is known.[23] The molecule structure of 2,6-dichlorobiphenyl and its $^1$H NMR spectrum are shown in FIG. 79. $^1$H NMR (300 MHz, CDCl$_3$) δ 7.18-7.30 (m, 3H), 7.38-7.50 (m, 5H).

Using t-BuOLi Base:

Copper(I) iodide (19 mg, 0.1 mmol), iodobenzene (204 mg, 1.0 mmol), 1,10-phenanthroline (18 mg, 0.1 mmol), 1,3-dichlorobenzene (220 mg, 1.5 mmol), tBuOLi (160 mg, 2.0 mmol), and DMPU (0.5 mL), 125° C., 12 hours. After column chromatography (hexanes) 40 mg (18%) of a colorless oil was obtained.

3-Nitro-2-(pyridin-2-yl)benzonitrile (Entry 15, Table VI)

Figure 80:
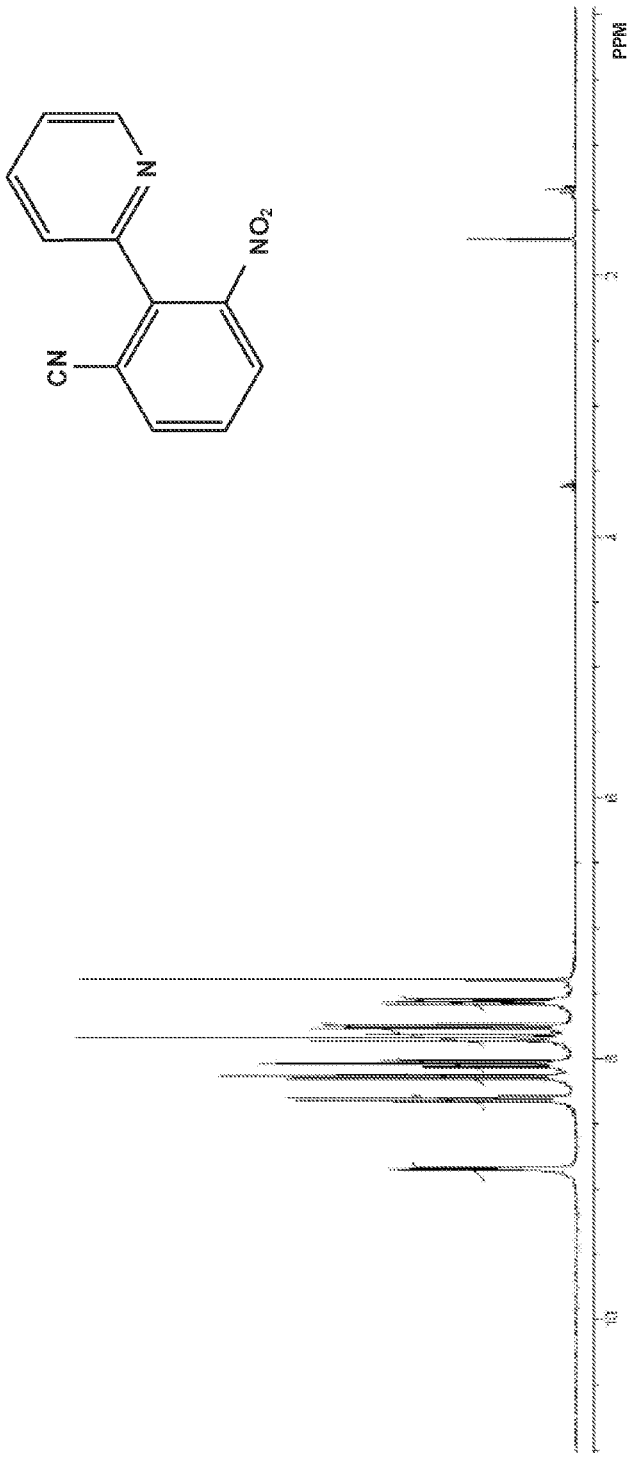
FIG. 80 depicts the molecule structure of 3-nitro-2-(pyridin-2-yl)benzonitrile and its $^1$H NMR spectrum.

Copper(I) iodide (19 mg, 0.1 mmol), 2-iodopyridine (410 mg, 2.0 mmol), 1,10-phenanthroline (18 mg, 0.1 mmol), 3-nitrobenzonitrile (148 mg, 1.0 mmol), K$_3$PO$_4$ (424 mg, 2.0 mmol), and anhydrous DMPU (0.6 mL), 125° C., 24 hours. After column chromatography (hexanes, then 1/1 ethyl acetate/hexanes) 115 mg (51%) of a light tan solid was obtained. R$_f$=0.45 (1/1 ethyl acetate/hexanes), mp 107-109° C. (from ether). The molecule structure of 3-nitro-2-(pyridin-2-yl)benzonitrile and its $^1$H NMR spectrum are shown in FIG. 80. $^1$H NMR (300 MHz, CDCl$_3$) δ 7.41 (ddd, J=8.0 Hz, 4.5 Hz, 1.0 Hz, 1H), 7.60 (dt, J=8.0 Hz, 1.0 Hz, 1H), 7.69 (t, J=8.0 Hz, 1H), 7.89 (dt, J=8.0 Hz, 1.7 Hz, 1H), 7.99 (dd, J=8.0 Hz, 1.0 Hz, 1H), 8.16 (dd, J=8.0 Hz, 1 Hz, 1H), 8.69 (dt, J=4.5 Hz, 1.0 Hz, 1H). $^{13}$C NMR (75 MHz, CDCl$_3$) δ 115.8, 116.4, 124.4, 124.7, 128.8, 130.3, 132.8, 137.3, 137.5, 139.4, 150.7, 152.4. FT-IR (neat, cm-1) u 2230, 1589, 1548, 1528, 1372, 815, 799, 783, 754, 733 Anal calcd for C$_{12}$H$_7$N$_3$O$_2$ (225.20 g/mol): C, 64.00; H, 3.13; N, 18.66. Found. C, 64.27; H, 3.13; N, 18.40.

2-(2,6-Dinitrophenyl)pyridine (Entry 16, Table VI)

Figure 81:
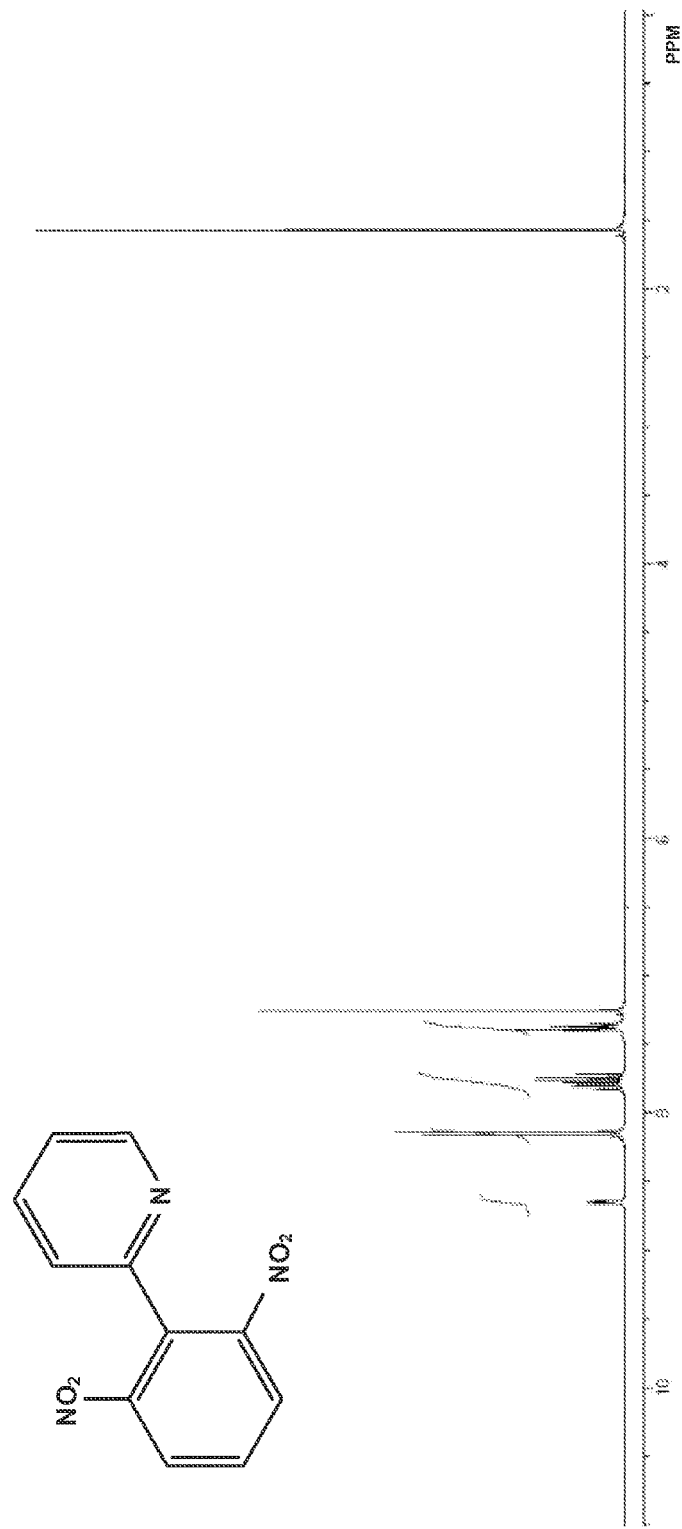
FIG. 81 depicts the molecule structure of 2-(2,6-dinitrophenyl)pyridine and its $^1$H NMR spectrum.

Copper(I) iodide (19 mg, 0.1 mmol), 2-iodopyridine (205 mg, 1.0 mmol), 1,10-phenanthroline (18 mg, 0.1 mmol), 1,3-dinitrobenzene (336 mg, 2.0 mmol), K$_3$PO$_4$ (424 mg, 2.0 mmol), and anhydrous DMPU (0.6 mL), 125° C., 22 hours. After column chromatography (hexanes, then 35% ethyl acetate in hexanes) 176 mg (72%) of a colorless solid was obtained. R$_f$=0.47 (1/1 ethyl acetate/hexanes), mp 160-162° C. (from hexanes). The molecule structure of 2-(2,6-dinitrophenyl)pyridine and its $^1$H NMR spectrum are shown in FIG. 81. $^1$H NMR (300 MHz, CDCl$_3$) δ 7.34-7.41 (m, 2H), 7.71-7.83 (m, 2H), 8.15 (d, J=7.8 Hz, 2H), 8.63-8.67 (m, 1H). $^{13}$C NMR (75 MHz, CDCl$_3$) δ 124.0, 124.2, 128.2, 130.4, 130.6, 137.2, 150.6, 150.8, 151.2. FT-IR (neat, cm-1) u 1524, 1362, 821, 793, 752, 721, 706 Anal calcd for C$_{12}$H$_7$N$_3$O$_2$ (245.19 g/mol): C, 53.88; H, 2.88; N, 17.14. Found. C, 53.86; H, 2.71; N, 16.87.

Control Arylation Reaction (CuI Omitted)

Using 4-Iodotoluene as the Coupling Partner:

1,10-phenanthroline (18 mg, 0.1 mmol), pentafluorobenzene (252 mg, 1.5 mmol), 4-iodotoluene (218 mg, 1.0 mmol), K$_3$PO$_4$ (424 mg, 2.0 mmol), and DMF (0.6 mL) at 125° C., 12 h. No product was detected. —Using 2-iodopyridine as the coupling partner: 1,10-phenanthroline (18 mg, 0.1 mmol), pentafluorobenzene (252 mg, 1.5 mmol), 2-iodopyridine (205 mg, 1.0 mmol), K$_3$PO$_4$ (424 mg, 2.0 mmol), and DMF (0.6 mL) at 125° C., 12 h. A trace of arylated product was detected.

Reaction of Benzothiophene and Iodoarenes in the Presence of t-BuOD:

Using Iodobenzene:

Copper(I) iodide (19 mg, 0.1 mmol), iodobenzene (408 mg, 2.0 mmol), 1,10-phenanthroline (18 mg, 0.1 mmol), benzothiophene (134 mg, 1.0 mmol), t-BuOLi (160 mg, 2.0 mmol), t-BuOD (150 mg, 2.0 mmol), and anhydrous DMPU (0.5 mL), 125° C. The reaction was stopped after 1 hour (15% conversion by GC). The unreacted starting material was recovered by column chromatography (hexanes). NMR integration showed 20% D incorporation in starting material at 2-position.

Using 4-Iodotoluene:

Copper(I) iodide (19 mg, 0.1 mmol), 4-iodotoluene (436 mg, 2.0 mmol), 1,10-phenanthroline (18 mg, 0.11 mmol), benzothiophene (134 mg, 1.0 mmol), t-BuOLi (160 mg, 2.0 mmol), t-BuOD (150 mg, 2.0 mmol), and anhydrous DMPU (0.5 mL), 125° C. The reaction was stopped after 1 hour (13% conversion by GC). The unreacted starting material was recovered by column chromatography (hexanes). NMR integration showed 25% D incorporation in starting material at 2-position.

Using 4-Iodobenzotrifluoride:

Copper(I) iodide (19 mg, 0.1 mmol), 4-iodobenzotrifluoride (544 mg, 2.0 mmol), 1,10-phenanthroline (18 mg, 0.1 mmol), benzothiophene (134 mg, 1.0 mmol), t-BuOLi (160 mg, 2.0 mmol), t-BuOD (150 mg, 2.0 mmol), and DMPU (0.5 mL), 125° C. The reaction was stopped after 1 hour (34% conversion by GC). The unreacted starting material was recovered by column chromatography (hexanes). NMR integration showed 26% of D incorporation in starting material at 2-position.

$^{19}$F NMR Study of the Reaction Intermediate:

Copper(I) iodide (190 mg, 1.0 mmol), 1,10-phenanthroline (180 mg, 1.0 mmol), pentafluorobenzene (252 mg, 1.5 mmol), K$_3$PO$_4$ (424 mg, 2.0 mmol), and DMF (3.0 mL) at 125° C. The reaction mixture was analyzed by $^9$F NMR at different reaction times. At t=0, only C6F5H was observed by $^{19}$F NMR. At t=1 h, only pentafluorophenylcopper phenanthroline complex was present in the reaction mixture.

TABLE S1

| | $^{19}$F NMR Spectrum of the Reaction Mixture and C$_6$F$_5$Cu(Phen) Complex | | |
|---|---|---|---|
| | Reaction mixture at t = 0 | Reaction mixture at t = 1 h | C$_6$F$_5$Cu(Phen) |
| o-F | −142.2 (d, J$_{F-F}$ = 10 Hz, 2F) | −113.5--113.0 (m, 2F) | −112.9--112.4 (m, 2F) |
| m-F | −166.3--166.0 (m, 2F) | −166.4--166.0 (m, 2F) | −166.2--165.9 (m, 2F) |
| p-F | −158.5 (t, J$_F$ = 20 Hz, 1F) | −165.2 (t, J$_F$ = 20 Hz, 1F) | −165.2 (t, J$_F$ = 20 Hz, 1F) |

H/D Exchange Reactions:

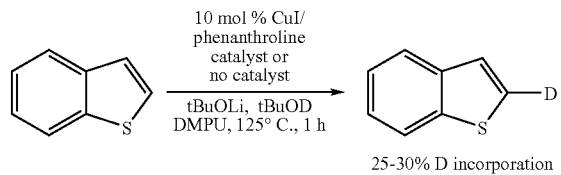 [SMILES: c1ccc2sccc2c1 ; [2H]c1cc2ccccc2s1]

25-30% D incorporation

With Copper(I) Catalyst:
Copper(I) iodide (19 mg, 0.1 mmol), benzothiophene (134 mg, 1.0 mmol), 1,10-phenanthroline (18 mg, 0.1 μmol), t-BuOD (375 mg, 5 mmol), t-BuOLi (160 mg, 2.0 mmol), and DMPU (0.7 mL) at 125° C. for 1 h. Benzothiophene was recovered by column chromatography (hexanes). NMR integration of the C-2 proton (δ 7.45 ppm) showed 30% D incorporation.

Without Copper(I) Catalyst:
Benzothiophene (134 mg, 1.0 mmol), t-BuOD (375 mg, 5 mmol), t-BuOLi (160 mg, 2.0 mmol), and DMPU (0.7 mL) at 125° C. for 1 h. Benzothiophene was recovered by column chromatography (hexanes). NMR integration of the C-2 proton (δ 7.45 ppm) showed 30% D incorporation.

Using t-BuOCu:
t-BuOCu (68.5 mg, 0.5 mmol), benzothiophene (67 mg, 0.5 mmol), 1,10-phenanthroline (90 mg, 0.5 mmol), t-BuOD (187.5 mg, 2.5 mmol), and anhydrous DMPU (0.4 mL) at 125° C. for 1 h. Benzothiophene was recovered by column chromatography (hexanes). NMR integration of the C-2 proton (δ 7.45 ppm) showed 60% D incorporation.

Using LiI:
LiI (134 mg, 1.0 mmol), benzothiophene (134 mg, 1.0 mmol), t-BuOD (375 mg, 5 mmol), and anhydrous DMPU (0.7 mL) at 125° C. for 1 h. Benzothiophene was recovered by column chromatography (hexanes). Deuterium incorporation in starting material was not detected.

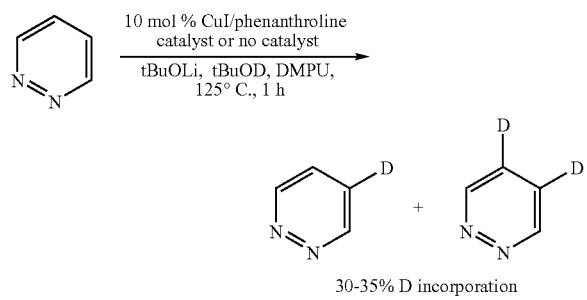

30-35% D incorporation

With Copper(I) Catalyst:
Copper(I) iodide (19 mg, 0.1 mmol), pyridazine (80 mg, 1.0 mmol), 1,10-phenanthroline (18 mg, 0.1 mmol), t-BuOD (375 mg, 5 mmol), t-BuOLi (160 mg, 2.0 mmol), and anhydrous DMPU (0.7 mL) at 125° C. for 1 h. After column chromatography (5% MeOH in ethyl acetate) a mixture of pyridazine and DMPU was recovered. NMR integration showed 30% D incorporation in starting material.

Without Copper(I) Catalyst:
Pyridazine (80 mg, 1.0 mmol), t-BuOD (375 mg, 5 mmol), t-BuOLi (160 mg, 2.0 mmol), and anhydrous DMPU (0.7 mL) at 125° C. for 1 h. After column chromatography (5% MeOH in ethyl acetate) a mixture of pyridazine and DMPU was recovered. NMR integration showed 30% D incorporation in starting material.

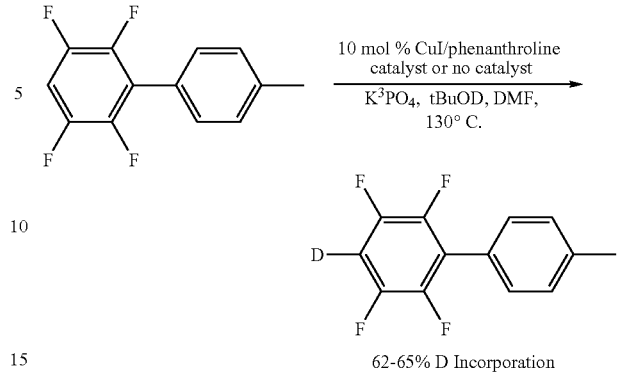

62-65% D Incorporation

With Copper(I) Catalyst:
Copper(I) iodide (9.6 mg, 0.05 mmol), 1,10-phenanthroline (9 mg, 0.05 mmol), 2,3,5,6-tetrafluoro-4'-methylbiphenyl (120 mg, 0.5 mmol), t-BuOD (375 mg, 5 mmol), $K_3PO_4$ (212 mg, 1.0 mmol), and DMF (0.4 mL) at 130° C. for 24 h. The unreacted starting material was recovered by column chromatography (hexanes). NMR integration showed 65% of D incorporation in starting material.

Without Copper(I) Catalyst:
2,3,5,6-Tetrafluoro-4'-methylbiphenyl (120 mg, 0.5 mmol), t-BuOD (375 mg, 5 mmol), $K_3PO_4$ (212 mg, 1.0 mmol), and DMF (0.4 mL) at 130° C. for 24 h. The unreacted starting material was recovered by column chromatography (hexanes). NMR integration showed 62% of D incorporation in starting material.

Competition Reaction of pentafluorobenzene and 1,2,4,5-tetrafluorobenzene
Copper(I) iodide (19 mg, 0.1 mmol), 4-iodotoluene (218 mg, 1.0 mmol), 1,10-phenanthroline (18 mg, 0.1 mmol), pentafluorobenzene (1176 mg, 7.0 mmol), 1,2,4,5-tetrafluorobenzene (1050 mg, 7.0 mmol), $K_3PO_4$ (488 mg, 2.3 mmol), and DMF (0.8 mL) at 125° C., 15 h. The molar ratio of arylation products 2,3,4,5,6-pentafluoro-4'-methylbiphenyl/2,3,5,6-tetrafluoro-4'-methylbiphenyl was determined to be 3.0 by GC analysis of crude reaction mixture.

Competition Reaction of 4-iodotoluene and 4-iodobenzotrifluoride:
Copper(I) iodide (19 mg, 0.1 mmol), 4-iodotoluene (1526 mg, 7.0 mmol), 4-iodobenzotrifluoride (1904 mg, 7.0 mmol), 1,10-phenanthroline (18 mg, 0.1 mmol), pentafluorobenzene (168 mg, 1.0 mmol), $K_3PO_4$ (424 mg, 2.0 mmol), and DMF (1.0 mL) at 125° C., 1 h. The molar ratio of arylation products 2,3,4,5,6-pentafluoro-4'-(trifluoromethyl)-biphenyl/2,3,4,5,6-pentafluoro-4'-methylbiphenyl was determined to be 4.0 by GC analysis of crude reaction mixture.

Competition Reaction of 4-Bromotoluene and 4-bromobenzotrifluoride:
Copper(I) iodide (19 mg, 0.1 mmol), 4-iodotoluene (1526 mg, 7.0 mmol), 4-iodobenzotrifluoride (1904 mg, 7.0 mmol), 1,10-phenanthroline (18 mg, 0.1 mmol), pentafluorobenzene (168 mg, 1.0 mmol), $K_3PO_4$ (424 mg, 2.0 mmol), and DMF (1.0 mL) at 125° C., 1 h. The molar ratio of arylation products 2,3,4,5,6-pentafluoro-4'-(trifluoromethyl)-biphenyl/2,3,4,5,6-pentafluoro-4'-methylbiphenyl was determined to be 4.0 by GC analysis of crude reaction mixture.

X-Ray Data for 4-Methoxy-2,3,5,6-tetrafluorophenylcopperphenanthroline Complex 2
All measurements were made with a Siemens SMART platform diffractometer equipped with a 4K CCD APEX II detector. A hemisphere of data (1271 frames at 6 cm detector distance) was collected using a narrow-frame algorithm with scan widths of 0.30\% in omega and an exposure time of 30 s/frame. The data were integrated using the Bruker-Nonius SAINT program, with the intensities corrected for Lorentz factor, polarization, air absorption, and absorption due to variation in the path length through the detector faceplate. A psi scan absorption correction was applied based on the entire data set. Redundant reflections were averaged. Final cell constants were refined using 3841 reflections having I>10\s(I), and these, along with other information pertinent to data collection and refinement, are listed in Table IV. The Laue symmetry was determined to be 2/m, and from the systematic absences noted the space group was shown unambiguously to be P2(1)/n. The asymmetric unit consists of one-half dimer situated about an inversion center.

TABLE S2

Crystal Data and Structure Refinement for 4-Methoxy-2,3,5,6-tetrafluorophenylcopper-phenanthroline Complex 2

| | |
|---|---|
| Empirical formula | $C_{38}H_{22}Cu_2F_8N_4O_2$ |
| Formula weight | 845.68 |
| Temperature | 223(2) K |
| Wavelength | 0.71073 A |
| Crystal system, space group | Monoclinic, P2(1)/n |
| Unit cell dimensions | a = 9.3839(6) A alpha = 90 deg. |
| | b = 17.3423(11) A beta = 93.516(1) deg. |
| | c = 10.0786(6) A gamma = 90 deg. |
| Volume | 1637.09(18) $A^3$ |
| Z, Calculated density | 2, 1.716 $Mg/m^3$ |
| Absorption coefficient | 1.389 $mm^{-1}$ |
| F(000) | 848 |
| Crystal color and shape | Bright red column |
| Crystal size | 0.45 × 0.15 × 0.15 mm |
| Theta range for data collection | 2.34 to 25.09 deg. |
| Limiting indices | −11 <= h <= 11, 0 <= k <= 20, 0 <= l <= 11 |
| Reflections collected/unique | 8401/3001 [R(int) = 0.0434] |
| Completeness to theta = 25.09 | 99.5% |
| Absorption correction | Empirical |
| Max. and min. transmission | 0.9856 and 0.6505 |
| Refinement method | Full-matrix least-squares on $F^2$ |
| Data/restraints/parameters | 2082/0/245 |
| Goodness-of-fit on $F^2$ | 0.996 |
| Final R indices [I > 4sigma(I)] | R1 = 0.0282, wR2 = 0.0760 |
| R indices (all data) | R1 = 0.0400, wR2 = 0.0834 |
| Largest diff. peak and hole | 0.513 and −0.207 $e.A^{-3}$ |

Procedure for Aerobic Copper-Catalyzed Dimerization of 2,3,5,6-Tetrafluoroanisole The present invention also provides a method for a one-step dimerization of heterocycles or electron-poor arenes, where the method includes contacting a substrate selected from the group consisting of electron-rich heterocyclic substrates, electron-poor heterocyclic substrates, electron-poor aromatic substrates, and mixtures or combinations thereof in the presence of a copper catalyst and stoichiometric oxygen or air reoxidant. The reaction can also include ligands to modify catalyst activity, where the ligands are generally of the same type used in the other reactions disclosed herein.

Outside the glovebox a 1-dram vial equipped with a magnetic stir bar was charged with 2,3,5,6-tetrafluoroanisole (180 mg, 1.0 mmol), copper(II) chloride (6.8 mg, 0.05 mmol) and commercial, non-anhydrous DMF (0.5 mL). The vial was flushed with argon, capped by an open screw cap with silicone septa and placed inside a glovebox. To this mixture was added t-BuOLi (160 mg, 2.0 mmol). The sealed vial was taken out of the glovebox and connect to dry oxygen source through a needle and then placed in a preheated oil bath (50° C.) for the 1 hour. The reaction mixture was allowed to cool to room temperature subjected to flash chromatography on silica gel. After column chromatography (10% AcoEt in hexanes) 115 mg (64%) of a colorless solid was obtained. $R_f$=0.51 ($SiO_2$, hexanes). $^1$H NMR (300 MHz, $CDCl_3$) δ 4.15 (s, 6H). $^{19}$F NMR (282 MHz, $CDCl_3$) δ−155.8 (d, $J_F$=18.7 Hz, 4F), −138.1 (d, $J_F$=18.7 Hz, 4F).

REFERENCES CITED IN THE INVENTION

The following references were cited in the Detailed Description Section of the Application.
1. Hassan, J.; Sévignon, M.; Gozzi, C.; Schultz, E.; Lemaire, M. *Chem. Rev.* 2002, 102, 1359.
2. Ullmann, F.; Bielecki, J. *Chem. Ber.* 1901, 34, 2174.
3. Reviews: (a) Suzuki, A. *Chem. Commun.* 2005, 4759. (b) Nicolaou, K. C.; Bulger, P. G.; Sarlah, D. *Angew. Chem. Int. Ed.* 2005, 44, 4442. (c) Miura, M. *Angew. Chem. Int. Ed.* 2004, 43, 2201. (d) Stanforth, S. P. *Tetrahedron* 1998, 54, 263.
4. (a) Allred, G. D.; Liebeskind, L. S. *J. Am. Chem. Soc.* 1996, 118, 2748. (b) Thathagar, M. B.; Beckers, J.; Rothenberg, G. *J. Am. Chem. Soc.* 2002, 124, 11858. (c) Ma, D.; Liu, F. *Chem. Commun.* 2004, 1934. (d) Kamata, K.; Yamaguchi, S.; Kotani, M.; Yamaguchi, K.; Mizuno, N. *Angew. Chem. Int. Ed.* 2008, 47, 2407. (e) Usui, S.; Hashimoto, Y.; Morey, J. V.; Wheatley, A. E. H.; Uchiyama, M. *J. Am. Chem. Soc.* 2007, 129, 15102.
5. (a) Klapars, A.; Antilla, J. C.; Huang, X.; Buchwald, S. L. *J. Am. Chem. Soc.* 2001, 123, 7727. (b) Campbell, M. J.; Johnson, J. S. *Org. Lett.* 2007, 9, 1521. (c) Hamada, T.; Ye, X.; Stahl, S. S. *J. Am. Chem. Soc.* 2008, 130, 833. (d) Bolshan, Y.; Batey, R. A. *Angew. Chem. Int. Ed.* 2008, 47, 2109. (e) Antilla, J. C.; Baskin, J. M.; Barder, T. E.; Buchwald, S. L. *J. Org. Chem.* 2004, 69, 5578. (f) del Amo, V.; Dubbaka, S. R.; Krasovskiy, A.; Knochel, P. *Angew. Chem. Int Ed.* 2006, 45, 7838. (g) Shafir, A.; Lichtor, P. A.; Buchwald, S. L. *J. Am. Chem. Soc.* 2007, 129, 3490. (h) Munro-Leighton, C.; Blue, E. D.; Gunnoe, T. B. *J. Am. Chem. Soc.* 2006, 128, 1446. (i) Taillefer, M.; Xia, N.; Ouali, A. *Angew. Chem. Int. Ed.* 2007, 46, 934.
6. (a) Altman, R. A.; Shafir, A.; Choi, A.; Lichtor, P. A.; Buchwald, S. L. *J. Org. Chem.* 2008, 73, 284. (b) Cai, Q.; Zou, B.; Ma, D. *Angew. Chem. Int. Ed.* 2006, 45, 1276.
7. (a) Steinkopf, W.; Leitsmann, R.; Hofmann, K. H. *Liebigs Ann. Chem.* 1941, 546, 180. (b) Sease, J. W.; Zechmeister, L. *J. Am. Chem. Soc.* 1947, 69, 270.
8. Reviews: (a) Dick, A. R.; Sanford, M. S. *Tetrahedron* 2006, 62, 2439. (b) Kakiuchi, F.; Chatani, N. *Adv. Synth. Catal.* 2003, 345, 1077. (c) Seregin, I. V.; Gevorgyan, V. *Chem. Soc. Rev.* 2007, 36, 1173. (d) Dyker, G. *Angew. Chem. Int. Ed.* 1999, 38, 1698. (e) Ritleng, V.; Sirlin, C.; Pfeffer, M. *Chem. Rev.* 2002, 102, 1731. (f) Alberico, D.; Scott, M. E.; Lautens, M. *Chem. Rev.* 2007, 107, 174. (g) Ackermann, L. *Synlett* 2007, 507. (h) Campeau, L.-C.; Fagnou, K. *Chem. Commun.* 2006, 1253. (i) Yu, J.-Q.; Giri, R.; Chen, X. *Org. Biomol. Chem.* 2006, 4, 4041. (J) Lewis, J. C.; Bergman, R. G.; Ellman, J. A. *Acc. Chem. Res.* 2008, ASAP article.
9. (a) Björklund, C.; Nilsson, M. *Acta Chem. Scand.* 1968, 22, 2338. (b) Ljusberg, H.; Wahren, R. *Acta Chem. Scand.* 1973, 27, 2717. (c) Nilsson, M. *Tetrahedron Lett.* 1966, 7, 679. (d) Forrest, J. *J. Chem. Soc.* 1960, 574.
10. (a) Fujita, K.-i.; Nonogawa, M.; Yamaguchi, R. *Chem. Commun.* 2004, 1926. (b) Fuchita, Y.; Oka, H.; Okamura, M. *Inorg. Chim. Acta* 1992, 194, 213. (c) Tani, M.; Sakaguchi, S.; Ishii, Y. *J. Org. Chem.* 2004, 69, 1221. (d) Jintoku, T.; Fujiwara, Y.; Kawata, I.; Kawauchi, T.; Taniguchi, H. *J. Organomet. Chem.* 1990, 385, 297. (e) Ackerman, L. J.; Sadighi, J. P.; Kurtz, D. M.; Labinger, J. A.; Bercaw, J. E. *Organometallics* 2003, 22, 3884. (f) Proch, S.; Kempe, R. *Angew. Chem. Int. Ed.* 2007, 46, 3135. (g) Hull, K. L.; Sanford, M. S. *J. Am. Chem. Soc.* 2007, 129, 11904. (h) Brasche, G.; Garcia-Fortanet, J.; Buchwald, S. L. *Org. Lett.* 2008, 10, 2207. (i) Dwight, T. A.; Rue, N. R.; Charyk, D.; Josselyn, R.; DeBoef, B. *Org. Lett.* 2007, 9, 3137. (J) Stuart, D. R.; Fagnou, K. *Science* 2007, 316, 1172.
11. (a) Lafrance, M.; Rowley, C. N.; Woo, T. K.; Fagnou, K. *J. Am. Chem. Soc.* 2006, 128, 8754. (b) Lafrance, M.; Shore, D.; Fagnou, K. *Org. Lett.* 2006, 8, 5097.
12. (a) Brasche, G.; Buchwald, S. L. *Angew. Chem. Int. Ed.* 2008, 47, 1932. (b) Norinder, J.; Matsumoto, A.; Yoshikai, N.; Nakamura, E. *J. Am. Chem. Soc.* 2008, 130, 5858. (c) Zhang, Y.; Li, C.-J. *Angew. Chem. Int. Ed.* 2006, 45, 1949. (d) Chen, X.; Hao, X.-S.; Goodhue, C. E.; Yu, J.-Q. *J. Am. Chem. Soc.* 2006, 128, 6790. (e) Uemura, T.; Imoto, S.; Chatani, N. *Chem. Lett.* 2006, 35, 842. (f) Li, Z.; Cao, L.; Li, C.-J. *Angew. Chem. Int. Ed.* 2007, 46, 6505. (g) Phipps, R. J.; Grimster, N. P.; Gaunt, M. J. *J. Am. Chem. Soc.* 2008, 130, 8172.
13. (a) Do, H.-Q.; Daugulis, O. *J. Am. Chem. Soc.* 2007, 129, 12404. (b) Do, H.-Q.; Daugulis, O. *J. Am. Chem. Soc.*, 2008, 130, 1128.
14. (a) Pellissier, H.; Santelli, M. *Tetrahedron* 2003, 59, 701. (b) Liu, Z.; Larock, R. C. *J. Org. Chem.* 2007, 72, 223.
15. (a) Shen, K.; Fu, Y.; Li, J.-N.; Liu, L.; Guo, Q.-X. *Tetrahedron* 2007, 63, 1568. (b) Bordwell, F. G. *Acc. Chem. Res.* 1988, 21, 456.
16. Helm, M. D.; Moore, J. E.; Plant, A.; Harrity, J. P. A. *Angew. Chem. Int. Ed.* 2005, 44, 3889.
17. (a) Beckwith, A. L. J.; Gara, W. B. *J. Chem. Soc. Perkin Trans.* 2 1975, 7, 795. (b) Branchi, B.; Galli, C.; Gentili, P. *Eur. J. Org. Chem.* 2002, 2844.
18. Tye, J. W.; Weng, Z.; Johns, A. M.; Incarvito, C. D.; Hartwig, J. F. *J. Am. Chem. Soc.* 2008, ASAP article.
19. (a) Bondi, A. *J. Phys. Chem.* 1964, 68, 441. (b) Carvajal, M. A.; Alvarez, S.; Novoa, J. *J. Chem. Eur. J.* 2004, 10, 2117.
20. Sundararaman, A.; Lalancette, R. A.; Zakharov, L. N.; Rheingold, A. L.; Jökle, F. *Organometallics* 2003, 22, 3526.
21. Sundararaman, A.; Zakharov, L. N.; Rheingold, A. L.; Jökle, F. *Chem. Commun.* 2005, 1708.
22. Camus, A.; Marsich, N. *J. Organomet. Chem.* 1970, 21, 249.
23. (a) Ishiyama, T.; Takagi, J.; Ishida, K.; Miyaura, N.; Anastasi, N. R.; Hartwig, J. F. *J. Am. Chem. Soc.* 2002, 124, 390. (b) Cho, J.-Y.; Tse, M. K.; Holmes, D.; Maleczka Jr., R. E.; Smith III, M. R. *Science* 2002, 295, 305.
24. (a) Anctil, E. J.-G.; Snieckus, V. *J. Organomet. Chem.* 2002, 653, 150. (b) Snieckus, V. *Chem. Rev.* 1990, 90, 879.

REFERENCE CITED IN THE EXPERIMENT SECTION OF THE INVENTION

The following references were cited in the Experiment Section of the Application.
(1) Martins, A.; Marquardt, U.; Kasravi, N.; Alberico, D.; Lautens, M. *J. Org. Chem.* 2006, 71, 4937.
(2) Delia, T. J.; Olsen, M. J.; Bosworth Brown, G. *J. Org. Chem.* 1965, 30, 2766.
(3) Brown, H. C.; Carlson, B. A.; Prager, R. H. *J. Am. Chem. Soc.* 1971, 93, 2070.
(4) Vemin, G.; Dou, H. J. M.; Metzger, J. *J. Chem. Soc., Perkin Transactions* 2 1973, 1093.
(5) Haneda, S.; Gan, Z.; Eda, K.; Hayashi, M. *Organometallics* 2007, 26, 6551.
(6) Vollmann, K.; Muller, C. E. *Heterocycles* 2002, 57, 871.
(7) Do, H.-Q.; Daugulis, O. *J. Am. Chem. Soc.* 2007, 129, 12404.
(8) Pivsa-Art, S.; Satoh, T.; Kawamura, Y.; Miura, M.; Nomura, M. *Bull. Chem. Soc. Jpn.* 1998, 71, 467.
(9) Estrada, L. A.; Montes, V. A.; Zyryanov, G.; Anzenbacher, P., Jr. *J. Phys. Chem. B* 2007, 111, 6983.
(10) Bagley, M. C.; Lubinu, M. C.; Mason, C. *Synlett* 2007, 704.
(11) Liang, Y.; Tang, S.; Zhang, X.-D.; Mao, L.-Q.; Xie, Y.-X.; Li, J.-H. *Org. Lett.* 2006, 8, 3017.
(12) Katritzky, A. R.; Hands, A. R. *J. Chem. Soc.* 1958, 2195.
(13) Bair, J. S.; Harrison, R. G. *J. Org. Chem.* 2007, 72, 6653.
(14) Tiecco, M.; Testaferri, L.; Bagnoli, L.; Marini, F.; Santi, C.; Temperini, A. *Heterocycles* 1996, 43, 2679.
(15) Boger, D. L.; Coleman, R. S.; Panek, J. S.; Yohannes, D. *J. Org. Chem.* 1984, 49, 4405.
(16) Mino, T.; Shirae, Y.; Sakamoto, M.; Fujita, T. *J. Org. Chem.* 2005, 70, 2191.
(17) Lafrance, M.; Rowley, C. N.; Woo, T. K.; Fagnou, K. *J. Am. Chem. Soc.* 2006, 128, 8754.
(18) Xiao, J.-C.; Ye, C.; Shreeve, J. n. M. *Org. Lett.* 2005, 7, 1963.
(19) Black, A.; Brown, J. M.; Pichon, C. *Chem. Commun.* 2005, 42, 5284.
(20) Birchall, J. M.; Haszeldine, R. N.; Speight, J. G. *J. Chem. Soc. Organic* 1970, 2187.
(21) Burukin, A. S.; Vasil'ev, A. A.; Chizhov, A. O.; Zlotin, S. G. *Russ. Chem. Bull.* 2005, 54, 970.
(22) Anklam, E.; Asmus, K. D.; Robertson, L. W. *J. Chem. Soc., Perkin Transactions* 2 1989, 1573.
(23) Nakada, M.; Miura, C.; Nishiyama, H.; Higashi, F.; Mori, T.; Hirota, M.; Ishii, T. *Bull. Chem. Soc. Jpn.* 1989, 62, 3122.

All references cited herein are incorporated by reference. Although the invention has been disclosed with reference to its embodiments, from reading this description those of skill in the art may appreciate changes and modification that may be made which do not depart from the scope and spirit of the invention as described above and claimed hereafter.

We claim:

1. A method for the direct conversion of C—H bonds to carbon-carbon bonds comprising the step of contacting a substrate including an acidic $sp^2$ C—H bond and an aryl halide in the presence of a catalyst comprising a copper(I) salt and a base in the absence of a palladium, rhodium, or ruthenium salt, where the catalyst is capable of deprotonating the hydrogen atom of the acidic $sp^2$ C—H bond, where the substrate comprises an electron-rich heterocyclic substrate having an acidic $sp^2$ C—H bond or a plurality of electron-rich heterocyclic substrates having an acidic $sp^2$ C—H bond, and where the carbon-carbon bonds form between the $sp^2$ carbon atoms of the acidic $sp^2$ C—H bonds and a carbon atom of the aryl halide.

2. The method of claim 1, wherein the catalyst further includes a ligand.

3. The method of claim 2, wherein the ligand comprises a nitrogen, sulfur, oxygen ligand or mixtures or combinations thereof.

4. The method of claim 3, wherein the ligand is selected from the group consisting of dimethylformamide, dimethylacetamide, N-methylpyrrolidone, bipyridine, phenanthroline, and mixtures or combinations thereof.

5. A method for the direct conversion of C—H bonds to carbon-carbon bonds comprising the step of contacting a substrate including an acidic sp$^2$ C—H bond and an aryl halide in the presence of a catalyst comprising a copper(I) salt and a base in the absence of a palladium, rhodium, or ruthenium salt, where the catalyst is capable of deprotonating the hydrogen atom of the acidic sp$^2$ C—H bond, where the substrate comprises an electron-poor heterocyclic substrate having an acidic sp$^2$ C—H bond or a plurality of electron-poor heterocyclic substrates having an acidic sp$^2$ C—H bond, and where the carbon-carbon bonds form between the sp$^2$ carbon atoms of the acidic sp$^2$ C—H bonds and a carbon atom of the aryl halide.

6. The method of claim 5, wherein the catalyst further includes a ligand.

7. The method of claim 6, wherein the ligand comprises a nitrogen, sulfur, oxygen ligand or mixtures or combinations thereof.

8. The method of claim 7, wherein the ligand is selected from the group consisting of dimethylformamide, dimethylacetamide, N-methylpyrrolidone, bipyridine, phenanthroline, and mixtures or combinations thereof.

9. A method for a one-step dimerization or polymerization of heterocycles or electron-poor arenes, comprising the step of contacting a substrate including an electron-rich heterocyclic substrate having an acidic sp$^2$ C—H bond, an electron-poor heterocyclic substrate having an acidic sp$^2$ C—H bond, an electron-poor aromatic substrate having an acidic sp$^2$ C—H bond, or mixtures and combinations thereof, a catalyst comprising a copper (I) salt, a base capable of deprotonating the hydrogen atom of the acidic sp$^2$ C—H bond and a stoichiometric oxygen or air reoxidant in the absence of a palladium, rhodium, or ruthenium salt to form a dimer or polymer of the substrate, where each new C—C bond is formed between two sp$^2$ carbon atoms of the acidic sp$^2$ C—H bond on each substrate, where the electron-poor aromatic substrate is selected from the group consisting of halogenated arenes, nitrile substituted arenes, nitrile and halogen substituted arenes, nitro substituted arenes, nitro and nitrile substituted arenes, nitro, nitrile and halogen substituted arenes, arenes bearing halogenated substitutents comprise halogenated alkyl groups and mixtures or combinations thereof and where the halogenated alkyl groups comprise fluorinated alkyl groups, perfluoroalkyl group, chlorinated alkyl groups, perchloroalkyl group, fluorinated/chlorinated alkyl groups, and mixtures or combinations thereof.

10. The method of claim 9, wherein the electron-poor aromatic substrate comprises halogenated arenes.

11. The method of claim 10, wherein the halogenated arenes comprise fluorinated arenes, perfluorinated arenes, chlorinated arenes, perchlorinated arenes, fluorinated/chlorinated arenes, or mixtures or combinations thereof.

12. A method for a one-step dimerization or polymerization of electron-poor arenes, comprising the step of contacting a halogenated arene having an acidic sp$^2$ C—H bond a catalyst comprising a copper (I) salt, a base capable of deprotonating the hydrogen atom of the acidic sp$^2$ C—H bond and a stoichiometric oxygen or air reoxidant to form a dimer or polymer of the substrate, where each new C—C bond is formed between two sp$^2$ carbon atoms of the acidic sp$^2$ C—H bond on each substrate, where the halogenated arenes comprise fluorinated arenes, perfluorinated arenes, chlorinated arenes, perchlorinated arenes, fluorinated/chlorinated arenes, or mixtures or combinations thereof, where the halogenated substituents comprise halogenated alkyl groups and where the halogenated alkyl groups comprise fluorinated alkyl groups, perfluoroalkyl group, chlorinated alkyl groups, perchloroalkyl group, fluorinated/chlorinated alkyl groups, and mixtures or combinations thereof.

* * * * *